US012281313B2

(12) United States Patent
Holt et al.

(10) Patent No.: US 12,281,313 B2
(45) Date of Patent: Apr. 22, 2025

(54) COMPOSITIONS AND METHODS FOR DELIVERING NUCLEIC ACIDS TO COCHLEAR AND VESTIBULAR CELLS

(71) Applicants: Children's Medical Center Corporation, Boston, MA (US); École Polytechnique Fédérale de Lausanne, Lausanne (CH)

(72) Inventors: Jeffrey R. Holt, Boston, MA (US); Yukako Asai, Boston, MA (US); Paola Andrea Solanes Vega, Lausanne (CH); Bernard Schneider, Lausanne (CH)

(73) Assignee: Children's Medical Center Corporation, Boston, MA (US)

( * ) Notice: Subject to any disclaimer, the term of this patent is extended or adjusted under 35 U.S.C. 154(b) by 1040 days.

(21) Appl. No.: 17/010,556

(22) Filed: Sep. 2, 2020

(65) Prior Publication Data

US 2020/0392516 A1 Dec. 17, 2020

Related U.S. Application Data

(63) Continuation of application No. PCT/US2019/020794, filed on Mar. 5, 2019.

(60) Provisional application No. 62/638,697, filed on Mar. 5, 2018.

(51) Int. Cl.
*C12N 15/64* (2006.01)
*A61P 27/16* (2006.01)

(52) U.S. Cl.
CPC .............. *C12N 15/64* (2013.01); *A61P 27/16* (2018.01)

(58) Field of Classification Search
None
See application file for complete search history.

(56) References Cited

U.S. PATENT DOCUMENTS

| | | | |
|---|---|---|---|
| 11,730,827 | B2 | 8/2023 | Holt et al. |
| 2005/0287127 | A1 | 12/2005 | Li et al. |
| 2013/0095071 | A1 | 4/2013 | Bance et al. |
| 2017/0166926 | A1 | 6/2017 | Deverman et al. |
| 2017/0204144 | A1 | 7/2017 | Deverman et al. |
| 2018/0055908 | A1 | 3/2018 | Petit et al. |
| 2019/0351072 | A1 | 11/2019 | Holt et al. |
| 2023/0330268 | A1 | 10/2023 | Holt et al. |

FOREIGN PATENT DOCUMENTS

| | | | |
|---|---|---|---|
| JP | 2016536011 | A | 11/2016 |
| JP | 2018536420 | A | 12/2018 |
| WO | 2006026570 | A2 | 3/2006 |
| WO | 2011075838 | A1 | 6/2011 |
| WO | 2015054653 | A2 | 4/2015 |
| WO | 2015089462 | A1 | 6/2015 |
| WO | 2017100791 | A1 | 6/2017 |
| WO | 2017136764 | A1 | 8/2017 |
| WO | 2017189964 | A2 | 11/2017 |
| WO | 2018017834 | A1 | 1/2018 |
| WO | 2019200016 | A1 | 10/2019 |

OTHER PUBLICATIONS

Sekerkova, et al. (2006) "Espins and the actin cytoskeleton of hair cell stereocilia and sensory cell microvilli", Cell and Molecular Life Sciences, 63: 2329-41. (Year: 2006).*
Zheng, et al. (2008) "Evaluation of Promoters for Use in Tissue-Specific Gene Delivery", in Meths Mol Bio, Gene Ther Prot, vol. 2: Design and Charact Gene Trans Vects, 3rd Ed, Ed by J M. Le Doux, Humana Press, Springer Sci and Buis Media, LLC, Totowa, NJ, USA, pp. 205-219. (Year: 2008).*
Gyorgy, et al. (Nov. 20, 2018) "Gene Transfer with AAV9-PHP.B rescues Hearing a Mouse Model of Usher Syndrome 3A and Transduces Hair Cells in a Non-human Primate", Molecular Therapy, 13: 1-13. (Year: 2018).*
Kawashima, et al. (2011) "Mechanotransduction in mouse inner ear hair cells requires transmembrane channel-like genes", 121(12): 4796-4809. (Year: 2011).*
Nakanishi, et al. (2014) "Mutations of TMC1 cause deafness by disrupting mechanoelectrical transduction", Auris Nasus Larynx, 41(5): 399-408. (Year: 2014).*
Gao, et al. (2018) "Treatment of autosomal dominant hearing loss by in vivo delivery of genome editing agents", 553: 217, 21 pages long. (Year: 2018).*
Zincarelli, et al. (2008) "Analysis of AAV Serotypes 1-9 Mediated Gene Expression and Tropism in Mice After Systemic Injection", Molecular Therapy, 16(6): 1073-80. (Year: 2008).*
Arnold et al., "Novel Slow- and Fast-Type Drug Release Round-Window Microimplants for Local Drug Application to the Cochlea: An Experimental Study in Guinea Pigs," Audiology & Neuro-Otology, 2005, vol. 10, pp. 53-63.
Deverman et al., "Cre-dependent selection yields AAV variants for widespread gene transfer to the adult brain," Nature Biotechnology, Feb. 2016, vol. 34, No. 2, pp. 204-209.
Landegger et al., "A synthetic AAV vector enables safe and efficient gene transfer to the mammalian inner ear," Nature Biotechnology, Mar. 2017, vol. 35, No. 3, pp. 280-284.
Mathur et al., "Usher syndrome: Hearing loss, retinal degeneration and associated abnormalities," Biochimica et Biophysica Acta, 2015, vol. 1852, No. 3, pp. 406-420.
Extended European Search Report dated Dec. 3, 2021 in corresponding European Patent Application No. 19764479.2 (7 pages).
Alagramam et al., "Promoter, alternative splice forms, and genomic structure of protocadherin 15," Genomics, 2007, vol. 90, pp. 482-492.
Durymanov et al., "Non-viral Delivery of Nucleic Acids: Insight Into Mechanisms of Overcoming Intracellular Barriers," Frontiers in Pharmacology, 2018, vol. 9, Article No. 971, pp. 1-15.
Géléoc et al., "35 Gene Therapy Restores Auditory and Vestibular Function in a Mouse Model of Usher Syndrome, Type 1C," Symposium—New horizons in hearing rehabilitation, Abstract Book, Inner Ear Biology 2016, Montpellier, Sep. 18, 2016.
GenBank Accession No. AKU89595.1.

(Continued)

*Primary Examiner* — Robert M Kelly
(74) *Attorney, Agent, or Firm* — Greenberg Traurig, LLP; Melissa Hunter-Ensor; Evelyn M. Kwon

(57) ABSTRACT

Provided herein are materials and methods for efficiently delivering nucleic acids to cochlear and vestibular cells, and methods of treating sensory transduction disorders associated with a genetic defect.

13 Claims, 27 Drawing Sheets

Specification includes a Sequence Listing.

(56) References Cited

OTHER PUBLICATIONS

Goodyear et al., "A Receptor-Like Inositol Lipid Phosphatase Is Required for the Maturation of Developing Cochlear Hair Bundles," The Journal of Neuroscience, Oct. 8, 2003, vol. 23, No. 27, pp. 9208-9219.
Grimm et al., "Helper Virus-Free, Optically Controllable, and Two-Plasmid-Based Production of Adeno-associated Virus Vectors of Serotypes 1 to 6," Molecular Therapy, Jun. 2003, vol. 7, No. 6, pp. 839-850.
György et al., "Rescue of Hearing by Gene Delivery to Inner-Ear Hair Cells Using Exosome-Associated AAV," Molecular Therapy, 2017, vol. 25, No. 2, pp. 379-391.
Kawashima et al., "Mechanotransduction in mouse inner ear hair cells requires transmembrane channel-like genes," The Journal of Clinical Investigation, 2011, vol. 121, No. 12, pp. 4796-4809.
Kotterman et al., "Engineering adeno-associated viruses for clinical gene therapy," Nature Reviews Genetics, 2014, vol. 15, pp. 445-451.
Landegger et al., "269. Novel Synthetic AAV Efficiently Transduces Neurosensory Hair Cells in the Cochlea," Molecular Therapy, May 1, 2016, vol. 24, Suppl. 1, p. S107.
Lenzi et al., NCBI Bookshelf, A Service of the National Library of Medicine, National Institute of Health, Oversight and Review of Clinical Gene Transfer Protocols: Assessing the Role of the Recombinant DNA Advisory Committee, 2014, pp. 1-16.
Longo-Guess et al., "Targeted knockout and lacZ reporter expression of the mouse Tmhs deafness gene and characterization of the hscy-2J mutation," Mammalian Genome, 2007, vol. 18, pp. 646-656.
Maison et al., "Muscarinic Signaling in the Cochlea: Presynaptic and Postsynaptic Effects on Efferent Feedback and Afferent Excitability," The Journal of Neuroscience, May 12, 2010, vol. 30, No. 19, pp. 6751-6762.
MedlinePlus "Usher syndrome," National Institute of Health / National Library of Medicine, 2022, pp. 1-8.
Parker et al., "Genetic investigations in childhood deafness," Archives of Disease in Childhood, 2015, vol. 100, No. 3, pp. 271-278.
Shim et al., "Nonviral Delivery Systems for Cancer Gene Therapy: Strategies and Challenges," Current Gene Therapy, 2017, vol. 17, No. 5, pp. 1-18.
Shu et al., "Identification of Adeno-Associated Viral Vectors That Target Neonatal and Adult Mammalian Inner Ear Cell Subtypes," Human Gene Therapy, Sep. 1, 2016, vol. 27, No. 9, pp. 687-699.
Office Action dated Jul. 5, 2023 in corresponding Japanese Patent Application No. 2020-570406 (4 pages).
English translation of Office Action dated Jul. 5, 2023 in corresponding Japanese Patent Application No. 2020-570406 (4 pages).
Askew et al., "Tmc gene therapy restores auditory function in deaf mice," Science Translational Medicine, Jul. 8, 2015, vol. 7, No. 295, 295ra108, pp. 1-28.
Shibata et al., "Intravenous rAAV2/9 injection for murine cochlear gene delivery," Scientific Reports, 2017, vol. 7, No. 9609, pp. 1-11.
Xia et al., "Inner Ear Gene Transfection in Neonatal Mice Using Adeno-Associated Viral Vector: A Comparison of Two Approaches," PLoS One, Aug. 2012, vol. 7, No. 8, e43218, pp. 1-8.
Office Action dated Feb. 1, 2023 in corresponding Japanese Patent Application No. 2020-570406 (4 pages).
English translation of the Office Action dated Feb. 1, 2023 in corresponding Japanese Patent Application No. 2020-570406 (5 pages).
György et al., "Gene Transfer with AAV9-PHP.B Rescues Hearing in a Mouse Model of Usher Syndrome 3A and Transduces Hair Cells in a Non-human Primate," Molecular Therapy: Methods & Clinical Development, Nov. 19, 2018, vol. 13, pp. 1-13.
Morabito et al., "AAV-PHP.B-Mediated Global-Scale Expression in the Mouse Nervous System Enables GBA1 Gene Therapy for Wide Protection from Synucleinopathy," Molecular Therapy, Aug. 10, 2017, vol. 25, pp. 2727-2742.
Pan et al., "Gene Therapy Restores Auditory and Vestibular Function in a Mouse Model of Usher Syndrome Type 1c," Nature Biotechnology, Feb. 6, 2017, vol. 35, pp. 264-272.
International Search Report and Written Opinion issued in corresponding International Patent Application No. PCT/US2019/020794, mailed Jul. 5, 2019 (12 pages).
Office Action dated Feb. 8, 2024 in corresponding Chinese Patent Application No. 201980030614.5 (10 pages).
English translation of Office Action dated Feb. 8, 2024 in corresponding Chinese Patent Application No. 201980030614.5 (9 pages).
Office Action dated Nov. 25, 2024 in corresponding Japanese Patent Application No. 2023-186434 (2 pages).
English translation of Office Action dated Nov. 25, 2024 in corresponding Japanese Patent Application No. 2023-186434 (2 pages).

* cited by examiner

COMPOSITIONS AND METHODS FOR DELIVERING NUCLEIC ACIDS TO COCHLEAR AND VESTIBULAR CELLS

CROSS-REFERENCE TO RELATED APPLICATIONS

This application is a U.S. National Stage filed under 35 U.S.C. § 111 (a), which is a continuation of and claims priority to PCT/US2019/020794, filed Mar. 5, 2019, which claims the benefit of and priority to U.S. Provisional Application No. 62/638,697, filed Mar. 5, 2018, the entire contents of each of which are incorporated herein by reference.

SEQUENCE LISTING

The instant application contains a Sequence Listing which has been submitted electronically in ASCII format and is hereby incorporated by reference in its entirety. Said ASCII copy, created on Apr. 4, 2019, is named 167705_015302US.txt and is 126,376 bytes in size.

BACKGROUND

Genetically-based hearing loss is a significant problem with few therapeutic options other than cochlear implants. Inherited hearing problems are often due to single gene defects. Prelingual deafness is diagnosed in 1/500 infants, of which about 50% have a genetic etiology. Usher syndrome, which is associated with a number of different clinical subtypes, each of which can be caused by a mutation in any of a number of different genes, is responsible for 3 to 6% of early childhood deafness. One of the more prevalent genetic defects, estimated to be 1-2% of all genetic deafness, occurs in the TMC1 gene. The most severe form of Usher Syndrome, USH1, is associated with defects in six genes: USH1, MYO7A (myosin 7a), USH1C (harmonin), CDH23 (cadherin 23), PCDH15 (protocadherin 15), SANS (sans; also known as USH1G) and CIB2 (calcium and integrin binding protein2).

The inner ear, e.g., cochlea, particularly the inner and outer hair cells (IHCs and OHCs) in the cochlea, is an attractive target for polynucleotide therapy approaches to intervene in hearing loss and deafness of various etiologies, most immediately monogenic forms of inherited deafness. However, it has been a challenge to efficiently target and transduce IHCs and OHCs as well as other inner ear cells that may be relevant to gene therapy approaches.

SUMMARY

The invention provides an AAV9-php.b vector comprising a transgene encoding a polypeptide of interest (e.g., TMC1, TMC2, MYO7A, USCH1C, CDH23, PCDH15, SANS, CIB2, USH2A, VLGR1, WHRN, CLRN1, PDZD7, KCNQ4, TMPRSS3, STRC, EYA4, USH1C (e.g., harmonin-a, b, or c), OTOF, GPR98, MYO6, MYO15A, LOXHD1, POU3F4, EYA1, WFS1, ACTG1, TMIE, PJVK, SYNE4, and FAM65B) and methods for administering the vector to the inner ear of a subject having a genetic defect in auditory and/or vestibular mechanosensation, thereby treating the subject.

The invention is based, at least in part, on the discovery that AAV9-php.b-CMV-GFP (also termed AAV-php.b-CMV-GFP) efficiently and specifically targeted the sensory cell of the inner ear, including inner and outer hair cells in vivo.

In one aspect, the invention provides a AAV9-php.b vector, where the vector contains a polynucleotide encoding myosin 7a, harmonin (e.g., harmonin-a, harmonin-b, or harmonin-c), cadherin 23, protocadherin 15, USH2A, ADGRV1/VLGR1/GPR98, WHRN, CLRN1, HARS, SANS and calcium and integrin binding protein 2, or any other polypeptide described herein.

In another aspect, the invention provides a AAV9-php.b vector, where the vector encodes a capsid having at least about 85% sequence identity to AAV9-php.b, and contains a promoter that directs expression of a human TMC1 polynucleotide.

In another aspect, the invention provides an AAV9-php.b vector, where the vector contains a promoter that is an Espin promoter, a PCDH15 promoter, a PTPRQ promoter, a Myo6 promoter, a KCNQ4 promoter, a Myo7a promoter, a synapsin promoter, a GFAP promoter, a CMV promoter, a CAG promoter, a CBH promoter, a CBA promoter, a U6 promoter, or a TMHS (LHFPL5) promoter that directs expression of a downstream polynucleotide.

In another aspect, the invention provides a cell containing the AAV9-php.b vector of a previous aspect.

In another aspect, the invention provides a method of expressing a polypeptide in the inner ear of a subject, the method involving contacting a cell of the inner ear with a AAV9-php.b vector encoding a polypeptide of interest, where the AAV9-php.b vector transfects at least about 85, 90, 95 percent or more of inner and outer hair cells.

In another aspect, the invention provides a method of expressing a polypeptide in the inner ear of a subject, the method involving contacting a cell of the inner ear with a AAV9-php.b vector encoding a human polypeptide of interest.

In another aspect, the invention provides a method of treating an inner ear disorder associated with a genetic defect in a subject, the method involving contacting a cell of the subject with a AAV9-php.b vector, where the vector contains a polynucleotide encoding any one or more of myosin 7a, harmonin, cadherin 23, protocadherin 15, USH2A, ADGRV1/VLGR1/GPR98, WHRN, CLRN1, HARS, SANS and calcium and integrin binding protein 2.

In another aspect, the invention provides a method of treating an inner ear disorder associated with a genetic defect in a subject, the method involving contacting a cell of the subject with a AAV9-php.b vector, where the vector contains a promoter is any of an Espin promoter, a PCDH15 promoter, a PTPRQ promoter, a Myo6 promoter, a KCNQ4 promoter, a Myo7a promoter, a synapsin promoter, a GFAP promoter, a CMV promoter, a CAG promoter, a CBH promoter, a CBA promoter, a U6 promoter, and a TMHS (LHFPL5) promoter.

In another aspect, the invention provides a method of treating an inner ear disorder associated with a genetic defect in a subject, the method involving contacting a cell of the subject with a AAV9-php.b vector, where the vector encodes a capsid having at least about 85% sequence identity to AAV9-php.b, and contains a promoter operably linked to a polynucleotide encoding an USH1 polypeptide that is myosin 7a, harmonin, cadherin 23, protocadherin 15, USH2A, ADGRV1/VLGR1/GPR98, WHRN, CLRN1, HARS, SANS and calcium or integrin binding protein 2.

In various embodiments of the above-aspects or any other aspect of the invention described herein, the inner ear defect is a genetic disorder associated with a genetic alteration in a polypeptide expressed in the inner ear. In other embodiments, the genetic defect is associated with partial hearing loss, complete deafness, or partial or complete vestibular dysfunction. In other embodiments of the above aspects, the promoter is any one or more of an Espin promoter, a PCDH15 promoter, a PTPRQ promoter, a Myo6 promoter, a KCNQ4 promoter, a Myo7a promoter, a synapsin promoter, a GFAP promoter, a CMV promoter, a CAG promoter, a CBH promoter, a CBA promoter, a U6 promoter, and a TMHS (LHFPL5) promoter. In other embodiments of the above aspects, the vector transduces inner and outer hair cells, vestibular hair cells, spiral ganglions, or vestibular ganglions with at least about 70% or greater efficiency. In other embodiments of the above aspects, the harmonin polypeptide is harmonin-a, harmonin-b, or harmonin-c. In other embodiments of the above aspects, the cell is outer or inner hair cell, vestibular hair cell, a spiral ganglion, or a vestibular ganglion. In other embodiments of the above aspects, the vector contains a promoter directing expression of a downstream polynucleotide, and the promoter is an Espin promoter, a PCDH15 promoter, a PTPRQ promoter, a Myo6 promoter, a KCNQ4 promoter, a Myo7a promoter, a synapsin promoter, a GFAP promoter, a CMV promoter, a CAG promoter, a CBH promoter, a CBA promoter, a U6 promoter, or a TMHS (LHFPL5) promoter. In other embodiments of the above aspects, the downstream polynucleotide is TMC1, TMC2 or an USH1 polypeptide that is myosin 7a, harmonin, cadherin 23, protocadherin 15, USH2A, ADGRV1/VLGR1/GPR98, WHRN, CLRN1, HARS, SANS and calcium or integrin binding protein 2. In particular embodiments of the above aspects, the harmonin polypeptide is harmonin-a, harmonin-b, or harmonin-c. In other embodiments of the above aspects, the AAV9-php.b vector targets inner and outer hair cells with at least about 70%, 80%, 90%, 95% or greater efficiency, even as high as 100% efficiency. In other embodiments of the above aspects, the human polypeptide is TMC1, TMC2, harmonin-a, harmonin-b, or harmonin-c. In other embodiments of the above aspects, the inner ear defect is a hearing disorder or vestibular disorder. In other embodiments, administering the vector improves or maintains auditory and/or vestibular function in the subject. In some embodiments, improved or maintained auditory and/or vestibular function is associated with preservation of hair bundle morphology and/or restoration of mechanotransduction. In other embodiments of the above aspects, the inner ear disorder is Usher Syndrome.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "AAV9-php.b vector" is meant a viral vector comprising an AAV9-php.b polynucleotide or fragment thereof that transfects a cell of the inner ear. In one embodiment, the AAV9-php.b vector transfects at least 70% of inner hair cells and 70% of outer hair cells following administration to the inner ear of a subject or contact with a cell derived from an inner ear in vitro. In other embodiments, at least 85%, 90%, 95% or virtually 100% of inner hair cells and/or 85%, 90%, 95% or virtually 100% of outer hair cells are transfected. The transfection efficiency may be assessed using a gene encoding GFP in a mouse model. The sequence of an exemplary AAV9-php.b vector is provided below.

```
AAV9-php.b
CCAATGATACGCGTCGGTGCGGGCCTCTTCGCTATTACGCCAGCTGGCGAAAGGGGGATGTGCTGCAAGG

CGATTAAGTTGGGTAACGCCAGGGTTTTCCCAGTCACGACGTTGTAAAACGACGGCCAGTGAGCGCGCGT

AATACGACTCACTATAGGGCGAATTGGGTACATCGACGGTATCGGGGGAGCTCGCAGGGTCTCCATTTTG

AAGCGGGAGGTTTGAACGCGCAGCCGCCATGCCGGGGTTTTACGAGATTGTGATTAAGGTCCCCAGCGAC

CTTGACGAGCATCTGCCCGGCATTTCTGACAGCTTTGTGAACTGGGTGGCCGAGAAGGAATGGGAGTTGC

CGCCAGATTCTGACATGGATCTGAATCTGATTGAGCAGGCACCCCTGACCGTGGCCGAGAAGCTGCAGCG

CGACTTTCTGACGGAATGGCGCCGTGTGAGTAAGGCCCCGGAGGCTCTTTTCTTTGTGCAATTTGAGAAG

GGAGAGAGCTACTTCCACATGCACGTGCTCGTGGAAACCACCGGGGTGAAATCCATGGTTTTGGGACGTT

TCCTGAGTCAGATTCGCGAAAAACTGATTCAGAGAATTTACCGCGGGATCGAGCCGACTTTGCCAAACTG

GTTCGCGGTCACAAAGACCAGAAATGGCGCCGGAGGCGGGAACAAGGTGGTGGATGAGTGCTACATCCCC

AATTACTTGCTCCCCAAAACCCAGCCTGAGCTCCAGTGGGCGTGGACTAATATGGAACAGTATTTAAGCG

CCTGTTTGAATCTCACGGAGCGTAAACGGTTGGTGGCGCAGCATCTGACGCACGTGTCGCAGACGCAGGA

GCAGAACAAAGAGAATCAGAATCCCAATTCTGATGCGCCGGTGATCAGATCAAAAACTTCAGCCAGGTAC

ATGGAGCTGGTCGGGTGGCTCGTGGACAAGGGGATTACCTCGGAGAAGCAGTGGATCCAGGAGGACCAGG

CCTCATACATCTCCTTCAATGCGGCCTCCAACTCGCGGTCCCAAATCAAGGCTGCCTTGGACAATGCGGG

AAAGATTATGAGCCTGACTAAAACCGCCCCCGACTACCTGGTGGGCCAGCAGCCCGTGGAGGACATTTCC

AGCAATCGGATTTATAAAATTTTGGAACTAAACGGGTACGATCCCCAATATGCGGCTTCCGTCTTTCTGG

GATGGGCCACGAAAAAGTTCGGCAAGAGGAACACCATCTGGCTGTTTGGGCCTGCAACTACCGGGAAGAC
```

-continued

CAACATCGCGGAGGCCATAGCCCACACTGTGCCCTTCTACGGGTGCGTAAACTGGACCAATGAGAACTTT
CCCTTCAACGACTGTGTGGACAAGATGGTGATCTGGTGGGAGGAGGGGAAGATGACCGCCAAGGTCGTGG
AGTCGGCCAAAGCCATTCTCGGAGGAAGCAAGGTGCGCGTGGACCAGAAATGCAAGTCCTCGGCCCAGAT
AGACCCGACTCCCGTGATCGTCACCTCCAACACCAATATGTGCGCCGTGATTGACGGGAACTCAACGACC
TTCGAACACCAGCAGCCGTTGCAAGACCGGATGTTCAAATTTGAACTCACCCGCCGTCTGGATCATGACT
TTGGGAAGGTCACCAAGCAGGAAGTCAAAGACTTTTTCCGGTGGGCAAAGGATCACGTGGTTGAGGTGGA
GCATGAATTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAACTACGCGG
ACAGGTACCAAAACAAATGTTCTCGTCACGTGGGCATGAATCTGATGCTGTTTCCCTGCAGACAATGCGA
GAGACTGAATCAGAATTCAAATATCTGCTTCACTCACGGTGTCAAAGACTGTTTAGAGTGCTTTCCCGTG
TCAGAATCTCAACCCGTTTCTGTCGTCAAAAAGGCGTATCAGAAACTGTGCTACATTCATCACATCATGG
GAAAGGTGCCAGACGCTTGCACTGCTTGCGACCTGGTCAATGTGGACTTGGATGACTGTGTTTCTGAACA
ATAAATGACTTAAACCAGGTATGAGTCGGCTGGATAAATCTAAAGTCATAAACGGCGCTCTGGAATTACT
CAATGAAGTCGGTATCGAAGGCCTGACGACAAGGAAACTCGCTCAAAAGCTGGGAGTTGAGCAGCCTACC
CTGTACTGGCACGTGAAGAACAAGCGGGCCCTGCTCGATGCCCTGGCCATCGAGATGCTGGACAGGCATC
ATACCCACTTCTGCCCCCTGGAAGGCGAGTCATGGCAAGACTTTCTGCGGAACAACGCCAAGTCATTCCG
CTGTGCTCTCCTCTCACATCGCGACGGGGCTAAAGTGCATCTCGGCACCCGCCCAACAGAGAAACAGTAC
GAAACCCTGGAAAATCAGCTCGCGTTCCTGTGTCAGCAAGGCTTCTCCCTGGAGAACGCACTGTACGCTC
TGTCCGCCGTGGGCCACTTTACACTGGGCTGCGTATTGGAGGAACAGGAGCATCAAGTAGCAAAAGAGGA
AAGAGAGACACCTACCACCGATTCTATGCCCCCACTTCTGAGACAAGCAATTGAGCTGTTCGACCGGCAG
GGAGCCGAACCTGCCTTCCTTTTCGGCCTGGAACTAATCATATGTGGCCTGGAGAAACAGCTAAAGTGCG
AAAGCGGCGGGCCGGCCGACGCCCTTGACGATTTTGACTTAGACATGCTCCCAGCCGATGCCCTTGACGA
CTTTGACCTTGATATGCTGCCTGCTGACGCTCTTGACGATTTTGACCTTGACATGCTCCCCGGGTAAATG
CATGAATTCGATCTAGAGGGCCCTATTCTATAGTGTCACCTAAATGCTAGAGCTCGCTGATCAGCCTCGA
CTGTGCCTTCTAGTTGCCAGCCATCTGTTGTTTGCCCCTCCCCCGTGCCTTCCTTGACCCTGGAAGGTGC
CACTCCCACTGTCCTTTCCTAATAAAATGAGGAAATTGCATCGCATTGTCTGAGTAGGTGTCATTCTATT
CTGGGGGGTGGGGTGGGGCAGGACAGCAAGGGGGAGGATTGGGAAGACAATAGCAGGCATGCTGGGGATG
CGGTGGGCTCTATGGCTTCTGAGGCGGAAAGAACCAGCTGGGGCTCGAATCAAGCTATCAAGTGCCACCT
GACGTCTCCCTATCAGTGATAGAGAAGTCGACACGTCTCGAGCTCCCTATCAGTGATAGAGAAGGTACGT
CTAGAACGTCTCCCTATCAGTGATAGAGAAGTCGACACGTCTCGAGCTCCCTATCAGTGATAGAGAAGGT
ACGTCTAGAACGTCTCCCTATCAGTGATAGAGAAGTCGACACGTCTCGAGCTCCCTATCAGTGATAGAGA
AGGTACGTCTAGAACGTCTCCCTATCAGTGATAGAGAAGTCGACACGTCTCGAGCTCCCTATCAGTGATA
GAGAAGGTACCCCCTATATAAGCAGAGAGATCTGTTCAAATTTGAACTGACTAAGCGGCTCCCGCCAGAT
TTTGGCAAGATTACTAAGCAGGAAGTCAAGGACTTTTTTGCTTGGGCAAAGGTCAATCAGGTGCCGGTGA
CTCACGAGTTTAAAGTTCCCAGGGAATTGGCGGGAACTAAAGGGGCGGAGAAATCTCTAAAACGCCCACT
GGGTGACGTCACCAATACTAGCTATAAAAGTCTGGAGAAGCGGGCCAGGCTCTCATTTGTTCCCGAGACG
CCTCGCAGTTCAGACGTGACTGTTGATCCCGCTCCTCTGCGACCGCTAGCTTCGATCAACTACGCAGACA
GGTACCAAAACAAGTGTTCTCGTCACGTGGGCATTAATCTGATTCTGTTTCCCTGCAGACAATGCGAGAG
AATGAATCAGAACTCAAATATCTGCTTCACTCACGGACAGAAAGACTGTTTAGAGTGCTTTCCCGTGTCA
GAATCTCAACCCGTTTCTGTCGTCAAAAAGGCGTATCAGAAACTGTGCTACATTCATCATATCATGGGAA

-continued

AGGTGCCAGACGCTTGCACTGCCTGCGATCTGGTCAATGTGGATTTGGATGACTGCATCTTTGAACAATA

AATGACTTAAGCCAGGTATGGCTGCCGATGGTTATCTTCCAGATTGGCTCGAGGACAACCTTAGTGAAGG

AATTCGCGAGTGGTGGGCTTTGAAACCTGGAGCCCCTCAACCCAAGGCAAATCAACAACATCAAGACAAC

GCTAGAGGTCTTGTGCTTCCGGGTTACAAATACCTTGGACCCGGCAACGGACTCGACAAGGGGGAGCCGG

TCAACGCAGCAGACGCGGCGGCCCTCGAGCACGACAAAGCCTACGACCAGCAGCTCAAGGCCGGAGACAA

CCCGTACCTCAAGTACAACCACGCCGACGCCGAGTTCCAGGAGCGGCTCAAAGAAGATACGTCTTTTGGG

GGCAACCTCGGGCGAGCAGTCTTCCAGGCCAAAAAGAGGCTTCTTGAACCTCTTGGTCTGGTTGAGGAAG

CGGCTAAGACGGCTCCTGGAAAGAAGAGGCCTGTAGAGCAGTCTCCTCAGGAACCGGACTCCTCCGCGGG

TATTGGCAAATCGGGTGCACAGCCCGCTAAAAAGAGACTCAATTTCGGTCAGACTGGCGACACAGAGTCA

GTCCCAGACCCTCAACCAATCGGAGAACCTCCCGCAGCCCCCTCAGGTGTGGGATCTCTTACAATGGCTT

CAGGTGGTGGCGCACCAGTGGCAGACAATAACGAAGGTGCCGATGGAGTGGGTAGTTCCTCGGGAAATTG

GCATTGCGATTCCCAATGGCTGGGGGACAGAGTCATCACCACCAGCACCCGAACCTGGGCCCTGCCCACC

TACAACAATCACCTCTACAAGCAAATCTCCAACAGCACATCTGGAGGATCTTCAAATGACAACGCCTACT

TCGGCTACAGCACCCCCTGGGGGTATTTTGACTTCAACAGATTCCACTGCCACTTCTCACCACGTGACTG

GCAGCGACTCATCAACAACAACTGGGGATTCCGGCCTAAGCGACTCAACTTCAAGCTCTTTAACATTCAG

GTCAAAGAGGTTACGGACAACAATGGAGTCAAGACCATCGCCAATAACCTTACCAGCACGGTCCAGGTCT

TCACGGACTCAGACTATCAGCTCCCGTACGTGCTCGGGTCGGCTCACGAGGGCTGCCTCCCGCCGTTCCC

AGCGGACGTTTTCATGATTCCTCAGTACGGGTATCTGACGCTTAATGATGGAAGCCAGGCCGTGGGTCGT

TCGTCCTTTTACTGCCTGGAATATTTCCCGTCGCAAATGCTAAGAACGGGTAACAACTTCCAGTTCAGCT

ACGAGTTTGAGAACGTACCTTTCCATAGCAGCTACGCTCACAGCCAAAGCCTGGACCGACTAATGAATCC

ACTCATCGACCAATACTTGTACTATCTCTCTAGAACTATTAACGGTTCTGGACAGAATCAACAAACGCTA

AAATTCAGTGTGGCCGGACCCAGCAACATGGCTGTCCAGGGAAGAAACTACATACCTGGACCCAGCTACC

GACAACAACGTGTCTCAACCACTGTGACTCAAAACAACAACAGCGAATTTGCTTGGCCTGGAGCTTCTTC

TTGGGCTCTCAATGGACGTAATAGCTTGATGAATCCTGGACCTGCTATGGCCTCTCACAAAGAAGGAGAG

GACCGTTTCTTTCCTTTGTCTGGATCTTTAATTTTTGGCAAACAAGGTACTGGCAGAGACAACGTGGATG

CGGACAAAGTCATGATAACCAACGAAGAAGAAATTAAAACTACTAACCCGGTAGCAACGGAGTCCTATGG

ACAAGTGGCCACAAACCACCAGAGTGCCCAAACTTTGGCGGTGCCTTTTAAGGCACAGGCGCAGACCGGT

TGGGTTCAAAACCAAGGAATACTTCCGGGTATGGTTTGGCAGGACAGAGATGTGTACCTGCAAGGACCCA

TTTGGGCCAAAATTCCTCACACGGACGGCAACTTTCACCCTTCTCCGCTGATGGGAGGGTTTGGAATGAA

GCACCCGCCTCCTCAGATCCTCATCAAAAACACACCTGTACCTGCGGATCCTCCAACGGCCTTCAACAAG

GACAAGCTGAACTCTTTCATCACCCAGTATTCTACTGGTCAAGTCAGCGTGGAGATCGAGTGGGAGCTGC

AGAAGGAAAACAGCAAGCGCTGGAACCCGGAGATCCAGTACACTTCCAACTATTACAAGTCTAATAATGT

TGAATTTGCTGTTAATACTGAAGGTGTATATAGTGAACCCCGCCCCATTGGCACCAGATACCTGACTCGT

AATCTGTAAGTCGACTTGCTTGTTAATCAATAAACCGTTTAATTCGTTTCAGTTGAACTTTGGTCTCTGC

GAAGGGCAATTCGTTTAAACCTGCAGGACTAGAGGTCCTGTATTAGAGGTCACGTGAGTGTTTTGCGACA

TTTTGCGACACCATGTGGTCACGCTGGGTATTTAAGCCCGAGTGAGCACGCAGGGTCTCCATTTTGAAGC

GGGAGGTTTGAACGCGCAGCCGCCAAGCCGAATTCTGCAGATATCACATGTCCTAGGAACTATCGATCCA

TCACACTGGCGGCCGCTCGACTAGAGCGGCCGCCACCGCGGTGGAGCTCCAGCTTTTGCGGACCGAATCG

GAAAGAACATGTGAGCAAAAGGCCAGCAAAAGGCCAGGAACCGTAAAAAGGCCGCGTTGCTGGCGTTTTT

CCATAGGCTCCGCCCCCCTGACGAGCATCACAAAAATCGACGCTCAAGTCAGAGGTGGCGAAACCCGACA

GGACTATAAAGATACCAGGCGTTTCCCCCTGGAAGCTCCCTCGTGCGCTCTCCTGTTCCGACCCTGCCGC

-continued

TTACCGGATACCTGTCCGCCTTTCTCCCTTCGGGAAGCGTGGCGCTTTCTCATAGCTCACGCTGTAGGTA

TCTCAGTTCGGTGTAGGTCGTTCGCTCCAAGCTGGGCTGTGTGCACGAACCCCCCGTTCAGCCCGACCGC

TGCGCCTTATCCGGTAACTATCGTCTTGAGTCCAACCCGGTAAGACACGACTTATCGCCACTGGCAGCAG

CCACTGGTAACAGGATTAGCAGAGCGAGGTATGTAGGCGGTGCTACAGAGTTCTTGAAGTGGTGGCCTAA

CTACGGCTACACTAGAAGAACAGTATTTGGTATCTGCGCTCTGCTGAAGCCAGTTACCTTCGGAAAAAGA

GTTGGTAGCTCTTGATCCGGCAAACAAACCACCGCTGGTAGCGGTGGTTTTTTTGTTTGCAAGCAGCAGA

TTACGCGCAGAAAAAAAGGATCTCAAGAAGATCCTTTGATCTTTTCTACGGGGTCTGACGCTCAGTGGAA

CGAAAACTCACGTTAAGGGATTTTGGTCATGAGATTATCAAAAAGGATCTTCACCTAGATCCTTTTAAAT

TAAAAATGAAGTTTTAAATCAATCTAAAGTATATATGAGTAAACTTGGTCTGACAGTTACCAATGCTTAA

TCAGTGAGGCACCTATCTCAGCGATCTGTCTATTTCGTTCATCCATAGTTGCCTGACTCCCCGTCGTGTA

GATAACTACGATACGGGAGGGCTTACCATCTGGCCCCAGTGCTGCAATGATACCGCGAGACCCACGCTCA

CCGGCTCCAGATTTATCAGCAATAAACCAGCCAGCCGGAAGGGCCGAGCGCAGAAGTGGTCCTGCAACTT

TATCCGCCTCCATCCAGTCTATTAATTGTTGCCGGGAAGCTAGAGTAAGTAGTTCGCCAGTTAATAGTTT

GCGCAACGTTGTTGCCATTGCTACAGGCATCGTGGTGTCACGCTCGTCGTTTGGTATGGCTTCATTCAGC

TCCGGTTCCCAACGATCAAGGCGAGTTACATGATCCCCCATGTTGTGCAAAAAAGCGGTTAGCTCCTTCG

GTCCTCCGATCGTTGTCAGAAGTAAGTTGGCCGCAGTGTTATCACTCATGGTTATGGCAGCACTGCATAA

TTCTCTTACTGTCATGCCATCCGTAAGATGCTTTTCTGTGACTGGTGAGTACTCAACCAAGTCATTCTGA

GAATAGTGTATGCGGCGACCGAGTTGCTCTTGCCCGGCGTCAATACGGGATAATACCGCGCCACATAGCA

GAACTTTAAAAGTGCTCATCATTGGAAAACGTTCTTCGGGGCGAAAACTCTCAAGGATCTTACCGCTGTT

GAGATCCAGTTCGATGTAACCCACTCGTGCACCCAACTGATCTTCAGCATCTTTTACTTTCACCAGCGTT

TCTGGGTGAGCAAAAACAGGAAGGCAAAATGCCGCAAAAAAGGGAATAAGGGCGACACGGAAATGTTGAA

TACTCATACTCTTCCTTTTTCAATATTATTGAAGCATTTATCAGGGTTATTGTCTCATGAGCGGATACAT

ATTTGAATGTATTTAGAAAAATAAACAAATAGGGGTTCCGCGCACATTTCCCCGAAAAGTGCCACCTGAC

GTC

By “mechanosensation” is meant a response to a mechanical stimulus. Touch, hearing, and balance are examples of the conversion of a mechanical stimulus into a neuronal signal. Mechanosensory input is converted into a response to a mechanical stimulus through a process termed “mechanotransduction.”

By “myosin 6 (Myo6) promoter” is meant a regulatory polynucleotide sequence comprising or consisting of a nucleic acid sequence sufficient to direct expression of a downstream polynucleotide in an outer or inner hair cell, a vestibular hair cell, a spiral ganglion, or a vestibular ganglion and having at least about 85% sequencing identity to the following nucleotide sequence:

TGCAAGAACCCTCACTGGCTGAACTATCTTGCCAGCCCCTTATTTTGTTT

TCATATTAACCT

CTTTTTTCTAGTAAAGGAGATGTTTGCTCTCAAATTTGCATAGGAATGTA

ATATTTAATTTAAAAAGATGACCCACATATGACCTTATAAGGACAGTAAA

ATTAAACAACCGGAAAGATAAAGCGGGCCAGTTGGCTCAGTTCTATAAAA

CCAGCCCACAAGGATTGTCACTATTCTTAGGCTTGCGCGGGCTACATGAT

-continued

GAGTTCCAGGACTGCCTGGTTACAGACCGAGACTCTCTCAAGAGTCCAGA

TAAACAACAACAAAGGGGGCGAGGTGGAAATACAGGGGCTGTAAGAAGTA

AATATGATATCTGCATGGGAGGCTAGCCAGAGAAGAAAAAATTTTCTTCC

GTGGTTCAATCCTCCAAGGGCTGAACAGGAAGTTGACGCAGGCAGGTGAG

GAGCACGAGCCTAGATGGGCTGCGGTGCCACCCTTAATCCCCACAAGCGA

GTTCCTCCGCAATTCGCCTGTCCCACTCTCAACTTTTCTTCAACTGACTC

TTTGCTGTGGTCCCTCGCTGTGGCAGTGGAAACAACTACCACTGCGAGGT

AGGGAATGTCATGAGGGGCTACCTGCAGCCCTTGGCTTGCAGGGATGCAG

GGATGCGGTCGGAACCTGAGGCCCCGCCCTTCTCTTGCCCCACGCCATTA

GGCCACGCCCCTACCCAGCACTCCTTCAACCACCCCCTTCCCCGGCGCCT

CATGAGGTCCCGCCCCTCTCAACCCTAGCTCTTGAGGCCTCCCCTTCACA

GCCGCCCCGGCGTTCCTTGACTTGAGGCCACGTCCCTCTGCTCCTTCATT

CCCAAGACCCTACGCTTTGCGAGTCCTCCCTGTCCTGCTGCCTAGGACCC

CGCCCCTCTCAGCCCTTCTGCCCCAAGACCCCGCCCCTTAGGCTGTTCCC

GCCCACTGGCCAATGAAGACCCGCCCTTTCTTTAGCCGCCCCGCCCCGGT

-continued

```
CCCACAAAATCCCGCCTCCGGCCCCGCCTCCCGCCCCCTTGGGCGCTCCG
TAGCAGTGACGTGCGCAGGCTGGGCACTCTGCAGGGCTCTCTGGCCGGCG
GGTGGAGACCGATCCGGGATCTGTCCCAGCAGGAPGCGTATCCCGGCCGC
CGTCGTGCTGTCGTCTCCGGTGCTCGCTCTCGGCCGCGGTGTCGCGCTTG
CCCTTCGCGCCCGCAGCCCGGCAGCCTCTC
```

By “myosin 7A (Myo7A) promoter” is meant a regulatory polynucleotide sequence comprising or consisting of a nucleic acid sequence sufficient to direct expression of a downstream polynucleotide in an outer or inner hair cell, a vestibular hair cell, a spiral ganglion, or a vestibular ganglion and having at least about 85% sequence identity to the following nucleotide sequence:

```
AGACACCCCAGTTATGGGGGCTAGGGACCCAAAAGAGACATCCTTCTGC
CACCCAGAGCTGCCCTGGCGAGGTGCACTATGGGGCCGCCGACAGCTGC
GTGGCTGCCGAGGGCGGAAAGGAGAAACTGTCATGTCCCGATAGGGCCG
CGCGAGGTCTCCATCCTCGACAACGCTAATAACAAAGACGTGTGCTCCT
CTTTGCTTGGTTCCCCCCACTCCTTTAAATCACAGATTTCACTTCAGTT
TATCTGTGTCGCTGTCACACGTGGGGTGGCTCCCAGTCAGCTGGTTTGG
CAAAGTTTCTGGATGATTACGGAATAACATGTGTCCCCAACCCGCAGAG
CAGGTTGTGGGGGCAATGTTGCATTGACCAGCGTCAGAGAACACACATC
AGAGGCAAGGGTGGGTGTGCAGGAGGGAGAAGGCGCAGAAGGCAGGGCT
TTAGCTCAGCACTCTCCCTCCTGCCATGCTCTGCCTGACCGTTCCCTCT
CTGAGTCCCAAACAGCCAGGTAGAGGAGGAAGAAATGGGGCTGAGACCC
CAGCACATCAGTGATTAAGTCAGGATCAGGTGCGGTTTCCTGCTCAGGT
GCTGAGACAGCAGGCGGTGTCCTGCAAACAACAGGAGGCACCTGAAGCT
AGCCTGGGGGGCCCACGCCCAGGTGCGGTGCATTCAGCAGCACAGCCAG
AGACAGACCCCAATGACCCCGCCTCCCTGTCGGCAGCCAGTGCTCTGCA
CAGAGCCCTGAGCAGCCTCTGGACATTAGTCCCAGCCCCAGCACGGCCC
GTCCCCCACGCTGATGTCACCGCACCCAGACCTTGGAGGCCCCCTCCGG
CTCCGCCTCCTGGGAGAAGGCTCTGGAGTGAGGAGGGGAGGGCAGCAGT
GCTGGCTGGACAGCTGCTCTGGGCAGGAGAGAGAGGGAGAGACAAGAGA
CACACACAGAGAGACGGCGAGGAAGGGAAAGACCCAGAGGGACGCCTAG
AACGAGACTTGGAGCCAGACAGAGGAAGAGGGGACGTGTGTTTGCAGAC
TGGCTGGGCCCGTGACCCAGCTTCCTGAGTCCTCCGTGCAGGTGGCAGC
TGTACCAGGCTGGCAGGTCACTGAGAGTGGGCAGCTGGGCCCCAGGTAA
GGATGGGCTGCCCACTGTCCTGGGCATTGGGAGGGGTTTGGATGTGGAG
GAGTCATGGACTTGAGCTACCTCTAGAGCCTCTGCCCCACAGCCACTTG
CTCCTGGGACTGGGCTTCCTGCCACCCTTGAGGGCTCAGCCACCACAGC
CACTGAATGAAACTGTCCCGAGCCTGGGAAGATGGATGTGTGTCCCCTG
GAGGAGGGAAGAGCCAAGGAGCATGTTGTCCATCGAATCTTCTCTGAGC
TGGGGCTGGGGTTAGTGGCATCCTGGGGCCAGGGGAATAGACATGCTGT
GGTGGCAGAGAGAAGAGTCCGTTCTCTCTGTCTCCTTTGCTTTCTCTCT
```

-continued

```
GACACTCTTTATCTCCGTTTTTGGATAAGTCACTTCCTTCCTCTATGCC
CCAAATATCCCATCTGTGAAATGGGAGTATGAAGCCCCAACAGCCAGGG
TTGTAGTGGGGAAGAGGTAAAATCAGGTATAGACATAGAAATACAAATA
CAGTCTATGCCCCCTGTTGTCAGTTGGAAAAGAAATTAACTTGAAGGTG
GTCTAGTTCTCATTTTTAGAAATGAAATGTCTGTCTGGTCATTTTAAAA
TGTGGCCCTTAAATTTCACGCCCTCACCGCTCTCCCCCATCCCTTGGAG
CCCCATGTCTCTAGTGAAAGCACTGGCTCTGCCCCCAGCCCTCATGGCT
CATGCTGGCATAGGGCGCCTGCTCCACAGCCTGGGCACCATCTTCAGAC
AAGTGCCCGGTGGCAACTGCCTGCTGGCCCTGTTGAATCCACATCTCCA
CCAGGCATCCAGACTAGTTCAGGTCTCTGGAAGGACCGTGGGTTTGCTG
TGTCCCAGAGCTCCAGGGCAGGGGTCAGGGCTCGGATGTCGGGCAGTGT
CATGGGCAGAGGATCGAATGCCCCGGCGGCTCTGAATGGGCCCTTGTGA
AAAATTGATGCGCATTCTAGGAGACAGGTTGGGAGCCAGAGGGGCCTCA
TACCAGGGTCTGTAGGCTGGGGCTGCCTTTTAAGCTCCTTCCTGAGGCC
GTCTCTGGGTCTGGCCCTGTGCTGGACAAGGCTGGAGACAAGGCAATGT
CTCAGACCCTCTCCCATTGGCCACATCCTGCCCTGGATCAACTCGCCAA
CTTTGGGGGCAGAGGTGGGACTGACCCTTACCCTGACAACATAATGCAT
ATAGTCAAAATGGGATAAAGGGGAATATAGAGGCTCTTGGCAGCTTGGG
AGTGGTCAGGGAAGGCTTCCTGGAGGAGGTATCATCTGAACTGAGCCAT
GAACCATAAGTGGAAATTCACTAGTCAAAATTTCAGGTAGAAGGGCCAG
TGTGTGAAGGCCAGGAGATGGCAAGAGCTGGCGTATTTCAGGAACAGTG
AGTCACTGAGGATGTCCAAGTATAAGGGTAGGAAAGGGAGTGAGCAGTG
AGAGAAAAGACCGAGGCATCAGCAGGGGCCAGATTGTGCTGGGCCTAGC
GGGGCGGGCCCGGGCCCGGGCCCAGGCCCAGGTGCGGTGCATTCAGCAG
CACAGCCAGAGACAGACCCCAATGACCCTGCCTCCCCGTCAGCAGCCAG
TGCTCTGCACAGAGCCATCCTGAGGGCAGTGGGTGCTCTTGAGAGGTTT
CAGGCAGGGTGTGCTGTGAGCAGGTCATGCCCAGCCCTTGACCTTCTGC
TCAGTCAGGCTTGTCCTTGTCACCCACATTCCTGGGGCAGTCCCTAAGC
TGAGTGCCGGAGATTAAGTCCTAGTCCTAAATTTGCTCTGGCTAGCTGT
GTGACCCTGGGCAAGTCTTGGTCCCTCTCTGGGCCCCTTTGCCGTAGGT
CCCTGGTGGGGCCAGACTTGCTACTTTCTAGGAGCCCTTTGGGAATCTC
TGAATGACAGTGGCTGAGAGAAGAATTCAGCTGCTCTGGGCAGTGGTGC
TGGTGACAGTGGCTGAGGCTCAGGTCACACAGGCTGGGCAGTGGTCAGA
GGGAGAGAAGCCAAGGAGGGTTCCCTTGAGGGAGGAGGAGCTGGGGCTT
TGGGAGGAGCCCAGGTGACCCCAGCCAGGCTCAAGGCTTCCAGGGCTGG
CCTGCCCAGAAGCATGACATGGTCTCTCTCCCTGCA
```

By “TMC1 polypeptide” is meant a polypeptide having at least about 85% or greater amino acid sequence identity to NCBI Reference Sequence: NP_619636.2 or a fragment thereof having mechanotransduction channel activity. An exemplary amino acid sequence of TMC1 is provided below:

```
  1 mspkkvqikv eekedetees sseeeeeved klprreslrp krkrtrdvin eddpepeped
 61 eetrkareke rrrrlkrgae eeeideeele rlkaeldekr qiiatvkckp wkmekkievl
121 keakkfvsen egalgkgkgk rwfafkmmma kkwakflrdf enfkaacvpw enkikaiesq
181 fgssvasyfl flrwmygvnm vlfiltfsli mlpeylwglp ygslprktvp raeeasaanf
241 gvlydfngla qysvlfygyy dnkrtigwmn frlplsyflv gimcigysfl vvlkamtkni
301 gddgggddnt fnfswkvfts wdylignpet adnkfnsitm nfkeaiteek aagveenvhl
361 irflrflanf fvfltlggsg ylifwavkrs qefaqqdpdt lgwweknemn mvmsllgmfc
421 ptlfdlfael edyhplialk wllgrifall lgnlyvfila lmdeinnkie eeklvkanit
481 lweanmikay nasfsenstg ppffvhpadv prgpcwetmv gqefvrltvs dvlttyvtil
541 igdflracfv rfcnycwcwd leygypsyte fdisgnvlal ifnqgmiwmg sffapslpgi
601 nilrlhtsmy fqcwavmccn vpearvfkas rsnnfylgml llilflstmp vlymivslpp
661 sfdcgpfsgk nrmfeviget lehdfpswma kilrqlsnpg lviavilvmv laiyylnata
721 kgqkaanldl kkkmkmqale nkmrnkkmaa araaaaagrq
```

By "TMC1 polynucleotide" is meant a polynucleotide encoding a TMC1 polypeptide. The sequence of an exemplary TMC1 polynucleotide is provided at NCBI Reference Sequence: NM_138691.2, which is reproduced below:

```
   1 cagaaactat gagggcagaa cccagcaatc tgtgctttct ttcacaagcc ctccaggagt
  61 tgctgaaatt taggaatcat tgccccaaaa agtggccctc ataatgatgc cagatgggat
 121 cttactctgt tgcccaggct ggagtgcagt ggtgcgatct cggctctctg caacctccgc
 181 ctcccaggtt caagtgattc tcctgcctcg gcctcctgag tagctgggat ttcaggccat
 241 gaaagatcac tgttttagtc tgcgtggtgc agtggaacag atagacctcg gtttgaatct
 301 cagctctact gtttactaga catgaaatgg ggaaatctaa aatgagatgc cagaagcctc
 361 aaaaatggaa aaccccctgt gcttcacatc tgaaaatctc tgctgggggc agcaactttg
 421 agcctgtggg gaaggaactg tccacgtgga gtggtctggt gaatgcttaa ggagctgcag
 481 aagggaagtc cctctccaaa ctagccagcc actgagacct tctgacagga cacccccagg
 541 atgtcaccca aaaaagtaca aatcaaagtg gaggaaaaag aagacgagac tgaggaaagc
 601 tcaagtgaag aggaagagga ggtggaagat aagctacctc gaagagagag cttgagacca
 661 aagaggaaac ggaccagaga tgttatcaat gaggatgacc cagaacctga accagaggat
 721 gaagaaacaa ggaaggcaag agaaaaagag aggaggagga ggctaaagag aggagcagaa
 781 gaagaagaaa ttgatgaaga ggaattggaa agattgaagg cagagttaga tgagaaaaga
 841 caaataattg ctactgtcaa atgcaaacca tggaagatgg agaagaaaat tgaagttctc
 901 aaggaggcaa aaaaatttgt gagtgaaaat gaaggggctc ttgggaaagg aaaaggaaaa
 961 cggtggtttg catttaagat gatgatggcc aagaaatggg caaaattcct ccgtgatttt
1021 gagaacttca aagctgcgtg tgtcccatgg gaaaataaaa tcaaggctat tgaaagtcag
1081 tttggctcct cagtggcctc atacttcctc ttcttgagat ggatgtatgg agtcaatatg
1141 gttctcttta tcctgacatt tagcctcatc atgttgccag agtacctctg gggtttgcca
1201 tatggcagtt tacctaggaa aaccgttccc agagccgaag aggcatcggc agcaaacttt
1261 ggtgtgttgt acgacttcaa tggtttggca caatattccg ttctctttta tggctattat
1321 gacaataaac gaacaattgg atggatgaat ttcaggttgc cgctctccta ttttctagtg
1381 gggattatgt gcattggata cagctttctg gttgtcctca aagcaatgac caaaaacatt
1441 ggtgatgatg gaggtggaga tgacaacact ttcaatttca gctggaaggt ctttaccagc
```

-continued

```
1501   tgggactacc tgatcggcaa tcctgaaaca gcagacaaca aatttaattc tatcacaatg
1561   aactttaagg aagctatcac agaagaaaaa gcagcccaag tagaagaaaa cgtccacttg
1621   atcagattcc tgaggtttct ggctaacttc ttcgtgtttc taacacttgg agggagtgga
1681   tacctcatct tttgggctgt gaagcgatcc caggaatttg cacagcaaga tcctgacacc
1741   cttgggtggt gggaaaaaaa tgaaatgaac atggttatgt ccctcctagg gatgttctgt
1801   ccaacattgt ttgacttatt tgctgaatta gaagactacc atcctctcat cgctttgaaa
1861   tggctactgg gacgcatttt tgctcttctt ttaggcaatt tatacgtatt tattcttgca
1921   ttaatggatg agattaacaa caagattgaa gaggagaagc tagtaaaggc caatattacc
1981   ctttgggaag ccaatatgat caaggcctac aatgcatcat tctctgaaaa tagcactgga
2041   ccaccctttt ttgttcaccc tgcagatgta cctcgaggac cttgctggga aacaatggtg
2101   ggacaggagt ttgtgaggct gacagtctct gatgttctga ccacctacgt cacaatcctc
2161   attggggact ttctaagggc atgttttgtg aggttttgca attattgctg gtgctgggac
2221   ttggagtatg gatatccttc atacaccgaa ttcgacatca gtggcaacgt cctcgctctg
2281   atcttcaacc aaggcatgat ctggatgggc tccttctttg ctcccagcct cccaggcatc
2341   aatatccttc gactccatac atccatgtac ttccagtgct gggccgttat gtgctgcaat
2401   gttcctgagg ccagggtctt caaagcttcc agatcaaata acttctacct gggcatgcta
2461   ctgctcatcc tcttcctgtc cacaatgcct gtcttgtaca tgatcgtgtc cctcccacca
2521   tcttttgatt gtggtccatt cagtggcaaa aatagaatgt ttgaagtcat tggagagacc
2581   ctggagcacg atttcccaag ctggatggcg aagatcttga gacagctttc aaaccctggg
2641   ctggtcattg ctgtcatttt ggtgatggtt ttggccatct attatctcaa tgctactgcc
2701   aagggccaga aggcagcgaa tctggatctc aaaaagaaga tgaaaatgca agctttggag
2761   aacaaaatgc gaaacaagaa aatggcagct gcacgagcag ctgcagctgc tggtcgccag
2821   taataagtat cctgagagcc cagaaaaggt acactttgcc ttgctgttta aaagtaatgc
2881   aatatgtgaa cgcccagaga acaagcactg tggaactgct attttcctgt tctacccttg
2941   atggattttc aaggtcatgc tggccaatta aggcatcatc agtcctacct gagcaacaag
3001   aatctaaact ttattccaag tcagaaactg tttctgcaga gccactctct cccctgctcc
3061   atttcgtgac ttttttttt tttttaacaa attgagttta gaagtgagtg taatccagca
3121   atacagttta ctggtttagt tggtgggtta attaaaaaaa atttgctcat atgaactttc
3181   attttatatg tttcttttgc c
```

By “TMC2 polypeptide” is meant a polypeptide having at least about 85% or greater amino acid sequence identity to NCBI Reference Sequence: NP_542789 or a fragment thereof that functions in mechanosensation. An exemplary amino acid sequence of TMC2 is provided below:

```
  1  mshqvkglke earggvkgrv ksgsphtgdr lgrrssskra lkaegtpgrr gaqrsqkera
 61  ggspspgspr rkqtgrrrhr eelgeqerge aertcegrrk rderasfqer taapkrekei
121  prreekskrq kkprssslas sasggeslse eelaqileqv eekkkliatm rskpwpmakk
181  ltelreaqef vekyegalgk gkgkqlyayk mlmakkwvkf krdfdnfktq cipwemkikd
241  ieshfgssva syfiflrwmy gvnlvlfgli fglviipevl mgmpygsipr ktvpraeeek
301  amdfsvlwdf egyikysalf ygyynnqrti gwlryrlpma yfmvgvsvfg ysliivirsm
361  asntqgstge gesdnftfsf kmftswdyli gnsetadnky asittsfkes ivdeqesnke
```

-continued

```
421  enihltrflr vlanfliicc lcgsgyliyf vvkrsqqfsk mqnvswyern eveivmsllg
481  mfcpplfeti aalenyhprt glkwqlgrif alflgnlytf llalmddvhl klaneetikn
541  ithwtlfnyy nssgwnesvp rpplhpadvp rgscwetavg iefmrltvsd mlvtyitill
601  gdflracfvr fmnycwcwdl eagfpsyaef disgnvlgli fnqgmiwmgs fyapglvgin
661  vlrlltsmyf qcwavmssnv phervfkasr snnfymglll lvlflsllpv aytimslpps
721  fdcgpfsgkn rmydvlqeti endfptflgk ifaflanpgl iipaillmfl aiyylnsysk
781  slsranaqlr kkiqvlreve kshksvkgka tardsedtpk sssknatqlq ltkeettpps
841  asgsgamdkk aqgpgtsnsa srttlpasgh lpisrppgig pdsghapsqt hpwrsasgks
901  aqrpph
```

By "TMC2 polynucleotide" is meant a polynucleotide encoding a TMC2 polypeptide. An exemplary polynucleotide sequence is provided below:

```
   1  gcagtgctgc tgaccatgag ccaccaggta aagggcctga aagaggaagc acgaggcgga
  61  gtgaaagggc gggtgaagag cggctctcca cacacaggtg acaggctggg aaggagatcc
 121  tcaagcaagc gggctctcaa agccgagggg accccaggca ggcgcggagc tcagcgaagc
 181  cagaaggagc gcgccggggg cagcccaagc ccggggtctc cccggaggaa gcaaacaggg
 241  cgcaggagac acagagaaga gctgggggag caggagcggg gcgaggcaga gaggacctgc
 301  gagggcagga gaaagcgcga cgagagggcc tccttccagg agcggacagc agccccaaag
 361  agggaaaagg agattccgag gagggaggag aagtcgaagc ggcagaagaa acccaggtca
 421  tcctccttgg cctccagtgc ctctggtggg gagtccctgt ccgaggagga actggcccag
 481  atcctggagc aggtggaaga aaaaaagaag ctcattgcca ccatgcggag caagccctgg
 541  cccatggcga agaagctgac agagctcagg gaggcccagg aatttgtgga gaagtatgaa
 601  ggtgccttgg gaaaggggaa aggcaagcaa ctatatgcct acaagatgct gatggccaag
 661  aaatgggtca aatttaagag agactttgat aatttcaaga ctcaatgtat cccctgggaa
 721  atgaagatca aggacattga aagtcacttt ggttcttcag tggcatcgta tttcatcttt
 781  ctccgatgga tgtatggagt taaccttgtc ctttttggct taatatttgg tctagtcata
 841  atcccagagg tactgatggg catgccctat gggagtattc ccagaaagac agtgcctcgg
 901  gctgaggaag aaaaggccat ggatttttct gtcctttggg attttgaggg ctatatcaag
 961  tactctgcac tcttctatgg ctactacaac aaccagagga ccatcgggtg gctgaggtac
1021  cggctgccta tggcttactt tatggtgggg gtcagcgtgt tcggctacag cctgattatt
1081  gtcattcgat cgatggccag caatacccaa ggaagcacag gcgaagggga gagtgacaac
1141  ttcacattca gcttcaagat gttcaccagc tgggactacc tgatcgggaa ttcagagaca
1201  gctgataaca aatatgcatc catcaccacc agcttcaagg aatcaatagt ggatgaacaa
1261  gagagtaaca aagaagaaaa tatccatctg acaagatttc ttcgtgtcct ggccaacttt
1321  ctcatcatct gctgtttgtg tggaagtggg tacctcattt actttgtggt taagcgatct
1381  cagcaattct ccaaaatgca gaatgtcagc tggtatgaaa ggaatgaggt agagatcgtg
1441  atgtccctgc ttggaatgtt ttgtcccccct ctgtttgaaa ccatcgctgc cctggagaat
1501  taccacccac gcactggact gaagtggcag ctgggacgca tctttgcact cttcctgggg
1561  aacctctaca catttctctt ggccctgatg gatgacgtcc acctcaagct tgctaatgaa
1621  gagacaataa agaacatcac tcactggact ctgtttaact attacaactc ttctggttgg
```

-continued

```
1681  aacgagagtg tcccccgacc acccctgcac cctgcagatg tgccccgggg ttcttgctgg
1741  gagacagctg tgggcattga attcatgagg ctgacggtgt ctgacatgct ggtaacgtac
1801  atcaccatcc tgctggggga cttcctacgg gcttgttttg tgcggttcat gaactactgc
1861  tggtgctggg acttggaggc tggatttcct tcatatgctg agtttgatat tagtggaaat
1921  gtgctgggtt tgatcttcaa ccaaggaatg atctggatgg gctccttcta tgctccaggc
1981  ctggtgggca ttaatgtgct gcgcctgctg acctccatgt acttccagtg ctgggcggtg
2041  atgagcagca acgtacccca tgaacgcgtg ttcaaagcct cccgatccaa caacttctac
2101  atgggcctcc tgctgctggt gctcttcctc agcctcctgc cggtggccta caccatcatg
2161  tccctcccac cctcctttga ctgcgggccg ttcagtggga aaaacagaat gtacgatgtc
2221  ctccaagaga ccattgaaaa cgatttccca accttcctgg gcaagatctt tgctttcctc
2281  gccaatccag gcctgatcat cccagccatc ctgctgatgt tcttggccat ttactacctg
2341  aactcagttt ccaaaagcct ttcccgagct aatgcccagc tgaggaagaa aatccaagtg
2401  ctccgtgaag ttgagaagag tcacaaatct gtaaaaggca aagccacagc cagagattca
2461  gaggacacac ctaaaagcag ctccaaaaat gccacccagc tccaactcac caaggaagag
2521  accactcctc cctctgccag ccaaagccag gccatggaca agaaggcgca gggccctggg
2581  acctccaatt ctgccagcag gaccacactg cctgcctctg gacaccttcc tatatctcgg
2641  ccccctggaa tcggaccaga ttctggccac gccccatctc agactcatcc gtggaggtca
2701  gcctctggaa agagtgctca gagacctccc cactgatggc taggactcca gggagcctcg
2761  accctagggc tgatcctcaa gtaccccagt ttcacacata ccaaaccaag gttctctccc
2821  ctctttcctc tcacatacat gctctgtctc ctctcttgga atgcatgaac tttgattcct
2881  tcaggccctt gtcagctacc gaaggaggaa gacagtggct tcacctgtcc tttagggaag
2941  ctggagccat ctctgcacta actgccctcc caaatatctt ggttcagaca gctctgaacc
3001  ccacgctcac agtggtcgac cttgcctccc gattttcgga gttggggaag ggccatgacc
3061  accctcgtag actttttcca tgggatacag tttaggacac gggtttctgc cagcttccct
3121  aaccaggagg gggatggaga agggcctaca tttctcaatc cagaggaag
```

By "harmonin" polypeptide is meant a polypeptide having at least about 85% amino acid sequence identity to Q9Y6N9-1 (isoform 1), Q9Y6N9-2, Q9Y6N9-3, Q9Y6N9-4, Q9Y6N9-5 or a fragment thereof that functions in mechanosensation or that interacts with any one or more of USH1C, USH1G, CDH23 and MYO7A. The sequence of an exemplary harmonin-a polypeptide (isoform 1) is provided below:

>sp|Q9Y6N9|USH1C_HUMAN Harmonin OS = *Homo sapiens* GN = USH1C PE = 1 SV = 3

```
MDRKVAREFRHKVDFLIENDAEKDYLYDVLRMYHQTMDVAVLVGDLKLVI
NEPSRLPLFDAIRPLIPLKHQVEYDQLTPRRSRKLKEVRLDRLHPEGLGL
SVRGGLEFGCGLFISHLIKGGQADSVGLQVGDEIVRINGYSISSCTHEEV
INLIRTKKTVSIKVRHIGLIPVKSSPDEPLTWQYVDQFVSESGGVRGSLG
```

-continued

```
SPGNRENKEKKVFISLVGSRGLGCSISSGPIQKPGIFISHVKPGSLSAEV
GLEIGDQIVEVNGVDFSNLDHKEAVNVLKSSRSLTISIVAAAGRELEMTD
RERLAEARQRELQRQELLMQKRLAMESNKILQEQQEMERQRRKEIAQKAA
EENERYRKEMEQIVEEEEKFKKQWEEDWGSKEQLLLPKTITAEVHPVPLR
KPKYDQGVEPELEPADDLDGGTEEQGEQDFRKYEEGFDPYSMFTPEQIMG
KDVRLLRIKKEGSLDLALEGGVDSPIGKVVVSAVYERGAAERHGGIVKGD
EIMAINGKIVTDYTLAEAEAALQKAWNQGGDWIDLVVAVCPPKEYDDELT
FF
```

By "Ush1C polynucleotide" is meant a nucleic acid molecule encoding a harmonin polypeptide. The sequence of exemplary Ush1C polynucleotide NM_005709 is provided below:

```
 1  agctccgagg gcggctggcc cggtcgcggt cgcggctctt tccagctcct ggcagccggg
61  cacccgaagg aacgggtcgt gcaacgacgc agctggacct ggcccagcca tggaccgaaa
```

-continued

```
121   agtggcccga gaattccggc ataaggtgga ttttctgatt gaaaatgatg cagagaagga
181   ctatctctat gatgtgctgc gaatgtacca ccagaccatg gacgtggccg tgctcgtggg
241   agacctgaag ctggtcatca atgaacccag ccgtctgcct ctgtttgatg ccattcggcc
301   gctgatccca ctgaagcacc aggtggaata tgatcagctg acccccccggc gctccaggaa
361   gctgaaggag gtgcgtctgg accgtctgca ccccgaaggc ctcggcctga gtgtgcgtgg
421   tggcctggag tttggctgtg ggctcttcat ctcccacctc atcaaaggcg gtcaggcaga
481   cagcgtcggg ctccaggtag gggacgagat cgtccggatc aatggatatt ccatctcctc
541   ctgtacccat gaggaggtca tcaacctcat tcgaaccaag aaaactgtgt ccatcaaagt
601   gagacacatc ggcctgatcc ccgtgaaaag ctctcctgat gagcccctca cttggcagta
661   tgtggatcag tttgtgtcgg aatctggggg cgtgcgaggc agcctgggct cccctggaaa
721   tcgggaaaac aaggagaaga aggtcttcat cagcctggta ggctcccgag gccttggctg
781   cagcatttcc agcggcccca tccagaagcc tggcatcttt atcagccatg tgaaacctgg
841   ctccctgtct gctgaggtgg gattggagat aggggaccag attgtcgaag tcaatggcgt
901   cgacttctct aacctggatc acaaggaggc tgtaaatgtg ctgaagagta gccgcagcct
961   gaccatctcc attgtagctg cagctggccg ggagctgttc atgacagacc gggagcggct
1021  ggcagaggcg cggcagcgtg agctgcagcg gcaggagctt ctcatgcaga agcggctggc
1081  gatggagtcc aacaagatcc tccaggagca gcaggagatg gagcggcaaa ggagaaaaga
1141  aattgcccag aaggcagcag aggaaaatga gagataccgg aaggagatgg aacagattgt
1201  agaggaggaa gagaagttta agaagcaatg ggaagaagac tggggctcaa aggaacagct
1261  actcttgcct aaaaccatca ctgctgaggt acacccagta ccccttcgca agccaaagta
1321  tgatcaggga gtggaacctg agctcgagcc cgcagatgac ctggatggag gcacggagga
1381  gcagggagag caggatttcc ggaaatatga ggaaggcttt gacccctact ctatgttcac
1441  cccagagcag atcatgggga aggatgtccg gctcctacgc atcaagaagg agggatcctt
1501  agacctggcc ctggaaggcg gtgtggactc ccccattggg aaggtggtcg tttctgctgt
1561  gtatgagcgg ggagctgctg agcggcatgg tggcattgtg aaaggggacg agatcatggc
1621  aatcaacggc aagattgtga cagactacac cctggctgag gctgaggctg ccctgcagaa
1681  ggcctggaat cagggcgggg actggatcga ccttgtggtt gccgtctgcc ccccaaagga
1741  gtatgacgat gagctgacct tcttctgaag tccaaaaggg gaaaccaaat tcaccgttag
1801  gaaacagtga gctccggccc cacctcgtga acacaaagcc tcggatcagc cttgagagag
1861  gccacactac acacaccaga tggcatcctt gggacctgaa tctatcaccc aggaatctca
1921  aactcccttt ggccctgaac cagggccaga taaggaacag ctcgggccac tcttctgaag
1981  gccaacgtgg aggaaaggga gcagccagcc atttgggaga agatctcaag gatccagact
2041  ctcattcctt tcctctggcc cagtgaattt ggtctctccc agctctgggg gactccttcc
2101  ttgaacccta ataagacccc actggagtct ctctctctcc atccctctcc tctgccctct
2161  gctctaattg ctgccaggat tgtcactcca aaccttactc tgagctcatt aataaaatag
2221  atttattttc cagctta
```

Other Exemplary harmonin sequences are provided below:

Harmonin-B
>XM_011519832.2 PREDICTED: *Homo sapiens* USH1 protein network component harmonin (USH1C), transcript variant X3, mRNA
AGCTCCGAGGGCGGCTGGCCCGGTCGCGGTCGCGGCTCTTTCCAGCTCCTGGCAGCCGGGCACCCGAAGG

AACGGGTCGTGCAACGACGCAGCTGGACCTGGCCCAGCCATGGACCGAAAAGTGGCCCGAGAATTCCGGC

ATAAGGTGGATTTTCTGATTGAAAATGATGCAGAGAAGGACTATCTCTATGATGTGCTGCGAATGTACCA

CCAGACCATGGACGTGGCCGTGCTCGTGGGAGACCTGAAGCTGGTCATCAATGAACCCAGCCGTCTGCCT

CTGTTTGATGCCATTCGGCCGCTGATCCCACTGAAGCACCAGGTGGAATATGATCAGCTGACCCCCCGGC

GCTCCAGGAAGCTGAAGGAGGTGCGTCTGGACCGTCTGCACCCCGAAGGCCTCGGCCTGAGTGTGCGTGG

TGGCCTGGAGTTTGGCTGTGGGCTCTTCATCTCCCACCTCATCAAAGGCGGTCAGGCAGACAGCGTCGGG

CTCCAGGTAGGGGACGAGATCGTCCGGATCAATGGATATTCCATCTCCTCCTGTACCCATGAGGAGGTCA

TCAACCTCATTCGAACCAAGAAAACTGTGTCCATCAAAGTGAGACACATCGGCCTGATCCCCGTGAAAAG

CTCTCCTGATGAGCCCCTCACTTGGCAGTATGTGGATCAGTTTGTGTCGGAATCTGGGGGCGTGCGAGGC

AGCCTGGGCTCCCCTGGAAATCGGGAAAACAAGGAGAAGAAGGTCTTCATCAGCCTGGTAGGCTCCCGAG

GCCTTGGCTGCAGCATTTCCAGCGGCCCCATCCAGAAGCCTGGCATCTTTATCAGCCATGTGAAACCTGG

CTCCCTGTCTGCTGAGGTGGGATTGGAGATAGGGGACCAGATTGTCGAAGTCAATGGCGTCGACTTCTCT

AACCTGGATCACAAGGAGGCTGTAAATGTGCTGAAGAGTAGCCGCAGCCTGACCATCTCCATTGTAGCTG

CAGCTGGCCGGGAGCTGTTCATGACAGACCGGGAGCGGCTGGCAGAGGCGCGGCAGCGTGAGCTGCAGCG

GCAGGAGCTTCTCATGCAGAAGCGGCTGGCGATGGAGTCCAACAAGATCCTCCAGGAGCAGCAGGAGATG

GAGCGGCAAAGGAGAAAAGAAATTGCCCAGAAGGCAGCAGAGGAAAATGAGAGATACCGGAAGGAGATGG

AACAGATTGTAGAGGAGGAAGAGAAGTTTAAGAAGCAATGGGAAGAAGACTGGGGCTCAAAGGAACAGCT

ACTCTTGCCTAAAACCATCACTGCTGAGGTACACCCAGTACCCCTTCGCAAGCCAAAGTATGATCAGGGA

GTGGAACCTGAGCTCGAGCCCGCAGATGACCTGGATGGAGGCACGGAGGAGCAGGGAGAGCAGAAAGGAA

AAGATAAGAAGAAAGCCAAGTATGGCAGCCTGCAGGACTTGAGAAAGAATAAGAAAGAACTGGAGTTTGA

GCAAAAGCTTTACAAAGAGAAAGAGGAAATGCTGGAGAAGGAAAAGCAGCTAAAGATCAACCGGCTGGCC

CAGGAGGATTTCCGGAAATATGAGGAAGGCTTTGACCCCTACTCTATGTTCACCCCAGAGCAGATCATGG

GGAAGGATGTCCGGCTCCTACGCATCAAGAAGGAGGGATCCTTAGACCTGGCCCTGGAAGGCGGTGTGGA

CTCCCCCATTGGGAAGGTGGTCGTTTCTGCTGTGTATGAGCGGGGAGCTGCTGAGCGGCATGGTGGCATT

GTGAAAGGGGACGAGATCATGGCAATCAACGGCAAGATTGTGACAGACTACACCCTGGCTGAGGCTGAGG

CTGCCCTGCAGAAGGCCTGGAATCAGGGCGGGGACTGGATCGACCTTGTGGTTGCCGTCTGCCCCCCAAA

GGAGTATGACGATGAGCTGACCTTCTTCTGAAGTCCAAAAGGGGAAACCAAATTCACCGTTAGGAAACAG

TGAGCTCCGGCCCCACCTCGTGAACACAAAGCCTCGGATCAGCCTTGAGAGAGGCCACACTACACACACC

AGATGGCATCCTTGGGACCTGAATCTATCACCCAGGAATCTCAAACTCCCTTTGGCCCTGAACCAGGGCC

AGATAAGGAACAGCTCGGGCCACTCTTCTGAAGGCCAACGTGGAGGAAAGGGAGCAGCCAGCCATTTGGG

AGAAGATCTCAAGGATCCAGACTCTCATTCCTTTCCTCTGGCCCAGTGAATTTGGTCTCTCCCAGCTCTG

GGGGACTCCTTCCTTGAACCCTAATAAGACCCCACTGGAGTCTCTCTCTCTCCATCCCTCTCCTCTGCCC

TCTGCTCTAATTGCTGCCAGGATTGTCACTCCAAACCTTACTCTGAGCTCATTAATAAAATAGATTTATT

TTCCA

Harmonin-B Polypeptide
MDRKVAREFRHKVDFLIENDAEKDYLYDVLRMYHQTMDVAVLVGDLKLVINEPSRLPLFDAIRPLIPLKHQVEY

DQLTPRRSRKLKEVRLDRLHPEGLGLSVRGGLEFGCGLFISHLIKGGQADSVGLQVGDEIVRINGYSISSCTHE

-continued

EVINLIRTKKTVSIKVRHIGLIPVKSSPDEPLTWQYVDQFVSESGGVRGSLGSPGNRENKEKKVFISLVGSRGL

GCSISSGPIQKPGIFISHVKPGSLSAEVGLEIGDQIVEVNGVDFSNLDHKEAVNVLKSSRSLTISIVAAAGREL

FMTDRERLAEARQRELQRQELLMQKRLAMESNKILQEQQEMERQRRKEIAQKAAEENERYRKEMEQIVEEEEKF

KKQWEEDWGSKEQLLLPKTITAEVHPVPLRKPKSFGWFYRYDGKEPTIRKKGKDKKKAKYGSLQDLRKNKKELE

FEQKLYKEKEEMLEKEKQLKINRLAQEVSETEREDLEESEKIQYWVERLCQTRLEQISSADNEISEMTTGPPPP

PPSVSPLAPPLRRFAGGLHLHTTDLDDIPLDMFYYPPKTPSALPVMPHPPPSNPPHKVPAPPVLPLSGHVSASS

SPWVQRTPPPIPIPPPPSVPTQDLTPTRPLPSALEEALSNHPERTGDTGNPVEDWEAKNHSGKPTNSPVPEQSF

PPTPKTFCPSPQPPRGPGVSTISKPVMVHQEPNFIYRPAVKSEVLPQEMLKRMVVYQTAFRQDFRKYEEGFDPY

SMFTPEQIMGKDVRLLRIKKEGSLDLALEGGVDSPIGKVVVSAVYERGAAERHGGIVKGDEIMAINGKIVTDYT

LAEAEAALQKAWNQGGDWIDLVVAVCPPKEYDDELASLPSSVAESPQPVRKLLEDRAAVHRHGFLLQLEPTDLL

LKSKRGNQIHR

Harmonin-C
>NM_001297764.1 *Homo sapiens* USH1 protein network component harmonin (USH1C), transcript variant 3, mRNA
AGCTCCGAGGGCGGCTGGCCCGGTCGCGGTCGCGGCTCTTTCCAGCTCCTGGCAGCCGGGCACCCGAAGG

AACGGGTCGTGCAACGACGCAGCTGGACCTGGCCCAGCCATGGACCGAAAAGTGGCCCGAGAATTCCGGC

ATAAGGTGGATTTTCTGATTGAAAATGATGCAGAGAAGGACTATCTCTATGATGTGCTGCGAATGTACCA

CCAGACCATGGACGTGGCCGTGCTCGTGGGAGACCTGAAGCTGGTCATCAATGAACCCAGCCGTCTGCCT

CTGTTTGATGCCATTCGGCCGCTGATCCCACTGAAGCACCAGGTGGAATATGATCAGCTGACCCCCCGGC

GCTCCAGGAAGCTGAAGGAGGTGCGTCTGGACCGTCTGCACCCCGAAGGCCTCGGCCTGAGTGTGCGTGG

TGGCCTGGAGTTTGGCTGTGGGCTCTTCATCTCCCACCTCATCAAAGGCGGTCAGGCAGACAGCGTCGGG

CTCCAGGTAGGGGACGAGATCGTCCGGATCAATGGATATTCCATCTCCTCCTGTACCCATGAGGAGGTCA

TCAACCTCATTCGAACCAAGAAAACTGTGTCCATCAAAGTGAGACACATCGGCCTGATCCCCGTGAAAAG

CTCTCCTGATGAGCCCCTCACTTGGCAGTATGTGGATCAGTTTGTGTCGGAATCTGGGGGCGTGCGAGGC

AGCCTGGGCTCCCCTGGAAATCGGGAAAACAAGGAGAAGAAGGTCTTCATCAGCCTGGTAGGCTCCCGAG

GCCTTGGCTGCAGCATTTCCAGCGGCCCCATCCAGAAGCCTGGCATCTTTATCAGCCATGTGAAACCTGG

CTCCCTGTCTGCTGAGGTGGGATTGGAGATAGGGGACCAGATTGTCGAAGTCAATGGCGTCGACTTCTCT

AACCTGGATCACAAGGAGGGCCGGGAGCTGTTCATGACAGACCGGGAGCGGCTGGCAGAGGCGCGGCAGC

GTGAGCTGCAGCGGCAGGAGCTTCTCATGCAGAAGCGGCTGGCGATGGAGTCCAACAAGATCCTCCAGGA

GCAGCAGGAGATGGAGCGGCAAAGGAGAAAAGAAATTGCCCAGAAGGCAGCAGAGGAAAATGAGAGATAC

CGGAAGGAGATGGAACAGATTGTAGAGGAGGAAGAGAAGTTTAAGAAGCAATGGGAAGAAGACTGGGGCT

CAAAGGAACAGCTACTCTTGCCTAAAACCATCACTGCTGAGGTACACCCAGTACCCCTTCGCAAGCCAAA

GTATGATCAGGGAGTGGAACCTGAGCTCGAGCCCGCAGATGACCTGGATGGAGGCACGGAGGAGCAGGGA

GAGCAGGATTTCCGGAAATATGAGGAAGGCTTTGACCCCTACTCTATGTTCACCCCAGAGCAGATCATGG

GGAAGGATGTCCGGCTCCTACGCATCAAGAAGGAGGGATCCTTAGACCTGGCCCTGGAAGGCGGTGTGGA

CTCCCCCATTGGGAAGGTGGTCGTTTCTGCTGTGTATGAGCGGGGAGCTGCTGAGCGGCATGGTGGCATT

GTGAAAGGGGACGAGATCATGGCAATCAACGGCAAGATTGTGACAGACTACACCCTGGCTGAGGCTGAGG

CTGCCCTGCAGAAGGCCTGGAATCAGGGCGGGGACTGGATCGACCTTGTGGTTGCCGTCTGCCCCCCAAA

GGAGTATGACGATGAGCTGACCTTCTTCTGAAGTCCAAAAGGGGAAACCAAATTCACCGTTAGGAAACAG

TGAGCTCCGGCCCCACCTCGTGAACACAAAGCCTCGGATCAGCCTTGAGAGAGGCCACACTACACACACC

AGATGGCATCCTTGGGACCTGAATCTATCACCCAGGAATCTCAAACTCCCTTTGGCCCTGAACCAGGGCC

AGATAAGGAACAGCTCGGGCCACTCTTCTGAAGGCCAACGTGGAGGAAAGGGAGCAGCCAGCCATTTGGG

-continued

AGAAGATCTCAAGGATCCAGACTCTCATTCCTTTCCTCTGGCCCAGTGAATTTGGTCTCTCCCAGCTCTG

GGGGACTCCTTCCTTGAACCCTAATAAGACCCCACTGGAGTCTCTCTCTCCATCCCTCTCCTCTGCCC

TCTGCTCTAATTGCTGCCAGGATTGTCACTCCAAACCTTACTCTGAGCTCATTAATAAAATAGATTTATT

TTCCAGCTTA

Harmonin-C Polypeptide
MDRKVAREFRHKVDFLIENDAEKDYLYDVLRMYHQTMDVAVLVGDLKLVINEPSRLPLFDAIRPLIPLKHQVEY

DQLTPRRSRKLKEVRLDRLHPEGLGLSVRGGLEFGCGLFISHLIKGGQADSVGLQVGDEIVRINGYSISSCTHE

EVINLIRTKKTVSIKVRHIGLIPVKSSPDEPLTWQYVDQFVSESGGVRGSLGSPGNRENKEKKVFISLVGSRGL

GCSISSGPIQKPGIFISHVKPGSLSAEVGLEIGDQIVEVNGVDFSNLDHKEGRELEMTDRERLAEARQRELQRQ

ELLMQKRLAMESNKILQEQQEMERQRRKEIAQKAAEENERYRKEMEQIVEEEEKEKKQWEEDWGSKEQLLLPKT

ITAEVHPVPLRKPKYDQGVEPELEPADDLDGGTEEQGEQDFRKYEEGFDPYSMFTPEQIMGKDVRLLRIKKEGS

LDLALEGGVDSPIGKVVVSAVYERGAAERHGGIVKGDEIMAINGKIVTDYTLAEAEAALQKAWNQGGDWIDLVV

AVCPPKEYDDELTFF

By "KCNQ4 polypeptide" is meant a polypeptide having at least about 85% identity to NP_004691.2 or a fragment thereof and having potassium voltage-gated channel activity. An exemplary amino acid sequence is provided at NP_004691.2, the sequence of which follows:

```
  1  MAEAPPRRLG LGPPPGDAPR AELVALTAVQ SEQGEAGGGG SPRRLGLLGS PLPPGAPLPG
 61  PGSGSGSACG QRSSAAHKRY RRLQNWVYNV LERPRGWAFV YHVFIFLLVF SCLVLSVLST
121  IQEHQELANE CLLILEFVMI VVFGLEYIVR VWSAGCCCRY RGWQGRFRFA RKPFCVIDFI
181  VFVASVAVIA AGTQGNIFAT SALRSMRFLQ ILRMVRMDRR GGTWKLLGSV VYAHSKELIT
241  AWYIGFLVLI FASFLVYLAE KDANSDFSSY ADSLWWGTIT LTTIGYGDKT PHTWLGRVLA
301  AGFALLGISF FALPAGILGS GFALKVQEQH RQKHFEKRRM PAANLIQAAW RLYSTDMSRA
361  YLTATWYYYD SILPSFRELA LLFEHVQRAR NGGLRPLEVR RAPVPDGAPS RYPPVATCHR
421  PGSTSFCPGE SSRMGIKDRI RMGSSQRRTG PSKQHLAPPT MPTSPSSEQV GEATSPTKVQ
481  KSWSFNDRTR FRASLRLKPR TSAEDAPSEE VAEEKSYQCE LTVDDIMPAV KTVIRSIRIL
541  KFLVAKRKFK ETLRPYDVKD VIEQYSAGHL DMLGRIKSLQ TRVDQIVGRG PGDRKAREKG
601  DKGPSDAEVV DEISMMGRVV KVEKQVQSIE HKLDLLLGFY SRCLRSGTSA SLGAVQVPLF
661  DPDITSDYHS PVDHEDISVS AQTLSISRSV STNMD
```

By KCNQ4 polynucleotide is meant a polynucleotide encoding a KCNQ4 polypeptide. An exemplary KCNQ4 polynucleotide sequence is provided at NM_004700, which is reproduced below.

```
  1  agccatgcgt ctctgagcgc cccgagcgcg cccccgcccc ggaccgtgcc cgggccccgg
 61  cgcccccagc ccggcgccgc ccatggccga ggcccccccg cgccgcctcg gcctgggtcc
121  cccgcccggg gacgcccccc gcgcggagct agtggcgctc acggccgtgc agagcgaaca
181  gggcgaggcg ggcgggggcg gctccccgcg ccgcctcggc ctcctgggca gccccctgcc
241  gccgggcgcg cccctccctg ggccgggctc cggctcgggc tccgcctgcg gccagcgctc
301  ctcggccgcg cacaagcgct accgccgcct gcagaactgg gtctacaacg tgctggagcg
361  gccccgcggc tgggccttcg tctaccacgt cttcatattt ttgctggtct tcagctgcct
421  ggtgctgtct gtgctgtcca ctatccagga gcaccaggaa cttgccaacg agtgtctcct
```

-continued

```
481   catcttggaa ttcgtgatga tcgtggtttt cggcttggag tacatcgtcc gggtctggtc
541   cgccggatgc tgctgccgct accgaggatg gcagggtcgc ttccgctttg ccagaaagcc
601   cttctgtgtc atcgacttca tcgtgttcgt ggcctcggtg gccgtcatcg ccgcgggtac
661   ccagggcaac atcttcgcca cgtccgcgct gcgcagcatg cgcttcctgc agatcctgcg
721   catggtgcgc atggaccgcc gcggcggcac ctggaagctg ctgggctcag tggtctacgc
781   gcatagcaag gagctgatca ccgcctggta catcgggttc ctggtgctca tcttcgcctc
841   cttcctggtc tacctggctg agaaggacgc caactccgac ttctcctcct acgccgactc
901   gctctggtgg gggacgatta cattgacaac catcggctat ggtgacaaga caccgcacac
961   atggctgggc agggtcctgg ctgctggctt cgccttactg ggcatctctt tctttgccct
1021  gcctgccggc atcctaggct ccggctttgc cctgaaggtc caggagcagc accggcagaa
1081  gcacttcgag aagcggagga tgccggcagc caacctcatc caggctgcct ggcgcctgta
1141  ctccaccgat atgagccggg cctacctgac agccacctgg tactactatg acagtatcct
1201  cccatccttc agagagctgg ccctcttgtt tgagcacgtg caacgggccc gcaatggggg
1261  cctacggccc ctggaggtgc ggcgggcgcc ggtacccgac ggagcaccct cccgttaccc
1321  gcccgttgcc acctgccacc ggccgggcag cacctccttc tgccctgggg aaagcagccg
1381  gatgggcatc aaagaccgca tccgcatggg cagctcccag cggcggacgg gtccttccaa
1441  gcagcatctg gcacctccaa caatgcccac ctccccaagc agcgagcagg tgggtgaggc
1501  caccagcccc accaaggtgc aaaagagctg gagcttcaat gaccgcaccc gcttccgggc
1561  atctctgaga ctcaaacccc gcacctctgc tgaggatgcc ccctcagagg aagtagcaga
1621  ggagaagagc taccagtgtg agctcacggt ggacgacatc atgcctgctg tgaagacagt
1681  catccgctcc atcaggattc tcaagttcct ggtggccaaa aggaaattca aggagacact
1741  gcgaccgtac gacgtgaagg acgtcattga gcagtactca gcaggccacc tggacatgct
1801  gggccggatc aagagcctgc aaactcgggt ggaccaaatt gtgggtcggg ggcccgggga
1861  caggaaggcc cgggagaagg gcgacaaggg gccctccgac gcggaggtgg tggatgaaat
1921  cagcatgatg ggacgcgtgg tcaaggtgga gaagcaggtg cagtccatcg agcacaagct
1981  ggacctgctg ttgggcttct attcgcgctg cctgcgctct ggcacctcgg ccagcctggg
2041  cgccgtgcaa gtgccgctgt tcgaccccga catcacctcc gactaccaca gccctgtgga
2101  ccacgaggac atctccgtct ccgcacagac gctcagcatc tcccgctcgg tcagcaccaa
2161  catggactga gggacttctc agaggcaggg cagcacacgg ccagccccgc ggcctggcgc
2221  tccgactgcc ctctgaggcc tccggactcc tctcgtactt gaactcactc cctcacgggg
2281  agagagacca cacgcagtat tgagctgcct gagtgggcgt ggtacctgct gtgggtgcca
2341  gcgccccttc cccacctcag gagcgtgaga tgccaggtcg cacagagggc agcagcagcg
2401  gccgtcccgc ggcctctggg ccccccagtg ccctgcccac tccatcaagg ccctatgtgg
2461  cccacctggc aggggcacag ccccgggagt gggagcgggc gctggggccc tgggccctga
2521  cccagcttcc agctatgcaa ggtgaggtct ctggcccacc cttcggacac agcagggaag
2581  ccctcccgcc aagtccccgc cccacttggg ggtgggccaa ggtgccccca caggtaccca
2641  caaagcacag gaccctgcca caaggcaggt ggacaccata tatgcaaacc atgttaaata
2701  tgcaactttg gggaccccca tggggtctct ctgtccctcc cccattggga gctgggcccc
2761  cagcagtagc tggtctcagg ctgcttggcc accaccctgt ccctattctt tggcttatca
2821  ctccttcccc tcccagcatg gggcctgttt ctcccctgcc ctctcctaag ggcaatgcct
```

-continued

```
2881 gggcctttct tcccatttgc aagtgtcagc tcccaggggc tccctcctcc tgctgggtgg
2941 ccactcccct ccttggccct ccagacacca ctcatagtca gcacaggttt ctgtatcctc
3001 cccaaaactc ccagacagtg cttcgtggac gatcgcacaa acatagcctt ttagtttctc
3061 cagacaggaa gaaagcctct cacacttaaa catgcaatga cgtgacacac ttggagacat
3121 gagtgcagag ccactcagcc gctcctgggc ctctgcagca gatgccagtg gactggcctt
3181 gcagggtgac gaccactaag aggaagaccc ccaactccat ctgagcagga gaaggagctt
3241 tgaagtaacc cgagagctct ccaggcccca cccagacctt tacccgctcc ccttcttcaa
3301 gaagatctcc tcctctctgg tccaggagcc ctaacccact gcctctgcct gtccccaagg
3361 gcccgcctcc gtgtctccac agcacaactc gggcccaggc ctgacaccac tggagagacc
3421 ccaggcccac ttctagccag gcctgtgcct tcctagtcac tctaactccc agagagaata
3481 agaatgcatg taatagctat accaaccgcg catccggctt tcacatgcac tgtctcccct
3541 ccctccacac cccacttctt cacttcaatt ggcagcgcca catccaggcg tcagccccca
3601 ttcactccag gaacactttc ttatccccac ccctttgctc ctcttctgca aagccaatgc
3661 aggtggcagg aaggtgaggg gtagtggacc aatggcaacc ctctgtggga acaaggggcc
3721 gaggccacgc tgcctgcatc tcgtgctggg gacctgcatg cgccagcacc agggcttgga
3781 ctggatctta ctcagtccat ggtgcccagc ctctgcccca acatgccctc tgcatgtgac
3841 cgtcatgccc tggatggagc cactcctggc tcaccccacc tgcactgcac tgtccccaga
3901 gagccacccc tccacccact cagagacagc tgtggagagg gccaggagaa tgggattacc
3961 ctatgaccaa ggagacatgg gaagaagccc tccttccttc cacgatcgag gttccgccat
4021 caactcggtt ctcggatatg caagtacctc actttgttaa cttattaact tattggtttc
4081 attaaagttt tcaagaggaa aaaaaaaaaa aaaaaa
```

By “KCNQ4 promoter” is meant a regulatory polynucleotide sequence comprising or consisting of a nucleic acid sequence sufficient to direct expression of a downstream polynucleotide in an outer or inner hair cell, a vestibular hair cell, a spiral ganglion, or a vestibular ganglion and having at least about 85% nucleotide sequence identity to the following nucleotide sequence:

```
ACGCGTCCGGCTTCCCGGCCCCGCGCGCTGCCCCCGCCACGCGGTTCGG
CCCAGGCACCAACTCGGCCGCCCGTGCGCCCTGCCCCGCCGCCTGCTCC
GCGCGTTCCCTCCCTCCGCCTCGCCTCGCTTGCTCGCTCGCTCCCTCCC
GATTTGGGAAGGCGGCCGCGGGGCGGGCGGGGGAGGGGCGGGGCGGGGG
AGGGTGACATGTGAGCGGCGCGCGCCGGTGGCAGGTGGAAAGGCGAGCG
GCATGGAGCGCGTAATAAGAGAGTTGGAGTCGGAAAGAGCAGCCCCAGT
CGCCGGGGAAGCGGGAGGTCAGTGCGGGCTCCGGCGGCCCCCAGGCTCC
GAGCGCCCGCCCGCGGCCCCGGCCCGGCCCCTAGCCCCCGCCGCCCGCG
CCCGCCCCGGGTCGCCCCTCTGGCCCCGGGTCCGAGCCATGCGTCTCTG
AGCGCCCCGAGCGCGCCCCCGCCCCGGACCGTGCCCGGGCCCCGGCGCC
CCCAGCCCGGCGCCGCCc
```

By “TMPRSS3 polypeptide” is meant a protein having at least about 85% amino acid sequence identify to NP_001243246 or a fragment thereof having protease activity. An exemplary TMPRSS3 sequence follows:

Transmembrane Protease Serine 3 Isoform 4 [*Homo sapiens*]

```
NCBI Reference Sequence: NP_001243246.1
>NP_001243246.1 transmembrane protease
serine 3 isoform 4 [Homo sapiens]
MGENDPPAVEAPFSFRSLFGLDDLKISPVAPDADAVAAQILSLLPLKFF
PIIVIGIIALILALAIGLGIHFDCSGKYRCRSSFKCIELIARCDGVSDC
KDGEDEYRCVRVGGQNAVLQVFTAASWKTMCSDDWKGHYANVACAQLGF
PSYVSSDNLRVSSLEGQFREEFVSIDHLLPDDKVTALHHSVYVREGCAS
GHVVTLQCTACGHRRGYSSRIVGGNMSLLSQWPWQASLQFQGYHLCGGS
VITPLWIITAAHCVYDLYLPKSWTIQVGLVSLLDNPAPSHLVEKIVYHS
KYKPKRLGNDIALMKLAGPLTFNEMIQPVCLPNSEENFPDGKVCWTSGW
GATEDGGDASPVLNHAAVPLISNKICNHRDVYGGIISPSMLCAGYLTGG
VDSCQGDSGGPLVCQERRLWKLVGATSFGIGCAEVNKPGVYTRVTSFLD
WIHEQMERDLKT
```

By “TMPRSS3 polynucleotide” is meant a polynucleotide encoding a TMPRSS3 polypeptide. An exemplary TMPRSS3 sequence is provided at NCBI NM_001256317, which is reproduced below:

>NM_001256317.1 *Homo sapiens* transmembrane serine protease 3 (TMPRSS3), transcript variant F, mRNA

ACCGGGCACCGGACGGCTCGGGTACTTTCGTTCTTAATTAGGTCATGCC

CGTGTGAGCCAGGAAAGGGCTGTGTTTATGGGAAGCCAGTAACACTGTG

GCCTACTATCTCTTCCGTGGTGCCATCTACATTTTTGGGACTCGGGAAT

TATGAGGTAGAGGTGGAGGCGGAGCCGGATGTCAGAGGTCCTGAAATAG

TCACCATGGGGGAAAATGATCCGCCTGCTGTTGAAGCCCCCTTCTCATT

CCGATCGCTTTTTGGCCTTGATGATTTGAAAATAAGTCCTGTTGCACCA

GATGCAGATGCTGTTGCTGCACAGATCCTGTCACTGCTGCCATTGAAGT

TTTTTCCAATCATCGTCATTGGGATCATTGCATTGATATTAGCACTGGC

CATTGGTCTGGGCATCCACTTCGACTGCTCAGGGAAGTACAGATGTCGC

TCATCCTTTAAGTGTATCGAGCTGATAGCTCGATGTGACGGAGTCTCGG

ATTGCAAAGACGGGGAGGACGAGTACCGCTGTGTCCGGGTGGGTGGTCA

GAATGCCGTGCTCCAGGTGTTCACAGCTGCTTCGTGGAAGACCATGTGC

TCCGATGACTGGAAGGGTCACTACGCAAATGTTGCCTGTGCCCAACTGG

GTTTCCCAAGCTATGTGAGTTCAGATAACCTCAGAGTGAGCTCGCTGGA

GGGGCAGTTCCGGGAGGAGTTTGTGTCCATCGATCACCTCTTGCCAGAT

GACAAGGTGACTGCATTACACCACTCAGTATATGTGAGGGAGGGATGTG

CCTCTGGCCACGTGGTTACCTTGCAGTGCACAGCCTGTGGTCATAGAAG

GGGCTACAGCTCACGCATCGTGGGTGGAAACATGTCCTTGCTCTCGCAG

TGGCCCTGGCAGGCCAGCCTTCAGTTCCAGGGCTACCACCTGTGCGGGG

GCTCTGTCATCACGCCCCTGTGGATCATCACTGCTGCACACTGTGTTTA

TGACTTGTACCTCCCCAAGTCATGGACCATCCAGGTGGGTCTAGTTTCC

CTGTTGGACAATCCAGCCCCATCCCACTTGGTGGAGAAGATTGTCTACC

ACAGCAAGTACAAGCCAAAGAGGCTGGGCAATGACATCGCCCTTATGAA

GCTGGCCGGGCCACTCACGTTCAATGAAATGATCCAGCCTGTGTGCCTG

CCCAACTCTGAAGAGAACTTCCCCGATGGAAAAGTGTGCTGGACGTCAG

GATGGGGGCCACAGAGGATGGAGGTGACGCCTCCCCTGTCCTGAACCA

CGCGGCCGTCCCTTTGATTTCCAACAAGATCTGCAACCACAGGGACGTG

TACGGTGGCATCATCTCCCCCTCCATGCTCTGCGCGGGCTACCTGACGG

GTGGCGTGGACAGCTGCCAGGGGGACAGCGGGGGGCCCCTGGTGTGTCA

AGAGAGGAGGCTGTGGAAGTTAGTGGGAGCGACCAGCTTTGGCATCGGC

TGCGCAGAGGTGAACAAGCCTGGGGTGTACACCCGTGTCACCTCCTTCC

TGGACTGGATCCACGAGCAGATGGAGAGAGACCTAAAAACCTGAAGAGG

AAGGGGACAAGTAGCCACCTGAGTTCCTGAGGTGATGAAGACAGCCCGA

TCCTCCCCTGGACTCCCGTGTAGGAACCTGCACACGAGCAGACACCCTT

GGAGCTCTGAGTTCCGGCACCAGTAGCAGGCCCGAAAGAGGCACCCTTC

CATCTGATTCCAGCACAACCTTCAAGCTGCTTTTTGTTTTTTGTTTTTT

TGAGATGGAGTCTCGCTCTGTTGCCCAGGCTGGAGTGCAGTGGCGAAAT

CCCTGCTCACTGCAGCCTCCGCTTCCCTGGTTCAAGCGATTCTCTTGCC

TCAGCTTCCCCAGTAGCTGGGACCACAGGTGCCCGCCACCACACCCAAC

-continued

TAATTTTTGTATTTTTAGTAGAGACAGGGTTTCACCATGTTGGCCAGGC

TGCTCTCAAACCCCTGACCTCAAATGATGTGCCTGCTTCAGCCTCCCAC

AGTGCTGGGATTACAGGCATGGGCCACCACGCCTAGCCTCACGCTCCTT

TCTGATCTTCACTAAGAACAAAAGAAGCAGCAACTTGCAAGGGCGGCCT

TTCCCACTGGTCCATCTGGTTTTCTCTCCAGGGGTCTTGCAAAATTCCT

GACGAGATAAGCAGTTATGTGACCTCACGTGCAAAGCCACCAACAGCCA

CTCAGAAAAGACGCACCAGCCCAGAAGTGCAGAACTGCAGTCACTGCAC

GTTTTCATCTCTAGGGACCAGAACCAAACCCACCCTTTCTACTTCCAAG

ACTTATTTTCACATGTGGGGAGGTTAATCTAGGAATGACTCGTTTAAGG

CCTATTTTCATGATTTCTTTGTAGCATTTGGTGCTTGACGTATTATTGT

CCTTTGATTCCAAATAATATGTTTCCTTCCCTCATTGAAAAAAAAAAAA

AAAAAAA

By “STRC polypeptide” is meant a protein having at least about 85% amino acid sequence identity to NP_714544 or a fragment thereof that associates with a hair bundle in the inner ear. An exemplary STRC amino acid sequence follows:

MALSLWPLLLLLLLLLLLSFAVTLAPTGPHSLDPGLSFLKSLLSTLDQA

PQGSLSRSRFFTFLANISSSFEPGRMGEGPVGEPPPLQPPALRLHDFLV

TLRGSPDWEPMLGLLGDMLALLGQEQTPRDFLVHQAGVLGGLVEVLLGA

LVPGGPPTPTRPPCTRDGPSDCVLAADWLPSLLLLLEGTRWQALVQVQP

SVDPTNATGLDGREAAPHFLQGLLGLLTPTGELGSKEALWGGLLRTVGA

PLYAAFQEGLLRVTHSLQDEVFSILGQPEPDTNGQCQGGNLQQLLLWGV

RHNLSWDVQALGFLSGSPPPPPALLHCLSTGVPLPRASQPSAHISPRQR

RAITVEALCENHLGPAPPYSISNFSIHLLCQHTKPATPQPHPSTTAICQ

TAVWYAVSWAPGAQGWLQACHDQFPDEFLDAICSNLSFSALSGSNRRLV

KRLCAGLLPPPTSCPEGLPPVPLTPDIFWGCFLENETLWAERLCGEASL

QAVPPSNQAWVQHVCQGPTPDVTASPPCHIGPCGERCPDGGSFLVMVCA

NDTMYEVLVPFWPWLAGQCRISRGGNDTCFLEGLLGPLLPSLPPLGPSP

LCLTPGPFLLGMLSQLPRCQSSVPALAHPTRLHYLLRLLTFLLGPGAGG

AEAQGMLGRALLLSSLPDNCSFWDAFRPEGRRSVLRTIGEYLEQDEEQP

TPSGFEPTVNPSSGISKMELLACFSPVLWDLLQREKSVWALQILVQAYL

HMPPENLQQLVLSAEREAAQGFLTLMLQGKLQGKLQVPPSEEQALGRLT

ALLLQRYPRLTSQLFIDLSPLIPFLAVSDLMRFPPSLLANDSVLAAIRD

YSPGMRPEQKEALAKRLLAPELFGEVPAWPQELLWAVLPLLPHLPLENF

LQLSPHQIQALEDSWPAAGLGPGHARHVLRSLVNQSVQDGEEQVRRLGP

LACFLSPEELQSLVPLSDPTGPVERGLLECAANGTLSPEGRVAYELLGV

LRSSGGAVLSPRELRVWAPLFSQLGLRFLQELSEPQLRAMLPVLQGTSV

TPAQAVLLLGRLLPRHDLSLEELCSLHLLLPGLSPQTLQAIPRRVLVGA

CSCLAPELSRLSACQTAALLQTFRVKDGVKNMGTTGAGPAVCIPGQPIP

TTWPDCLLPLLPLKLLQLDSLALLANRRRYWELPWSEQQAQFLWKKMQV

-continued

PTNLTLRNLQALGTLAGGMSCEFLQQINSMVDFLEVVHMIYQLPTRVRG

SLRACIWAELQRRMAMPEPEWTTVGPELNGLDSKLLLDLPIQLMDRLSN

ESIMLVVELVQRAPEQLLALTPLHQAALAERALQNLAPKETPVSGEVLE

TLGPLVGFLGTESTRQIPLQILLSHLSQLQGFCLGETFATELGWLLLQE

SVLGKPELWSQDEVEQAGRLVFTLSTEATSLIPREALGPETLERLLEKQ

QSWEQSRVGQLCREPQLAAKKAALVAGVVRPAAEDLPEPVPNCADVRGT

FPAAWSATQTAEMELSDFEDCLTLFAGDPGLGPEELRAAMGKAKQLWGP

PRGFRPEQILQLGRLLIGLGDRELQELILVDWGVLSTLGQIDGWSTTQL

RIVVSSFLRQSGRHVSHLDFVHLTALGYTLCGLRPEELQHISSWEFSQA

ALFLGTLHLQCSEEQLEVLAHLLVLPGGFGPISNWGPEIFTEIGTIAAG

IPDLALSALLRGQIQGVTPLAISVIPPPKFAVVFSPIQLSSLTSAQAVA

VTPEQMAFLSPEQRRAVAWAQHEGKESPEQQGRSTAWGLQDWSRPSWSL

VLTISFLGHLL"

By "STRC polynucleotide" is meant a nucleic acid molecule encoding an STRC polypeptide. An exemplary STRC polynucleotide sequence follows:

>NM_153700.2 *Homo sapiens* stereocilin (STRC), mRNA

GCCCTGCCCTCACCTGGCTATCCCACACAGGTGAGAATAACCAGAACTC

ACCTCCGGTACCAGTGTTCACTTGGAAACATGGCTCTCAGCCTCTGGCC

CCTGCTGCTGCTGCTGCTGCTGCTGCTGCTGCTGTCCTTTGCAGTGACT

CTGGCCCCTACTGGGCCTCATTCCCTGGACCCTGGTCTCTCCTTCCTGA

AGTCATTGCTCTCCACTCTGGACCAGGCTCCCCAGGGCTCCCTGAGCCG

CTCACGGTTCTTTACATTCCTGGCCAACATTTCTTCTTCCTTTGAGCCT

GGGAGAATGGGGGAAGGACCAGTAGGAGAGCCCCCACCTCTCCAGCCGC

CTGCTCTGCGGCTCCATGATTTTCTAGTGACACTGAGAGGTAGCCCCGA

CTGGGAGCCAATGCTAGGGCTGCTAGGGGATATGCTGGCACTGCTGGGA

CAGGAGCAGACTCCCCGAGATTTCCTGGTGCACCAGGCAGGGGTGCTGG

GTGGACTTGTGGAGGTGCTGCTGGGAGCCTTAGTTCCTGGGGGCCCCCC

TACCCCAACTCGGCCCCCATGCACCCGTGATGGGCCGTCTGACTGTGTC

CTGGCTGCTGACTGGTTGCCTTCTCTGCTGCTGTTGTTAGAGGGCACAC

GCTGGCAAGCTCTGGTGCAGGTGCAGCCCAGTGTGGACCCCACCAATGC

CACAGGCCTCGATGGGAGGGAGGCAGCTCCTCACTTTTTGCAGGGTCTG

TTGGGTTTGCTTACCCCAACAGGGGAGCTAGGCTCCAAGGAGGCTCTTT

GGGGCGGTCTGCTACGCACAGTGGGGGCCCCCCTCTATGCTGCCTTTCA

GGAGGGGCTGCTCCGTGTCACTCACTCCCTGCAGGATGAGGTCTTCTCC

ATTTTGGGGCAGCCAGAGCCTGATACCAATGGGCAGTGCCAGGGAGGTA

ACCTTCAACAGCTGCTCTTATGGGGCGTCCGGCACAACCTTTCCTGGGA

TGTCCAGGCGCTGGGCTTTCTGTCTGGATCACCACCCCCACCCCCTGCC

CTCCTTCACTGCCTGAGCACGGGCGTGCCTCTGCCCAGAGCTTCTCAGC

CGTCAGCCCACATCAGCCCACGCCAACGGCGAGCCATCACTGTGGAGGC

CCTCTGTGAGAACCACTTAGGCCCAGCACCACCCTACAGCATTTCCAAC

-continued

TTCTCCATCCACTTGCTCTGCCAGCACACCAAGCCTGCCACTCCACAGC

CCCATCCCAGCACCACTGCCATCTGCCAGACAGCTGTGTGGTATGCAGT

GTCCTGGGCACCAGGTGCCCAAGGCTGGCTACAGGCCTGCCACGACCAG

TTTCCTGATGAGTTTTTGGATGCGATCTGCAGTAACCTCTCCTTTTCAG

CCCTGTCTGGCTCCAACCGCCGCCTGGTGAAGCGGCTCTGTGCTGGCCT

GCTCCCACCCCCTACCAGCTGCCCTGAAGGCCTGCCCCCTGTTCCCCTC

ACCCCAGACATCTTTTGGGGCTGCTTCTTGGAGAATGAGACTCTGTGGG

CTGAGCGACTGTGTGGGGAGGCAAGTCTACAGGCTGTGCCCCCCAGCAA

CCAGGCTTGGGTCCAGCATGTGTGCCAGGGCCCCACCCCAGATGTCACT

GCCTCCCCACCATGCCACATTGGACCCTGTGGGGAACGCTGCCCGGATG

GGGGCAGCTTCCTGGTGATGGTCTGTGCCAATGACACCATGTATGAGGT

CCTGGTGCCCTTCTGGCCTTGGCTAGCAGGCCAATGCAGGATAAGTCGT

GGGGGCAATGACACTTGCTTCCTAGAAGGGCTGCTGGGCCCCCTTCTGC

CCTCTCTGCCACCACTGGGACCATCCCCACTCTGTCTGACCCCTGGCCC

CTTCCTCCTTGGCATGCTATCCCAGTTGCCACGCTGTCAGTCCTCTGTC

CCAGCTCTTGCTCACCCCACACGCCTACACTATCTCCTCCGCCTGCTGA

CCTTCCTCTTGGGTCCAGGGGCTGGGGGCGCTGAGGCCCAGGGGATGCT

GGGTCGGGCCCTACTGCTCTCCAGTCTCCCAGACAACTGCTCCTTCTGG

GATGCCTTTCGCCCAGAGGGCCGGCGCAGTGTGCTACGGACGATTGGGG

AATACCTGGAACAAGATGAGGAGCAGCCAACCCCATCAGGCTTTGAACC

CACTGTCAACCCCAGCTCTGGTATAAGCAAGATGGAGCTGCTGGCCTGC

TTTAGTCCTGTGCTGTGGGATCTGCTCCAGAGGGAAAAGAGTGTTTGGG

CCCTGCAGATTCTAGTGCAGGCGTACCTGCATATGCCCCCAGAAAACCT

CCAGCAGCTGGTGCTTTCAGCAGAGAGGGAGGCTGCACAGGGCTTCCTG

ACACTCATGCTGCAGGGGAAGCTGCAGGGGAAGCTGCAGGTACCACCAT

CCGAGGAGCAGGCCCTGGGTCGCCTGACAGCCCTGCTGCTCCAGCGGTA

CCCACGCCTCACCTCCCAGCTCTTCATTGACCTGTCACCACTCATCCCT

TTCTTGGCTGTCTCTGACCTGATGCGCTTCCCACCATCCCTGTTAGCCA

ACGACAGTGTCCTGGCTGCCATCCGGGATTACAGCCCAGGAATGAGGCC

TGAACAGAAGGAGGCTCTGGCAAAGCGACTGCTGGCCCCTGAACTGTTT

GGGGAAGTGCCTGCCTGGCCCCAGGAGCTGCTGTGGGCAGTGCTGCCCC

TGCTCCCCCACCTCCCTCTGGAGAACTTTTTGCAGCTCAGCCCTCACCA

GATCCAGGCCCTGGAGGATAGCTGGCCAGCAGCAGGTCTGGGGCCAGGG

CATGCCCGCCATGTGCTGCGCAGCCTGGTAAACCAGAGTGTCCAGGATG

GTGAGGAGCAGGTACGCAGGCTTGGGCCCCTCGCCTGTTTCCTGAGCCC

TGAGGAGCTGCAGAGCCTAGTGCCCCTGAGTGATCCAACGGGGCCAGTA

GAACGGGGGCTGCTGGAATGTGCAGCCAATGGGACCCTCAGCCCAGAAG

GACGGGTGGCATATGAACTTCTGGGTGTGTTGCGCTCATCTGGAGGAGC

GGTGCTGAGCCCCCGGGAGCTGCGGGTCTGGGCCCCTCTCTTCTCTCAG

CTGGGCCTCCGCTTCCTTCAGGAGCTGTCAGAGCCCCAGCTTAGAGCCA

-continued

TGCTTCCTGTCCTGCAGGGAACTAGTGTTACACCTGCTCAGGCTGTCCT

GCTGCTTGGACGGCTCCTTCCTAGGCACGATCTATCCCTGGAGGAACTC

TGCTCCTTGCACCTTCTGCTACCAGGCCTCAGCCCCCAGACACTCCAGG

CCATCCCTAGGCGAGTCCTGGTCGGGGCTTGTTCCTGCCTGGCCCCTGA

ACTGTCACGCCTCTCAGCCTGCCAGACCGCAGCACTGCTGCAGACCTTT

CGGGTTAAAGATGGTGTTAAAAATATGGGTACAACAGGTGCTGGTCCAG

CTGTGTGTATCCCTGGTCAGCCTATTCCCACCACCTGGCCAGACTGCCT

GCTTCCCCTGCTCCCATTAAAGCTGCTACAACTGGATTCCTTGGCTCTT

CTGGCAAATCGAAGACGCTACTGGGAGCTGCCCTGGTCTGAGCAGCAGG

CACAGTTTCTCTGGAAGAAGATGCAAGTACCCACCAACCTTACCCTCAG

GAATCTGCAGGCTCTGGGCACCCTGGCAGGAGGCATGTCCTGTGAGTTT

CTGCAGCAGATCAACTCCATGGTAGACTTCCTTGAAGTGGTGCACATGA

TCTATCAGCTGCCCACTAGAGTTCGAGGGAGCCTGAGGGCCTGTATCTG

GGCAGAGCTACAGCGGAGGATGGCAATGCCAGAACCAGAATGGACAACT

GTAGGGCCAGAACTGAACGGGCTGGATAGCAAGCTACTCCTGGACTTAC

CGATCCAGTTGATGGACAGACTATCCAATGAATCCATTATGTTGGTGGT

GGAGCTGGTGCAAAGAGCTCCAGAGCAGCTGCTGGCACTGACCCCCCTC

CACCAGGCAGCCCTGGCAGAGAGGGCACTACAAAACCTGGCTCCAAAGG

AGACTCCAGTCTCAGGGGAAGTGCTGGAGACCTTAGGCCCTTTGGTTGG

ATTCCTGGGGACAGAGAGCACACGACAGATCCCCCTACAGATCCTGCTG

TCCCATCTCAGTCAGCTGCAAGGCTTCTGCCTAGGAGAGACATTTGCCA

CAGAGCTGGGATGGCTGCTATTGCAGGAGTCTGTTCTTGGGAAACCAGA

GTTGTGGAGCCAGGATGAAGTAGAGCAAGCTGGACGCCTAGTATTCACT

CTGTCTACTGAGGCAATTTCCTTGATCCCCAGGGAGGCCTTGGGTCCAG

AGACCCTGGAGCGGCTTCTAGAAAAGCAGCAGAGCTGGGAGCAGAGCAG

AGTTGGACAGCTGTGTAGGGAGCCACAGCTTGCTGCCAAGAAAGCAGCC

CTGGTAGCAGGGGTGGTGCGACCAGCTGCTGAGGATCTTCCAGAACCTG

TGCCAAATTGTGCAGATGTACGAGGGACATTCCCAGCAGCCTGGTCTGC

AACCCAGATTGCAGAGATGGAGCTCTCAGACTTTGAGGACTGCCTGACA

TTATTTGCAGGAGACCCAGGACTTGGGCCTGAGGAACTGCGGGCAGCCA

TGGGCAAAGCAAAACAGTTGTGGGGTCCCCCCCGGGGATTTCGTCCTGA

GCAGATCCTGCAGCTTGGTAGGCTCTTAATAGGTCTAGGAGATCGGGAA

CTACAGGAGCTGATCCTAGTGGACTGGGGAGTGCTGAGCACCCTGGGGC

AGATAGATGGCTGGAGCACCACTCAGCTCCCGCATTGTGGTCTCCAGTTT

CCTACGGCAGAGTGGTCGGCATGTGAGCCACCTGGACTTCGTTCATCTG

ACAGCGCTGGGTTATACTCTCTGTGGACTGCGGCCAGAGGAGCTCCAGC

ACATCAGCAGTTGGGAGTTCAGCCAAGCAGCTCTCTTCCTCGGCACCCT

GCATCTCCAGTGCTCTGAGGAACAACTGGAGGTTCTGGCCCACCTACTT

GTACTGCCTGGTGGGTTTGGCCCAATCAGTAACTGGGGGCCTGAGATCT

TCACTGAAATTGGCACCATAGCAGCTGGGATCCCAGACCTGGCTCTTTC

AGCACTGCTGCGGGGACAGATCCAGGGCGTTACTCCTCTTGCCATTTCT

-continued

GTCATCCCTCCTCCTAAATTTGCTGTGGTGTTTAGTCCCATCCAACTAT

CTAGTCTCACCAGTGCTCAGGCTGTGGCTGTCACTCCTGAGCAAATGGC

CTTTCTGAGTCCTGAGCAGCGACGAGCAGTTGCATGGGCCCAACATGAG

GGAAAGGAGAGCCCAGAACAGCAAGGTCGAAGTACAGCCTGGGGCCTCC

AGGACTGGTCACGACCTTCCTGGTCCCTGGTATTGACTATCAGCTTCCT

TGGCCACCTGCTATGAGCCTGTCTCTACAGTAGAAGGAGATTGTGGGGA

GAGAAATCTTAAGTCATAATGAATAAAGTGCAAACAGAAGTGCATCCTG

ATTATTTTCAGAAGCTGATGAGGAATA

By "EYA4 polypeptide" is meant a protein having at least about 85% identity to NP 001287941.1 or a fragment thereof having transcriptional regulatory activity.

>NP_001287941.1 eyes absent homolog 4 isoform e [*Homo sapiens*]
MEDSQDLNEQSVKKTCTESDVSQSQNSRSMEMQDLASPHTLVGGGDTPG

SSKLEKSNLSSTSVTTNGTGVITSSGYSPRSAHQYSPQLYPSKPYPHIL

STPAAQTMSAYAGQTQYSGMQQPAVYTAYSQTGQPYSLPTYDLGVMLPA

IKTESGLSQTQSPLQSGCLSYSPGFSTPQPGQTPYSYQMPGSSFAPSST

IYANNSVSNSTNFSGSQQDYPSYTAFGQNQYAQYYSASTYGAYMTSNNT

ADGTPSSTSTYQLQESLPGLTNQPGEFDTMQSPSTPIKDLDERTCRSSG

SKSRGRGRKNNPSPPPDSDLERVFVWDLDETIIVEHSLLTGSYAQKYGK

DPPMAVTLGLRMEEMIFNLADTHLFFNDLEECDQVHIDDVSSDDNGQDL

STYSFATDGFHAAASSANLCLPTGVRGGVDWMRKLAFRYRRVKELYNTY

KNNVGGLLGPAKRDAWLQLRAEIEGLTDSWLTNALKSLSIISTRSNCIN

VLVTTTQLIPALAKVLLYSLGGAFPIENTYSATKIGKESCFERIVSRFG

TNITYVVIGDGRDEEHAANQHNMPFWRISSHSDLLALHQALELEYL

By "EYA4 polynucleotide" is meant a nucleic acid molecule that encodes an EYA4 polypeptide. An exemplary EYA4 polynucleotide sequence is provided at NCBI Ref: NM_001301012.1, which is reproduced below:

>NM_001301012.1 *Homo sapiens* EYA transcriptional coactivator and phosphatase 4 (EYA4), transcript variant 5, mRNA
TCCGGAGTTTTGGCTCCTCTCCTTTCCTCCTCCCCCTCGGAGCCGGCTT

CTCCCTCCGCCCCGCTTCTCCCCCGCTTGTGTACGCTATTTGTTGTGGG

GTGGCCGAAGGGGATGTCCTGTTTTCACCAGAGGCACAGCGCGAAGGGG

AAACTTCGACACTGGAAGGAACGAGAATAAATACTTAATTACGGACGCA

CTGAACCGCGGCTGGGACAGACACTTCGGGAACCCGAGGCGGACCGGGC

GACGAGATAGTCATTTTTACTTGAAGGAAGCTGCTTCTACTTGGGAGTG

GCAGGAGAAGTGAGAAAACCACATGGAAGACTCCCAGGATTTAAATGAA

CAATCAGTAAAGAAAACGTGCACAGAATCAGATGTTTCACAATCTCAGA

ATTCCAGGTCTATGGAAATGCAGGACCTAGCAAGTCCTCATACTCTTGT

TGGAGGTGGTGATACTCCAGGTAGCTCCAAACTGGAAAAATCTAATCTC

AGCAGCACATCAGTTACTACAAATGGGACAGGAGTAATTACAAGTAGTG

-continued

GCTACAGCCCCAGATCAGCACATCAGTATTCCCCACAGCTGTATCCTTC
CAAGCCCTATCCACACATTCTTTCTACACCAGCAGCTCAAACAATGTCT
GCCTATGCAGGCCAGACTCAGTATTCGGGGATGCAGCAGCCAGCCGTCT
ACACAGCCTACTCACAGACAGGACAGCCCTACAGCTTGCCCACTTACGA
TTTGGGTGTGATGTTGCCAGCCATCAAGACAGAGAGTGGACTTTCCCAA
ACTCAGTCCCCATTACAGAGTGGCTGCCTCAGTTACAGCCCAGGGTTCT
CTACCCCACAGCCAGGCCAGACACCTTATTCTTACCAAATGCCAGGTTC
TAGTTTTGCACCATCATCTACTATTTATGCAAATAATTCAGTTTCCAAT
TCAACGAATTTCAGTGGTTCACAACAGGATTATCCATCCTATACAGCCT
TTGGCCAAAACCAGTATGCACAGTATTATTCAGCATCAACGTATGGAGC
GTATATGACATCGAATAACACAGCCGATGGCACACCCTCTTCAACCTCT
ACTTATCAGTTGCAGGAATCTCTCCCAGGACTGACTAACCAACCAGGAG
AGTTCGATACCATGCAGAGTCCCTCCACACCCATCAAAGATCTTGATGA
GAGAACCTGTAGGAGTTCTGGGTCAAAGTCCAGAGGAAGAGGCCGGAAA
AATAATCCCTCCCCGCCTCCTGATAGTGACCTGGAGCGTGTGTTTGTCT
GGGATTTGGATGAAACCATCATTGTTTTTCACTCACTGCTCACCGGGTC
TTATGCACAGAAGTATGGCAAGGATCCCCCCATGGCTGTAACCCTTGGA
CTCCGCATGGAAGAAATGATTTTTAATCTTGCTGATACTCATTTGTTTT
TTAATGATTTAGAGGAGTGTGATCAAGTTCATATAGATGATGTTTCCTC
TGATGATAATGGGCAGGACTTAAGTACCTACAGTTTTGCAACTGATGGC
TTCCATGCAGCTGCAAGTAGTGCAAACCTTTGTTTGCCAACAGGTGTAA
GAGGAGGGGTTGACTGGATGAGGAAGTTGGCTTTTCGTTACAGAAGAGT
AAAAGAATTATATAACACCTACAAGAACAACGTTGGAGGACTCCTTGGC
CCTGCCAAGAGGGATGCCTGGCTACAGTTAAGGGCAGAGATTGAAGGTC
TGACAGATTCCTGGCTAACAAATGCACTTAAGTCTTTATCAATTATTAG
CACTAGGAGTAACTGCATAAATGTCTTGGTAACGACAACTCAACTGATC
CCAGCACTTGCGAAGGTTCTACTCTATAGTTTAGGAGGTGCTTTCCCCA
TTGAGAATATTTACAGTGCAACTAAAATAGGCAAGGAAAGCTGTTTTGA
GCGTATAGTGTCCAGATTTGGCACTAACATAACTTATGTTGTGATTGGA
GATGGCCGAGATGAGGAGCATGCCGCTAACCAGCACAACATGCCCTTCT
GGAGGATATCCAGTCACTCAGACCTCCTGGCTCTCCACCAAGCACTGGA
ATTAGAGTATTTGTAACTGTGTTCTTTAGCCGGAGATCCATTTTTTATA
TTTCAAGTACACTGAATTTTTATGTGTGATTCAATGCCTCTGGCTCTAC
ACATATAAATTGTCTTAATGGATGAAATCATATTTGGAATAAAAATTCC
AGAATGAAGAATTCAGATTGCTGAATGGAGTTAAACTTTAGTGCTACAG
AAAAGAAACTCTATGGTCTTATATTTACAACACTTTAATGGGTTTTTTA
AAAATCTGTGGAGGTTGCTGGTACACACCAAATGAGTCCAAACTGGAAT
GAGCAGCTTTAGCAAAGAACTCTTACCCTGGCAAAGCAGCAACACACAT
GCTCCGTCTGACAAGGTGGTCAACAACATTCCTCAAAATGGGAGATCTT
CTCAGCCCTGAGGTTTGAATCTGACTTTAGCCTACCTAACCCAGAAAAT
CTGAATTGGAATGCACTCAGACTGTATAAGGACAGTCCTATTTAGACAT

-continued

GTAATTTGTGTAAATTATTGATGAAAATAATTTACTGTGACTTTATTAG
CAGCTGACTTTCAAAGTGGATGCAATTTTTCTTTCTTTTGTTGGGGAGG
GGAATGGGAGGGGAAATGGGAATATAATATTGTCTCTTTTTTAAGTTTG
GCAAACAGAATGTTCATACTGATGTGTTGTGCCTTAAAGACAAGACAGC
ATTTGTGTGTTACAATGTAACTTTGGTTAAAATCTCTGTAGATAATGAA
AAAAAACAAAAAAAAAAACCTTTGTGATGATTCTTAACATGACCAAATT
TAAAAGTCAAGCTCTCAGAGCTTAATTACCGCATCAGCAAGAAACTGAG
TATTTTTTGCAATAAGAAAACAACAATAATAAAGGAAAGCTTGTGTTTC
ATTTGGGTTCTTAATAATTCCAATAATTGTATGAGGCAACTATTTGCGC
ATCCAACCATGAGTGGAAGGTTTGGGAAAGACTGTGGGACCTTTACTTA
GAAAGTGAAATGTATGTAGAAGTCTCAAGTACCCCTTCTACAGTTTTAC
TGGAGAAAACTAAGAGCCATATTCATGACAACTTGCACAGTTTTGAGGT
TGAGACTTTTGATATGTGTAAGTTGCATAGAGGAGGATATTATCATGCA
AATCATGAGCAATTATCACATAAACTTTTTTAGAATGTGCCATGAACAT
GGCATAAAATTCACATTGAGTGCACAGGGCTTAAAATAAAGCTAAGTAT
GTTTATTCCCAATGCCATGGCAAAAATGATAATATCATCAGAAATGGAA
GGCAGTTCTCCCAGATGGTGTCTAATGAAAGCAATGAGTCTATGAAAAT
TTTACCTAGAATATCATCATAAATTAAATTAGCAAGTGCGCTGGATCTT
GGCAGCGCTGCTGAAATGACAACAGTAAAATAATACCTGGTTCTCCATC
TGAATACATCAATGCAGGTTCTCCTCGTAACAGACTTGCATATGTTTGT
TAGTTTCTGCCTGTATTGTCACTGCGCAACGGATGGCATTCATTACAAG
AAGAGCCCATCATCGTTGTGTTTGCATGGTTTTTTCCTTGTGTGTAGC
CCATGTTGGGAACACGATACAGGTTCTCCTCTTATTTCCTATGACACGA
TTTCCCTTGTGGAAATTTAAGACTTTAAGAACTAGAGTATTTTTATGGT
GTCTGCACCTGCAGTTCTGTGTTTAAAATGTCATAATGTGGATCCTGGA
GTCAGGCTACTAGTCAGTGCCCCTAGCCAGAGGCTGGTTCATGAGTTCA
TCAACTGAGGCCTCTGTGGCTTCAATAAAGTCTACATTTTGCTCACAGA
TCACAACATTCACTGTGGAAATATGATTTCATTTCTTTAGGCTACAAAC
CTGTATTTCTTTACTGAATGCTAAGGCCATGTTTATATTGGGTAGAAAG
ATATTGAGATCCCAATTTTGTACAAGATTGTGATTTCATTATCTAAACC
TTAAACTTAATCCTTTAAATTTTGTAGCTTTTGGCTGCATCTGCCCCAA
GTACTATTCCAGGCAAATTAAAGTTGGAATACCTTTAATAATATAAAAA
TAATGATAGTAAATCTTATACTTCTGTTGGCCCTTAGCTTGAAAATAGC
AGTTAAAAAAATTTAAATGTTGCCTTGATTATCAGTACTTAATTATGTT
GTGCACTAAAACCTTAAATATTTATTACTGTGAATAAAAACAAATTATC
TTTACTGTATAGCTGGTTTCTTTAAATGTTGATAGAATTGTGGCATTAC
ATCTAAATTTGTAAGTCTTTTCATATCAAACAAGCAAGGCTTTTTATGC
TGCTAAGTCTGTGGGTGCAGAAAGAAACACCCCTTGGAAGGGCAAAGAG
AAGCCGGCTGGTTGCATCACCCCGTGCAGTTTCTCACACACATCTCTTT
TTCTGATTCTGTGTTCAGAAGAGGCTGCCGGCATAAAACCTAAATGCAA

-continued

GGTTGACGGAGAACAGCTTGTCTGGCACAACAATGGTGCAGGCCCACGA

GCCAGCATCACAGCTTGGCCATGGGACGTTGAGTATGCACAAACTAGAA

CTCTTCCCTTCCCACCTTAGGAATAGAAAATCCTCTTCCTTTCTAATCT

GAAAAACGAAAACTGAACAAACACAAAACCAACCCCTTGGCAGTTCCCA

CCTCCTATTGACATATGGAATATTGTGCCTTATTGTAAACCAGTTTGAA

AAATGTTCTGTAACTAAAGTGGGTTTTCGGCTATTATGTATACAGCTTG

GTATATTACTACGAAAGATAACCACCTTGTGTTGCACCTTAAAAATATC

AAGACCATGTAATTTCCATAACAAAATAGGTGGCCTGGCTATGGTATTA

TAGCATACAATTAGGACACTATGCCCCTGCAAAATTTTGTAAATCAAAT

TCAGAGGCAAAAACATATTTTAGAATCATACAGTTTGCACACGACAAGT

AGGTAATAACTGTCTCTAAAAATGTTTTCTCCTTAGTCCGCAATGAGCT

AAGATTCAGAATAGTGTCAACAGCATGCTCCTATATGAAGTTGTTTTTT

TTAAAGCACATTTGTTTATGACAAGCCTACATTCTCAGTGAATATGGCA

TTTAGTATTTCTTTTGAAAACAAACTTAAGCATCATGAGCCAAAGTTGC

ACTTTGACTCCCAACTACGGTAGCATTATGGACATCTCACAATGTCAAG

GGTTTCTGTTATGTATTAGTAAAGTATAGATTATTGGGGCCTACATAAT

TTAAAAGAAATGTAAATTAATATTAAAAGCTTGTAAAAATATGTATATC

TTTACTATTTCTCAATAAATACCTTTGCAATTGTTTTCATTTCCTTCAA

AAA

By “Espin promoter” is meant a regulatory polynucleotide sequence derived from NCBI Reference Sequence: NG_015866.1 that is sufficient to direct expression of a downstream polynucleotide in an outer or inner hair cell, vestibular hair cell, a spiral ganglion, or a vestibular ganglion. In one embodiment, the Espin promoter comprises or consists of at least about 350, 500, 1000, 2000, 3000, 4000, 5000, or more base pairs upstream of an Espin coding sequence.

By “protocadherin related 15 (PCDH15) promoter” is meant a regulatory polynucleotide sequence derived from NCBI Reference Sequence: NG_009191 that is sufficient to direct expression of a downstream polynucleotide in an outer or inner hair cell, vestibular hair cell, a spiral ganglion, or a vestibular ganglion. In one embodiment, the PCDH15 promoter comprises at least about 350, 500, 1000, 2000, 3000, 4000, 5000, or more base pairs upstream of an PCDH15 coding sequence. In some embodiments, the PCDH15 promoter comprises or consists of a nucleic acid sequence having at least about 85% sequence identity to the following nucleotide sequence:

TCTTCACCTGTCATTTTCAACCAGCCTCAGCCTATCTGCTCTGTCACAA

TCACTACTAAAATATGTTCCTAAATTGCTTGTTTCTAGATCCTTCCTTC

TCATATGCTCAGGTGAACACATGGGTGAAATTTAATATGGAATTGAAAT

ATGTACTATGCAAGATAGATTCCTTAAGAAATGTTTCTCTGATTTATAT

GACATAATTGTATTTTACTAGTTTACCTGTCCATCTGTAAAACTTTGTT

TTGGAGATTTCATATATTACAATGTTTAAGAAATATGCTATAATGTTTT

GTATAGTATATTTCTTCGTGATAACCTTATATACTACCAGTCACACGTG

-continued

TTTGTAAAAATCTAAAGAGTACTTTTGGCTCCTACAGAATGTGTGAAGT

TGTGAAATTGTTTTTTTGTTTTGTTTTGTTTTGTTTTTATGCCCCAAAG

ATGTGGAGGGCTTCATATAAGAGGGTAGATTTAATGAGAGAGAGAGGGA

GAGACAGAGAGAATGATAAAAGAAGCTTAAGAGATTATTTTATCTTGTC

AACGACATTGTTATTGAATGTAAGCTGCTAAACTTCTTAGATAAAGTAA

AACAGTAAAAACAAACACACAAAACAGAACAGAGAATCATCAGACAGGC

TGACGAACACAGTACAATAAAGCAGCCAGTACCGATGATCAGTGGACAT

CAATTTGTCTTTTGGGCTGTAGCACCTGCTACTAATTGGTGCAAAGCGC

TCACCAGTCAGTGCGTGGTTTAGCGCACTCAGCTGTCTCCTGTATGTGC

TGCGAGAAGCAAGATAGCTAATTGCTGTTGCTTCAGTGCCAGTGAAATC

AACGTGCTGAGCTAATAGCGACAGATAGAGGGCAGACAGATTCCTGCTA

GCAGCTTAGTGTTAGTTGCTTGTGGTAACTAAGGCAGGTGGCATACATC

TCAGAACGTGGAGAATGATGGTATGCTTTCTGA

By “protein tyrosine phosphatase, receptor type Q (PTPRQ) promoter” is meant a regulatory polynucleotide sequence derived from GeneID: 374462 that is sufficient to direct expression of a downstream polynucleotide in an outer or inner hair cell, vestibular hair cell, a spiral ganglion, or a vestibular ganglion. In one embodiment, the PTPRQ promoter comprises at least about 350, 500, 1000, 2000, 3000, 4000, 5000, or more base pairs upstream of an PTPRQ coding sequence. In some embodiments, the PTPRQ promoter comprises or consists of a nucleic acid sequence having at least about 85% sequence identity to the following nucleotide sequence:

TGGTAGCCTCCCTAGAGACACAGAGCTGGGCCGGATGAGTCCAGGCACT

GACGTGATCCATTATCTTTCACCTTAAAGAGTAAAAGGGAAACTAAAGT

TAATTACCTCCACGAAACAAAAAGGTGCCTTCTTGTGCTTCAATTACAT

GGATATATTCTACTAGTCTAAAAGTATCTTCTCACTTCTTTCTGTCACT

GTGAGGACTTGAGTCAGAAGAAAGTTTAAATACAGTCATTGAGCTGGAA

AGAGTGGAAAGAGAAGCAAAGAGGGGGAAGCTGTAGGAAGGACGAAGTC

ACCCCCAAGATACATGGTTACTGCTTACACCAAGCAAGCTGCCTTGGGA

ACGCTTCCCCCGAGCAGCCAGAATGCTCAGCAGTGGAAGACACCTCTAT

TCCTGTAGGCGAGTCCTGGGAAGCTGGTCAATCTGCAAATGCCAATTCC

CAGCAGTGAGCTCGGTCCACGTGTAAATCAAGATTTGGGGAAAGAGTAG

GGTGGGTGGCATGGTTGACAATGTCATCAGCTCCCTCCTCTGACTCCTG

TGGTCGTGCCCCCATCTACTCTCACTCAGCTACACCCCACCTTCGGATT

TGTGATGGACGCTGGGTCCCTAGTAACCACAGCAAGTGTCTCCCCCGCA

CTTCCCCCTTCCCCACCCCCACCCCCACCCCCAACCACCACCCCAGCGA

TGGAGCCTACTCTGCTCCAAGCCGCCGCTAAGACCCGGAGAAGCGGAAT

TTCACTTTGAAATTCCCTTGCCTCGTGAGGGCCGGCGCTGGGCATGCTC

AGTAGCCGCGGCGCTGCTGCTGGGCTGCTGGGCTGGCGCGGAGTCCACC

CTGCCGTCTCCGCCTTGGCTTCTGGGCGTCCAGAAGGCCAGGCATTTGC

CGCCTCTGAGCGCTTCTGTTCCCCTTACCCGCAACCTCCTACTGCTCTT

-continued

CCTCTCTCCCTCTCTTAGGGAGGTTGAAGCTGGTGCTGGTTTCTGTCGG

CGCCACAGACTGACTGCTCTGCAAACCCCAGCCGAGGACCTGAATCCCG

GAGACTAGAAG

By "lipoma HMGIC fusion partner-like 5 (LHFPL5) promoter" also termed "TMHS promoter" is meant a regulatory polynucleotide sequence derived from NCBI Reference Sequence: GeneID: 222662 that is sufficient to direct expression of a downstream polynucleotide in an outer or inner hair cell, vestibular hair cell, a spiral ganglion, or a vestibular ganglion. In one embodiment, the TMHS promoter comprises at least about 350, 500, 1000, 2000, 3000, 4000, 5000, or more base pairs upstream of an PCDH15 coding sequence. In some embodiments, the TMHS promoter comprises or consists of a nucleic acid sequence having at least about 85% sequence identity to the following nucleotide sequence:

GCCCAGTGGAATTTTCCTAGTTCTTTACACTAGCCATGTATTTACCTAT

AAAATCAGGAGAAATATGTATATATATAATATATTAAAACATATATATA

TTTAAATGGGGAAATATGTAACAAACAAATAGAAACAAGGGGAGAAAGG

CATTGTATTTGACAAAACACATATGTTCAGGTCTGAGAAGGCTCATAAA

GAATGTTGTCTGCTATACTTTGTAGTTGCTTCTGTTATCACACAATCAG

TCTGCATATACAGGCGTTTTATATATATATTTATATAGACTACATATAT

ACGTATATTATATATGTAAATATTTCACTGTCTTTGAGGACGGGGGCCC

TGTCTTTTTTATCTGTGGTTTTGCTTAGATGTCCTCCAACATAATCTTA

ACACATAGTATGCTTTTAGAAATCGTTGACTGAATGCTAAGGACGAAAA

ACCGGTGACCAGAAGGCAACCAGGAAAGGCTTTGCTGACCTCCGGAGTG

GTGGAGTTGGAGGTTCTGGGAAGGCGACTAGGGAGCCAGGCAGGGGCGG

GGTGGGATGGGATGTGGACAGCGCTTTTGCGGGGGGAAAGCGTTTTTGC

TGCTGGAATTGAGCAGTAGGAATGTGTCAGTCACATCCCCACCTTCCCA

ATTCTTGTCATCTCGGTTCAGGAAGGTGAACGGTGTTCCGATTCCCCGC

GGCGGGGGCCTGTAGTGGGAGCTCTGCCCCTTCCCCGCCTCTGCTGCAG

GCCCCGCCCCTCGCCCGGAACCCCGGGGCGCTGGCCGCGGTGCTGAAAC

GGCGCCCTCCGCGGACGGAGGAGGGGGCGGGGCTCTCGGGAGCCGTGAG

CCGGGAAGAGGGAGACGGGCAGGGCGGCGCCAGCAGGCCCTGGTGGGCT

TGGGAGGAGGCAGGAGACTGGAGACAGCCTCGGCTAGAGCGGACACAGG

CACCTGGCAAGCTTTCCTTGACCAAATCAAGGT

By "synapsin promoter" also termed "Syn promoter" is meant a regulatory polynucleotide sequence comprising or consisting of a nucleic acid sequence sufficient to direct expression of a downstream polynucleotide in an outer or inner hair cell, a vestibular hair cell, a spiral ganglion, or a vestibular ganglion and having at least about 85% sequence identity to the following nucleotide sequence:

tctagactgcagagggccctgcgtatgagtgcaagtgggttttaggacc aggatgaggcggggtgggggtgcctacctgacgaccgaccccgacccac tggacaagcacccaacccccattccccaaattgcgcatcccctatcaga -continued gagggggagggggaaacaggatgcggcgaggcgcgtgcgcactgccagct tcagcaccgcggacagtgccttcgcccccgcctggcggcgcgcgccacc gccgcctcagcactgaaggcgcgctgacgtcactcgccggtcccccgca aactccccttcccggccaccttggtcgcgtccgcgccgccgccggccca gccggaccgcaccacgcgaggcgcgagataggggGcacgggcgcgacc atctgcgctgcggcgccggcgactcagcgctgcctcagtctgcggtggg cagcggaggagtcgtgtcgtgcctgagagcgcagtc By "agent" is meant a polypeptide, polynucleotide, or small compound.

By "ameliorate" is meant decrease, suppress, attenuate, diminish, arrest, or stabilize the development or progression of a disease or disorder.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages or interferes with the normal function of a cell, tissue, or organ. Examples of diseases include genetic disorders characterized by a loss of function in a protein that functions in mechanosensory transduction that is expressed, for example, in the inner ear of a subject. In another embodiment, the disease is Usher Syndrome (e.g., USH1) or age-related hearing loss. In one embodiment, a disease is an auditory disorder associated with a genetic defect, such as a defect in TMC1, TMC2, MYO7A, USCH1C, CDH23, PCDH15, SANS, CIB2, USH2A, VLGR1, WHRN, CLRN1, PDZD7, KCNQ4, TMPRSS3, STRC, EYA4, USH1C (e.g., harmonin-a, b, or c), OTOF, GPR98, MYO6, MYO15A, LOXHD1, POU3F4, EYA1, WFS1, ACTG1, TMIE, PJVK, SYNE4, and FAM65B.

By "effective amount" is meant the amount of an agent required to ameliorate the symptoms of a disease relative to an untreated patient. The effective amount of active agent(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

As used herein, "obtaining" as in "obtaining an agent" includes synthesizing, purchasing, or otherwise acquiring the agent.

By "promoter" is meant a polynucleotide sufficient to direct transcription of a downstream polynucleotide.

By "reduces" or "increases" is meant a negative or positive alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule.

By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152: 507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

By "transgene" is meant any piece of DNA that is inserted by artifice into a cell and becomes part of the genome of the organism that develops from that cell. Such a transgene may include a gene which is partly or entirely heterologous (i.e., foreign) to the transgenic organism, or may represent a gene homologous to an endogenous gene of the organism.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

BRIEF DESCRIPTION OF DRAWINGS

FIG. 5A is a confocal image of the cochlear apex transduced with AAV2/Anc80L65-GFP at P1 via utricle injection. FIG. 5B is a confocal image of the cochlear apex transduced with AAV2/Anc80L65-GFP at P1 via RWM injection. The scale bar in FIG. 5A applies to FIG. 5B and represents 0.2 mm. FIG. 5C is a series of high magnitude (630×) confocal images from the apex (top row), mid (middle row), and base (bottom row) regions of the cochlea transduced with Anc80-GFP at P1 via utricle and RWM injection. The scale bar shown in the top row represents 20 μm. FIG. 5D is a graphical comparion of the percentage of eGFP positive inner hair cells (IHCs) and outer hair cells (OHCs) from image sections after utricle (left) and RWM (right) injection.

FIG. 6A is a confocal image of the cochlear apex after utricle injection with AAV.9PHP.B-Cmv-eGFP generated at École Polytechnique Fédérale de Lausanne (EPFL) at P1. The scale bar in FIG. 6A applies to FIGS. 6A to 6C and represents 0.2 mm. FIG. 6A is a confocal image of the cochlear apex after utricle injection at P1 of AAV.9PHP.B-Cmv-eGFP prepared at Boston Children's Hospital (BCH). FIG. 6C is a confocal image of the cochlear apex after RWM injection of AAV.9PHP.B-Cmv-eGFP at P1. FIG. 6D is a series of 100 μm confocal images (63×) of apex, mid, and base regions of the cochlea after RWM or utricle injection at P1 of PHP.B-Cmv-eGFP prepared at EPFL.

FIG. 7A is a confocal image of the cochlear apex after utricle injection of the PHP.B adeno-associated vector (AAV). The scale bar applies to FIGS. 7A and 7B and represents 0.2 mm. FIG. 7B is a confocal image of the cochlear apex after utricle injection of Anc80 AAV. FIG. 7C are is a graphical comparison of the percentage of eGFP positive inner hair cells (IHCs) and outer hair cells (OHCs) after utricle injection of PHP.B AAV (left) and Anc80 AAV (right).

FIG. 8A is a series of confocal images of mouse cochlea injected via the utricle with Anc80-Cmv-eGFP-WPRE at P1 and harvested at P15. The scale bar in FIG. 8A applies to FIG. 8B and represents 100 μm. FIG. 8B is a series of confocal images of mouse cochlea injected via the utricle with PHP.B-Cmv-eGFP at P1 and harvested at P15.

FIG. 9A is a series of 100 μm confocal images (63×) of the apex, mid, and base regions of the cochlea after utricle injection with PHP.B-GFP at P7 and P16. The scale bars present in the images in the top row of FIG. 9A apply to all images in FIG. 9A and represent 20 μm. FIG. 9B is a graphical comparison of the percentage of eGFP positive inner and outer hair cells counted from the images in FIG. 9A.

FIG. 10A is a series of graphs illustrating representative current families of sensory transduction currents evoked by mechanical displacement of hair bundles from GFP positive outer hair cells at P7 (right panel, GFP positive inner hair cells at P7, and GFP positive inner hair cells at P29. FIG. 10B is a current-displacement plot of transduction current from P7 outer hair cells (OHC) for GFP negative and GFP positive cells. FIG. 10C is a chart showing the peak transduction current from GFP positive cells which are similar in amplitude to those of WT cells (Landegger et al., Nat. Biotech, 2017).

FIG. 11 shows panels of graphs illustrating ABR and DPOAE thresholds measured at ~P30 for uninjected WT mice (black dotted line) and WT mice following P1 (FIG. 11A), P7 (FIG. 11B) or P16 (FIG. 11C) injection of Anc80-Cmv-eGFP (light gray) or AAV9-Php.b-Cmv-eGFP (dark gray). FIG. 8A is a series of confocal images of utricles and horizontal and anterior cristae after utricle injection of PHP.B-Cmv-eGFP (top row) and Anc80-Cmv-eGFP (bottom row) at P1, P7, and P16. FIG. 8B is a series of confocal images of saccules after utricle injection of PHP.B-Cmv-eGFP (top row) and Anc80-Cmv-eGFP (bottom row) at P1, P7, and P16. The scale bar in FIG. 8A applies to all images and represents 100 μm.

FIG. 16A is a graph illustrating that auditory brainstem response (ABR) thresholds were superior to those of AAV1-CMV-TMC1 or Anc80-CMV-TMC1. The single trace (with no error bars) was transduced with PHP.B-CMV-TMC1 and had thresholds similar to wildtype (WT). FIG. 16B is a graph illustrating the distortion product otoacoustic emissions (DPOAE) thresholds for five mice injected with AAV9-PHP.B-Cmv-Tmc1.

FIG. 17A is a series of confocal images illustrating the ability of the Pcdh15 promoter to drive transgene expression in inner and outer hair cells. FIG. 17B is a confocal image demonstrating the ability of the Myo6 promoter to drive transgenes expression in inner and outer hair cells. FIG. 17C is an image showing the ability of the Myo7a promoter to drive expression in inner and outer hair cells. FIG. 17D is a series of images showing the ability of the KCNQ4 promoter to drive transgene expression specifically in outer hair cells.

DETAILED DESCRIPTION

Figure 1:
FIG. 1 shows sensory hair cells transduced with AAV9-PHP.B CMV-GFP. The left panel is an image of sensory hair cells transduced with AAV9-PHP.B CMV-GFP and stained with phalloidin red. The right panel is an image of sensory hair cells transduced with AAV9-PHP.B CMV-GFP showing that 100% of inner hair cells took up the vector and were positive for green fluorescent protein (GFP).

The invention provides compositions and methods for delivering and expressing a protein (e.g., TMC1, TMC2, MYO7A, USCH1C, CDH23, PCDH15, SANS, CIB2, USH2A, VLGR1, WHRN, CLRN1, PDZD7, KCNQ4, TMPRSS3, STRC, EYA4, USH1C (e.g., harmonin-a, b, or c), OTOF, GPR98, MYO6, MYO15A, LOXHD1, POU3F4, EYA1, WFS1, ACTG1, TMIE, PJVK, SYNE4, and FAM65B) required for mechanosensation, including hearing, and/or vestibular function, in a cell of the inner ear of a subject, such as a cochlear cell (e.g., inner or outer hair cell), wherein the subject has a loss or reduction in the level or activity of that protein.

The invention is based, at least in part, on the discoveries that an adeno-associated viral vector AAV-PHP.B, which encodes a capsid comprising the 7-mer sequence TLAVPFK (SEQ ID NO: 27) is extremely efficient and specific for expressing a protein of interest in inner and outer hair cells of the inner ear.

AAV-PHP.B

The AAV-PHP.B vector was generated using a Cre recombination-dependent approach to selectively recover capsids that transduce a predefined Cre expressing target cell population (also termed CREATE). This approach and vectors useful in the methods of the invention are described by Deverman et al., entitled "Cre-dependent selection yields AAV variants for widespread gene transfer to the adult brain," Nat Biotechnol. 2016 February; 34(2): 204-209) and in US Patent Publication No. 20170166926, each of which is incorporated herein by reference in their entirety. A library of AAV variants was generated by inserting 7 amino acids (AA) of randomized sequence (7-mer) between AA588-589 (VP1 position) of the AAV9 capsid. AAV-PHP.B encodes the 7-mer sequence TLAVPFK (SEQ ID NO: 27) and was tested for efficient transgene delivery to the cochlea, where it showed remarkably specific and robust expression in the inner and outer hair cells.

Usher Syndrome

Human Usher syndrome (USH) is a rare genetic condition responsible for combined deafness and blindness. Inherited as an autosomal recessive trait, it affects 16,000 to 20,000 people in the United States and is responsible for 3 to 6% of early childhood deafness. Usher syndrome is classified under three clinical subtypes (USH-1, -2 and -3) according to the severity of the symptoms. USH1 is the most severe form. Patients who are affected by USH1 suffer congenital bilateral profound sensorineural hearing loss, vestibular areflexia and pre-pubertal retinitis pigmentosa (a progressive, bilateral, symmetric degeneration of rod and cone function of the retina). Unless fitted with a cochlear implant, individuals do not typically develop the ability to generate speech. While no biological treatments currently exist for Usher patients, early reintroduction of the wild-type form of the defective gene may allow for reversal of the disease.

Six Usher genes are associated with USH1: MYO7A (myosin 7a), USH1C (harmonin), CDH23 (cadherin 23), PCDH15 (protocadherin 15), SANS (sans) and CIB2 (calcium and integrin binding protein 2). These genes encode proteins that are involved in hair bundle morphogenesis in the inner ear and are part of an interactome (see, for example, Mathur & Yang, 2015, Biochim. Biophys. Acta, 1852:406-20). Harmonin resides at the center of the USH1 interactome where it binds to other Usher 1 proteins. Because of its PDZ (PSD-59 95/Dlg/ZO-1) interaction domains, harmonin has been proposed to function as a scaffolding protein. In vitro binding studies have shown that all other known USH1 proteins bind to PDZ domains of harmonin as do two of the USH2 proteins, usherin, and VLGR1. The USH1C gene consists of 28 exons, which code for 10 alternative splice forms of harmonin, grouped into three different subclasses (a, b and c) depending on the domain composition of the protein. The three isoforms differ in the number of PDZ protein-protein interaction domains, coiled-coiled (CC) domains, and proline-serine-threonine (PST) rich domains.

USH1 proteins are localized to the apex of hair cells in mechanosenosory hair bundles, which are composed of hundreds of stereocilia interconnected by numerous extra-cellular links. Cadherin 23 and Protocadherin 15, products of Usher genes (USH1D and USH1E, respectively) form tip-links located at the distal end of the stereocilia. Harmonin-b binds to CDH23, PCDH15, F-actin and itself. It is found at the tips of the stereocilia near the tip-link insertion point in hair cells where it is thought to play a functional role in transduction and adaptation in hair cells. Harmonin-b is expressed during early postnatal stages but its expression diminishes around postnatal day 30 (P30) in both the cochlea and vestibule. Harmonin-a also binds to cadherin 23 and is found in the stereocilia. Recent reports reveal an additional role for harmonin-a at the synapse where it associates with Cav1.3 Ca2+ channels to limit channel availability through an ubiquitin-dependent pathway.

Several mouse models for Usher syndrome have been identified or engineered over the past decade, seven of which affect harmonin. Of these, only one model, the Ush1c c.216G>A model, reproduces both auditory and retinal deficits that characterize human Usher Syndrome. Ush1c c.216G>A is a knock-in mouse model that affects expression of all conventional harmonin isoforms due a point mutation similar to the one found in a cohort of French-Acadian USH1C patients. The mutation introduces a cryptic splice site at the end of exon three of the Ush1c gene. Use of this cryptic splice site produces a frame-shifted transcript with a 35 bp deletion and results in translation of a severely truncated protein lacking PDZ, PST and CC domains. Homozygous c.216AA knock-in mice suffer from severe hearing loss at 1 month of age while heterozygous c.216GA mice do not present any abnormal phenotype. Cochlear histology in c.216AA mice shows disorganized hair bundles, abnormal cell rows and loss of both inner and outer hair cells in middle and basal turns at P30.

It is demonstrated herein that a AAV9-PHP.B vector successfully transduced hair cells and drove expression of a protein of interest (i.e., GFP) in hair cells. Accordingly, this vector can be used to deliver other proteins of interest to hair cells for the treatment of Usher syndrome, as well as other auditory disorders.

TMC1/TMC2

Over 40 distinct mutations have been identified in TMC1 that cause deafness. These are subdivided into 35 recessive mutations and 5 dominant mutations. Most of the recessive mutations cause profound, congenital hearing loss (e.g., DFNB7/11) though a few cause later onset, moderate to severe hearing loss. All of the dominant mutations cause progressive hearing loss (e.g., DFNA36), with onset in the mid-teen years. In particular, a AAV9-PHP.B vector as described herein can be used to deliver a non-mutant (e.g., wild-type) TMC1 sequence or TMC2 sequence, thereby preventing hearing loss (e.g., further hearing loss) and/or restoring hearing function.

Therapeutic Strategies for the Treatment of Hearing Loss

Since the sensory cells of the adult mammalian cochlea lack the capacity for self-repair, current therapeutic strategies (depending on the level and exact position of impairment) rely on amplification (hearing aids), better transmission of sound (middle ear prostheses/active implants), or direct neuronal stimulation (cochlear implants) to compensate for permanent damage to primary sensory hair cells or spiral ganglion neurons which form the auditory nerve and relay acoustic information to the brain. While these approaches have been transformative, they remain far from optimal in restoring complex human hearing function important for modern life. Specifically, major problems still include limited frequency sensitivity, unnatural sound perception, and limited speech discrimination in noisy environments.

Therapeutic gene transfer to the cochlea has been considered to further improve upon the current standard of care ranging from age-related and environmentally induced hearing loss to genetic forms of deafness. More than 300 genetic loci have been linked to hereditary hearing loss with over 70 causative genes described (Parker & Bitner-Glindzicz, 2015, *Arch. Dis. Childhood,* 100:271-8). Therapeutic success in these approaches relies significantly on the safe and efficient delivery of exogenous gene constructs to the relevant therapeutic cell targets in the organ of *Corti* in the cochlea.

The organ of *Corti* includes two classes of sensory hair cells: inner hair cells, which convert mechanical information carried by sound into electrical signals transmitted to neuronal structures and outer hair cells which serve to amplify and tune the cochlear response, a process required for complex hearing function. Other potential targets in the inner ear include spiral ganglion neurons, columnar cells of the spiral limbus, which are important for the maintenance of the adjacent tectorial membrane or supporting cells, which have protective functions and can be triggered to trans-differentiate into hair cells up to an early neonatal stage.

Injection to the cochlear duct, which is filled with high potassium endolymph fluid, could provide direct access to hair cells. However, alterations to this delicate fluid environment may disrupt the endocochlear potential, heightening the risk for injection-related toxicity. The perilymph-filled spaces surrounding the cochlear duct, scala tympani and scala vestibuli, can be accessed from the middle ear, either through the oval or round window membrane. The round window membrane, which is the only non-bony opening into the inner ear, is relatively easily accessible in many animal models and administration of viral vector using this route is well tolerated. In humans, cochlear implant placement routinely relies on surgical electrode insertion through the RWM.

Previous studies evaluating AAV serotypes in organotypic cochlear explant and in vivo inner ear injection have resulted in only partial rescue of hearing in mouse models of inherited deafness. Unexpectedly, an AAV9-PHP.B vector transduced hair cells with high efficiency. This finding overcomes the low transduction rates that have limited successful development of cochlear gene therapy using conventional AAV serotypes. An AAV9-PHP.B vector as described herein provides a valuable platform for inner ear gene delivery to inner and outer hair cells, as well as an array of other inner ear cell types that are compromised by genetic hearing and balance disorders.

The AAV9-PHP.B vector provides for the highly efficient delivery of nucleic acids encoding proteins of interest. In particular, the invention provides a AAV9-PHP.B vector comprising one of the following promoters: an Espin promoter, a PCDH15 promoter, a PTPRQ promoter, a Myo6 promoter, a KCNQ4 promoter, a Myo7a promoter, a synapsin promoter, a GFAP promoter, a CMV promoter, a CAG promoter, a CBH promoter, a CBA promoter, a U6 promoter, or a TMHS (LHFPL5) promoter). In particular embodiments, the promoter directs expression of a polynucleotide encoding one or more of TMC1, TMC2, MYO7A, USCH1C, CDH23, PCDH15, SANS, CIB2, USH2A, VLGR1, WHRN, CLRN1, PDZD7, KCNQ4, TMPRSS3, STRC, EYA4, USH1C (e.g., harmonin-a, b, or c) OTOF, GPR98, MYO6, MYO15A, LOXHD1, POU3F4, EYA1, WFS1, ACTG1, TMIE, PJVK, SYNE4, and FAM65B to cells, particularly cells within the inner ear, e.g., in the cochlea (or cells of the cochlea or cochlear cells). As used herein, inner ear cells refer to, without limitation, inner hair cells (IHCs), outer hair cells (OHCs), spiral ganglion neurons, stria vascularis, vestibular hair cells, vestibular ganglion neurons, and supporting cells. Supporting cells refer to cells in the ear that are not excitable, e.g., cells that are not hair cells or neurons. An example of a supporting cell is a Schwann cell.

Delivery of one or more of the nucleic acids described herein to inner ear cells can be used to treat any number of inherited or acquired hearing disorders, which are typically defined by partial hearing loss or complete deafness. The methods described herein can be used to treat a hearing disorder such as, without limitation, recessive deafness, dominant deafness, Usher syndrome, and other syndromic deafness, as well as hearing loss due to trauma or aging.

Methods of Making Viruses Carrying Specific Transgenes

As described herein, AAV-PHP.B vectors are particularly efficient at delivering nucleic acids (e.g., transgenes, including but not limited to a polynucleotide encoding one or more of TMC1, TMC2, MYO7A, USCH1C, CDH23, PCDH15, SANS, CIB2, USH2A, VLGR1, WHRN, CLRN1, PDZD7, KCNQ4, TMPRSS3, STRC, EYA4, USH1C (e.g., harmonin-a, b, or c)) to inner ear cells. The AAV-PHP.B vector advantageously transduced greater than about 60%, 70%, 80%, 90%, 95%, or even 100% of inner or outer hair cells.

In particular embodiments the AAV-PHP.B vector has a natural or engineered tropism for hair cells. In some embodiments, AAV9-php.b delivers a transgene (e.g., a polynucleotide encoding one or more of TMC1, TMC2, MYO7A, USCH1C, CDH23, PCDH15, SANS, CIB2, USH2A, VLGR1, WHRN, CLRN1, PDZD7, KCNQ4, TMPRSS3, STRC, EYA4, USH1C (e.g., harmonin-a, b, or c), OTOF, GPR98, MYO6, MYO15A, LOXHD1, POU3F4, EYA1, WFS1, ACTG1, TMIE, PJVK, SYNE4, and FAM65B) to the inner ear in a subject.

In one embodiment, a AAV-PHP.B vector comprising a promoter (e.g., an Espin promoter, a PCDH15 promoter, a PTPRQ promoter, a Myo6 promoter, a KCNQ4 promoter, a Myo7a promoter, a synapsin promoter, a GFAP promoter, a CMV promoter, a CAG promoter, a CBH promoter, a CBA promoter, a U6 promoter, and a TMHS (LHFPL5) promoter) directing expression of a polynucleotide encoding one or more of TMC1, TMC2, MYO7A, CDH23, PCDH15, SANS, CIB2, USH2A, VLGR1, WHRN, CLRN1, PDZD7, KCNQ4, TMPRSS3, STRC, EYA4, USH1C (e.g., harmonin-a, b, or c), OTOF, GPR98, MYO6, MYO15A, LOXHD1, POU3F4, EYA1, WFS1, ACTG1, TMIE, PJVK, SYNE4, and FAM65B is used to treat a hearing disorder. A nucleic acid sequence delivered to a cell for the purpose of expression oftentimes is referred to as a transgene. Representative transgenes that can be delivered to, and expressed in, inner ear cells include, without limitation, a transgene encoding a polypeptide that functions in auditory and/or vestibular mechanosensation (e.g., TMC1, TMC2, MYO7A, USCH1C, CDH23, PCDH15, SANS, CIB2, USH2A, VLGR1, WHRN, CLRN1, PDZD7 (e.g., harmonin-a, b, or c), OTOF, GPR98, MYO6, MYO15A, LOXHD1, POU3F4, EYA1, WFS1, ACTG1, TMIE, PJVK, SYNE4, and FAM65B), KCNQ4, TMPRSS3, STRC, EYA4, a transgene that encodes a neurotrophic factor (e.g., GDNV, BDNF, or HSP70).

Expression of a transgene may be directed by the transgene's natural promoter (i.e., the promoter found naturally with the transgenic coding sequence) or expression of a transgene may be directed by a heterologous promoter (e.g., an Espin promoter, a PCDH15 promoter, a PTPRQ promoter, a Myo6 promoter, a KCNQ4 promoter, a Myo7a promoter, a synapsin promoter, a GFAP promoter, a CMV promoter, a CAG promoter, a CBH promoter, a CBA promoter, a U6 promoter, and a TMHS (LHFPL5) promoter). For example, any of the transgenes described herein can be used with its natural promoter. Alternatively, any of the transgenes described herein can be used with a heterologous promoter. As used herein, a heterologous promoter refers to a promoter that does not naturally direct expression of that sequence (i.e., is not found with that sequence in nature). Representative heterologous promoters that can be used to direct expression of any of the transgenes indicated herein include, for example, a CMV promoter, a CBA promoter, a CASI promoter, a P promoter, and a EF-1 promoter, an alpha9 nicotinic receptor promoter, a prestin promoter, a Gfi1 promoter, and a Vglut3 promoter. In addition, a promoter that naturally directs expression of one of the above-referenced transgenes (e.g., a KCNQ4 promoter, a Myo7a promoter, a Myo6 promoter or an Atoh1 promoter) can be used as a heterologous promoter to direct expression of a transgene. In other embodiments, the promoter is an Espin promoter, a PCDH15 promoter, a PTPRQ promoter, a Myo6 promoter, a KCNQ4 promoter, a Myo7a promoter, a synapsin promoter, a GFAP promoter, a CMV promoter, a CAG promoter, a CBH promoter, a CBA promoter, a U6 promoter, or a TMHS (LHFPL5) promoter.

Methods of making a transgene (e.g., TMC1, TMC2, USH1C (e.g., harmonin-a, b, or c), MYO7A, USCH1C, CDH23, PCDH15, SANS, CIB2, USH2A, VLGR1, WHRN, CLRN1, PDZD7, KCNQ4, TMPRSS3, STRC, EYA4) for packaging into a AAV-PHP.B vector are known in the art, and utilize conventional molecular biology and recombinant nucleic acid techniques.

The transgene can be packaged into an AAV-PHP.B vector using, for example, a packaging host cell. The components of a virus particle (e.g., rep sequences, cap sequences, inverted terminal repeat (ITR) sequences) can be introduced, transiently or stably, into a packaging host cell using one or more constructs as described herein.

In general, as used herein, "nucleic acids," can include DNA and RNA, and also can include nucleic acids that contain one or more nucleotide analogs or backbone modifications. Nucleic acids can be single-stranded or double-stranded, which usually depends upon its intended use. Nucleic acids that can be used in the methods described herein can be identical to a known nucleic acid sequence, or nucleic acids that can be used in the methods described herein can differ in sequence from such known sequences. Simply by way of example, nucleic acids (or the encoded polypeptides) can have at least 75% sequence identity (e.g., at least 80%, 81%, 82%, 83%, 84%, 85%, 86%, 87%, 88%, 89%, 90%, 91%, 92%, 93%, 94%, 95%, 96%, 97%, 98%, or 99% sequence identity) to a known sequence.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity is performed using the computer program ClustalW and default parameters, which allows alignments of nucleic acid or polypeptide sequences to be carried out across their entire length (global alignment). Chenna et al., 2003, Nucleic Acids Res., 31 (13): 3497-500. ClustalW calculates the best match between a query and one or more subject sequences, and aligns them so that identities, similarities and differences are determined. Gaps of one or more residues can be inserted into a query sequence, a subject sequence, or both, to maximize sequence alignments. For pairwise alignment of nucleic acid sequences, the default parameters are used (i.e., word size: 2; window size: 4; scoring method: percentage; number of top diagonals: 4; and gap penalty: 5); for an alignment of multiple nucleic acid sequences, the following parameters are used: gap opening penalty: 10.0; gap extension penalty: 5.0; and weight transitions: yes. For pairwise alignment of polypeptide sequences, the following parameters are used: word size: 1; window size: 5; scoring method: percentage; number of top diagonals: 5; and gap penalty: 3. For multiple alignment of polypeptide sequences, the following parameters are used: weight matrix: BLOSUM (blocks substitution matrix); gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

Changes can be introduced into a nucleic acid sequence, which can lead to changes in the amino acid sequence of the encoded polypeptide if the nucleic acid sequence is a coding sequence. For example, changes can be introduced into nucleic acid coding sequences using mutagenesis (e.g., site-directed mutagenesis, PCR-mediated mutagenesis) or by chemically synthesizing a nucleic acid molecule having such changes. Such nucleic acid changes can lead to conservative and/or non-conservative amino acid substitutions at one or more amino acid residues. A "conservative amino acid substitution" is one in which one amino acid residue is replaced with a different amino acid residue having a similar side chain (see, for example, Dayhoff et al. (1978, in Atlas of Protein Sequence and Structure, 5 (Suppl. 3): 345-352), which provides frequency tables for amino acid substitutions), and a non-conservative substitution is one in which an amino acid residue is replaced with an amino acid residue that does not have a similar side chain.

A nucleic acid can be contained within a construct, which also can be referred to as a vector or a plasmid. Constructs are commercially available or can be produced by recombinant techniques routine in the art. A construct containing a nucleic acid can have expression elements that direct and/or regulate expression of such a nucleic acid, and also can include sequences such as those for maintaining the construct (e.g., origin of replication, a selectable marker). Expression elements are known in the art and include, for example, promoters, introns, enhancer sequences, response elements, or inducible elements.

Pharmaceutical Compositions

A AAV-PHP.B vector comprising a promoter (e.g., an Espin promoter, a PCDH15 promoter, a PTPRQ promoter, a Myo6 promoter, a KCNQ4 promoter, a Myo7a promoter, a synapsin promoter, a GFAP promoter, a CMV promoter, a CAG promoter, a CBH promoter, a CBA promoter, a U6 promoter, and a TMHS (LHFPL5) promoter) and a polynucleotide that is one or more of USH1, MYO7A, USH1C (harmonin-a, b, c), CDH23, PCDH15, SANS and CIB2, usually suspended in a physiologically compatible excipient, can be administered to a subject (e.g., a human or non-human mammal) by injection to the inner ear of a subject through the round window or utricle. Suitable carriers include saline, which may be formulated with a variety of buffering solutions (e.g., phosphate buffered saline), lactose, sucrose, calcium phosphate, gelatin, dextran, agar, pectin, and water. The AAV-PHP.B vector is administered in sufficient amounts to transduce or infect the cells and to provide sufficient levels of gene transfer and expression to provide a therapeutic benefit without undue adverse effects.

The dose of the AAV-PHP.B vector administered to a subject will depend primarily on factors such as the condition being treated, and the age, weight, and health of the subject. For example, a therapeutically effective dosage of a AAV-PHP.B vector to be administered to a human subject generally is in the range of from about 0.1 ml to about 10 ml of a solution containing concentrations of from about 1×10' to 1×1012 genome copies (GCs) of AAVs (e.g., about 1×103 to 1×109 GCs).

Methods of Delivering Nucleic Acids to Inner Ear Cells

Methods of delivering nucleic acids to cells generally are known in the art, and methods of delivering viruses (which also can be referred to as viral particles) containing a transgene to inner ear cells in vivo are described herein. As described herein, about 108 to about 1012 viral particles can be administered to a subject, and the virus can be suspended within a suitable volume (e.g., 10 μL, 50 μL, 100 μL, 500 μL, or 1000 μL) of, for example, artificial perilymph solution.

A virus containing a promoter (e.g., an Espin promoter, a PCDH15 promoter, a PTPRQ promoter, a Myo6 promoter, a KCNQ4 promoter, a Myo7a promoter, a synapsin promoter, a GFAP promoter, a CMV promoter, a CAG promoter, a CBH promoter, a CBA promoter, a U6 promoter, and a TMHS (LHFPL5) promoter) and a transgene (e.g., TMC1, TMC2, USH1C (e.g., harmonin-a, b, or c), MYO7A, USCH1C, CDH23, PCDH15, SANS, CIB2, USH2A, VLGR1, WHRN, CLRN1, PDZD7, KCNQ4, TMPRSS3, STRC, EYA4, OTOF, GPR98, MYO6, MYO15A, LOXHD1, POU3F4, EYA1, WFS1, ACTG1, TMIE, PJVK, SYNE4, and FAM65B) as described herein can be delivered to inner ear cells (e.g., cells in the cochlea) using any number of means. For example, a therapeutically effective amount of a composition including virus particles containing one or more different types of transgenes as described herein can be injected through the round window or the oval window, or the utricle, typically in a relatively simple (e.g., outpatient) procedure. In some embodiments, a composition comprising a therapeutically effective number of virus particles containing a transgene, or containing one or more sets of different virus particles, wherein each particle in a set can contain the same type of transgene, but wherein each set of particles contains a different type of transgene than in the other sets, as described herein can be delivered to the appropriate position within the ear during surgery (e.g., a cochleostomy or a canalostomy).

In one embodiment, an AAV-PHP.B vector comprising a promoter (e.g., an Espin promoter, a PCDH15 promoter, a PTPRQ promoter, a Myo6 promoter, a KCNQ4 promoter, a Myo7a promoter, a synapsin promoter, a GFAP promoter, a CMV promoter, a CAG promoter, a CBH promoter, a CBA promoter, a U6 promoter, or a TMHS (LHFPL5) promoter) and a polynucleotide that is one or more of USH1, MYO7A, USH1C (harmonin-a, b, c), CDH23, PCDH15, SANS and CIB2 is injected through the round window or utricle of a subject in need thereof.

In addition, delivery vehicles (e.g., polymers) are available that facilitate the transfer of agents across the tympanic membrane and/or through the round window or utricle, and any such delivery vehicles can be used to deliver the viruses described herein. See, for example, Arnold et al., 2005, *Audiol. Neurootol.,* 10:53-63.

The compositions and methods described herein enable the highly efficient delivery of nucleic acids to inner ear cells, e.g., cochlear cells. For example, the compositions and methods described herein enable the delivery to, and expression of, a transgene in at least 80% (e.g., at least 85, 90, 91, 92, 93, 94, 95, 96, 97, 98, or 99%) of inner hair cells or delivery to, and expression in, at least 80% (e.g., at least 85, 90, 91, 92, 93, 94, 95, 96, 97, 98, or 99) of outer hair cells.

As demonstrated herein, expression of a transgene delivered using an AAV-PHP.B vector can result in regeneration of inner hair cells (IHCs), outer hair cells (OHCs), spiral ganglion neurons, stria vascularis, vestibular hair cells, and/or vestibular ganglion neurons (e.g. Atoh1, NF2) such that hearing or vestibular function is restored for an extended period of time (e.g., months, years, decades, a life time).

Kits

The invention also provides a pharmaceutical pack or kit comprising one or more containers filled with one or more of the ingredients of the pharmaceutical compositions of the invention including a AAV-PHP.B vector comprising a promoter (e.g., an Espin promoter, a PCDH15 promoter, a PTPRQ promoter, a Myo6 promoter, a KCNQ4 promoter, a Myo7a promoter, a synapsin promoter, a GFAP promoter, a CMV promoter, a CAG promoter, a CBH promoter, a CBA promoter, a U6 promoter, and a TMHS (LHFPL5) promoter) and a polynucleotide that is one or more of USH1, MYO7A, USH1C (harmonin-a, b, c), CDH23, PCDH15, SANS and CIB2). Associated with such container(s) can be a notice in the form prescribed by a governmental agency regulating the manufacture, use or sale of pharmaceuticals or biological products, which notice reflects approval by the agency of manufacture, use or sale for human administration.

The invention also provides kits for treatment or prevention of a disease or disorder (or symptoms) thereof associated with a defect in auditory and/or vestibular mechanosensation. In one embodiment, the kit includes an effective amount of a AAV-PHP.B vector comprising a promoter (e.g., an Espin promoter, a PCDH15 promoter, a PTPRQ promoter, a Myo6 promoter, a KCNQ4 promoter, a Myo7a promoter, a synapsin promoter, a GFAP promoter, a CMV promoter, a CAG promoter, a CBH promoter, a CBA promoter, a U6 promoter, and a TMHS (LHFPL5) promoter) and a polynucleotide that is one or more of USH1, MYO7A, USH1C (harmonin-a, b, c), CDH23, PCDH15, SANS and CIB2 in unit dosage form, together with instructions for administering the AAV-PHP.B vector to a subject suffering from or susceptible to a disease or disorder or symptoms thereof associated with a hearing disorder. In preferred embodiments, the kit comprises a sterile container which contains the AAV-PHP.B vector; such containers can be boxes, ampules, bottles, vials, tubes, bags, pouches, blister-packs, or other suitable container form known in the art. Such containers can be made of plastic, glass, laminated paper, metal foil, or other materials suitable for holding medicaments. The instructions will generally include information about the use of the AAV-PHP.B vector for treatment of a disease or disorder or symptoms thereof associated with a hearing disorder. The instructions may be printed directly on the container (when present), or as a label applied to the container, or as a separate sheet, pamphlet, card, or folder supplied in or with the container.

Conventional molecular biology, microbiology, biochemical, and recombinant DNA techniques within the skill of the art can be used in accordance with the present disclosure. Such techniques are explained fully in the literature. The invention will be further described in the following examples, which do not limit the scope of the methods and compositions of matter described in the claims.

EXAMPLES

Example 1: AAV-PHP.B Vectors Direct Transgene Expression in Outer and Inner Hair Cells In Vivo Injections Mouse pups (P0 to P2) were injected with AAV-PHP.B vector CMV GFP via the round window membrane (RWM) using beveled glass microinjection pipettes. Pipettes were pulled from capillary glass (WPI) on a P-2000 pipette puller (Sutter Instrument, Novato, CA) and were beveled (~20 μm tip diameter at a 28° angle) using a micropipette beveler (Sutter Instrument, Novato, CA). EMLA cream (lidocaine 2.5% and prilocaine 2.5%) was applied externally for analgesia using sterile swabs to cover the surgical site (left mastoid prominence). Body temperature was maintained on a 38° C. warming pad prior to surgery. Pups were anesthetized by rapid induction of hypothermia into ice/water for 2-3 minutes until loss of consciousness, and this state was maintained on a cooling platform for 5-10 minutes during the surgery. The surgical site was disinfected by scrubbing with Betadine and wiping with 70% Ethanol in repetition three times. A post-auricular incision was made to expose the transparent otic bulla, a micropipette was advanced manually through the bulla and overlying fascia, and the RWM was penetrated by the tip of the micropipette. Approximately 1 μL of virus was injected unilaterally within 1 min into the left ear manually in C57BL/6 animals. After the injection, the skin incision was closed using a 6-0 black monofilament suture (Surgical Specialties, Wyomissing, PA). Pups were subsequently returned to the 38° C. warming pad for 5-10 min and then put back to their mother for breeding.

Figure 2:
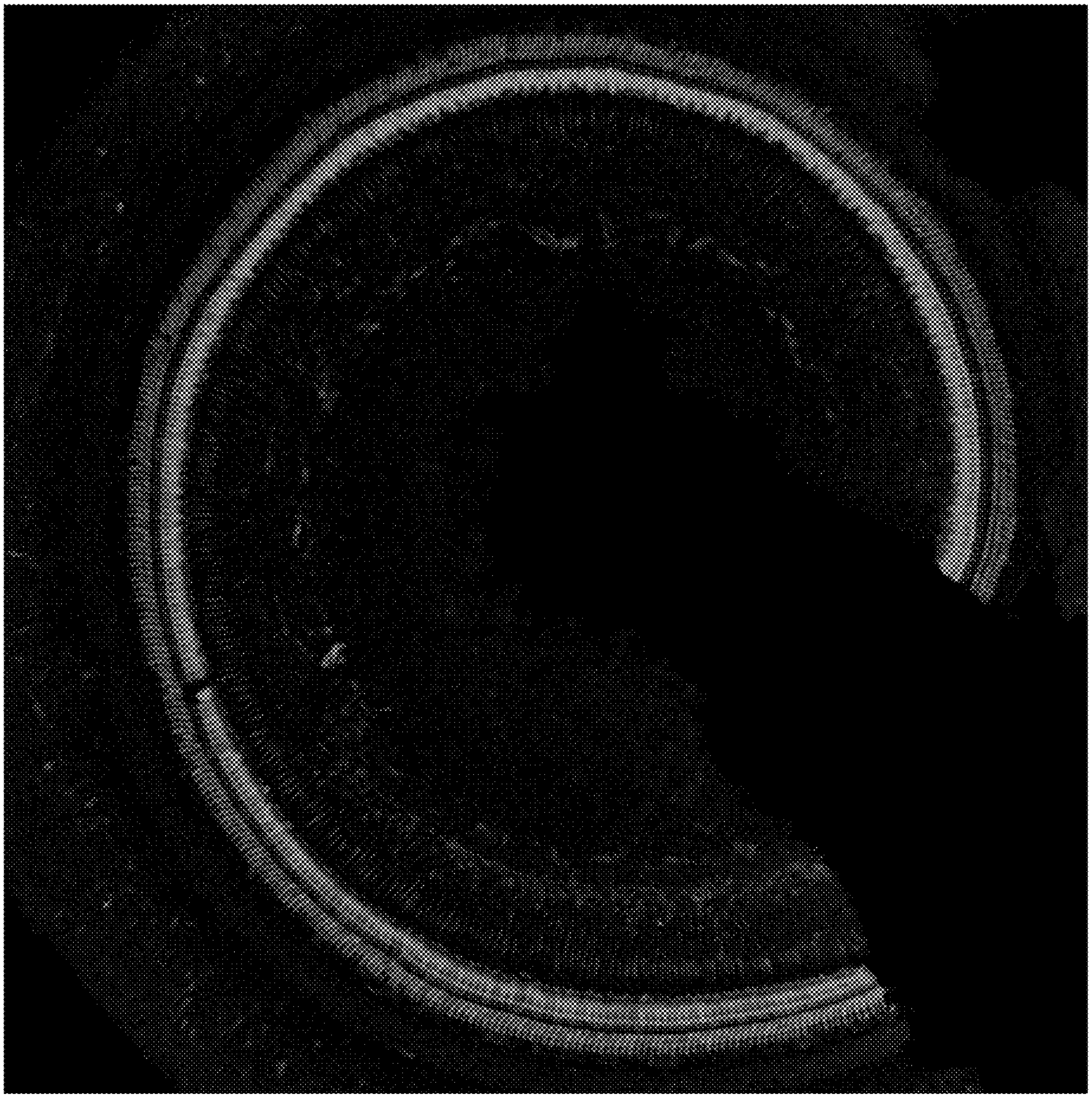
FIG. 2 is an image of sensory hair cells transduced with AAV9-PHP.B CMV-GFP from a different mouse and injection. 100% of inner hair cells and 100% of outer hair cells were transduced and are GFP-positive. Very few other cells express GFP. We have injected the inner ears of four mice. Three of four mice showed expression similar to that described herein below with 100% of sensory hair cells transduced. The fourth is shown in FIG. 1.
Figure 3:
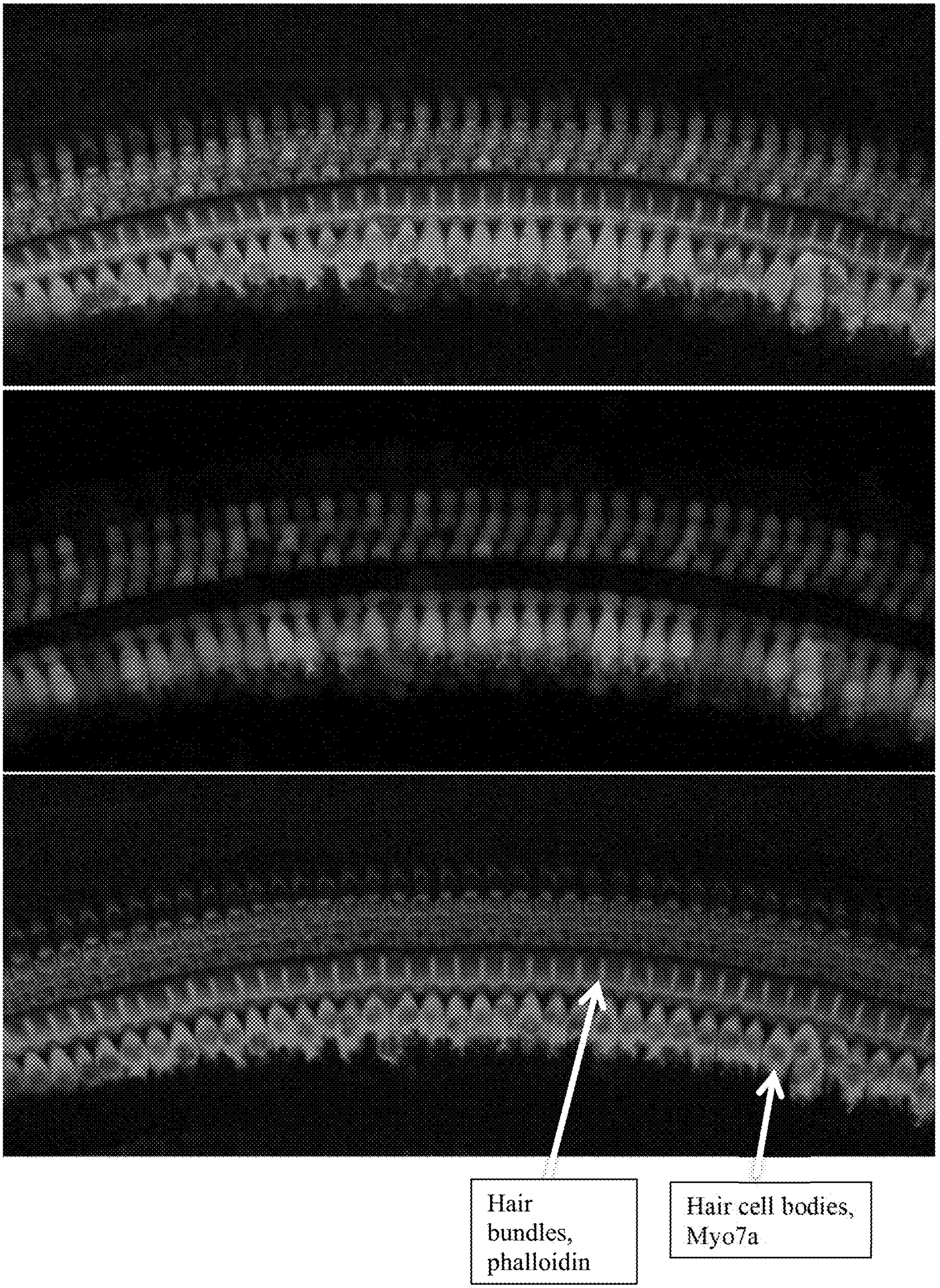
FIG. 3 shows a high magnification view from a different mouse. In this case, the tissue was stained with Myo7a to illuminate the hair cell cell-bodies (blue) and with phalloidin to stain to the hair bundles (red). The top panel shows a merge of all three color channels. The middle panel shows GFP (green) expression with 100% of inner hair cells transduced and 100% of outer hair cells transduced. The bottom panel shows Myo7a and phalloidin.

AAV-PHP.B vector transduced nearly 100% of IHCs and 100% of OHCs (FIGS. 1-3) with high specificity, i.e. very few non-hair cells were transduced.

The AAV-PHP.B CMV GFP vector-transduced samples were subsequently fixed, stained with phalloidin or Myo7 and imaged by confocal microscopy. The outer and inner hair cell targeting illustrates efficient transduction.

Example 2—Hair Cell Electrophysiology

Following transduction of an AAV-PHP.B vector comprising a transgene encoding a gene of interest, the electrophysiology of the hair cell is assayed. *Cochleae* are excised, mounted on glass coverslips and viewed on an Axio Examiner.A1 upright microscope (Carl Zeiss, Oberkochen, Germany) equipped with a 63× water-immersion objective and differential interference contrast optics. Electrophysiological recordings are performed at room temperature (22° C.-24° C.) in standard solutions containing (in mM): 137 NaCl, 5.8 KCl, 10 HEPES, 0.7 $NaH_2PO_4$, 1.3 $CaCl_2$), 0.9 $MgCl_2$, and 5.6 D-glucose, vitamins (1:100), and amino acids (1:50) as in MEM (Life Technologies, Carlsbad, CA) (pH 7.4; ~310 mOsm/kg). Recording electrodes (3-4 MΩ) are pulled from R-6 glass (King Precision Glass, Claremont, CA) and filled with intracellular solution containing (in mM): 140 CsCl, 5 EGTA-KOH, 5 HEPES, 2.5 $Na_2ATP$, 3.5 $MgCl_2$, and 0.1 $CaCl_2$) (pH 7.4; ~280 mOsm/kg). The whole-cell, tight-seal technique is used to record mechanotransduction currents using an Axopatch 200B (Molecular Devices, Sunnyvale, CA). Hair cells were held at −84 mV. Currents were filtered at 5 kHz with a low-pass Bessel filter, digitized at ≥20 kHz with a 12-bit acquisition board (Digidata 1440A, Molecular Devices, Sunnyvale, CA), and recorded using pCLAMP 10 software (Molecular Devices, Sunnyvale, CA). Hair bundles from IHCs and OHCs were deflected using stiff glass probes mounted on a PICMA chip piezo actuator (Physik Instrumente, Karlsruhe, Germany) driven by an LVPZT amplifier (E-500.00, Physik Instrumente, Karlsruhe, Germany) and filtered with an 8-pole Bessel filter (Model 3384 filter, Krohn-Hite Corporation, Brockton, MA) at 40 kHz to eliminate residual pipette resonance. Stiff glass probes are designed to fit into the concave aspect of the array of hair cell stereocilia for whole-bundle recordings (3-4 μm diameter for OHCs and 4-5 μm diameter for IHCs). For the whole cell electrophysiology recording at >P10, cochlea tissues are dissected at P5-7 and incubated in MEM (1×)+GlutaMAXTM-I medium with 1% FBS at 37° C., 5% CO2 for up to 30 days.

Example 3—Hearing Tests

Hearing is also assayed following transduction in mice having a genetic auditory defect. Auditory brainstem response (ABR) and distortion product otoacoustic emissions (DPOAE) data are collected. DPOAE is an assay for proper cochlear amplification and tuning and is a sensitive measure of outer hair cell viability. Stimuli tested in anesthetized mice varied between 10 and 90 dB sound pressure level at frequencies of 5.6, 8, 11.3, 16, 22.6, and 32 kHz. Minimal sound thresholds required to evoke ABRs are plotted.

Example 4—Rotarod Test

Mice are tested for balance behavior on the rotarod device. Mice with impaired vestibular function are known to perform poorly on the rotarod device. Previous studies highlighted the ability of this rotarod test to detect balance dysfunction when only one ear is affected. Mice are injected at P1 and tested at P36 and uninjected control mice at P79. All mice are tested using the following rotarod protocol. On day one, mice are trained to balance on a rod that is rotating at four RPM for five minutes. On day two, the mice are tested in five trials with each trial separated by five minutes. For each trial, the rod accelerated one RPM from a starting rate of two RPM. The time (in seconds) is recorded until the mice fell off the device.

Since the perilymphatic solutions of the cochlea is continuous with those of the vestibular labyrinth, it is evaluated whether AAV-PHP.B vector expressing a protein of interest injected via the cochlear RWM would transduce vestibular sensory organs. Thus, to address the safety concern that AAV-PHP.B vector transduction may affect balance, injected mice with confirmed vestibular expression perform the rotarod test for vestibular function relative to uninjected controls.

Example 5—Mouse Model of Usher Syndrome

Tissue Preparation

Utricle and organ of *Corti* from Ush1c c.216G>A heterozygous or homozygous mutant mice are harvested from postnatal day 0 to 8 (P0 to P8) for electrophysiological studies. Postnatal mouse pups are killed by rapid decapitation. The temporal bones are excised and bathed in MEM (Invitrogen, Carlsbad, CA) supplemented with 10 mM HEPES (pH 7.4). The organ of *Corti* is dissected away without the use of enzyme as described previously (53). Utricles are removed after 10 min protease treatment (Protease XXIV, Sigma) at 0.1 mg/ml. The excised organs are mounted on round glass coverslips. A pair of thin glass fibers previously glued to the coverslip is placed on the edge of the tissue to stabilize it in a flat position. Tissues are either used acutely or kept in culture in presence of 1% Fetal Bovine Serum. Cultures are maintained for 7 to 8 days and the media is replaced every 2 to 3 days for experiments that involve viral vectors infection in vitro.

Animals

Ush1c c.216G>A knock-in mice were obtained from Louisiana State University Health Science Center. The imported strain while on a C57BL6 background were previously bred out of the Cdh23 (Ahl) mutation causing age related hearing loss (48, 49). Mice str genotyped using toe clip (before P8) or ear punch (after P8) and PCR is performed as described previously (32). For all studies, both male and female mice are used in approximately equal proportions. No randomization paradigm was otherwise applied.

Round Window Membrane (RWM) Injection

AAV-PHP.B vectors expressing a gene of interest under a selected promoter are generated. 0.8 μl-1 μl of vector is injected in neonatal mice P0-P1 and P10-P12. P0-P1 mice are first anesthetized using hypothermia exposure while P10-P12 mice are anesthetized with isoflurane. Upon anesthesia, post-auricular incision is made to expose the otic bulla and visualize the cochlea. Injections are done through the RWM with a glass micropipette controlled by a micromanipulator (Askew et al. 2015). The volume of the injected materials is controlled at an approximately 0.02 μl/min for 10 min. Standard post-operative care is applied. Sample size for in vivo studies were determined on a continuing basis to optimize the sample size and decrease the variance.

Electrophysiological Recording

Recordings are performed in standard artificial perilymph solution containing (in mM): 144 NaCl, 0.7 NaH2PO4, 5.8 KCl, 1.3 CaCl2, 0.9 MgCl2, 5.6 D-glucose, and 10 HEPES-NaOH, adjusted to pH 7.4 and 320 mOsmol/kg. Vitamins (1:50) and amino acids (1:100) were added from concentrates (Invitrogen, Carlsbad, CA). Hair cells were viewed from the apical surface using an upright Axioskop FS microscope (Zeiss, Oberkochen, Germany) equipped with a 63× water immersion objective with differential interference contrast optics. Recording pipettes (3-5 M (2) were pulled from borosilicate capillary glass (Garner Glass, Claremont, CA) and filled with intracellular solution containing (in mM): 135 KCl, 5 EGTA-KOH, 10 HEPES, 2.5 $K_2ATP$, 3.5 $MgCl_2$, 0.1 $CaCl_2$), pH 7.4. Currents were recorded under whole-cell voltage-clamp at a holding potential of −64 mV at room temperature. Data were acquired using an Axopatch Multiclamp 700A or Axopatch 200A (Molecular devices, Palo Alto, CA) filtered at 10 kHz with a low pass Bessel filter, digitized at ≥20 kHz with a 12-bit acquisition board (Digidata 1322) and pClamp 8.2 and 10.5 (Molecular Devices, Palo Alto, CA). Data were analyzed offline with OriginLab software and are presented as means±standard deviations unless otherwise noted.

Example 6—Acoustic Startle Responses

The acoustic startle responses (ASR) is measured using the Startle Monitor (Kinder Scientific). Mice are placed in a small-sized, nonrestrictive, cubical Plexiglas recording chamber (27 cm×10 cm×652 12.5 cm) fixed on a piezo/plexiglass sensing assembly and allowed to acclimate for 5 min with a 60 db SPL background white noise. Each session consists of 35 trials, during which a single noise pulse ranging in 10 dB SPL intensities from 60-120 db SPL was delivered with an inter-trial interval averaging 30s (25-35s range). Pulses are arranged in a pseudorandom order, on a constant 60 dB SPL background noise to limit external noise interference. The Startle Monitor system reduced the response to each pulse into measurements of first N, max N, and max time of the response (ms), for calculations of peak startle response (ASR amplitude) and time from stimulus to peak startle response (ASR latency). ASR were all conducted blind.

To assess whether the ABR/DPOAE recovery yielded behaviorally relevant recovery of auditory function, acoustic startle responses are measured in mice injected with AAV-PHP.B vector alone and expressing a protein of interest and those injected with both vectors. Analysis of the startle response to white noise is assessed for rescue of the response in 6 weeks old mice.

Example 7—Immunofluorescence

Immunostaining is performed to determine the distribution of expression of a transgene delivered by a AAV-PHP.B vector. To do so, immunostaining is performed on freshly dissected organs of *Corti*, immersion fixed for 1 h at room temperature with 4% paraformaldehyde diluted in PBS. The tissue is then rinsed in PBS, permeabilized in 0.01-0.1% Triton X-100 for 30 minutes, and counterstained for 1 h with AlexaFluor546-phalloidin (Molecular Probes, 1:200 dilution) to label filamentous actin.

For localization of exogenously expressed TMC::FLAG fusion proteins, the tissue is blocked for 1 hour using 2% BSA and 5% Normal Goat Serum, and is incubated overnight at 4° C. with an antibody to the FLAG motif (BD Biosciences, 1:200 dilution). For hair cell counts, tissue is blocked in Normal Goat Serum for 1 hour, stained with a rabbit anti-Myosin VIIa primary antibody (Proteus Biosciences, 1:1000 dilution) at 4° C. overnight, and labeled with goat anti-rabbit antibody conjugated to AlexaFluor488 (Life Technologies, 1:200 dilution) for 1 h. Samples are mounted on glass coverslips with Vectashield mounting medium (Vector Laboratories), and imaged at 10×-63× magnification using a Zeiss LSM700 confocal microscope.

Example 8—Utricle Injection

A novel injection method was developed to deliver therapeutic vectors to the inner ear. Previous injection methods delivered vectors through the round window membrane, the oval window, or the posterior semicircular canal. While somewhat effective, these methods all suffer significant draw backs, including targets that are difficult to access surgically, uneven viral distribution, and significant variability in targeting perilymphatic or endolymphatic spaces. To circumvent these limitations, a novel method was designed that allows for efficient delivery to inner ear spaces without causing auditory or vestibular dysfunction.

Figure 4:
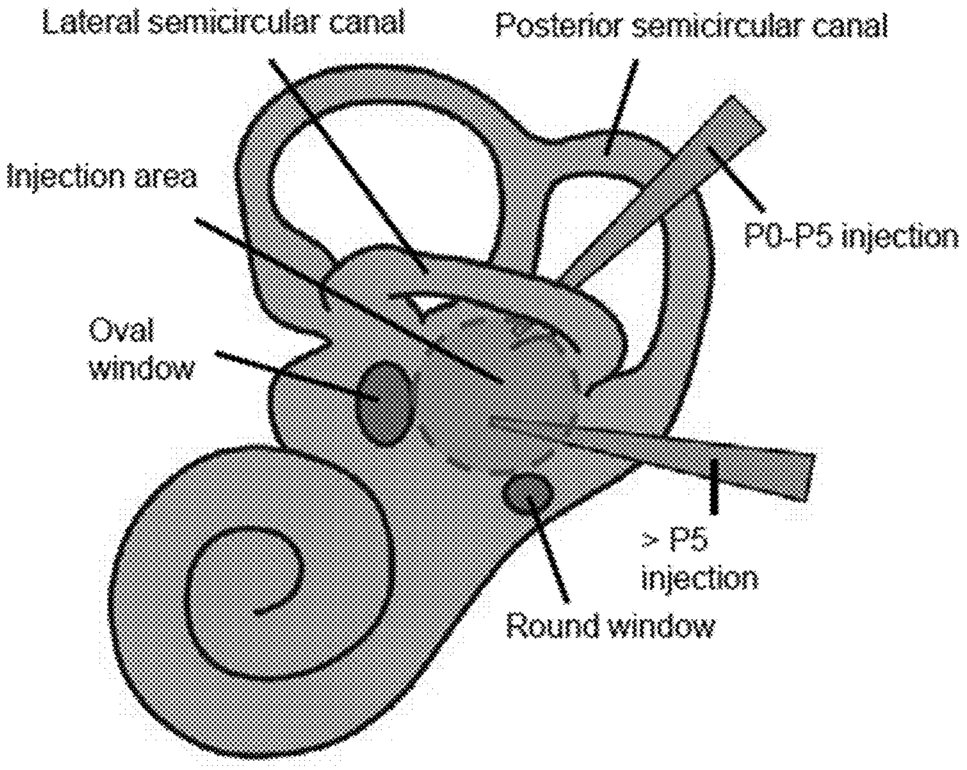
FIG. 4 is an illustration of the inner ear that shows the injection sites used to transduce mice. "P0-P4" and ">P5" refer to the injection at post-hearing stages P0 to P4 and post hearing stages later than stage P5, respectively.

This method comprises targeting the utricle, one of the vestibular organs, for injection. Injection is into the endolymphatic space. Two different routes were used for delivery depending on age of the mice. As illustrated below, between P0 and P5, the utricle was approached between the lateral and posterior semicircular canals. At stages later than P5, the utricle was injected between the round and oval windows (FIG. 4). Because the fluid filled spaces of the utricle are continuous with the other vestibular organs and the cochlea, significantly improved viral distribution throughout the inner ear was observed.

Figure 5A:
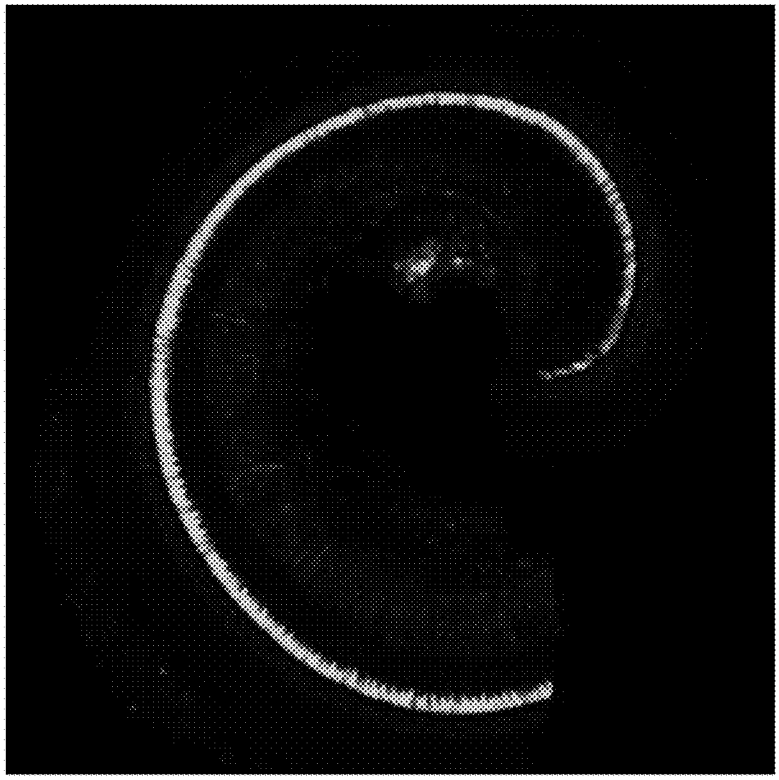
FIGS. 5A to 5D compare of utricle and round windown membrane (RWM) injection of Anc80-Cmv-eGFP.
Figure 5B:
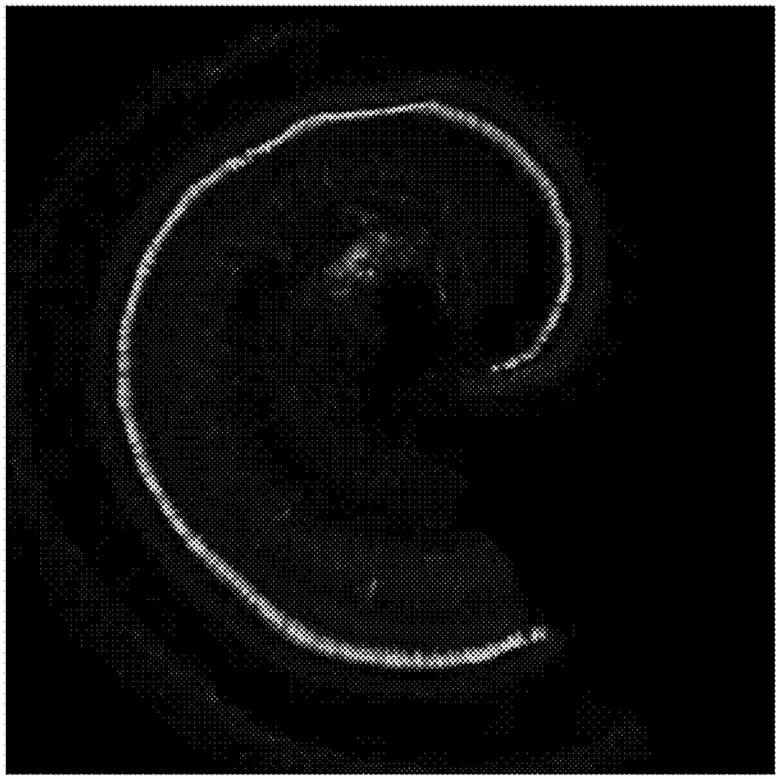
Figure 5C:
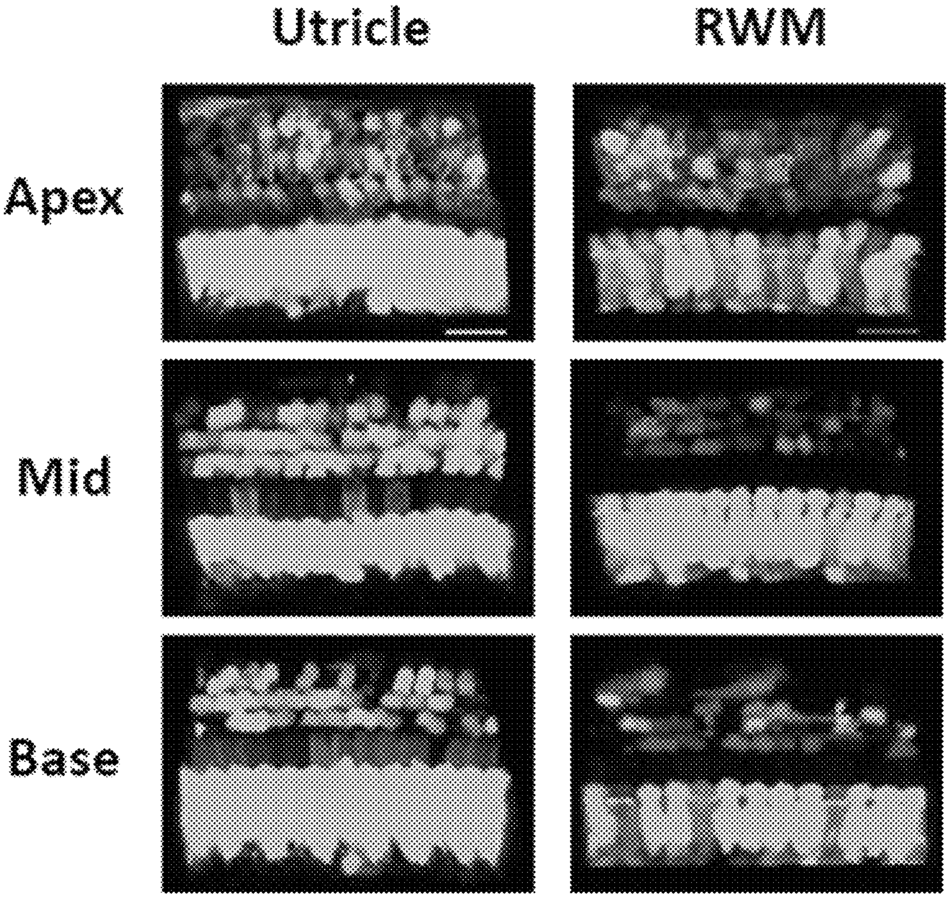
Figure 5D:
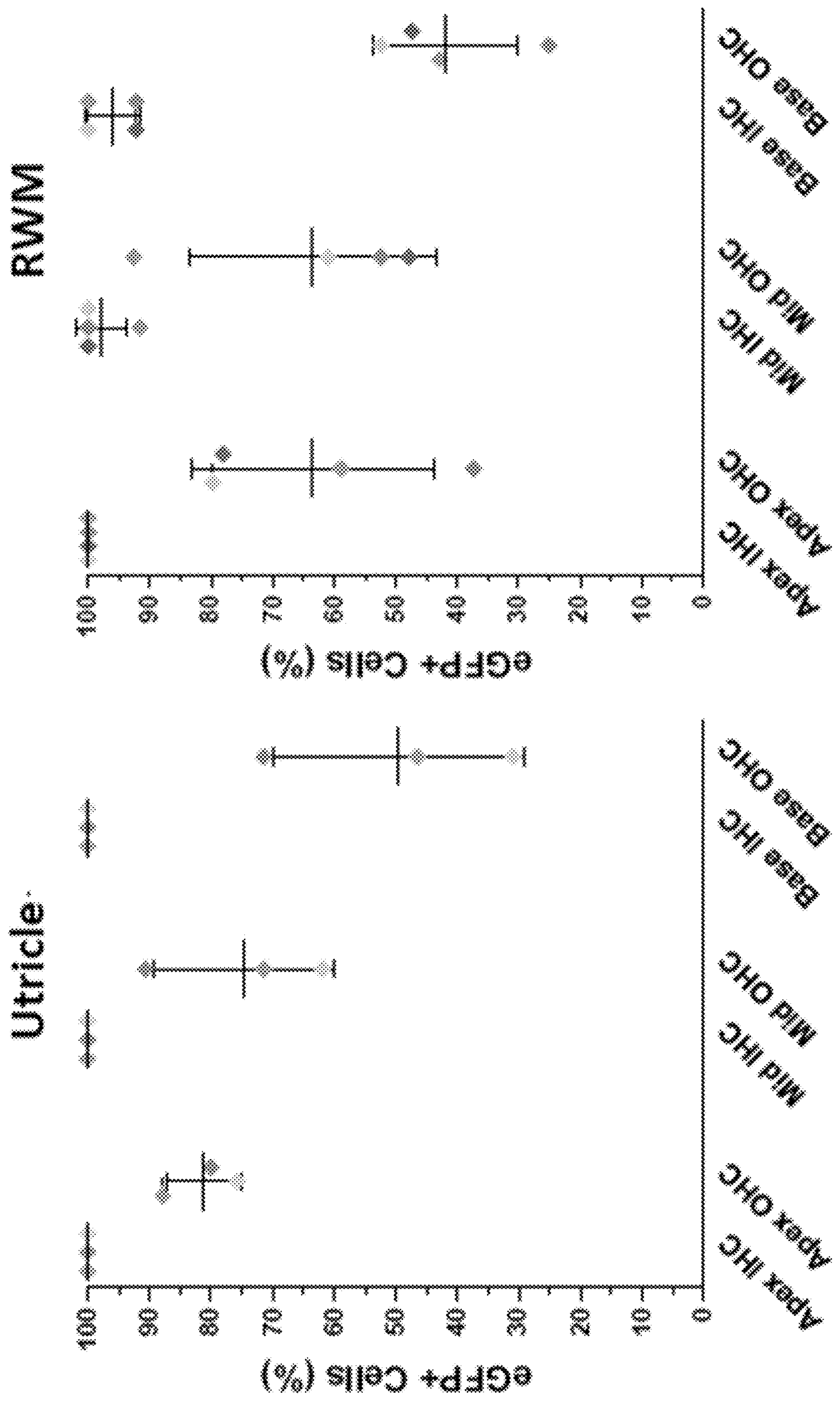

To compare this new method to an existing method of injecting into the round window membrane (RWM), P1 mice were injected in either the utricle or the RWM with AAV2-Anc80L65-GFP. Temporal bones were harvested at 4 weeks of age for imaging. Hair cells were stained with anti-Myosin VIIa antibody. Referring to FIGS. 5A and 5B, expression is detected in the cochlear apex of mice that received utricle and RWM injections, respectively. High resolution images of the apex, mid, and base regions of the cochlea showed enhanced GFP expression in mice that were administered utricle injections compared to those that received RWM injections (FIGS. 5C and 5D).

Figure 6C:
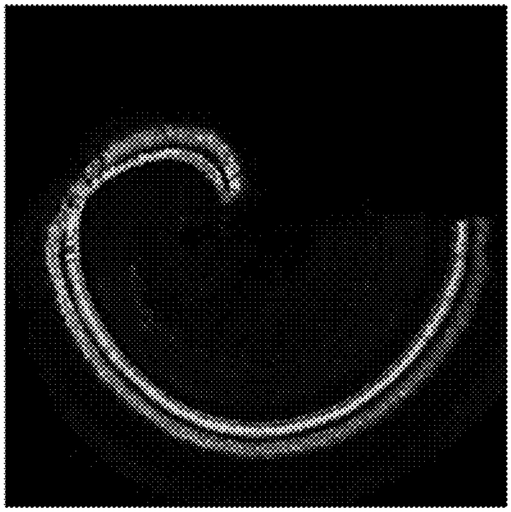
FIGS. 6A to 6D compare utricle and RWM injection of PHP.B-Cmv-eGFP.
Figure 6B:
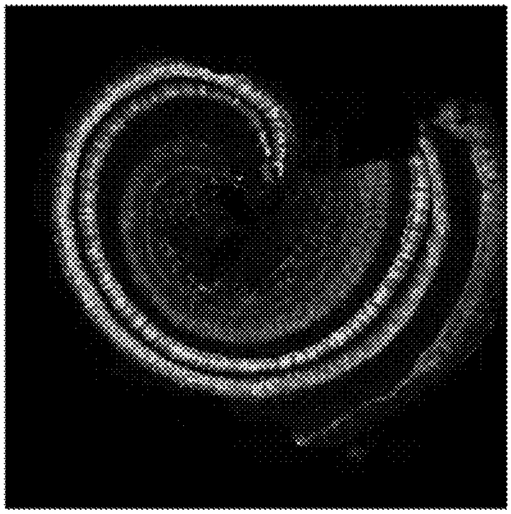
Figure 6A:
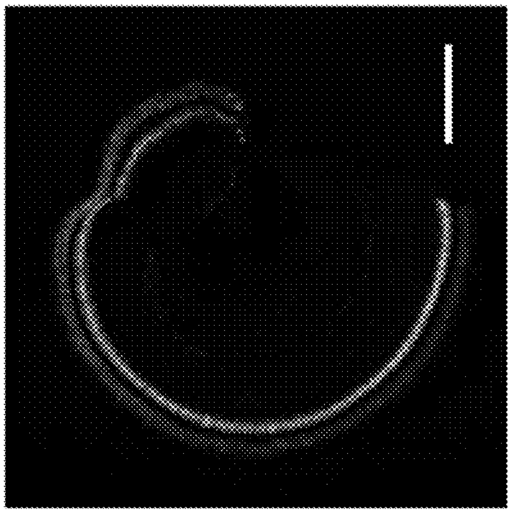
Figure 6D:
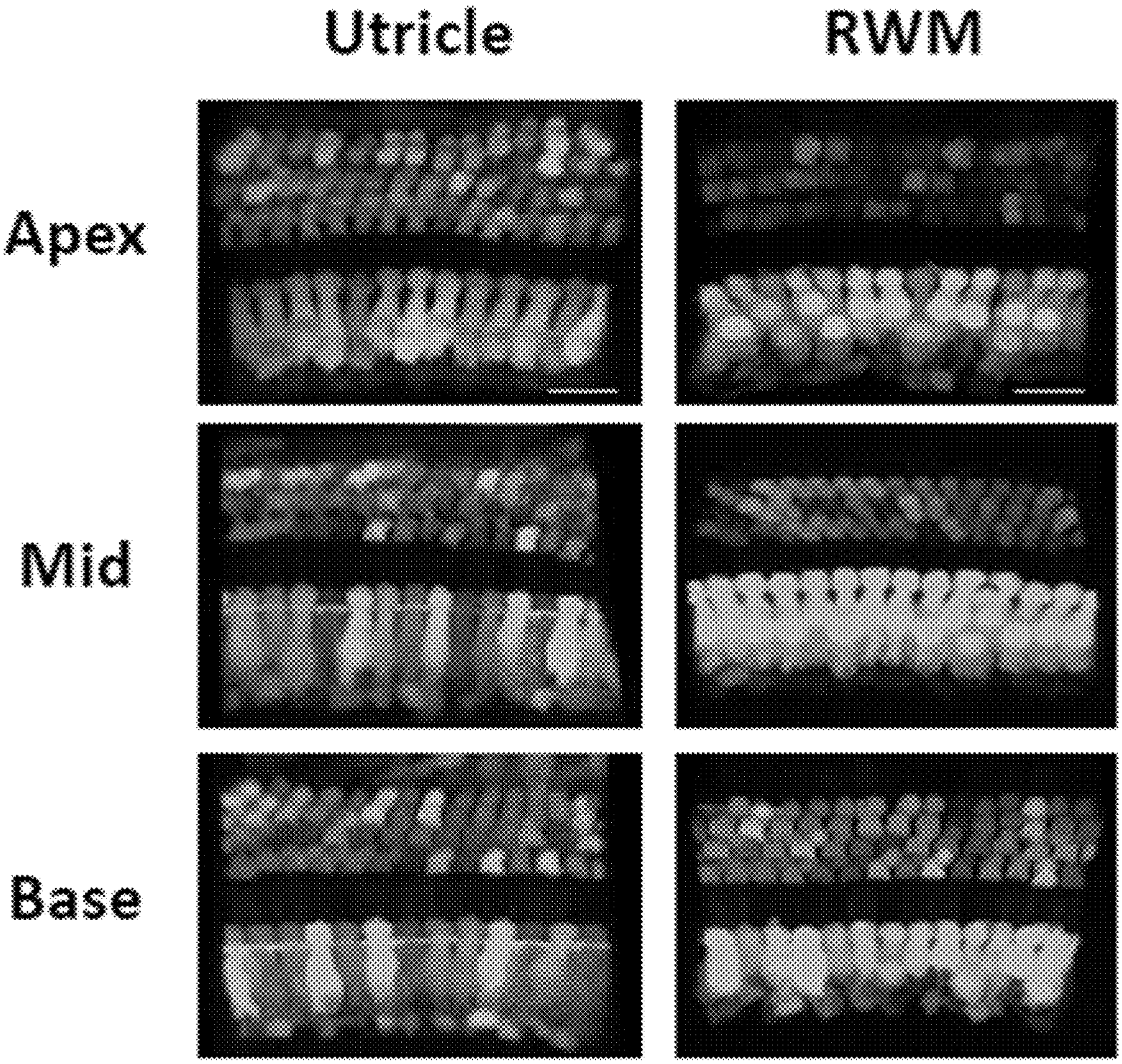
Figure 6E:
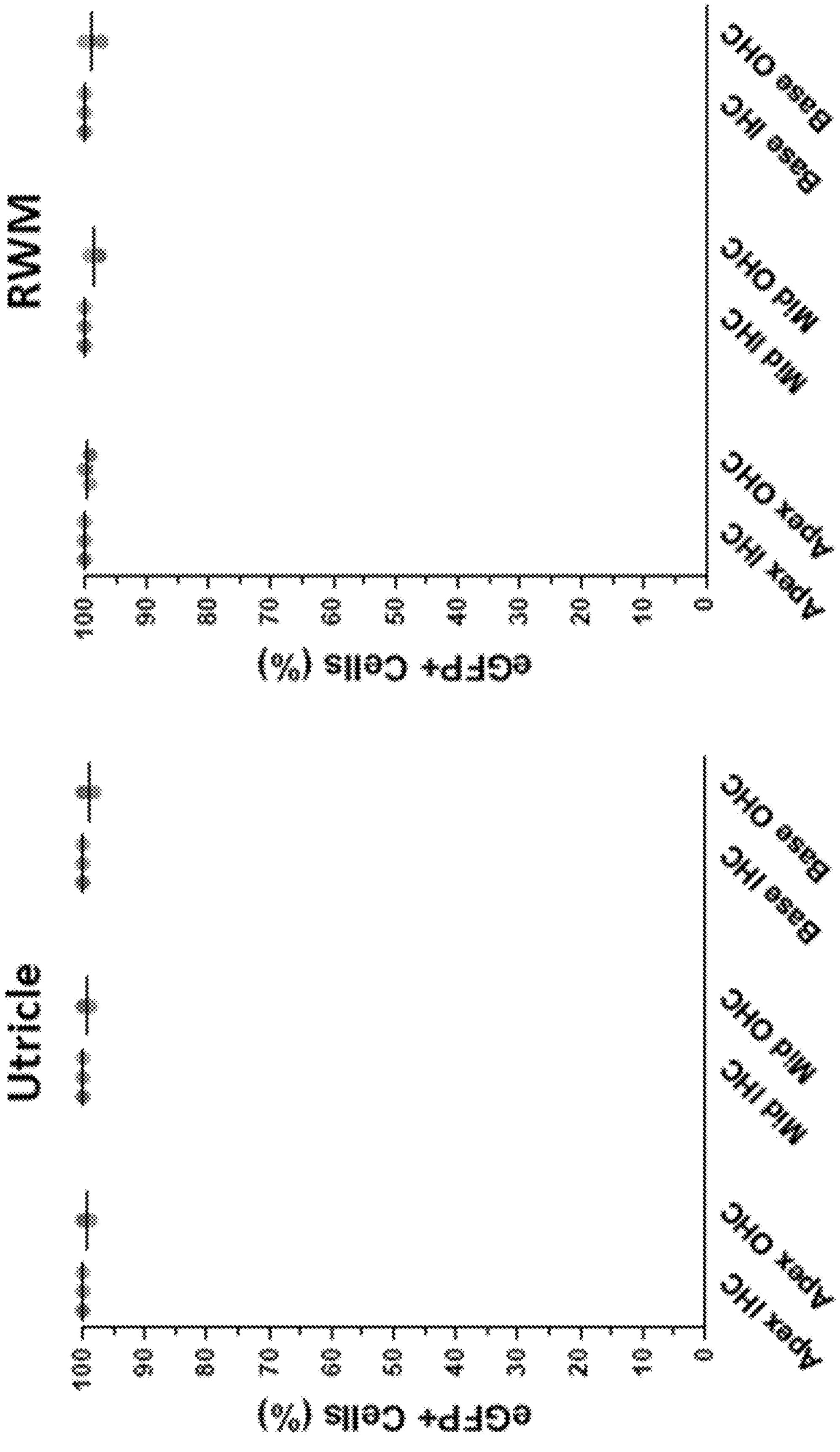
FIG. 6E is a graphical comparison of the percentage of eGFP positive inner hair cells (IHCs) and outer hair cells (OHCs) after utricle and RWM injection of AAV9.PHP.B-CMV-eGFP.

To determine if PHB.B-Cmv-eGFP efficiently and specifically transduced mice via utricle or RWM injection, mice were injected with the AAV9.PHP.B-Cmv-eGFP at P1 in either the utricle or the RWM. Referring to FIGS. 6A and 6B, efficient and specific transduction was observed in temporal bones harvested from P14 mice that received utricle injection at P1 of virus prepared at École Polytechnique Fédérale de Lausanne (EPFL) and virus prepared at Boston Children's Hospital (BCH), respectively. RWM transduction of the EPFL virus was also efficient and specific (FIG. 6C). Similar percentages of transduced cells were observed in the apex, mid, and base regions of the cochlea for both utricle and RWM injection (FIGS. 6D and E).

Figure 7A:
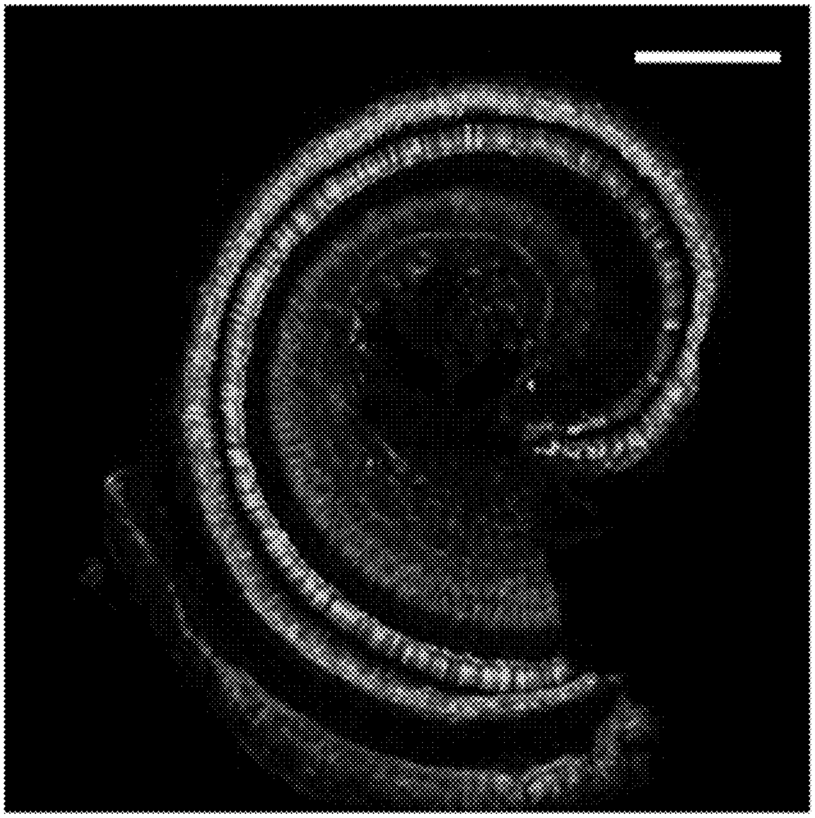
FIGS. 7A to 7C compare hair cell transduction efficiency with PHP.B and Anc80 at the same titer (3.5 E+12 viral genomes/mL).
Figure 7B:
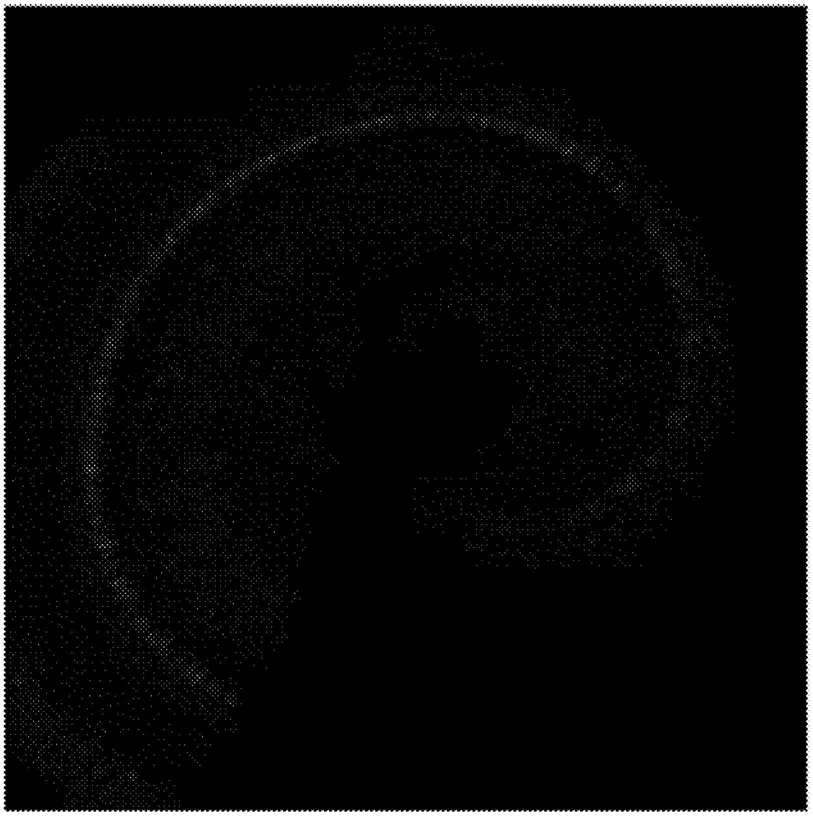
Figure 7C:
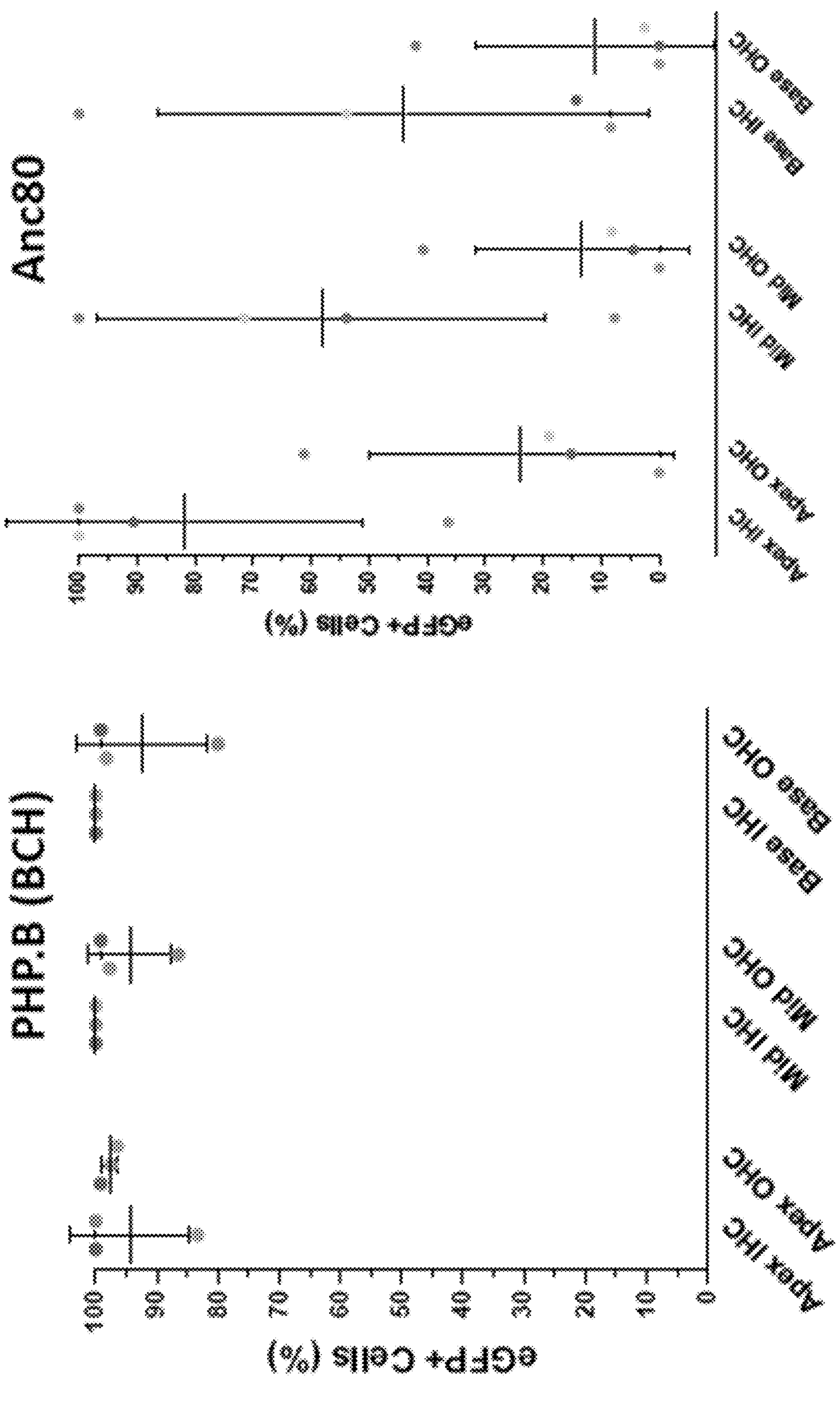

The AAV9-PHP.B vector transduces mice at higher rates than the Anc80 vector. Mice were administered utricle injections of AAV9.PHP.B-Cmv-eGFP or AAV-Anc80-Cmv-eGFP at P1. Temporal bones were harvested at P14, and increased rates of transduction were observed for PHP.B relative to Anc80 as determined by fluorescence detected in the cochlea (FIGS. 7A and 7B) and in the inner and outer hair cells of the apex, mid, and base regions of the cochlea (FIG. 7C).

Figure 8A:
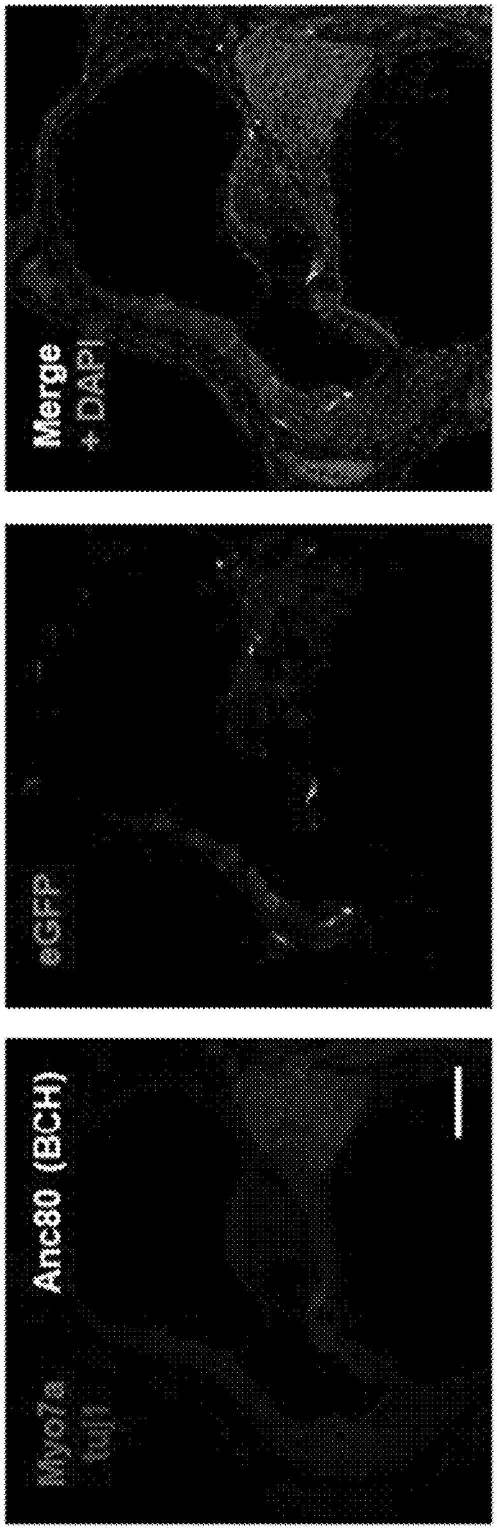
FIGS. 8A and 8B show that AAV9.PHP.B has a higher specificity than Anc80.
Figure 8B:
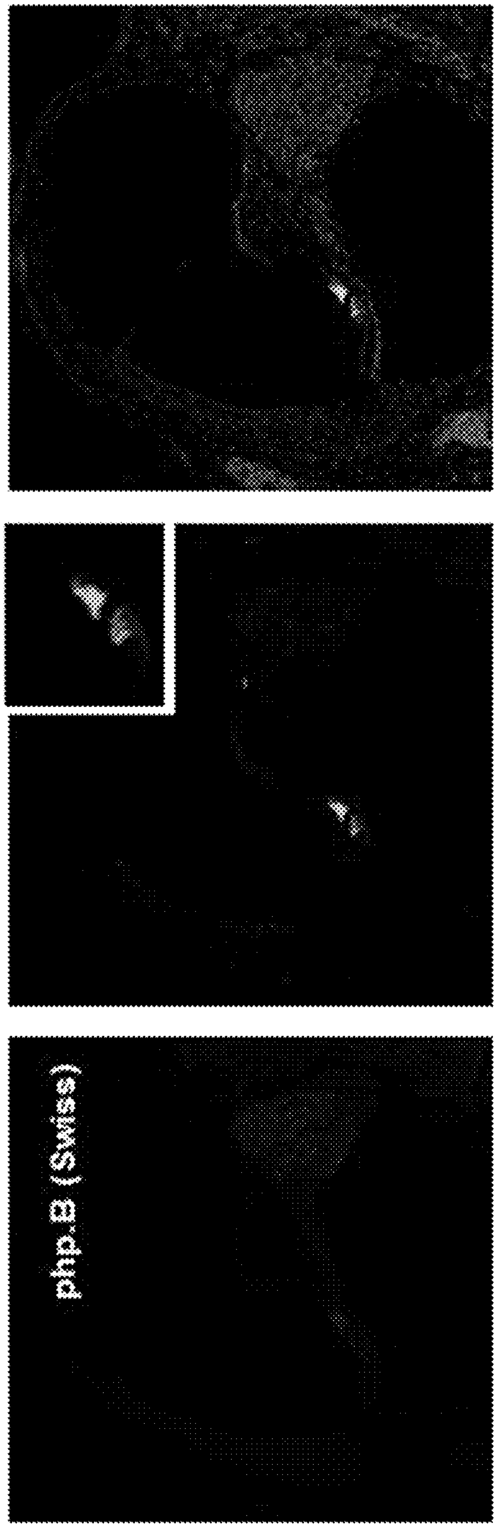

To determine if PHP.B has a higher specificity than Anc80, P1 mice were administered utricle injections of Anc80-Cmv-eGFP-EPRE or PHP.B-Cmv-eGFP. Cochleas were harvested at P15 mice, and cross sections were prepared. Referring to FIGS. 8A and 8B, increased specificity was observed for PHP.B as indicated by the green fluorescence observed in the lower middle panel.

Figure 9A:
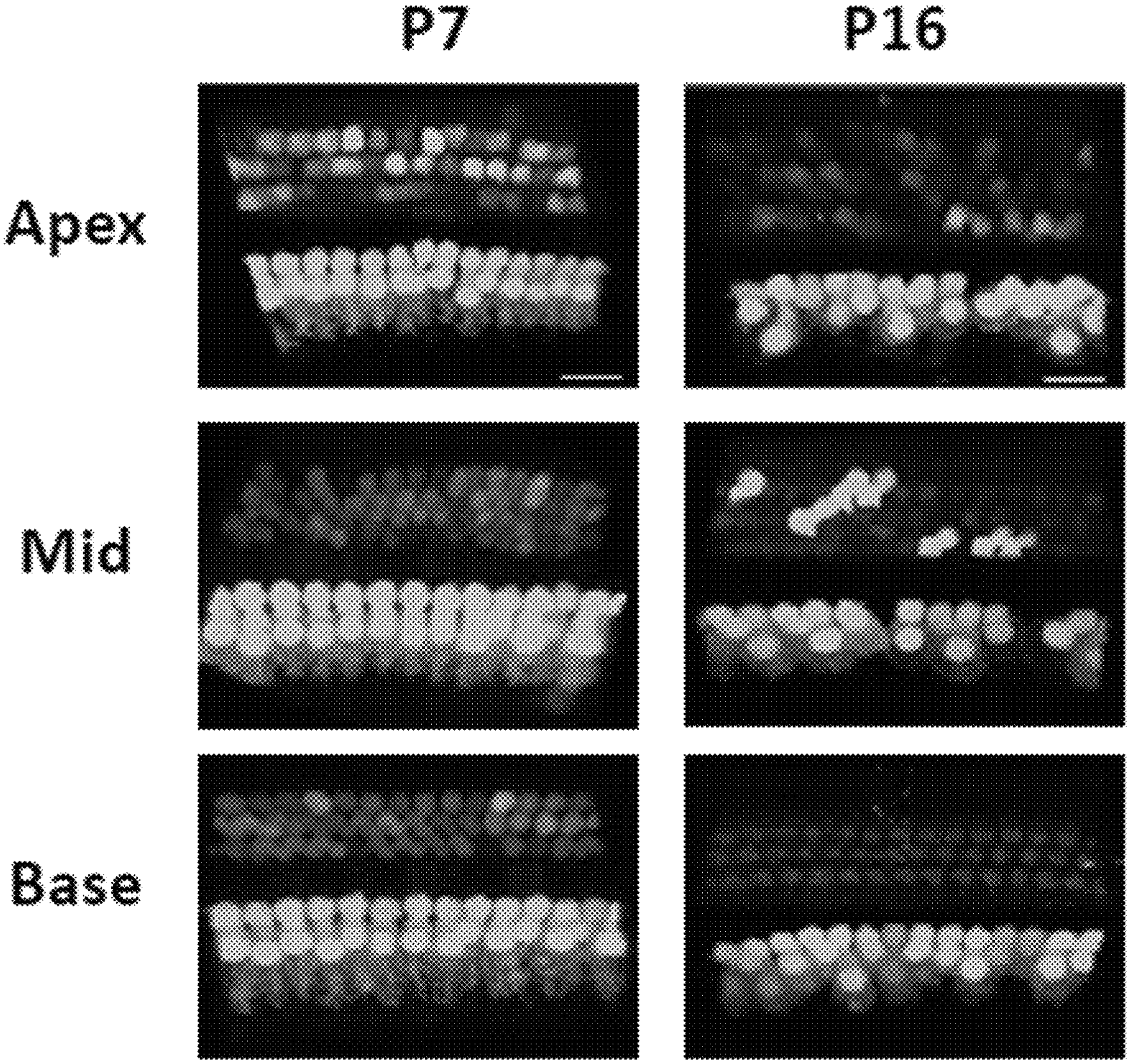
FIGS. 9A and 9B illustrate that PHP.B-Cmv-eGFP targets inner ear hair cells at postnatal and mature stages.
Figure 9B:
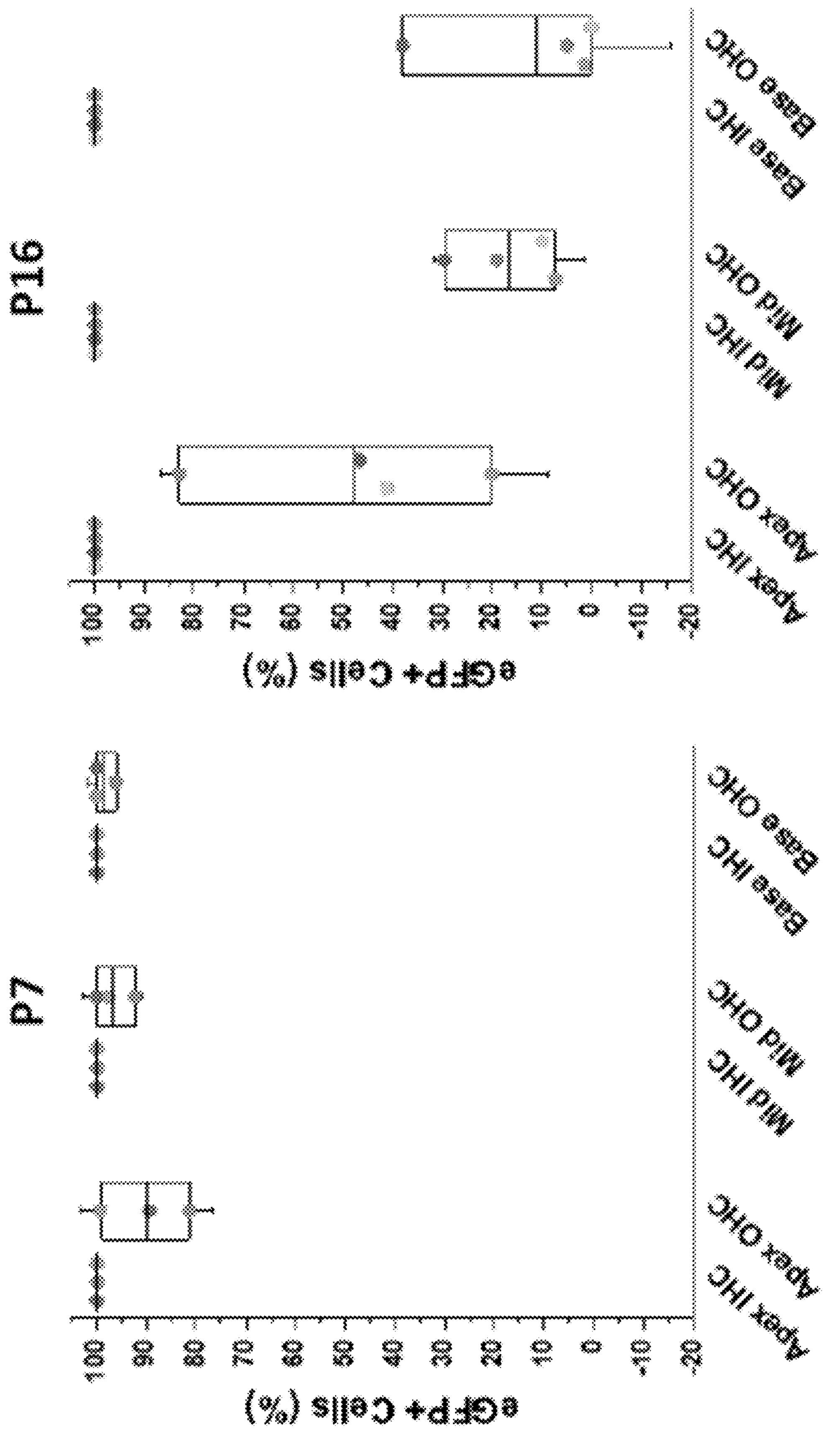

To determine the developmental stages at which PHP.B-Cmv-eGFP targets inner and outer hair cells, mice were administered utricle injections of the PHP.B vector at P7 and P16. Referring to FIG. 9A, increased eGFP positive cells were observed in the mice receiving injections at P7 relative to P16. However, PHP.B-Cmv-eGFP targeted inner ear hair cells at both postnatal and mature stages (FIG. 9B).

Figure 10A:
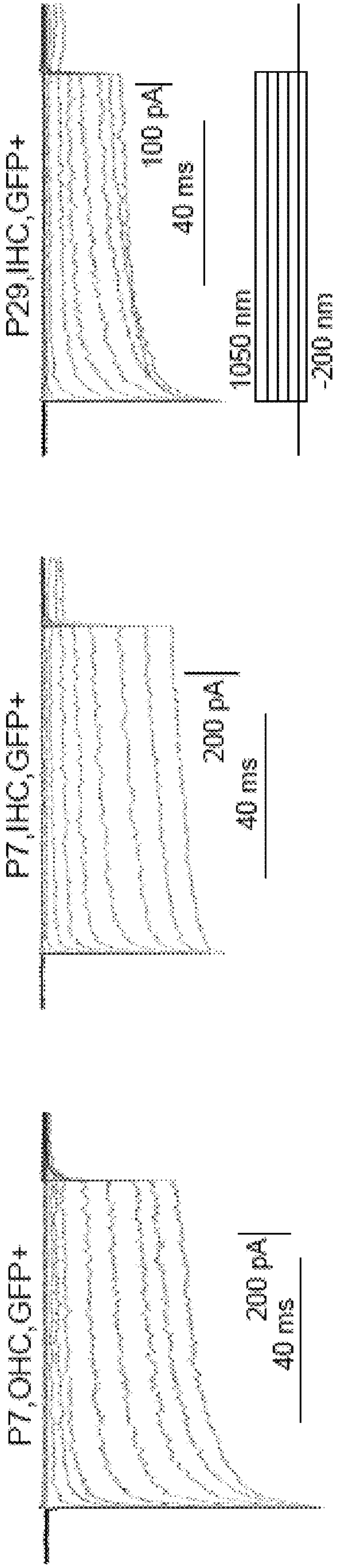
FIGS. 10A to 10C illustrate that hair cell transduction in wildtype mice was unaffected by injection of AAV9-Php.b-CMV-GFP at P1.
Figure 10B:
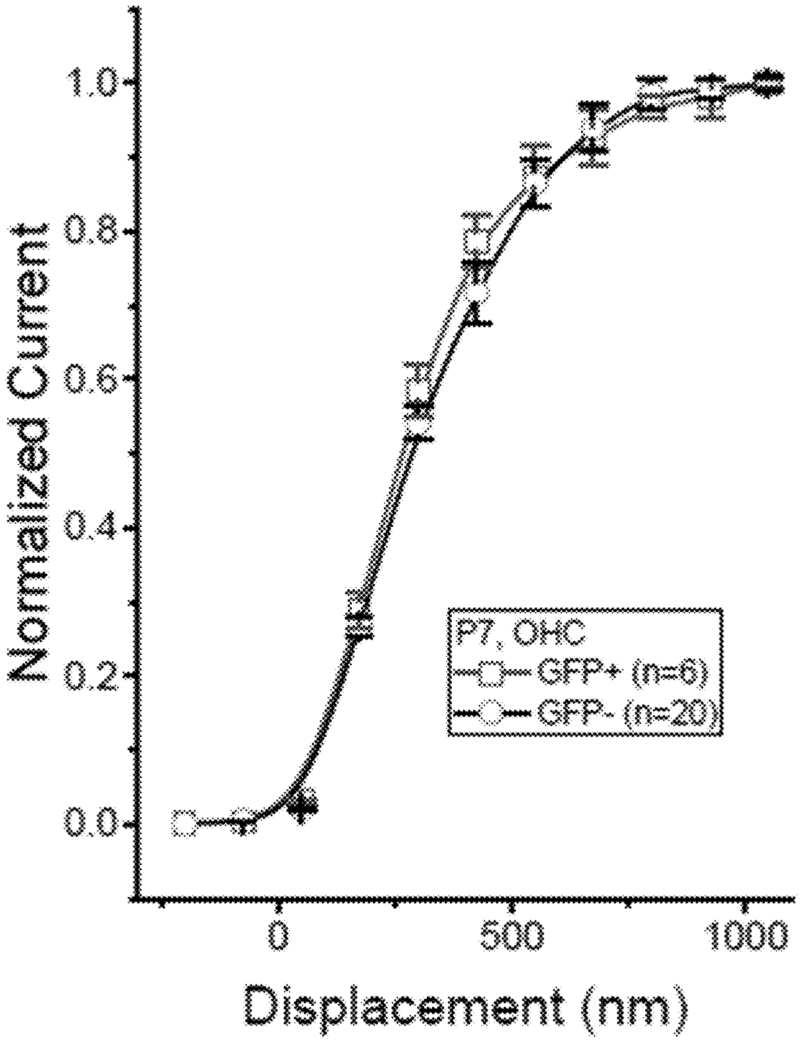
Figure 10C:
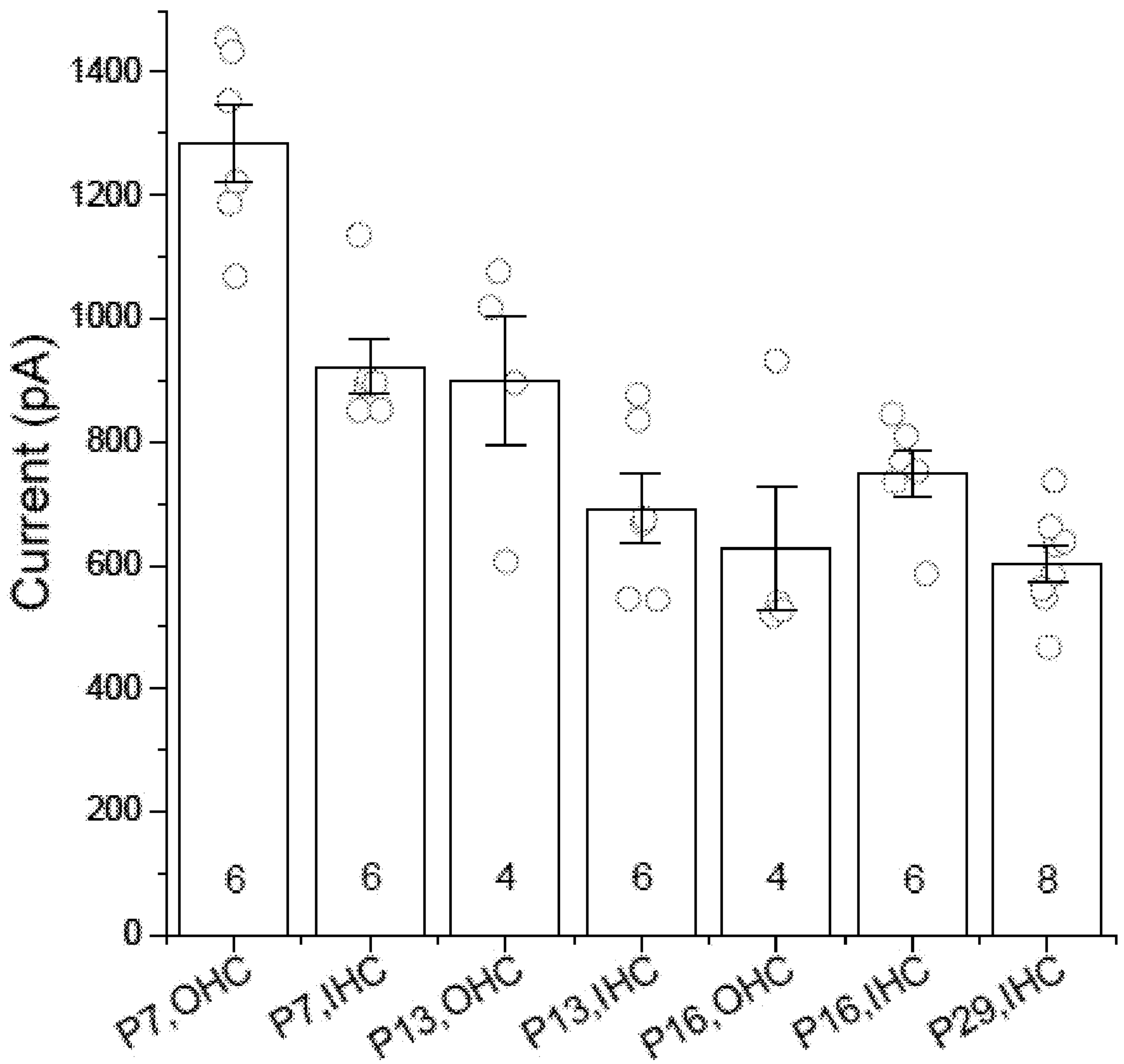

The effect of AAV9-PHP.B-Cmv-GFP injection on hair cell transduction in wildtype mice was assessed. Mice were administered utricle injections at P1 of the vector. FIG. 10A illustrates the representative current families of sensory transduction currents evoked by mechanical displacement of hair bundles from GFP positive cells. FIG. 10B shows that there was no difference in sensitivity between P7 GFP positive and GFP negative outer hair cells. Additionally, no difference was observed in the current amplitude for GFP positive and GFP negative inner and outer hair cells (FIG. 10C).

Figure 11A:
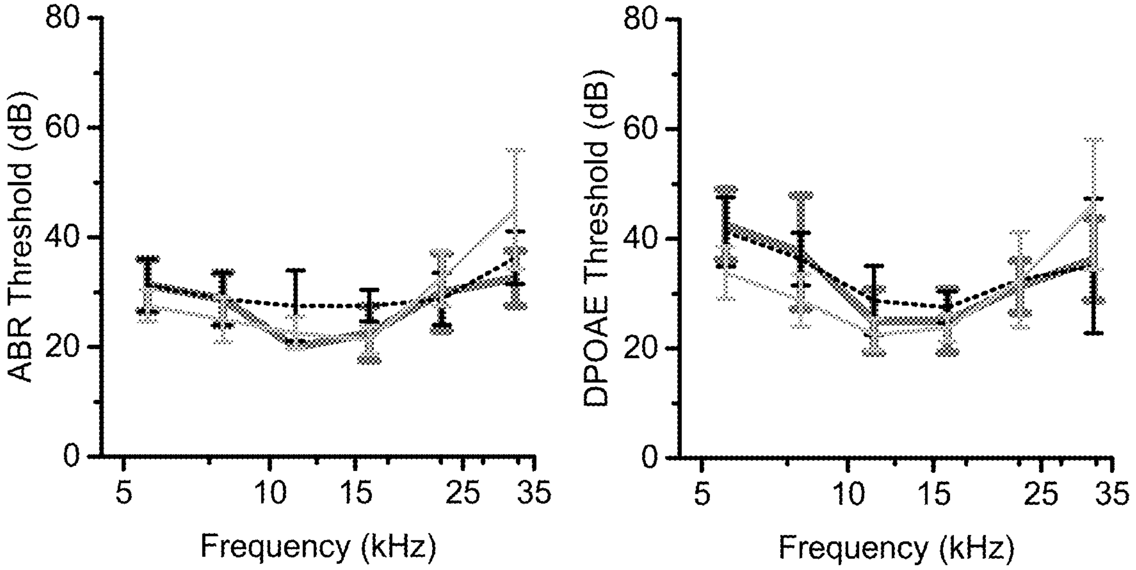
FIGS. 11A to 11C illustrate that auditory brainstem recording (ABR) and distortion product otoacoustic emissions (DPOAE) thresholds were unaffected by injection of PHP.B-Cmv-eGFP at P1, P7 and P16.
Figure 11B:
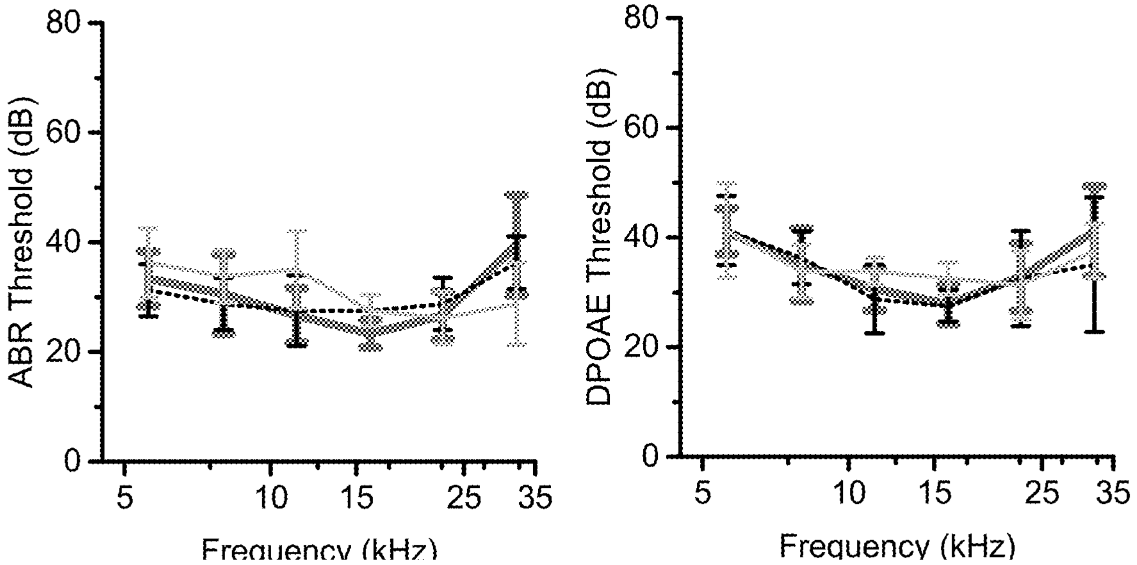
Figure 11C:
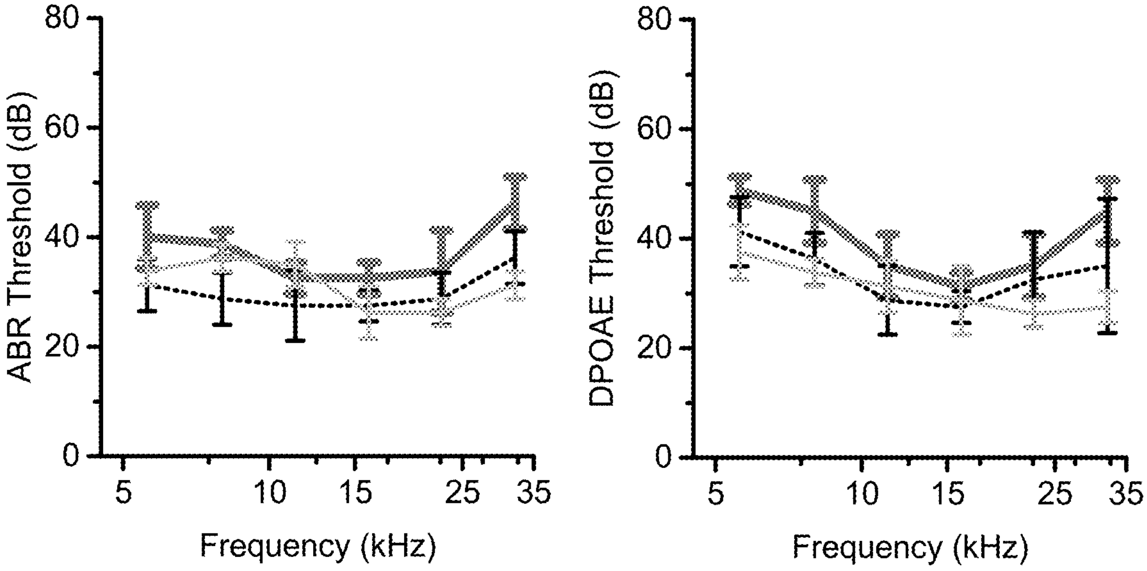

Auditory brainstem recording (ABR) and distortion product otoacoustic emissions (DPOAE) thresholds were assessed. FIG. 11A depicts the observed ABR and DPOAE thresholds for four C57 uninjected mice tested at P28 to P31 (black dotted line), four C57 mice administered utricle injections at P1 of Anc80-eGFP and tested at P30 (light gray), and four C57 mice administered utricle injections at P1 of AAV9.PHP.B-Cmv-eGFP prepared by BCH and tested at P29 (dark gray). Referring to FIG. 11B, thresholds were observed for ABR (left) and DPOAE (right) for four C57 uninjected mice tested at P28-P31 (black dotted line), four C57 mice administered utricle injections at P7 of Anc80-eGFP and tested at P30 (light gray), and nine C57 mice administered utricle injections at P7 of PHP.B-eGFP (EPFL) and tested at P27-P28 (dark gray). Referring to FIG. 11C, thresholds were also observed for ABR (left) and DPOAE (right) for four C57 uninjected mice tested at P28-P31 (black dotted line), four C57 mice administered utricle injections at P16 of Anc80-eGFP and tested at P31 (light gray) and four C57 mice administered utricle injections at P16 of PHP.B-eGFP (EPFL) and tested at P28 (dark gray). Taken together, these data indicate that the ABR and DPOAE thresholds were not affected by injection of AAV9.PHP.B-Cmv-eGFP at P1, P7 or P16.

Figure 12A:
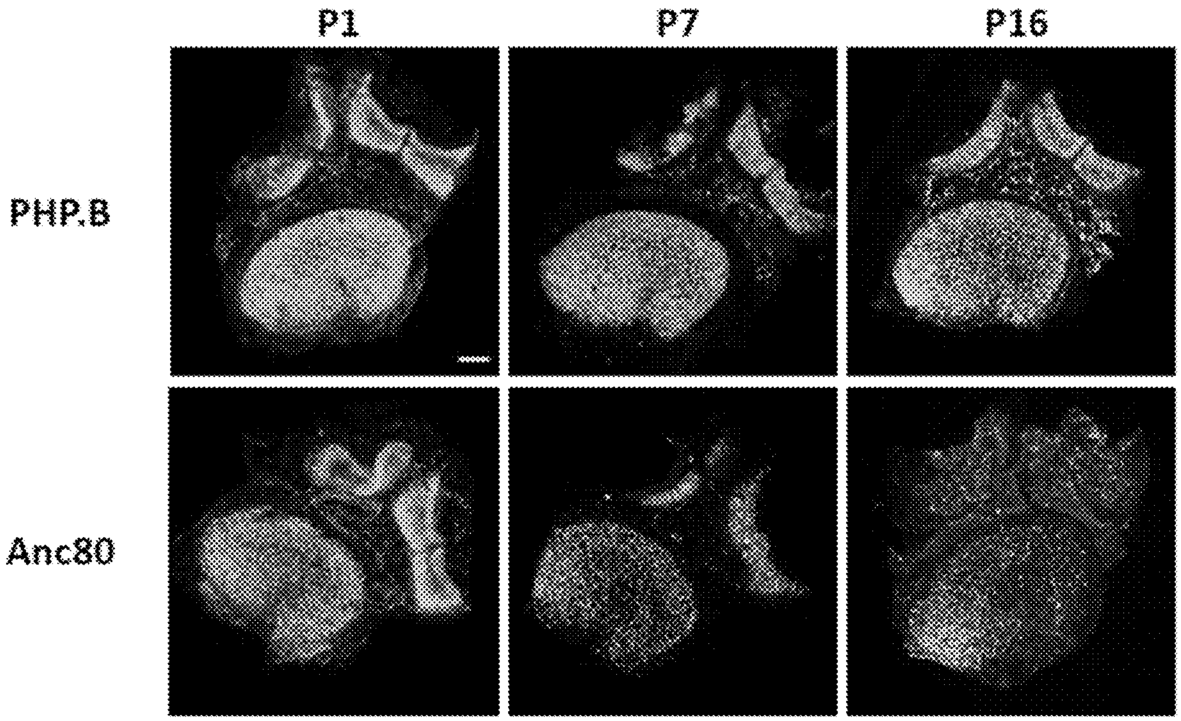
FIGS. 12A and 12B illustrate that PHP.B-Cmv-eGFP injected at P1, P7, and P16 has higher transduction rates in vestibular hair cells than Anc80-Cmv-eGFP.
Figure 12B:
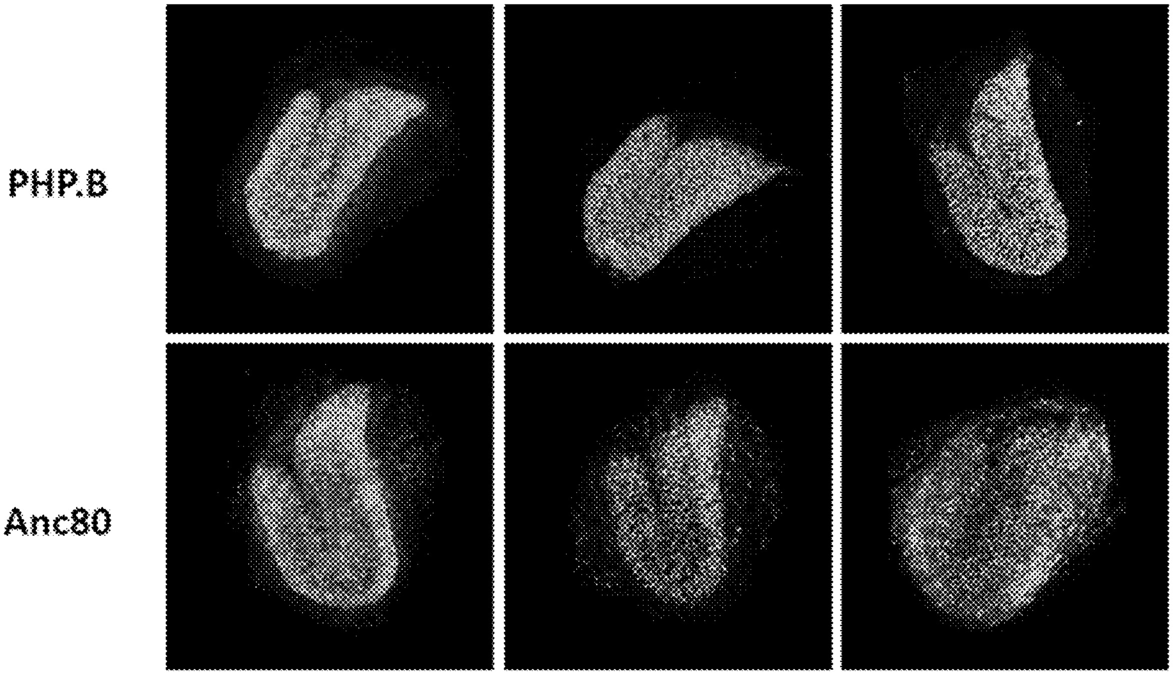
Figure 13:
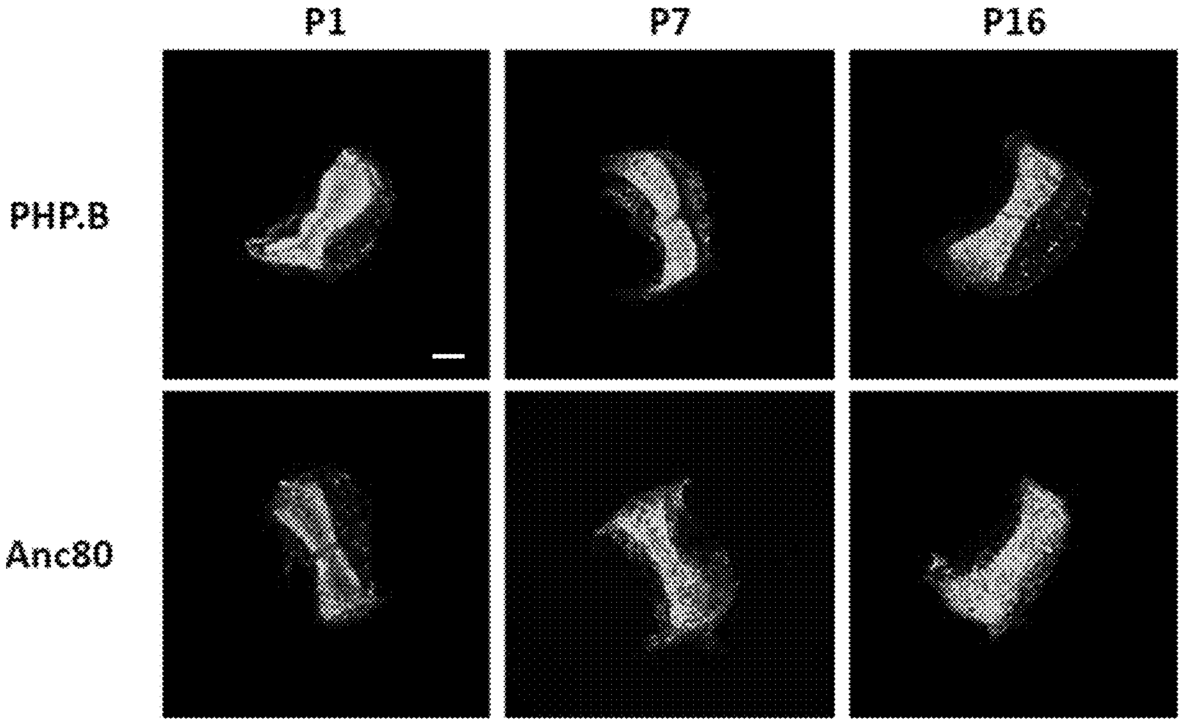
FIG. 13 is a series of images comparing vestibular transduction after P1, P7, and P16 utricle injections of PHP.B-Cmv-eGFP (top row) and Anc80-Cmv-eGFP (bottom row). The scale bar in the first panel applies to all panels and represents 100 μm.

The effects of injection timing on PHP.B and Anc80 transduction were compared. Mice were injected in the utricle at P1, P7, and P16 with either AAV9.PHP.B-Cmv-eGFP or with Anc80-Cmv-eGFP. Referring to FIGS. 12A and 12B, PHP.B-Cmv-eGFP had higher transduction rates in the utricles and saccules, respectively, than did the Anc80 construct. eGFP expression was also qualitatively more robust and specific to hair cells of the posterior semicircular canal in the mice receiving PHP.B-Cmv-eGFP compared to those receiving Anc80-Cmv-eGFP (FIG. 13).

Figure 14:
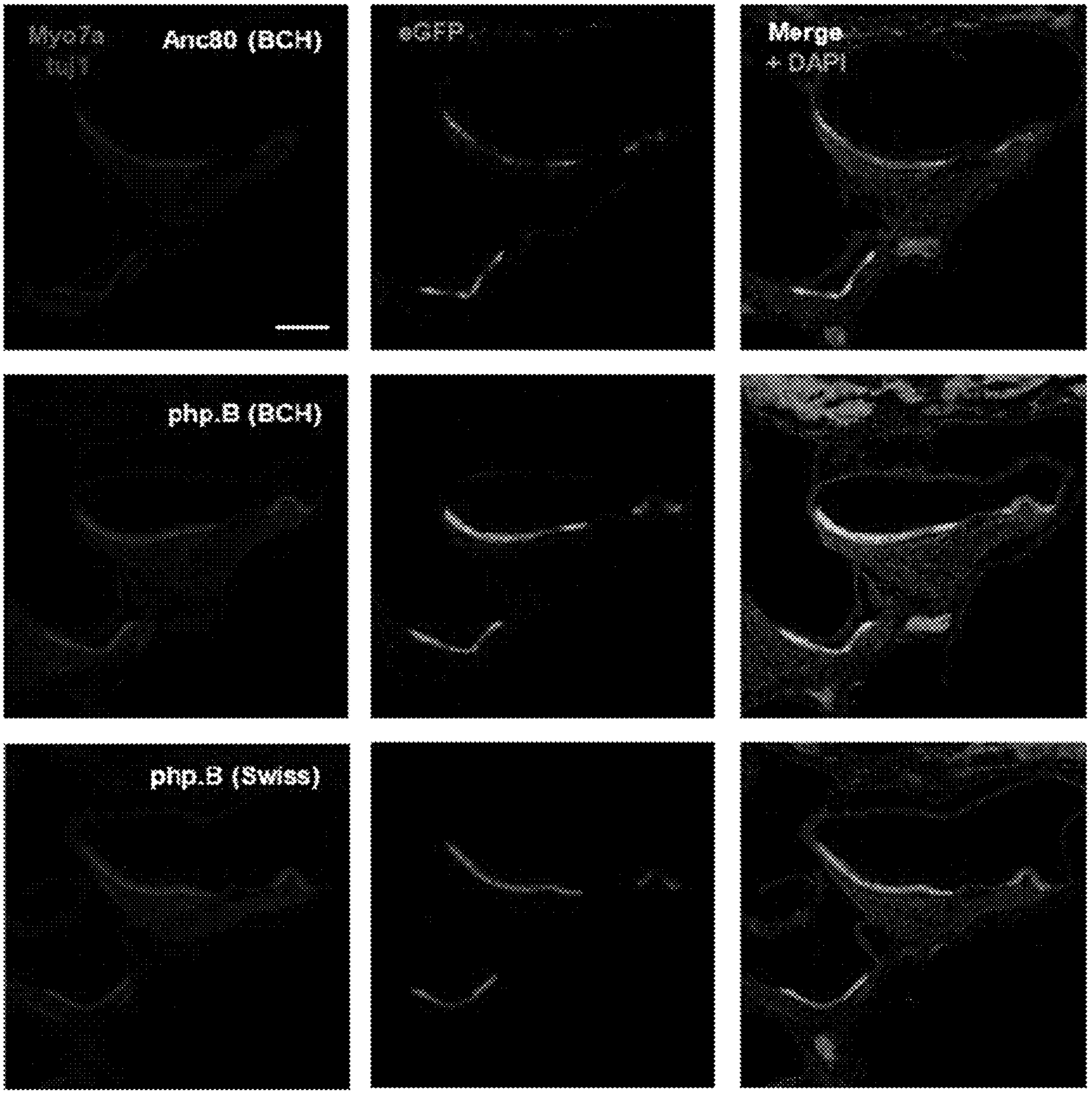
FIG. 14 is a series of confocal images illustrating that vestibular cryosections of mice injected via utricle with vectors driving eGFP expression. The scale bar in the first panel applies to all panels and represents 200 μm.

Viral vectors prepared by different entities were assessed. C57 mice were administered utricle injections at P1 of Anc80-Cmv-eGFP, PHP.B-Cmv-eGFP prepared at BCH, or PHP.B-Cmv-eGFP prepared at EPFL. Tissue was harvested at P15. Referring to FIG. 14, PHP.B-Cmv-eGFP (and especially the vector prepared at BCH) had higher transduction rates in vestibular hair cells than did the Anc80 vector.

Example 9: Neuronal Transduction

Figure 15:
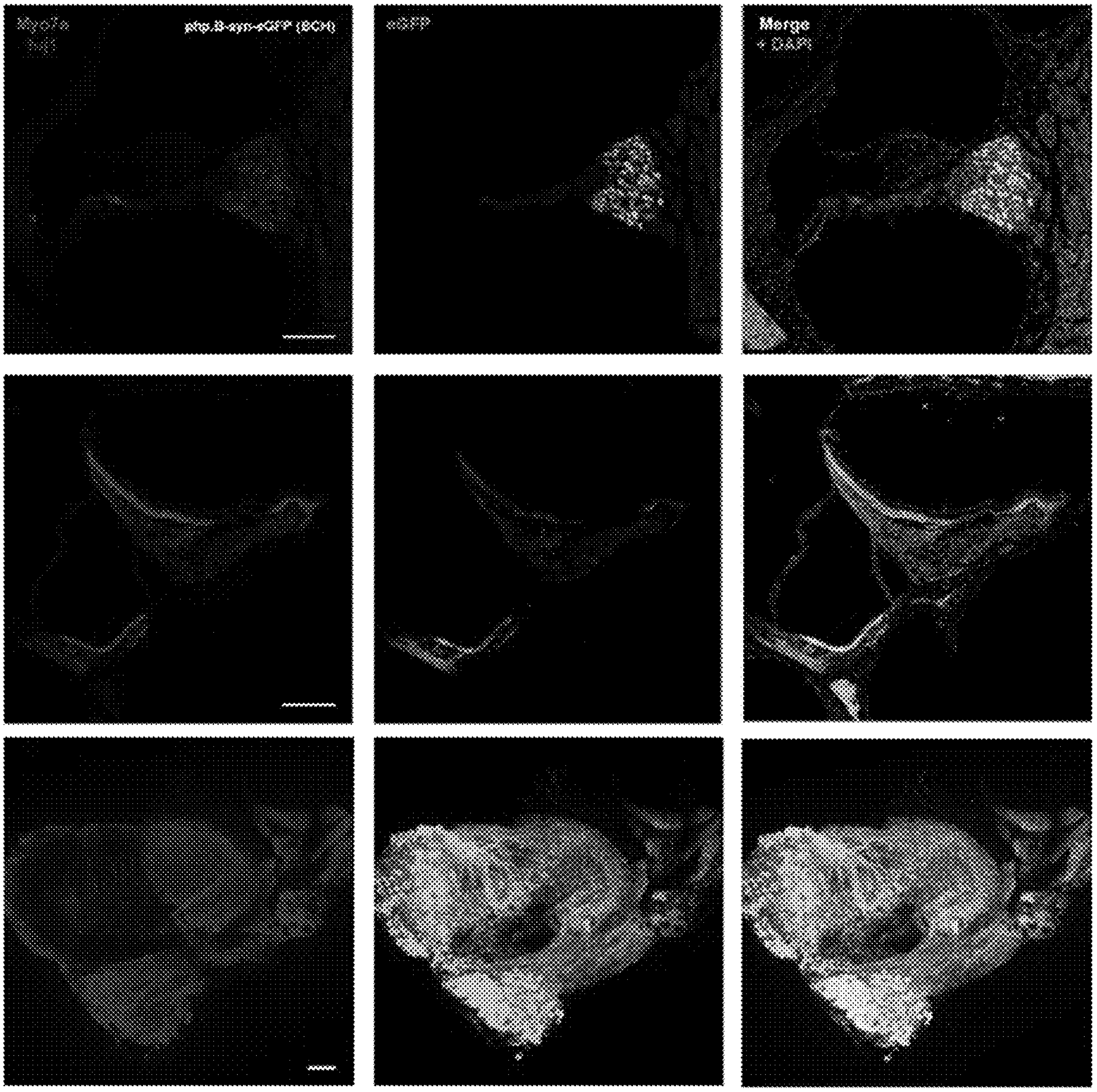
FIG. 15 is a series of confocal images of cochlear cyrosections (top row, scale bar represents 100 μm), vestibular cyrosections (middle row, scale bar represents 200 μm), and whole mount dissections (bottom row, scale bar represents 100 μm) of C57 mice injected at P1 via the utricle with PHP.B-Syn-eGFP.

To determine if cochlear and vestibular neurons could be effectively transduced, the AAV9-PHP.B vector was modified to comprise the synapsin promoter. C57 mice were administered utricle injections of PHP.B-Syn-eGFP at P1. Tissue was harvested at P15 and cross sections and whole mount dissections were prepared. Referring to FIG. 15, the cochlear and vestibular cross sections as well as the whole mount dissections demonstrate that AAV-PHP.B-Syn-eGFP has high specificity and efficiency for transducing spiral ganglion and vestibular neurons.

Example 10: Restoring Auditory Function

Figure 16A:
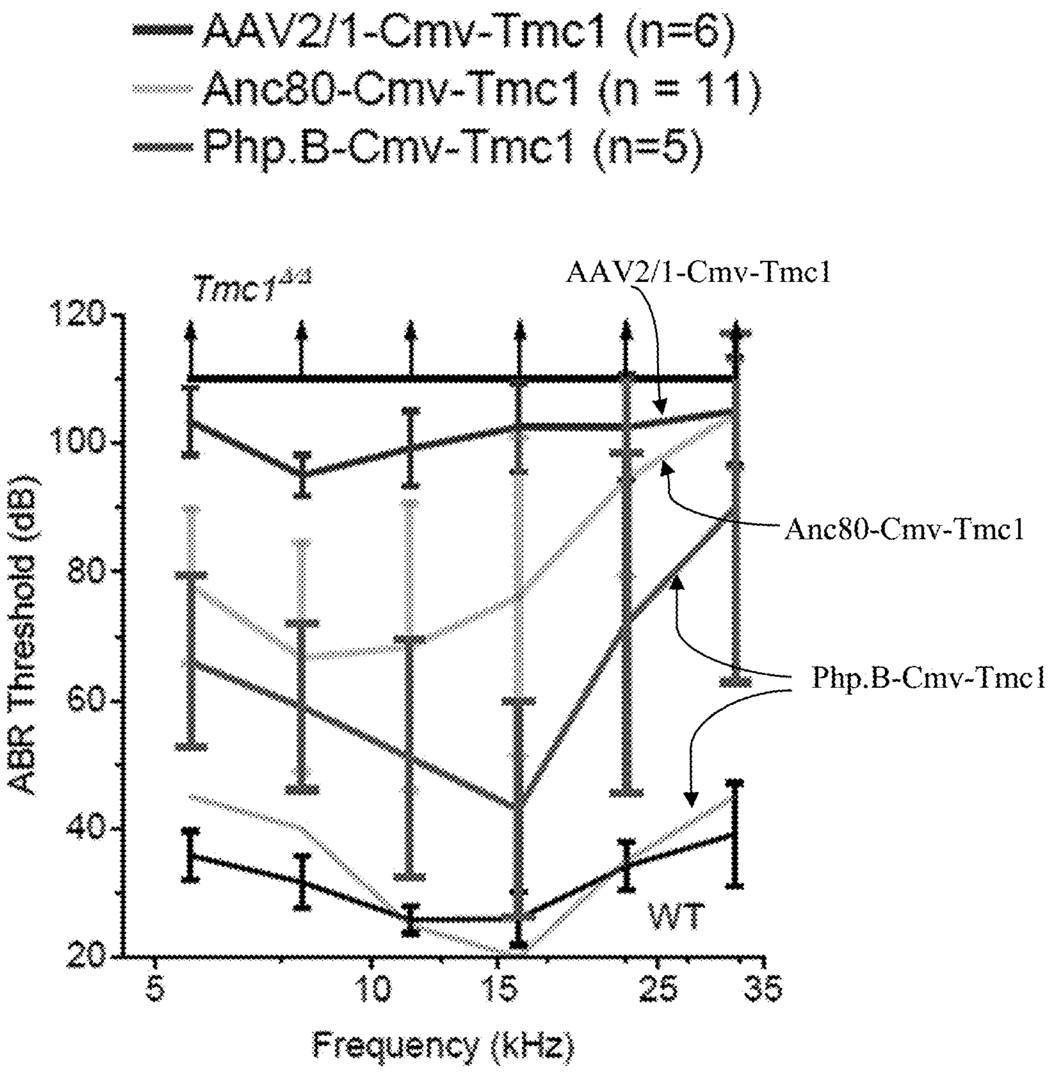
FIGS. 16A and 16B show that AAV9-PHP.B-Cmv-TMC1 restores auditory function in TMC1 mutant mice.
Figure 16B:
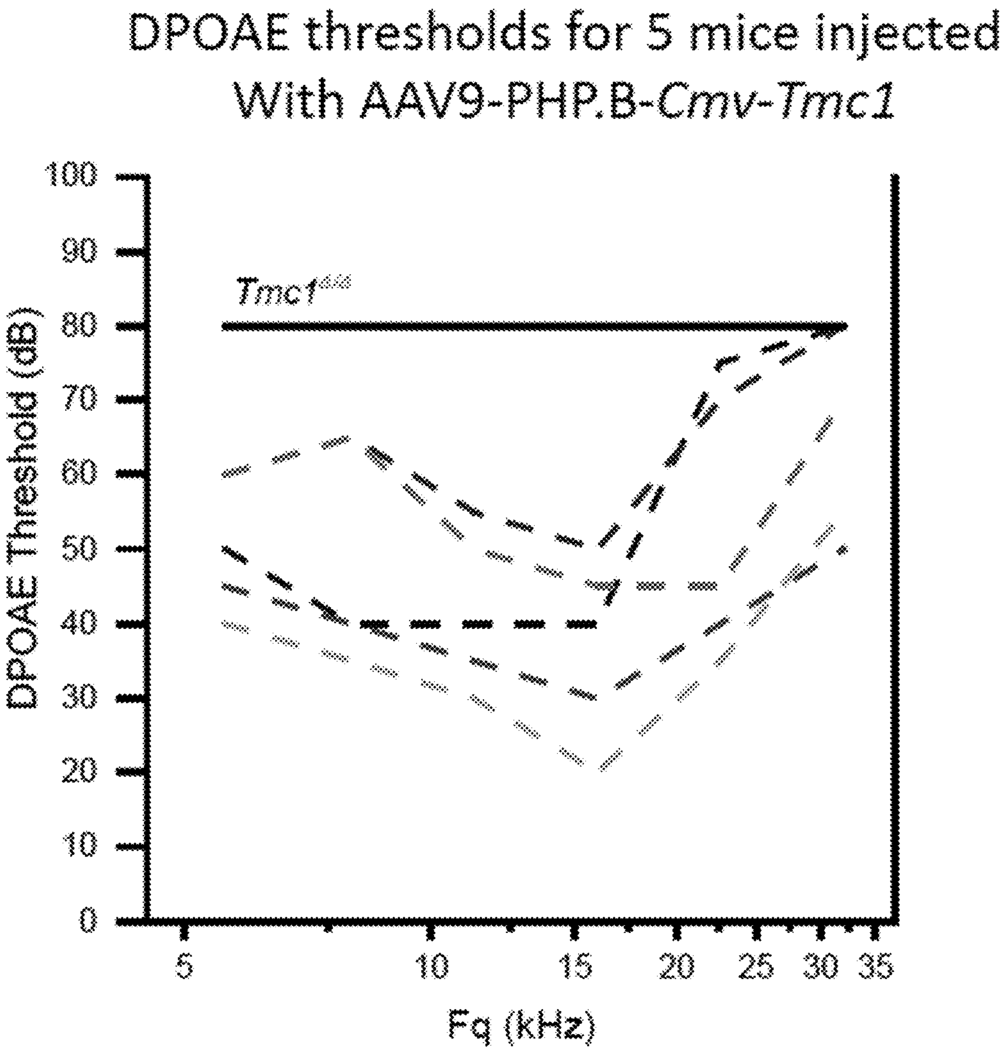

The ability of the PHP.B vector to drive the expression of a therapeutic polypeptide was assessed in homozygous Tmc1 mutant mice. Mice were injected at P1 and auditory function was measured at P30.] As measured by ABR and DPOAE thresholds, the AAV9-PHP.B-Cmv-Tmc1 vector restored auditory function in the mutant mice (FIGS. 16A and 16B). This vector outperformed AAV1-Cmv-Tmc1 and Anc80-Cmv-Tmc1, and one mouse that was administered the AAV9-PHP.B-Cmv-Tmc1 vector performed similarly to wildtype (FIG. 16A).

Example 11: Promoters for Expressing Transgenes in Inner and Outer Hair Cells

Figure 17A:
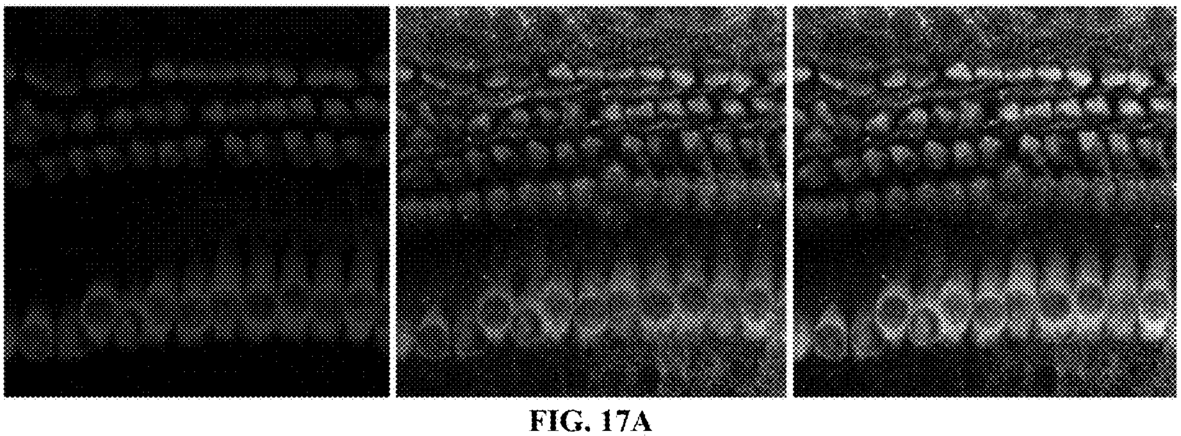
FIGS. 17A to 17D illustrate the ability of different promoters to drive expression of a transgene in the inner ear.
Figure 17B:
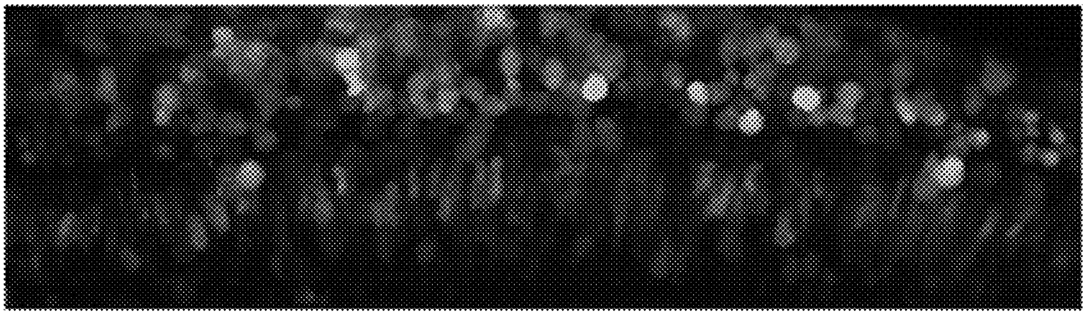
Figure 17C:
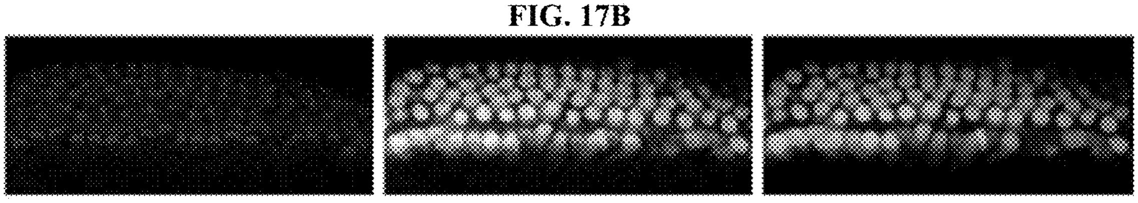
Figure 17D:

Promoters that drive expression in specific cells or tissues are particularly valuable for targeted delivery of therapeutic transgenes and minimizing off-target expression. The abilities of several promoters that drive expression specifically in vestibular cells was investigated. Referring to FIGS. 17A to 17C, the Pcdh15, Myosin 6, and Myosin 7a promoters drive expression in the inner and outer hair cells. The KCNQ4 promoter specifically drives expression in the outer hair cells (FIG. 17D).

OTHER EMBODIMENTS

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. An AAV vector, wherein the vector comprises:

a polynucleotide encoding:

a capsid comprising amino acid sequence: TLAVPFK (SEQ ID NO: 27); and a polypeptide selected from the group consisting of TMC1, TMC2, MYO7A, USH1C, CDH23, PCDH15, SANS, CIB2, USH2A, VLGR1, WHRN, CLRN1, PDZD7, KCNQ4, TMPRSS3, STRC, EYA4, harmonin-a, b, and c, OTOF, GPR98, MYO6, MYO15A, LOXHD1, POU3F4, EYA1, WFS1, ACTG1, TMIE, PJVK, SYNE4, and FAM65B; and a promoter that directs expression of the polynucleotide encoding the polypeptide.

2. The vector of claim 1, wherein the AAV vector is AAV9-php.b vector.

3. A cell comprising the AAV9-php.b vector of claim 2.

4. The cell of claim 3, wherein the cell is an outer or inner hair cell, vestibular hair cell, a spiral ganglion, or a vestibular ganglion.

5. The vector of claim 1, wherein the promoter is selected from the group consisting of an Espin promoter, a PCDH15 promoter, a PTPRQ promoter, a Myo6 promoter, a KCNQ4 promoter, a Myo7a promoter, a synapsin promoter, a GFAP promoter, a CMV promoter, a CAG promoter, a CBH promoter, a CBA promoter, a U6 promoter, and a TMHS (LHFPL5) promoter.

6. A method, comprising: administering the AAV vector of claim 1 to an inner ear of a subject having a recessive mutation in a gene selected from the group consisting of: TMC1, TMC2, MYO7A, USH1C, CDH23, PCDH15, SANS, CIB2, USH2A, VLGR1, WHRN, CLRN1, PDZD7, KCNQ4, TMPRSS3, STRC, EYA4, harmonin-a, harmonin-b, harmonin-c, OTOF, GPR98, MYO6, MYO15A, LOXHD1, POU3F4, EYA1, WFS1, ACTG1, TMIE, PJVK, SYNE4, and FAM65B, thereby forming an AAV vector-encoded transgene, wherein the AAV vector-encoded transgene is a wild-type form of the mutated gene in the subject, thereby expressing the polypeptide in the inner ear.

7. The method of claim 6, wherein the inner ear disorder is Usher Syndrome.

8. The method of claim 6, wherein administering transduces at least 70% of inner hair cells and outer hair cells of the inner ear.

9. The method of claim 6, wherein the cell is a cell of the inner ear.

10. The method of claim 6, wherein the administering improves or maintains auditory and/or vestibular function in the subject.

11. The method of claim 10, wherein increase in auditory function is associated with preservation of hair bundle morphology and/or restoration of mechanotransduction.

12. The method of claim 6, wherein the recessive mutation is associated with partial hearing loss, complete deafness, or partial or complete vestibular dysfunction.

13. A method of transducing an outer hair cell, an inner hair cell, a vestibular hair cell, a spiral ganglion, or a vestibular ganglion in a subject having a defective gene, the method comprising:

injecting the AAV vector of claim 1 into an inner ear of the subject, thereby forming an AAV vector-encoded transgene, wherein the AAV vector-encoded transgene is a wild-type form of the defective gene of the subject, thereby expressing the polypeptide in the outer hair cell, the inner hair cell, the vestibular hair cell, the spiral ganglion, or the vestibular ganglion, wherein the defective gene comprises a recessive mutation.

* * * * *

SEQUENCE LISTING

```
<160> NUMBER OF SEQ ID NOS: 27

<210> SEQ ID NO 1
<211> LENGTH: 8543
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

ccaatgatac gcgtcggtgc gggcctcttc gctattacgc cagctggcga aagggggatg      60

tgctgcaagg cgattaagtt gggtaacgcc agggttttcc cagtcacgac gttgtaaaac     120

gacggccagt gagcgcgcgt aatacgactc actatagggc gaattgggta catcgacggt     180

atcgggggag ctcgcagggt ctccattttg aagcgggagg tttgaacgcg cagccgccat     240

gccggggttt tacgagattg tgattaaggt ccccagcgac cttgacgagc atctgcccgg     300

catttctgac agctttgtga actgggtggc cgagaaggaa tgggagttgc cgccagattc     360

tgacatggat ctgaatctga ttgagcaggc acccctgacc gtggccgaga agctgcagcg     420

cgactttctg acggaatggc gccgtgtgag taaggccccg gaggctcttt tctttgtgca     480

atttgagaag ggagagagct acttccacat gcacgtgctc gtggaaacca ccggggtgaa     540

atccatggtt ttgggacgtt tcctgagtca gattcgcgaa aaactgattc agagaattta     600
```

-continued

```
ccgcgggatc gagccgactt tgccaaactg gttcgcggtc acaaagacca gaaatggcgc    660
cggaggcggg aacaaggtgg tggatgagtg ctacatcccc aattacttgc tccccaaaac    720
ccagcctgag ctccagtggg cgtggactaa tatggaacag tatttaagcg cctgtttgaa    780
tctcacggag cgtaaacggt tggtggcgca gcatctgacg cacgtgtcgc agacgcagga    840
gcagaacaaa gagaatcaga atcccaattc tgatgcgccg gtgatcagat caaaaacttc    900
agccaggtac atggagctgg tcgggtggct cgtggacaag gggattacct cggagaagca    960
gtggatccag gaggaccagg cctcatacat ctccttcaat gcggcctcca actcgcggtc   1020
ccaaatcaag gctgccttgg acaatgcggg aaagattatg agcctgacta aaaccgcccc   1080
cgactacctg gtgggccagc agcccgtgga ggacatttcc agcaatcgga tttataaaat   1140
tttggaacta aacgggtacg atccccaata tgcggcttcc gtctttctgg gatgggccac   1200
gaaaaagttc ggcaagagga acaccatctg gctgtttggg cctgcaacta ccgggaagac   1260
caacatcgcg gaggccatag cccacactgt gcccttctac gggtgcgtaa actggaccaa   1320
tgagaacttt cccttcaacg actgtgtgga caagatggtg atctggtggg aggaggggaa   1380
gatgaccgcc aaggtcgtgg agtcggccaa agccattctc ggaggaagca aggtgcgcgt   1440
ggaccagaaa tgcaagtcct cggcccagat agacccgact cccgtgatcg tcacctccaa   1500
caccaatatg tgcgccgtga ttgacgggaa ctcaacgacc ttcgaacacc agcagccgtt   1560
gcaagaccgg atgttcaaat ttgaactcac ccgccgtctg gatcatgact ttgggaaggt   1620
caccaagcag gaagtcaaag actttttccg gtgggcaaag gatcacgtgg ttgaggtgga   1680
gcatgaattc tacgtcaaaa agggtggagc caagaaaaga cccgcccccca gtgacgcaga   1740
tataagtgag cccaaacggg tgcgcgagtc agttgcgcag ccatcgacgt cagacgcgga   1800
agcttcgatc aactacgcgg acaggtacca aaacaaatgt tctcgtcacg tgggcatgaa   1860
tctgatgctg tttccctgca gacaatgcga gagactgaat cagaattcaa atatctgctt   1920
cactcacggt gtcaaagact gtttagagtg ctttcccgtg tcagaatctc aacccgtttc   1980
tgtcgtcaaa aaggcgtatc agaaactgtg ctacattcat cacatcatgg gaaaggtgcc   2040
agacgcttgc actgcttgcg acctggtcaa tgtggacttg gatgactgtg tttctgaaca   2100
ataaatgact taaaccaggt atgagtcggc tggataaatc taaagtcata aacggcgctc   2160
tggaattact caatgaagtc ggtatcgaag gcctgacgac aaggaaactc gctcaaaagc   2220
tgggagttga gcagcctacc ctgtactggc acgtgaagaa caagcgggcc ctgctcgatg   2280
ccctggccat cgagatgctg gacaggcatc atacccactt ctgcccccctg gaaggcgagt   2340
catggcaaga ctttctgcgg aacaacgcca agtcattccg ctgtgctctc ctctcacatc   2400
gcgacggggc taaagtgcat ctcggcaccc gcccaacaga gaaacagtac gaaaccctgg   2460
aaaatcagct cgcgttcctg tgtcagcaag gcttctccct ggagaacgca ctgtacgctc   2520
tgtccgccgt gggccacttt acactgggct gcgtattgga ggaacaggag catcaagtag   2580
caaaagagga aagagagaca cctaccaccg attctatgcc cccacttctg agacaagcaa   2640
ttgagctgtt cgaccggcag ggagccgaac ctgccttcct tttcggcctg gaactaatca   2700
tatgtggcct ggagaaacag ctaaagtgcg aaagcggcgg gccggccgac gcccttgacg   2760
attttgactt agacatgctc ccagccgatg cccttgacga ctttgacctt gatatgctgc   2820
ctgctgacgc tcttgacgat tttgaccttg acatgctccc cgggtaaatg catgaattcg   2880
atctagaggg ccctattcta tagtgtcacc taaatgctag agctcgctga tcagcctcga   2940
ctgtgccttc tagttgccag ccatctgttg tttgcccctc ccccgtgcct tccttgaccc   3000
```

-continued

```
tggaaggtgc cactcccact gtcctttcct aataaaatga ggaaattgca tcgcattgtc   3060
tgagtaggtg tcattctatt ctggggggtg gggtggggca ggacagcaag ggggaggatt   3120
gggaagacaa tagcaggcat gctggggatg cggtgggctc tatggcttct gaggcggaaa   3180
gaaccagctg gggctcgaat caagctatca agtgccacct gacgtctccc tatcagtgat   3240
agagaagtcg acacgtctcg agctccctat cagtgataga gaaggtacgt ctagaacgtc   3300
tccctatcag tgatagagaa gtcgacacgt ctcgagctcc ctatcagtga tagagaaggt   3360
acgtctagaa cgtctcccta tcagtgatag agaagtcgac acgtctcgag ctccctatca   3420
gtgatagaga aggtacgtct agaacgtctc cctatcagtg atagagaagt cgacacgtct   3480
cgagctccct atcagtgata gagaaggtac cccctatata agcagagaga tctgttcaaa   3540
tttgaactga ctaagcggct cccgccagat tttggcaaga ttactaagca ggaagtcaag   3600
gactttttg cttgggcaaa ggtcaatcag gtgccggtga ctcacgagtt taaagttccc   3660
agggaattgg cgggaactaa aggggcggag aaatctctaa aacgcccact gggtgacgtc   3720
accaatacta gctataaaag tctggagaag cgggccaggc tctcatttgt tcccgagacg   3780
cctcgcagtt cagacgtgac tgttgatccc gctcctctgc gaccgctagc ttcgatcaac   3840
tacgcagaca ggtaccaaaa caagtgttct cgtcacgtgg gcattaatct gattctgttt   3900
ccctgcagac aatgcgagag aatgaatcag aactcaaata tctgcttcac tcacggacag   3960
aaagactgtt tagagtgctt tcccgtgtca gaatctcaac ccgtttctgt cgtcaaaaag   4020
gcgtatcaga aactgtgcta cattcatcat atcatgggaa aggtgccaga cgcttgcact   4080
gcctgcgatc tggtcaatgt ggatttggat gactgcatct ttgaacaata aatgacttaa   4140
gccaggtatg gctgccgatg gttatcttcc agattggctc gaggacaacc ttagtgaagg   4200
aattcgcgag tggtgggctt tgaaacctgg agcccctcaa cccaaggcaa atcaacaaca   4260
tcaagacaac gctagaggtc ttgtgcttcc gggttacaaa taccttggac ccggcaacgg   4320
actcgacaag gggggagccgg tcaacgcagc agacgcggcg gccctcgagc acgacaaagc   4380
ctacgaccag cagctcaagg ccggagacaa cccgtacctc aagtacaacc acgccgacgc   4440
cgagttccag gagcggctca aagaagatac gtcttttggg ggcaacctcg ggcgagcagt   4500
cttccaggcc aaaaagaggc ttcttgaacc tcttggtctg gttgaggaag cggctaagac   4560
ggctcctgga aagaagaggc ctgtagagca gtctcctcag gaaccggact cctccgcggg   4620
tattggcaaa tcgggtgcac agcccgctaa aaagagactc aatttcggtc agactggcga   4680
cacagagtca gtcccagacc ctcaaccaat cggagaacct cccgcagccc cctcaggtgt   4740
gggatctctt acaatggctt caggtggtgg cgcaccagtg gcagacaata acgaaggtgc   4800
cgatggagtg ggtagttcct cgggaaattg gcattgcgat tcccaatggc tgggggacag   4860
agtcatcacc accagcaccc gaacctgggc cctgcccacc tacaacaatc acctctacaa   4920
gcaaatctcc aacagcacat ctggaggatc ttcaaatgac aacgcctact tcggctacag   4980
cacccccctgg gggtattttg acttcaacag attccactgc cacttctcac cacgtgactg   5040
gcagcgactc atcaacaaca actggggatt ccggcctaag cgactcaact tcaagctctt   5100
taacattcag gtcaaagagg ttacggacaa caatggagtc aagaccatcg ccaataacct   5160
taccagcacg gtccaggtct tcacggactc agactatcag ctcccgtacg tgctcgggtc   5220
ggctcacgag ggctgcctcc cgccgttccc agcggacgtt ttcatgattc ctcagtacgg   5280
gtatctgacg cttaatgatg gaagccaggc cgtgggtcgt tcgtcctttt actgcctgga   5340
```

-continued

```
atatttcccg tcgcaaatgc taagaacggg taacaacttc cagttcagct acgagtttga   5400
gaacgtacct ttccatagca gctacgctca cagccaaagc ctggaccgac taatgaatcc   5460
actcatcgac caatacttgt actatctctc tagaactatt aacggttctg gacagaatca   5520
acaaacgcta aaattcagtg tggccggacc cagcaacatg gctgtccagg gaagaaacta   5580
catacctgga cccagctacc gacaacaacg tgtctcaacc actgtgactc aaaacaacaa   5640
cagcgaattt gcttggcctg gagcttcttc ttgggctctc aatggacgta atagcttgat   5700
gaatcctgga cctgctatgg cctctcacaa agaaggagag gaccgtttct ttcctttgtc   5760
tggatcttta atttttggca aacaaggtac tggcagagac aacgtggatg cggacaaagt   5820
catgataacc aacgaagaag aaattaaaac tactaacccg gtagcaacgg agtcctatgg   5880
acaagtggcc acaaaccacc agagtgccca aactttggcg gtgcctttta aggcacaggc   5940
gcagaccggt tgggttcaaa accaaggaat acttccgggt atggtttggc aggacagaga   6000
tgtgtacctg caaggaccca tttgggccaa aattcctcac acggacggca actttcaccc   6060
ttctccgctg atgggagggt ttggaatgaa gcacccgcct cctcagatcc tcatcaaaaa   6120
cacacctgta cctgcggatc ctccaacggc cttcaacaag gacaagctga actctttcat   6180
cacccagtat tctactggtc aagtcagcgt ggagatcgag tgggagctgc agaaggaaaa   6240
cagcaagcgc tggaacccgg agatccagta cacttccaac tattacaagt ctaataatgt   6300
tgaatttgct gttaatactg aaggtgtata tagtgaaccc cgccccattg gcaccagata   6360
cctgactcgt aatctgtaag tcgacttgct tgttaatcaa taaaccgttt aattcgtttc   6420
agttgaactt tggtctctgc gaagggcaat tcgtttaaac ctgcaggact agaggtcctg   6480
tattagaggt cacgtgagtg ttttgcgaca ttttgcgaca ccatgtggtc acgctgggta   6540
tttaagcccg agtgagcacg cagggtctcc attttgaagc gggaggtttg aacgcgcagc   6600
cgccaagccg aattctgcag atatcacatg tcctaggaac tatcgatcca tcacactggc   6660
ggccgctcga ctagagcggc cgccaccgcg gtggagctcc agcttttgcg gaccgaatcg   6720
gaaagaacat gtgagcaaaa ggccagcaaa aggccaggaa ccgtaaaaag gccgcgttgc   6780
tggcgttttt ccataggctc cgcccccctg acgagcatca caaaaatcga cgctcaagtc   6840
agaggtggcg aaacccgaca ggactataaa gataccaggc gtttccccct ggaagctccc   6900
tcgtgcgctc tcctgttccg accctgccgc ttaccggata cctgtccgcc tttctccctt   6960
cgggaagcgt ggcgctttct catagctcac gctgtaggta tctcagttcg gtgtaggtcg   7020
ttcgctccaa gctgggctgt gtgcacgaac cccccgttca gcccgaccgc tgcgccttat   7080
ccggtaacta tcgtcttgag tccaacccgg taagacacga cttatcgcca ctggcagcag   7140
ccactggtaa caggattagc agagcgaggt atgtaggcgg tgctacagag ttcttgaagt   7200
ggtggcctaa ctacggctac actagaagaa cagtatttgg tatctgcgct ctgctgaagc   7260
cagttacctt cggaaaaaga gttggtagct cttgatccgg caaacaaacc accgctggta   7320
gcggtggttt ttttgtttgc aagcagcaga ttacgcgcag aaaaaaagga tctcaagaag   7380
atcctttgat cttttctacg gggtctgacg ctcagtggaa cgaaaactca cgttaaggga   7440
ttttggtcat gagattatca aaaaggatct tcacctagat ccttttaaat taaaaatgaa   7500
gttttaaatc aatctaaagt atatatgagt aaacttggtc tgacagttac caatgcttaa   7560
tcagtgaggc acctatctca gcgatctgtc tatttcgttc atccatagtt gcctgactcc   7620
ccgtcgtgta gataactacg atacgggagg gcttaccatc tggccccagt gctgcaatga   7680
taccgcgaga cccacgctca ccggctccag atttatcagc aataaaccag ccagccggaa   7740
```

-continued

```
gggccgagcg cagaagtggt cctgcaactt tatccgcctc catccagtct attaattgtt   7800

gccgggaagc tagagtaagt agttcgccag ttaatagttt gcgcaacgtt gttgccattg   7860

ctacaggcat cgtggtgtca cgctcgtcgt ttggtatggc ttcattcagc tccggttccc   7920

aacgatcaag gcgagttaca tgatccccca tgttgtgcaa aaaagcggtt agctccttcg   7980

gtcctccgat cgttgtcaga agtaagttgg ccgcagtgtt atcactcatg gttatggcag   8040

cactgcataa ttctcttact gtcatgccat ccgtaagatg cttttctgtg actggtgagt   8100

actcaaccaa gtcattctga gaatagtgta tgcggcgacc gagttgctct tgcccggcgt   8160

caatacggga taataccgcg ccacatagca gaactttaaa agtgctcatc attggaaaac   8220

gttcttcggg gcgaaaactc tcaaggatct taccgctgtt gagatccagt tcgatgtaac   8280

ccactcgtgc acccaactga tcttcagcat cttttacttt caccagcgtt tctgggtgag   8340

caaaaacagg aaggcaaaat gccgcaaaaa agggaataag ggcgacacgg aaatgttgaa   8400

tactcatact cttccttttt caatattatt gaagcattta tcagggttat tgtctcatga   8460

gcggatacat atttgaatgt atttagaaaa ataaacaaat aggggttccg cgcacatttc   8520

cccgaaaagt gccacctgac gtc                                           8543
```

<210> SEQ ID NO 2
<211> LENGTH: 1242
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
tgcaagaacc ctcactggct gaactatctt gccagcccct tattttgttt tcatattaac     60

ctctttttc tagtaaagga gatgtttgct ctcaaatttg cataggaatg taatatttaa     120

tttaaaaaga tgacccacat atgaccttat aaggacagta aaattaaaca accggaaaga    180

taaagcgggc cagttggctc agttctataa aaccagccca caaggattgt cactattctt    240

aggcttgcgc gggctacatg atgagttcca ggactgcctg gttacagacc gagactctct    300

caagagtcca gataaacaac aacaaagggg gcgaggtgga aatacagggg ctgtaagaag    360

taaatatgat atctgcatgg gaggctagcc agagaagaaa aaatttctt ccgtggttca     420

atcctccaag ggctgaacag gaagttgacg caggcaggtg aggagcacga gcctagatgg    480

gctgcggtgc cacccttaat ccccacaagc gagttcctcc gcaattcgcc tgtcccactc    540

tcaacttttc ttcaactgac tctttgctgt ggtccctcgc tgtggcagtg gaaacaacta    600

ccactgcgag gtagggaatg tcatgagggg ctacctgcag cccttggctt gcagggatgc    660

agggatgcgg tcggaacctg aggccccgcc cttctcttgc cccacgccat taggccacgc    720

ccctacccag cactccttca accacccccct tccccggcgc ctcatgaggt cccgcccctc    780

tcaaccctag ctcttgaggc ctccccttca cagccgcccc ggcgttcctt gacttgaggc    840

cacgtccctc tgctccttca ttcccaagac cctacgcttt gcgagtcctc cctgtcctgc    900

tgcctaggac cccgcccctc tcagcccttc tgccccaaga ccccgcccct taggctgttc    960

ccgcccactg gccaatgaag acccgccctt tctttagccg ccccgccccg gtcccacaaa   1020

atcccgcctc cggccccgcc tcccgccccc ttgggcgctc cgtagcagtg acgtgcgcag   1080

gctgggcact ctgcagggct ctctggccgg cgggtggaga ccgatccggg atctgtccca   1140

gcaggaagcg tatcccggcc gccgtcgtgc tgtcgtctcc ggtgctcgct ctcggccgcg   1200
```

gtgtcgcgct tgcccttcgc gcccgcagcc cggcagcctc tc 1242

<210> SEQ ID NO 3
<211> LENGTH: 3221
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3
agacacccca gttatggggg ctagggaccc aaaagagaca tccttctgcc acccagagct 60
gccctggcga ggtgcactat ggggccgccg acagctgcgt ggctgccgag ggcggaaagg 120
agaaactgtc atgtcccgat agggccgcgc gaggtctcca tcctcgacaa cgctaataac 180
aaagacgtgt gctcctcttt gcttggttcc ccccactcct ttaaatcaca gatttcactt 240
cagtttatct gtgtcgctgt cacacgtggg gtggctccca gtcagctggt ttggcaaagt 300
ttctggatga ttacggaata acatgtgtcc ccaacccgca gagcaggttg tgggggcaat 360
gttgcattga ccagcgtcag agaacacaca tcagaggcaa gggtgggtgt gcaggaggga 420
gaaggcgcag aaggcagggc tttagctcag cactctccct cctgccatgc tctgcctgac 480
cgttccctct ctgagtccca aacagccagg tagaggagga agaaatgggg ctgagacccc 540
agcacatcag tgattaagtc aggatcaggt gcggtttcct gctcaggtgc tgagacagca 600
ggcggtgtcc tgcaaacaac aggaggcacc tgaagctagc ctgggggccc cacgcccagg 660
tgcggtgcat tcagcagcac agccagagac agaccccaat gaccccgcct ccctgtcggc 720
agccagtgct ctgcacagag ccctgagcag cctctggaca ttagtcccag ccccagcacg 780
gcccgtcccc cacgctgatg tcaccgcacc cagaccttgg aggccccctc cggctccgcc 840
tcctgggaga aggctctgga gtgaggaggg gagggcagca gtgctggctg gacagctgct 900
ctgggcagga gagagaggga gagacaagag acacacacag agagacggcg aggaagggaa 960
agacccagag ggacgcctag aacgagactt ggagccagac agaggaagag gggacgtgtg 1020
tttgcagact ggctgggccc gtgacccagc ttcctgagtc ctccgtgcag gtggcagctg 1080
taccaggctg gcaggtcact gagagtgggc agctgggccc caggtaagga tgggctgccc 1140
actgtcctgg gcattgggag gggtttggat gtggaggagt catggacttg agctacctct 1200
agagcctctg ccccacagcc acttgctcct gggactgggc ttcctgccac ccttgagggc 1260
tcagccacca cagccactga atgaaactgt cccgagcctg ggaagatgga tgtgtgtccc 1320
ctggaggagg gaagagccaa ggagcatgtt gtccatcgaa tcttctctga gctggggctg 1380
gggttagtgg catcctgggg ccaggggaat agacatgctg tggtggcaga gagaagagtc 1440
cgttctctct gtctcctttg ctttctctct gacactcttt atctccgttt ttggataagt 1500
cacttccttc ctctatgccc caaatatccc atctgtgaaa tgggagtatg aagccccaac 1560
agccagggtt gtagtgggga agaggtaaaa tcaggtatag acatagaaat acaaatacag 1620
tctatgcccc ctgttgtcag ttggaaaaga aattaacttg aaggtggtct agttctcatt 1680
tttagaaatg aaatgtctgt ctggtcattt taaaatgtgg cccttaaatt tcacgccctc 1740
accgctctcc cccatccctt ggagccccat gtctctagtg aaagcactgg ctctgccccc 1800
agccctcatg gctcatgctg gcatagggcg cctgctccac agcctgggca ccatcttcag 1860
acaagtgccc ggtggcaact gcctgctggc cctgttgaat ccacatctcc accaggcatc 1920
cagactagtt caggtctctg gaaggaccgt gggtttgctg tgtcccagag ctccagggca 1980

-continued

```
ggggtcaggg ctcggatgtc gggcagtgtc atgggcagag gatcgaatgc cccggcggct   2040

ctgaatgggc ccttgtgaaa aattgatgcg cattctagga gacaggttgg gagccagagg   2100

ggcctcatac cagggtctgt aggctggggc tgccttttaa gctccttcct gaggccgtct   2160

ctgggtctgg ccctgtgctg gacaaggctg gagacaaggc aatgtctcag accctctccc   2220

attggccaca tcctgccctg gatcaactcg ccaactttgg gggcagaggt gggactgacc   2280

cttaccctga caacataatg catatagtca aaatgggata aaggggaata tagaggctct   2340

tggcagcttg ggagtggtca gggaaggctt cctggaggag gtatcatctg aactgagcca   2400

tgaaccataa gtggaaattc actagtcaaa atttcaggta gaagggccag tgtgtgaagg   2460

ccaggagatg gcaagagctg gcgtatttca ggaacagtga gtcactgagg atgtccaagt   2520

ataagggtag gaaagggagt gagcagtgag agaaaagacc gaggcatcag caggggccag   2580

attgtgctgg gcctagcggg gcgggcccgg gcccgggccc aggcccaggt gcggtgcatt   2640

cagcagcaca gccagagaca gaccccaatg accctgcctc cccgtcagca gccagtgctc   2700

tgcacagagc catcctgagg gcagtgggtg ctcttgagag gtttcaggca gggtgtgctg   2760

tgagcaggtc atgcccagcc cttgaccttc tgctcagtca ggcttgtcct tgtcacccac   2820

attcctgggg cagtccctaa gctgagtgcc ggagattaag tcctagtcct aaatttgctc   2880

tggctagctg tgtgaccctg ggcaagtctt ggtccctctc tgggcccctt tgccgtaggt   2940

ccctggtggg gccagacttg ctactttcta ggagcccttt gggaatctct gaatgacagt   3000

ggctgagaga agaattcagc tgctctgggc agtggtgctg gtgacagtgg ctgaggctca   3060

ggtcacacag gctgggcagt ggtcagaggg agagaagcca aggagggttc ccttgaggga   3120

ggaggagctg gggctttggg aggagcccag gtgaccccag ccaggctcaa ggcttccagg   3180

gctggcctgc ccagaagcat gacatggtct ctctccctgc a                        3221
```

```
<210> SEQ ID NO 4
<211> LENGTH: 760
<212> TYPE: PRT
<213> ORGANISM: Homo sapiens

<400> SEQUENCE: 4

Met Ser Pro Lys Lys Val Gln Ile Lys Val Glu Glu Lys Glu Asp Glu
1               5                   10                  15

Thr Glu Glu Ser Ser Ser Glu Glu Glu Glu Glu Val Glu Asp Lys Leu
            20                  25                  30

Pro Arg Arg Glu Ser Leu Arg Pro Lys Arg Lys Arg Thr Arg Asp Val
        35                  40                  45

Ile Asn Glu Asp Asp Pro Glu Pro Glu Pro Glu Asp Glu Glu Thr Arg
    50                  55                  60

Lys Ala Arg Glu Lys Glu Arg Arg Arg Arg Leu Lys Arg Gly Ala Glu
65                  70                  75                  80

Glu Glu Glu Ile Asp Glu Glu Glu Leu Glu Arg Leu Lys Ala Glu Leu
                85                  90                  95

Asp Glu Lys Arg Gln Ile Ile Ala Thr Val Lys Cys Lys Pro Trp Lys
            100                 105                 110

Met Glu Lys Lys Ile Glu Val Leu Lys Glu Ala Lys Lys Phe Val Ser
        115                 120                 125

Glu Asn Glu Gly Ala Leu Gly Lys Gly Lys Gly Lys Arg Trp Phe Ala
    130                 135                 140

Phe Lys Met Met Met Ala Lys Lys Trp Ala Lys Phe Leu Arg Asp Phe
```

-continued

```
145                 150                 155                 160

Glu Asn Phe Lys Ala Ala Cys Val Pro Trp Glu Asn Lys Ile Lys Ala
                165                 170                 175

Ile Glu Ser Gln Phe Gly Ser Ser Val Ala Ser Tyr Phe Leu Phe Leu
            180                 185                 190

Arg Trp Met Tyr Gly Val Asn Met Val Leu Phe Ile Leu Thr Phe Ser
        195                 200                 205

Leu Ile Met Leu Pro Glu Tyr Leu Trp Gly Leu Pro Tyr Gly Ser Leu
    210                 215                 220

Pro Arg Lys Thr Val Pro Arg Ala Glu Glu Ala Ser Ala Ala Asn Phe
225                 230                 235                 240

Gly Val Leu Tyr Asp Phe Asn Gly Leu Ala Gln Tyr Ser Val Leu Phe
                245                 250                 255

Tyr Gly Tyr Tyr Asp Asn Lys Arg Thr Ile Gly Trp Met Asn Phe Arg
            260                 265                 270

Leu Pro Leu Ser Tyr Phe Leu Val Gly Ile Met Cys Ile Gly Tyr Ser
        275                 280                 285

Phe Leu Val Val Leu Lys Ala Met Thr Lys Asn Ile Gly Asp Asp Gly
    290                 295                 300

Gly Gly Asp Asp Asn Thr Phe Asn Phe Ser Trp Lys Val Phe Thr Ser
305                 310                 315                 320

Trp Asp Tyr Leu Ile Gly Asn Pro Glu Thr Ala Asp Asn Lys Phe Asn
                325                 330                 335

Ser Ile Thr Met Asn Phe Lys Glu Ala Ile Thr Glu Glu Lys Ala Ala
            340                 345                 350

Gln Val Glu Glu Asn Val His Leu Ile Arg Phe Leu Arg Phe Leu Ala
        355                 360                 365

Asn Phe Phe Val Phe Leu Thr Leu Gly Gly Ser Gly Tyr Leu Ile Phe
    370                 375                 380

Trp Ala Val Lys Arg Ser Gln Glu Phe Ala Gln Gln Asp Pro Asp Thr
385                 390                 395                 400

Leu Gly Trp Trp Glu Lys Asn Glu Met Asn Met Val Met Ser Leu Leu
                405                 410                 415

Gly Met Phe Cys Pro Thr Leu Phe Asp Leu Phe Ala Glu Leu Glu Asp
            420                 425                 430

Tyr His Pro Leu Ile Ala Leu Lys Trp Leu Leu Gly Arg Ile Phe Ala
        435                 440                 445

Leu Leu Leu Gly Asn Leu Tyr Val Phe Ile Leu Ala Leu Met Asp Glu
    450                 455                 460

Ile Asn Asn Lys Ile Glu Glu Glu Lys Leu Val Lys Ala Asn Ile Thr
465                 470                 475                 480

Leu Trp Glu Ala Asn Met Ile Lys Ala Tyr Asn Ala Ser Phe Ser Glu
                485                 490                 495

Asn Ser Thr Gly Pro Pro Phe Phe Val His Pro Ala Asp Val Pro Arg
            500                 505                 510

Gly Pro Cys Trp Glu Thr Met Val Gly Gln Glu Phe Val Arg Leu Thr
        515                 520                 525

Val Ser Asp Val Leu Thr Thr Tyr Val Thr Ile Leu Ile Gly Asp Phe
    530                 535                 540

Leu Arg Ala Cys Phe Val Arg Phe Cys Asn Tyr Cys Trp Cys Trp Asp
545                 550                 555                 560

Leu Glu Tyr Gly Tyr Pro Ser Tyr Thr Glu Phe Asp Ile Ser Gly Asn
                565                 570                 575
```

-continued

```
Val Leu Ala Leu Ile Phe Asn Gln Gly Met Ile Trp Met Gly Ser Phe
            580                 585                 590

Phe Ala Pro Ser Leu Pro Gly Ile Asn Ile Leu Arg Leu His Thr Ser
        595                 600                 605

Met Tyr Phe Gln Cys Trp Ala Val Met Cys Cys Asn Val Pro Glu Ala
    610                 615                 620

Arg Val Phe Lys Ala Ser Arg Ser Asn Asn Phe Tyr Leu Gly Met Leu
625                 630                 635                 640

Leu Leu Ile Leu Phe Leu Ser Thr Met Pro Val Leu Tyr Met Ile Val
                645                 650                 655

Ser Leu Pro Pro Ser Phe Asp Cys Gly Pro Phe Ser Gly Lys Asn Arg
            660                 665                 670

Met Phe Glu Val Ile Gly Glu Thr Leu Glu His Asp Phe Pro Ser Trp
        675                 680                 685

Met Ala Lys Ile Leu Arg Gln Leu Ser Asn Pro Gly Leu Val Ile Ala
    690                 695                 700

Val Ile Leu Val Met Val Leu Ala Ile Tyr Tyr Leu Asn Ala Thr Ala
705                 710                 715                 720

Lys Gly Gln Lys Ala Ala Asn Leu Asp Leu Lys Lys Lys Met Lys Met
                725                 730                 735

Gln Ala Leu Glu Asn Lys Met Arg Asn Lys Lys Met Ala Ala Ala Arg
            740                 745                 750

Ala Ala Ala Ala Ala Gly Arg Gln
        755                 760
```

<210> SEQ ID NO 5
<211> LENGTH: 3201
<212> TYPE: DNA
<213> ORGANISM: Homo sapiens

<400> SEQUENCE: 5

```
cagaaactat gagggcagaa cccagcaatc tgtgctttct ttcacaagcc ctccaggagt     60

tgctgaaatt taggaatcat tgccccaaaa agtggccctc ataatgatgc cagatgggat    120

cttactctgt tgcccaggct ggagtgcagt ggtgcgatct cggctctctg caacctccgc    180

ctcccaggtt caagtgattc tcctgcctcg gcctcctgag tagctgggat ttcaggccat    240

gaaagatcac tgttttagtc tgcgtggtgc agtggaacag atagacctcg gtttgaatct    300

cagctctact gtttactaga catgaaatgg ggaaatctaa aatgagatgc cagaagcctc    360

aaaaatggaa aaccccctgt gcttcacatc tgaaaatctc tgctgggggc agcaactttg    420

agcctgtggg gaaggaactg tccacgtgga gtggtctggt gaatgcttaa ggagctgcag    480

aagggaagtc cctctccaaa ctagccagcc actgagacct tctgacagga cacccccagg    540

atgtcaccca aaaaagtaca aatcaaagtg gaggaaaaag aagacgagac tgaggaaagc    600

tcaagtgaag aggaagagga ggtggaagat aagctacctc gaagagagag cttgagacca    660

aagaggaaac ggaccagaga tgttatcaat gaggatgacc cagaacctga accagaggat    720

gaagaaacaa ggaaggcaag agaaaaagag aggaggagga ggctaaagag aggagcagaa    780

gaagaagaaa ttgatgaaga ggaattggaa agattgaagg cagagttaga tgagaaaaga    840

caaataattg ctactgtcaa atgcaaacca tggaagatgg agaagaaaat tgaagttctc    900

aaggaggcaa aaaaatttgt gagtgaaaat gaaggggctc ttgggaaagg aaaaggaaaa    960

cggtggtttg catttaagat gatgatggcc aagaaatggg caaaattcct ccgtgatttt   1020
```

-continued

```
gagaacttca aagctgcgtg tgtcccatgg gaaaataaaa tcaaggctat tgaaagtcag   1080
tttggctcct cagtggcctc atacttcctc ttcttgagat ggatgtatgg agtcaatatg   1140
gttctcttta tcctgacatt tagcctcatc atgttgccag agtacctctg ggtttgcca    1200
tatggcagtt tacctaggaa aaccgttccc agagccgaag aggcatcggc agcaaacttt   1260
ggtgtgttgt acgacttcaa tggtttggca caatattccg ttctctttta tggctattat   1320
gacaataaac gaacaattgg atggatgaat ttcaggttgc cgctctccta ttttctagtg   1380
gggattatgt gcattggata cagctttctg gttgtcctca aagcaatgac caaaaacatt   1440
ggtgatgatg gaggtggaga tgacaacact ttcaatttca gctggaaggt ctttaccagc   1500
tgggactacc tgatcggcaa tcctgaaaca gcagacaaca aatttaattc tatcacaatg   1560
aactttaagg aagctatcac agaagaaaaa gcagcccaag tagaagaaaa cgtccacttg   1620
atcagattcc tgaggtttct ggctaacttc ttcgtgtttc taacacttgg agggagtgga   1680
tacctcatct tttgggctgt gaagcgatcc caggaatttg cacagcaaga tcctgacacc   1740
cttgggtggt gggaaaaaaa tgaaatgaac atggttatgt ccctcctagg gatgttctgt   1800
ccaacattgt ttgacttatt tgctgaatta gaagactacc atcctctcat cgctttgaaa   1860
tggctactgg gacgcatttt tgctcttctt ttaggcaatt tatacgtatt tattcttgca   1920
ttaatggatg agattaacaa caagattgaa gaggagaagc tagtaaaggc caatattacc   1980
ctttgggaag ccaatatgat caaggcctac aatgcatcat tctctgaaaa tagcactgga   2040
ccaccctttt ttgttcaccc tgcagatgta cctcgaggac cttgctggga aacaatggtg   2100
ggacaggagt ttgtgaggct gacagtctct gatgttctga ccacctacgt cacaatcctc   2160
attgggggact ttctaagggc atgttttgtg aggttttgca attattgctg gtgctgggac  2220
ttggagtatg gatatccttc atacaccgaa ttcgacatca gtggcaacgt cctcgctctg   2280
atcttcaacc aaggcatgat ctggatgggc tccttctttg ctcccagcct cccaggcatc   2340
aatatccttc gactccatac atccatgtac ttccagtgct gggccgttat gtgctgcaat   2400
gttcctgagg ccagggtctt caaagcttcc agatcaaata acttctacct gggcatgcta   2460
ctgctcatcc tcttcctgtc cacaatgcct gtcttgtaca tgatcgtgtc cctcccacca   2520
tcttttgatt gtggtccatt cagtggcaaa aatagaatgt ttgaagtcat tggagagacc   2580
ctggagcacg atttcccaag ctggatggcg aagatcttga gacagctttc aaaccctggg   2640
ctggtcattg ctgtcatttt ggtgatggtt ttggccatct attatctcaa tgctactgcc   2700
aagggccaga aggcagcgaa tctggatctc aaaaagaaga tgaaaatgca agctttggag   2760
aacaaaatgc gaaacaagaa aatggcagct gcacgagcag ctgcagctgc tggtcgccag   2820
taataagtat cctgagagcc cagaaaaggt acactttgcc ttgctgttta aaagtaatgc   2880
aatatgtgaa cgcccagaga acaagcactg tggaactgct attttcctgt tctacccttg   2940
atggattttc aaggtcatgc tggccaatta aggcatcatc agtcctacct gagcaacaag   3000
aatctaaact ttattccaag tcagaaactg tttctgcaga gccactctct cccctgctcc   3060
atttcgtgac ttttttttt tttttaacaa attgagttta gaagtgagtg taatccagca    3120
atacagttta ctggtttagt tggtgggtta attaaaaaaa atttgctcat atgaactttc   3180
attttatatg tttcttttgc c                                             3201
```

<210> SEQ ID NO 6
<211> LENGTH: 906
<212> TYPE: PRT
<213> ORGANISM: Homo sapiens

<400> SEQUENCE: 6

Met Ser His Gln Val Lys Gly Leu Lys Glu Glu Ala Arg Gly Gly Val
1 5 10 15

Lys Gly Arg Val Lys Ser Gly Ser Pro His Thr Gly Asp Arg Leu Gly
20 25 30

Arg Arg Ser Ser Ser Lys Arg Ala Leu Lys Ala Glu Gly Thr Pro Gly
35 40 45

Arg Arg Gly Ala Gln Arg Ser Gln Lys Glu Arg Ala Gly Gly Ser Pro
50 55 60

Ser Pro Gly Ser Pro Arg Arg Lys Gln Thr Gly Arg Arg Arg His Arg
65 70 75 80

Glu Glu Leu Gly Glu Gln Glu Arg Gly Glu Ala Glu Arg Thr Cys Glu
85 90 95

Gly Arg Arg Lys Arg Asp Glu Arg Ala Ser Phe Gln Glu Arg Thr Ala
100 105 110

Ala Pro Lys Arg Glu Lys Glu Ile Pro Arg Arg Glu Glu Lys Ser Lys
115 120 125

Arg Gln Lys Lys Pro Arg Ser Ser Ser Leu Ala Ser Ser Ala Ser Gly
130 135 140

Gly Glu Ser Leu Ser Glu Glu Glu Leu Ala Gln Ile Leu Glu Gln Val
145 150 155 160

Glu Glu Lys Lys Lys Leu Ile Ala Thr Met Arg Ser Lys Pro Trp Pro
165 170 175

Met Ala Lys Lys Leu Thr Glu Leu Arg Glu Ala Gln Glu Phe Val Glu
180 185 190

Lys Tyr Glu Gly Ala Leu Gly Lys Gly Lys Gly Lys Gln Leu Tyr Ala
195 200 205

Tyr Lys Met Leu Met Ala Lys Lys Trp Val Lys Phe Lys Arg Asp Phe
210 215 220

Asp Asn Phe Lys Thr Gln Cys Ile Pro Trp Glu Met Lys Ile Lys Asp
225 230 235 240

Ile Glu Ser His Phe Gly Ser Ser Val Ala Ser Tyr Phe Ile Phe Leu
245 250 255

Arg Trp Met Tyr Gly Val Asn Leu Val Leu Phe Gly Leu Ile Phe Gly
260 265 270

Leu Val Ile Ile Pro Glu Val Leu Met Gly Met Pro Tyr Gly Ser Ile
275 280 285

Pro Arg Lys Thr Val Pro Arg Ala Glu Glu Glu Lys Ala Met Asp Phe
290 295 300

Ser Val Leu Trp Asp Phe Glu Gly Tyr Ile Lys Tyr Ser Ala Leu Phe
305 310 315 320

Tyr Gly Tyr Tyr Asn Asn Gln Arg Thr Ile Gly Trp Leu Arg Tyr Arg
325 330 335

Leu Pro Met Ala Tyr Phe Met Val Gly Val Ser Val Phe Gly Tyr Ser
340 345 350

Leu Ile Ile Val Ile Arg Ser Met Ala Ser Asn Thr Gln Gly Ser Thr
355 360 365

Gly Glu Gly Glu Ser Asp Asn Phe Thr Phe Ser Phe Lys Met Phe Thr
370 375 380

Ser Trp Asp Tyr Leu Ile Gly Asn Ser Glu Thr Ala Asp Asn Lys Tyr
385 390 395 400

Ala Ser Ile Thr Thr Ser Phe Lys Glu Ser Ile Val Asp Glu Gln Glu

-continued

```
                405                 410                 415

Ser Asn Lys Glu Glu Asn Ile His Leu Thr Arg Phe Leu Arg Val Leu
            420                 425                 430

Ala Asn Phe Leu Ile Ile Cys Cys Leu Cys Gly Ser Gly Tyr Leu Ile
        435                 440                 445

Tyr Phe Val Val Lys Arg Ser Gln Gln Phe Ser Lys Met Gln Asn Val
    450                 455                 460

Ser Trp Tyr Glu Arg Asn Glu Val Glu Ile Val Met Ser Leu Leu Gly
465                 470                 475                 480

Met Phe Cys Pro Pro Leu Phe Glu Thr Ile Ala Ala Leu Glu Asn Tyr
                485                 490                 495

His Pro Arg Thr Gly Leu Lys Trp Gln Leu Gly Arg Ile Phe Ala Leu
            500                 505                 510

Phe Leu Gly Asn Leu Tyr Thr Phe Leu Leu Ala Leu Met Asp Asp Val
        515                 520                 525

His Leu Lys Leu Ala Asn Glu Glu Thr Ile Lys Asn Ile Thr His Trp
    530                 535                 540

Thr Leu Phe Asn Tyr Tyr Asn Ser Ser Gly Trp Asn Glu Ser Val Pro
545                 550                 555                 560

Arg Pro Pro Leu His Pro Ala Asp Val Pro Arg Gly Ser Cys Trp Glu
                565                 570                 575

Thr Ala Val Gly Ile Glu Phe Met Arg Leu Thr Val Ser Asp Met Leu
            580                 585                 590

Val Thr Tyr Ile Thr Ile Leu Leu Gly Asp Phe Leu Arg Ala Cys Phe
        595                 600                 605

Val Arg Phe Met Asn Tyr Cys Trp Cys Trp Asp Leu Glu Ala Gly Phe
    610                 615                 620

Pro Ser Tyr Ala Glu Phe Asp Ile Ser Gly Asn Val Leu Gly Leu Ile
625                 630                 635                 640

Phe Asn Gln Gly Met Ile Trp Met Gly Ser Phe Tyr Ala Pro Gly Leu
                645                 650                 655

Val Gly Ile Asn Val Leu Arg Leu Leu Thr Ser Met Tyr Phe Gln Cys
            660                 665                 670

Trp Ala Val Met Ser Ser Asn Val Pro His Glu Arg Val Phe Lys Ala
        675                 680                 685

Ser Arg Ser Asn Asn Phe Tyr Met Gly Leu Leu Leu Leu Val Leu Phe
    690                 695                 700

Leu Ser Leu Leu Pro Val Ala Tyr Thr Ile Met Ser Leu Pro Pro Ser
705                 710                 715                 720

Phe Asp Cys Gly Pro Phe Ser Gly Lys Asn Arg Met Tyr Asp Val Leu
                725                 730                 735

Gln Glu Thr Ile Glu Asn Asp Phe Pro Thr Phe Leu Gly Lys Ile Phe
            740                 745                 750

Ala Phe Leu Ala Asn Pro Gly Leu Ile Ile Pro Ala Ile Leu Leu Met
        755                 760                 765

Phe Leu Ala Ile Tyr Tyr Leu Asn Ser Val Ser Lys Ser Leu Ser Arg
    770                 775                 780

Ala Asn Ala Gln Leu Arg Lys Lys Ile Gln Val Leu Arg Glu Val Glu
785                 790                 795                 800

Lys Ser His Lys Ser Val Lys Gly Lys Ala Thr Ala Arg Asp Ser Glu
                805                 810                 815

Asp Thr Pro Lys Ser Ser Ser Lys Asn Ala Thr Gln Leu Gln Leu Thr
            820                 825                 830
```

```
Lys Glu Glu Thr Thr Pro Pro Ser Ala Ser Gln Ser Gln Ala Met Asp
        835                 840                 845

Lys Lys Ala Gln Gly Pro Gly Thr Ser Asn Ser Ala Ser Arg Thr Thr
    850                 855                 860

Leu Pro Ala Ser Gly His Leu Pro Ile Ser Arg Pro Pro Gly Ile Gly
865                 870                 875                 880

Pro Asp Ser Gly His Ala Pro Ser Gln Thr His Pro Trp Arg Ser Ala
                885                 890                 895

Ser Gly Lys Ser Ala Gln Arg Pro Pro His
            900                 905


<210> SEQ ID NO 7
<211> LENGTH: 3169
<212> TYPE: DNA
<213> ORGANISM: Homo sapiens

<400> SEQUENCE: 7

gcagtgctgc tgaccatgag ccaccaggta aagggcctga aagaggaagc acgaggcgga     60

gtgaaagggc gggtgaagag cggctctcca cacacaggtg acaggctggg aaggagatcc    120

tcaagcaagc gggctctcaa agccgagggg accccaggca ggcgcggagc tcagcgaagc    180

cagaaggagc gcgccggggg cagcccaagc ccggggtctc cccggaggaa gcaaacaggg    240

cgcaggagac acagagaaga gctgggggag caggagcggg gcgaggcaga gaggacctgc    300

gagggcagga gaaagcgcga cgagagggcc tccttccagg agcggacagc agccccaaag    360

agggaaaagg agattccgag gagggaggag aagtcgaagc ggcagaagaa acccaggtca    420

tcctccttgg cctccagtgc ctctggtggg gagtccctgt ccgaggagga actggcccag    480

atcctggagc aggtggaaga aaaaaagaag ctcattgcca ccatgcggag caagccctgg    540

cccatggcga agaagctgac agagctcagg gaggcccagg aatttgtgga gaagtatgaa    600

ggtgccttgg gaaaggggaa aggcaagcaa ctatatgcct acaagatgct gatggccaag    660

aaatgggtca aatttaagag agactttgat aatttcaaga ctcaatgtat cccctgggaa    720

atgaagatca aggacattga aagtcacttt ggttcttcag tggcatcgta tttcatcttt    780

ctccgatgga tgtatggagt taaccttgtc ctttttggct taatatttgg tctagtcata    840

atcccagagg tactgatggg catgccctat gggagtattc ccagaaagac agtgcctcgg    900

gctgaggaag aaaaggccat ggatttttct gtcctttggg attttgaggg ctatatcaag    960

tactctgcac tcttctatgg ctactacaac aaccagagga ccatcgggtg gctgaggtac   1020

cggctgccta tggcttactt tatggtgggg gtcagcgtgt tcggctacag cctgattatt   1080

gtcattcgat cgatggccag caatacccaa ggaagcacag gcgaagggga gagtgacaac   1140

ttcacattca gcttcaagat gttcaccagc tgggactacc tgatcgggaa ttcagagaca   1200

gctgataaca aatatgcatc catcaccacc agcttcaagg aatcaatagt ggatgaacaa   1260

gagagtaaca aagaagaaaa tatccatctg acaagatttc ttcgtgtcct ggccaacttt   1320

ctcatcatct gctgtttgtg tggaagtggg tacctcattt actttgtggt taagcgatct   1380

cagcaattct ccaaaatgca gaatgtcagc tggtatgaaa ggaatgaggt agagatcgtg   1440

atgtccctgc ttggaatgtt ttgtccccct ctgtttgaaa ccatcgctgc cctggagaat   1500

taccacccac gcactggact gaagtggcag ctgggacgca tctttgcact cttcctgggg   1560

aacctctaca catttctctt ggccctgatg gatgacgtcc acctcaagct tgctaatgaa   1620

gagacaataa agaacatcac tcactggact ctgtttaact attacaactc ttctggttgg   1680
```

-continued

```
aacgagagtg tcccccgacc acccctgcac cctgcagatg tgccccgggg ttcttgctgg   1740

gagacagctg tgggcattga attcatgagg ctgacggtgt ctgacatgct ggtaacgtac   1800

atcaccatcc tgctggggga cttcctacgg gcttgttttg tgcggttcat gaactactgc   1860

tggtgctggg acttggaggc tggatttcct tcatatgctg agtttgatat tagtggaaat   1920

gtgctgggtt tgatcttcaa ccaaggaatg atctggatgg gctccttcta tgctccaggc   1980

ctggtgggca ttaatgtgct gcgcctgctg acctccatgt acttccagtg ctgggcggtg   2040

atgagcagca acgtacccca tgaacgcgtg ttcaaagcct cccgatccaa caacttctac   2100

atgggcctcc tgctgctggt gctcttcctc agcctcctgc cggtggccta caccatcatg   2160

tccctcccac cctcctttga ctgcgggccg ttcagtggga aaaacagaat gtacgatgtc   2220

ctccaagaga ccattgaaaa cgatttccca accttcctgg gcaagatctt tgctttcctc   2280

gccaatccag gcctgatcat cccagccatc ctgctgatgt tcttggccat ttactacctg   2340

aactcagttt ccaaaagcct ttcccgagct aatgcccagc tgaggaagaa aatccaagtg   2400

ctccgtgaag ttgagaagag tcacaaatct gtaaaaggca aagccacagc cagagattca   2460

gaggacacac ctaaaagcag ctccaaaaat gccacccagc tccaactcac caaggaagag   2520

accactcctc cctctgccag ccaaagccag gccatggaca agaaggcgca gggccctggg   2580

acctccaatt ctgccagcag gaccacactg cctgcctctg gacaccttcc tatatctcgg   2640

ccccctggaa tcggaccaga ttctggccac gccccatctc agactcatcc gtggaggtca   2700

gcctctggaa agagtgctca gagacctccc cactgatggc taggactcca gggagcctcg   2760

accctagggc tgatcctcaa gtaccccagt ttcacacata ccaaaccaag gttctctccc   2820

ctctttcctc tcacatacat gctctgtctc ctctcttgga atgcatgaac tttgattcct   2880

tcaggccctt gtcagctacc gaaggaggaa gacagtggct tcacctgtcc tttagggaag   2940

ctggagccat ctctgcacta actgccctcc caaatatctt ggttcagaca gctctgaacc   3000

ccacgctcac agtggtcgac cttgcctccc gattttcgga gttggggaag ggccatgacc   3060

accctcgtag actttttcca tgggatacag tttaggacac gggtttctgc cagcttccct   3120

aaccaggagg gggatggaga agggcctaca tttctcaatc cagaggaag              3169
```

<210> SEQ ID NO 8
<211> LENGTH: 552
<212> TYPE: PRT
<213> ORGANISM: Homo sapiens

<400> SEQUENCE: 8

```
Met Asp Arg Lys Val Ala Arg Glu Phe Arg His Lys Val Asp Phe Leu
1               5                   10                  15

Ile Glu Asn Asp Ala Glu Lys Asp Tyr Leu Tyr Asp Val Leu Arg Met
            20                  25                  30

Tyr His Gln Thr Met Asp Val Ala Val Leu Val Gly Asp Leu Lys Leu
        35                  40                  45

Val Ile Asn Glu Pro Ser Arg Leu Pro Leu Phe Asp Ala Ile Arg Pro
    50                  55                  60

Leu Ile Pro Leu Lys His Gln Val Glu Tyr Asp Gln Leu Thr Pro Arg
65                  70                  75                  80

Arg Ser Arg Lys Leu Lys Glu Val Arg Leu Asp Arg Leu His Pro Glu
                85                  90                  95

Gly Leu Gly Leu Ser Val Arg Gly Gly Leu Glu Phe Gly Cys Gly Leu
            100                 105                 110
```

```
Phe Ile Ser His Leu Ile Lys Gly Gly Gln Ala Asp Ser Val Gly Leu
        115                 120                 125

Gln Val Gly Asp Glu Ile Val Arg Ile Asn Gly Tyr Ser Ile Ser Ser
    130                 135                 140

Cys Thr His Glu Glu Val Ile Asn Leu Ile Arg Thr Lys Lys Thr Val
145                 150                 155                 160

Ser Ile Lys Val Arg His Ile Gly Leu Ile Pro Val Lys Ser Ser Pro
                165                 170                 175

Asp Glu Pro Leu Thr Trp Gln Tyr Val Asp Gln Phe Val Ser Glu Ser
            180                 185                 190

Gly Gly Val Arg Gly Ser Leu Gly Ser Pro Gly Asn Arg Glu Asn Lys
        195                 200                 205

Glu Lys Lys Val Phe Ile Ser Leu Val Gly Ser Arg Gly Leu Gly Cys
    210                 215                 220

Ser Ile Ser Ser Gly Pro Ile Gln Lys Pro Gly Ile Phe Ile Ser His
225                 230                 235                 240

Val Lys Pro Gly Ser Leu Ser Ala Glu Val Gly Leu Glu Ile Gly Asp
                245                 250                 255

Gln Ile Val Glu Val Asn Gly Val Asp Phe Ser Asn Leu Asp His Lys
            260                 265                 270

Glu Ala Val Asn Val Leu Lys Ser Ser Arg Ser Leu Thr Ile Ser Ile
        275                 280                 285

Val Ala Ala Ala Gly Arg Glu Leu Phe Met Thr Asp Arg Glu Arg Leu
    290                 295                 300

Ala Glu Ala Arg Gln Arg Glu Leu Gln Arg Gln Glu Leu Leu Met Gln
305                 310                 315                 320

Lys Arg Leu Ala Met Glu Ser Asn Lys Ile Leu Gln Glu Gln Gln Glu
                325                 330                 335

Met Glu Arg Gln Arg Arg Lys Glu Ile Ala Gln Lys Ala Ala Glu Glu
            340                 345                 350

Asn Glu Arg Tyr Arg Lys Glu Met Glu Gln Ile Val Glu Glu Glu Glu
        355                 360                 365

Lys Phe Lys Lys Gln Trp Glu Glu Asp Trp Gly Ser Lys Glu Gln Leu
    370                 375                 380

Leu Leu Pro Lys Thr Ile Thr Ala Glu Val His Pro Val Pro Leu Arg
385                 390                 395                 400

Lys Pro Lys Tyr Asp Gln Gly Val Glu Pro Glu Leu Glu Pro Ala Asp
                405                 410                 415

Asp Leu Asp Gly Gly Thr Glu Glu Gln Gly Glu Gln Asp Phe Arg Lys
            420                 425                 430

Tyr Glu Glu Gly Phe Asp Pro Tyr Ser Met Phe Thr Pro Glu Gln Ile
        435                 440                 445

Met Gly Lys Asp Val Arg Leu Leu Arg Ile Lys Lys Glu Gly Ser Leu
    450                 455                 460

Asp Leu Ala Leu Glu Gly Gly Val Asp Ser Pro Ile Gly Lys Val Val
465                 470                 475                 480

Val Ser Ala Val Tyr Glu Arg Gly Ala Ala Glu Arg His Gly Gly Ile
                485                 490                 495

Val Lys Gly Asp Glu Ile Met Ala Ile Asn Gly Lys Ile Val Thr Asp
            500                 505                 510

Tyr Thr Leu Ala Glu Ala Glu Ala Ala Leu Gln Lys Ala Trp Asn Gln
        515                 520                 525
```

-continued

```
Gly Gly Asp Trp Ile Asp Leu Val Val Ala Val Cys Pro Pro Lys Glu
    530                 535                 540

Tyr Asp Asp Glu Leu Thr Phe Phe
545                 550


<210> SEQ ID NO 9
<211> LENGTH: 2237
<212> TYPE: DNA
<213> ORGANISM: Homo sapiens

<400> SEQUENCE: 9

agctccgagg gcggctggcc cggtcgcggt cgcggctctt tccagctcct ggcagccggg      60

cacccgaagg aacgggtcgt gcaacgacgc agctggacct ggcccagcca tggaccgaaa     120

agtggcccga gaattccggc ataaggtgga ttttctgatt gaaaatgatg cagagaagga     180

ctatctctat gatgtgctgc gaatgtacca ccagaccatg gacgtggccg tgctcgtggg     240

agacctgaag ctggtcatca atgaacccag ccgtctgcct ctgtttgatg ccattcggcc     300

gctgatccca ctgaagcacc aggtggaata tgatcagctg acccccccggc gctccaggaa     360

gctgaaggag gtgcgtctgg accgtctgca ccccgaaggc ctcggcctga gtgtgcgtgg     420

tggcctggag tttggctgtg ggctcttcat ctcccacctc atcaaaggcg gtcaggcaga     480

cagcgtcggg ctccaggtag gggacgagat cgtccggatc aatggatatt ccatctcctc     540

ctgtacccat gaggaggtca tcaacctcat tcgaaccaag aaaactgtgt ccatcaaagt     600

gagacacatc ggcctgatcc ccgtgaaaag ctctcctgat gagcccctca cttggcagta     660

tgtggatcag tttgtgtcgg aatctggggg cgtgcgaggc agcctgggct cccctggaaa     720

tcgggaaaac aaggagaaga aggtcttcat cagcctggta ggctcccgag gccttggctg     780

cagcatttcc agcggcccca tccagaagcc tggcatcttt atcagccatg tgaaacctgg     840

ctccctgtct gctgaggtgg gattggagat aggggaccag attgtcgaag tcaatggcgt     900

cgacttctct aacctggatc acaaggaggc tgtaaatgtg ctgaagagta gccgcagcct     960

gaccatctcc attgtagctg cagctggccg ggagctgttc atgacagacc gggagcggct    1020

ggcagaggcg cggcagcgtg agctgcagcg gcaggagctt ctcatgcaga agcggctggc    1080

gatggagtcc aacaagatcc tccaggagca gcaggagatg gagcggcaaa ggagaaaaga    1140

aattgcccag aaggcagcag aggaaaatga gagataccgg aaggagatgg aacagattgt    1200

agaggaggaa gagaagttta agaagcaatg ggaagaagac tggggctcaa aggaacagct    1260

actcttgcct aaaaccatca ctgctgaggt acacccagta ccccttcgca agccaaagta    1320

tgatcaggga gtggaacctg agctcgagcc cgcagatgac ctggatggag gcacggagga    1380

gcagggagag caggatttcc ggaaatatga ggaaggcttt gacccctact ctatgttcac    1440

cccagagcag atcatgggga aggatgtccg gctcctacgc atcaagaagg agggatcctt    1500

agacctggcc ctggaaggcg gtgtggactc ccccattggg aaggtggtcg tttctgctgt    1560

gtatgagcgg ggagctgctg agcggcatgg tggcattgtg aaaggggacg agatcatggc    1620

aatcaacggc aagattgtga cagactacac cctggctgag gctgaggctg ccctgcagaa    1680

ggcctggaat cagggcgggg actggatcga ccttgtggtt gccgtctgcc ccccaaagga    1740

gtatgacgat gagctgacct tcttctgaag tccaaaaggg gaaaccaaat tcaccgttag    1800

gaaacagtga gctccggccc cacctcgtga acacaaagcc tcggatcagc cttgagagag    1860

gccacactac acacaccaga tggcatcctt gggacctgaa tctatcaccc aggaatctca    1920

aactcccttt ggccctgaac cagggccaga taaggaacag ctcgggccac tcttctgaag    1980
```

-continued gccaacgtgg aggaaaggga gcagccagcc atttgggaga agatctcaag gatccagact 2040
ctcattcctt tcctctggcc cagtgaattt ggtctctccc agctctgggg gactccttcc 2100
ttgaacccta ataagacccc actggagtct ctctctctcc atccctctcc tctgccctct 2160
gctctaattg ctgccaggat tgtcactcca aaccttactc tgagctcatt aataaaatag 2220
atttattttc cagctta 2237

<210> SEQ ID NO 10
<211> LENGTH: 2385
<212> TYPE: DNA
<213> ORGANISM: Homo sapiens

<400> SEQUENCE: 10
agctccgagg gcggctggcc cggtcgcggt cgcggctctt tccagctcct ggcagccggg 60
cacccgaagg aacgggtcgt gcaacgacgc agctggacct ggcccagcca tggaccgaaa 120
agtggcccga gaattccggc ataaggtgga ttttctgatt gaaaatgatg cagagaagga 180
ctatctctat gatgtgctgc gaatgtacca ccagaccatg gacgtggccg tgctcgtggg 240
agacctgaag ctggtcatca atgaacccag ccgtctgcct ctgtttgatg ccattcggcc 300
gctgatccca ctgaagcacc aggtggaata tgatcagctg accccccggc gctccaggaa 360
gctgaaggag gtgcgtctgg accgtctgca ccccgaaggc ctcggcctga gtgtgcgtgg 420
tggcctggag tttggctgtg ggctcttcat ctcccacctc atcaaaggcg gtcaggcaga 480
cagcgtcggg ctccaggtag gggacgagat cgtccggatc aatggatatt ccatctcctc 540
ctgtacccat gaggaggtca tcaacctcat tcgaaccaag aaaactgtgt ccatcaaagt 600
gagacacatc ggcctgatcc ccgtgaaaag ctctcctgat gagcccctca cttggcagta 660
tgtggatcag tttgtgtcgg aatctggggg cgtgcgaggc agcctgggct cccctggaaa 720
tcgggaaaac aaggagaaga aggtcttcat cagcctggta ggctcccgag gccttggctg 780
cagcatttcc agcggcccca tccagaagcc tggcatcttt atcagccatg tgaaacctgg 840
ctccctgtct gctgaggtgg gattggagat aggggaccag attgtcgaag tcaatggcgt 900
cgacttctct aacctggatc acaaggaggc tgtaaatgtg ctgaagagta gccgcagcct 960
gaccatctcc attgtagctg cagctggccg ggagctgttc atgacagacc gggagcggct 1020
ggcagaggcg cggcagcgtg agctgcagcg gcaggagctt ctcatgcaga agcggctggc 1080
gatggagtcc aacaagatcc tccaggagca gcaggagatg gagcggcaaa ggagaaaaga 1140
aattgcccag aaggcagcag aggaaaatga gagataccgg aaggagatgg aacagattgt 1200
agaggaggaa gagaagttta agaagcaatg ggaagaagac tggggctcaa aggaacagct 1260
actcttgcct aaaaccatca ctgctgaggt acacccagta ccccttcgca agccaaagta 1320
tgatcaggga gtggaacctg agctcgagcc cgcagatgac ctggatggag gcacggagga 1380
gcagggagag cagaaaggaa aagataagaa gaaagccaag tatggcagcc tgcaggactt 1440
gagaaagaat aagaaagaac tggagtttga gcaaaagctt tacaaagaga aagaggaaat 1500
gctggagaag gaaaagcagc taaagatcaa ccggctggcc caggaggatt tccggaaata 1560
tgaggaaggc tttgacccct actctatgtt caccccagag cagatcatgg ggaaggatgt 1620
ccggctccta cgcatcaaga aggagggatc cttagacctg gccctggaag gcggtgtgga 1680
ctcccccatt gggaaggtgg tcgtttctgc tgtgtatgag cggggagctg ctgagcggca 1740
tggtggcatt gtgaaagggg acgagatcat ggcaatcaac ggcaagattg tgacagacta 1800

```
caccctggct gaggctgagg ctgccctgca gaaggcctgg aatcagggcg gggactggat    1860

cgaccttgtg gttgccgtct gccccccaaa ggagtatgac gatgagctga ccttcttctg    1920

aagtccaaaa ggggaaacca aattcaccgt taggaaacag tgagctccgg ccccacctcg    1980

tgaacacaaa gcctcggatc agccttgaga gaggccacac tacacacacc agatggcatc    2040

cttgggacct gaatctatca cccaggaatc tcaaactccc tttggccctg aaccagggcc    2100

agataaggaa cagctcgggc cactcttctg aaggccaacg tggaggaaag ggagcagcca    2160

gccatttggg agaagatctc aaggatccag actctcattc ctttcctctg cccagtgaa    2220

tttggtctct cccagctctg ggggactcct tccttgaacc ctaataagac cccactggag    2280

tctctctctc tccatccctc tcctctgccc tctgctctaa ttgctgccag gattgtcact    2340

ccaaacctta ctctgagctc attaataaaa tagatttatt ttcca                    2385
```

<210> SEQ ID NO 11
<211> LENGTH: 899
<212> TYPE: PRT
<213> ORGANISM: Homo sapiens

<400> SEQUENCE: 11

```
Met Asp Arg Lys Val Ala Arg Glu Phe Arg His Lys Val Asp Phe Leu
1               5                   10                  15

Ile Glu Asn Asp Ala Glu Lys Asp Tyr Leu Tyr Asp Val Leu Arg Met
            20                  25                  30

Tyr His Gln Thr Met Asp Val Ala Val Leu Val Gly Asp Leu Lys Leu
        35                  40                  45

Val Ile Asn Glu Pro Ser Arg Leu Pro Leu Phe Asp Ala Ile Arg Pro
    50                  55                  60

Leu Ile Pro Leu Lys His Gln Val Glu Tyr Asp Gln Leu Thr Pro Arg
65                  70                  75                  80

Arg Ser Arg Lys Leu Lys Glu Val Arg Leu Asp Arg Leu His Pro Glu
                85                  90                  95

Gly Leu Gly Leu Ser Val Arg Gly Gly Leu Glu Phe Gly Cys Gly Leu
            100                 105                 110

Phe Ile Ser His Leu Ile Lys Gly Gly Gln Ala Asp Ser Val Gly Leu
        115                 120                 125

Gln Val Gly Asp Glu Ile Val Arg Ile Asn Gly Tyr Ser Ile Ser Ser
    130                 135                 140

Cys Thr His Glu Glu Val Ile Asn Leu Ile Arg Thr Lys Lys Thr Val
145                 150                 155                 160

Ser Ile Lys Val Arg His Ile Gly Leu Ile Pro Val Lys Ser Ser Pro
                165                 170                 175

Asp Glu Pro Leu Thr Trp Gln Tyr Val Asp Gln Phe Val Ser Glu Ser
            180                 185                 190

Gly Gly Val Arg Gly Ser Leu Gly Ser Pro Gly Asn Arg Glu Asn Lys
        195                 200                 205

Glu Lys Lys Val Phe Ile Ser Leu Val Gly Ser Arg Gly Leu Gly Cys
    210                 215                 220

Ser Ile Ser Ser Gly Pro Ile Gln Lys Pro Gly Ile Phe Ile Ser His
225                 230                 235                 240

Val Lys Pro Gly Ser Leu Ser Ala Glu Val Gly Leu Glu Ile Gly Asp
                245                 250                 255

Gln Ile Val Glu Val Asn Gly Val Asp Phe Ser Asn Leu Asp His Lys
            260                 265                 270
```

-continued

```
Glu Ala Val Asn Val Leu Lys Ser Ser Arg Ser Leu Thr Ile Ser Ile
        275                 280                 285

Val Ala Ala Ala Gly Arg Glu Leu Phe Met Thr Asp Arg Glu Arg Leu
    290                 295                 300

Ala Glu Ala Arg Gln Arg Glu Leu Gln Arg Gln Glu Leu Leu Met Gln
305                 310                 315                 320

Lys Arg Leu Ala Met Glu Ser Asn Lys Ile Leu Gln Glu Gln Gln Glu
                325                 330                 335

Met Glu Arg Gln Arg Arg Lys Glu Ile Ala Gln Lys Ala Ala Glu Glu
            340                 345                 350

Asn Glu Arg Tyr Arg Lys Glu Met Glu Gln Ile Val Glu Glu Glu Glu
        355                 360                 365

Lys Phe Lys Lys Gln Trp Glu Glu Asp Trp Gly Ser Lys Glu Gln Leu
    370                 375                 380

Leu Leu Pro Lys Thr Ile Thr Ala Glu Val His Pro Val Pro Leu Arg
385                 390                 395                 400

Lys Pro Lys Ser Phe Gly Trp Phe Tyr Arg Tyr Asp Gly Lys Phe Pro
                405                 410                 415

Thr Ile Arg Lys Lys Gly Lys Asp Lys Lys Lys Ala Lys Tyr Gly Ser
            420                 425                 430

Leu Gln Asp Leu Arg Lys Asn Lys Lys Glu Leu Glu Phe Glu Gln Lys
        435                 440                 445

Leu Tyr Lys Glu Lys Glu Glu Met Leu Glu Lys Glu Lys Gln Leu Lys
    450                 455                 460

Ile Asn Arg Leu Ala Gln Glu Val Ser Glu Thr Glu Arg Glu Asp Leu
465                 470                 475                 480

Glu Glu Ser Glu Lys Ile Gln Tyr Trp Val Glu Arg Leu Cys Gln Thr
                485                 490                 495

Arg Leu Glu Gln Ile Ser Ser Ala Asp Asn Glu Ile Ser Glu Met Thr
            500                 505                 510

Thr Gly Pro Pro Pro Pro Pro Pro Ser Val Ser Pro Leu Ala Pro Pro
        515                 520                 525

Leu Arg Arg Phe Ala Gly Gly Leu His Leu His Thr Thr Asp Leu Asp
    530                 535                 540

Asp Ile Pro Leu Asp Met Phe Tyr Tyr Pro Pro Lys Thr Pro Ser Ala
545                 550                 555                 560

Leu Pro Val Met Pro His Pro Pro Pro Ser Asn Pro Pro His Lys Val
                565                 570                 575

Pro Ala Pro Pro Val Leu Pro Leu Ser Gly His Val Ser Ala Ser Ser
            580                 585                 590

Ser Pro Trp Val Gln Arg Thr Pro Pro Pro Ile Pro Ile Pro Pro Pro
        595                 600                 605

Pro Ser Val Pro Thr Gln Asp Leu Thr Pro Thr Arg Pro Leu Pro Ser
    610                 615                 620

Ala Leu Glu Glu Ala Leu Ser Asn His Pro Phe Arg Thr Gly Asp Thr
625                 630                 635                 640

Gly Asn Pro Val Glu Asp Trp Glu Ala Lys Asn His Ser Gly Lys Pro
                645                 650                 655

Thr Asn Ser Pro Val Pro Glu Gln Ser Phe Pro Pro Thr Pro Lys Thr
            660                 665                 670

Phe Cys Pro Ser Pro Gln Pro Pro Arg Gly Pro Gly Val Ser Thr Ile
        675                 680                 685

Ser Lys Pro Val Met Val His Gln Glu Pro Asn Phe Ile Tyr Arg Pro
```

-continued

```
    690                 695                 700

Ala Val Lys Ser Glu Val Leu Pro Gln Glu Met Leu Lys Arg Met Val
705                 710                 715                 720

Val Tyr Gln Thr Ala Phe Arg Gln Asp Phe Arg Lys Tyr Glu Glu Gly
                725                 730                 735

Phe Asp Pro Tyr Ser Met Phe Thr Pro Glu Gln Ile Met Gly Lys Asp
            740                 745                 750

Val Arg Leu Leu Arg Ile Lys Lys Glu Gly Ser Leu Asp Leu Ala Leu
        755                 760                 765

Glu Gly Gly Val Asp Ser Pro Ile Gly Lys Val Val Val Ser Ala Val
    770                 775                 780

Tyr Glu Arg Gly Ala Ala Glu Arg His Gly Gly Ile Val Lys Gly Asp
785                 790                 795                 800

Glu Ile Met Ala Ile Asn Gly Lys Ile Val Thr Asp Tyr Thr Leu Ala
                805                 810                 815

Glu Ala Glu Ala Ala Leu Gln Lys Ala Trp Asn Gln Gly Gly Asp Trp
            820                 825                 830

Ile Asp Leu Val Val Ala Val Cys Pro Pro Lys Glu Tyr Asp Asp Glu
        835                 840                 845

Leu Ala Ser Leu Pro Ser Ser Val Ala Glu Ser Pro Gln Pro Val Arg
    850                 855                 860

Lys Leu Leu Glu Asp Arg Ala Ala Val His Arg His Gly Phe Leu Leu
865                 870                 875                 880

Gln Leu Glu Pro Thr Asp Leu Leu Leu Lys Ser Lys Arg Gly Asn Gln
                885                 890                 895

Ile His Arg


<210> SEQ ID NO 12
<211> LENGTH: 2180
<212> TYPE: DNA
<213> ORGANISM: Homo sapiens

<400> SEQUENCE: 12

agctccgagg gcggctggcc cggtcgcggt cgcggctctt tccagctcct ggcagccggg     60

cacccgaagg aacgggtcgt gcaacgacgc agctggacct ggcccagcca tggaccgaaa    120

agtggcccga gaattccggc ataaggtgga ttttctgatt gaaaatgatg cagagaagga    180

ctatctctat gatgtgctgc gaatgtacca ccagaccatg gacgtggccg tgctcgtggg    240

agacctgaag ctggtcatca atgaacccag ccgtctgcct ctgtttgatg ccattcggcc    300

gctgatccca ctgaagcacc aggtggaata tgatcagctg accccccggc gctccaggaa    360

gctgaaggag gtgcgtctgg accgtctgca ccccgaaggc ctcggcctga gtgtgcgtgg    420

tggcctggag tttggctgtg ggctcttcat ctcccacctc atcaaaggcg gtcaggcaga    480

cagcgtcggg ctccaggtag gggacgagat cgtccggatc aatggatatt ccatctcctc    540

ctgtacccat gaggaggtca tcaacctcat tcgaaccaag aaaactgtgt ccatcaaagt    600

gagacacatc ggcctgatcc ccgtgaaaag ctctcctgat gagcccctca cttggcagta    660

tgtggatcag tttgtgtcgg aatctggggg cgtgcgaggc agcctgggct cccctggaaa    720

tcgggaaaac aaggagaaga aggtcttcat cagcctggta ggctcccgag gccttggctg    780

cagcatttcc agcggcccca tccagaagcc tggcatcttt atcagccatg tgaaacctgg    840

ctccctgtct gctgaggtgg gattggagat aggggaccag attgtcgaag tcaatggcgt    900

cgacttctct aacctggatc acaaggaggg ccgggagctg ttcatgacag accgggagcg    960
```

```
gctggcagag gcgcggcagc gtgagctgca gcggcaggag cttctcatgc agaagcggct   1020

ggcgatggag tccaacaaga tcctccagga gcagcaggag atggagcggc aaaggagaaa   1080

agaaattgcc cagaaggcag cagaggaaaa tgagagatac cggaaggaga tggaacagat   1140

tgtagaggag gaagagaagt ttaagaagca atgggaagaa gactggggct caaaggaaca   1200

gctactcttg cctaaaacca tcactgctga ggtacaccca gtaccccttc gcaagccaaa   1260

gtatgatcag ggagtggaac ctgagctcga gcccgcagat gacctggatg gaggcacgga   1320

ggagcaggga gagcaggatt tccggaaata tgaggaaggc tttgacccct actctatgtt   1380

caccccagag cagatcatgg ggaaggatgt ccggctccta cgcatcaaga aggagggatc   1440

cttagacctg gccctggaag gcggtgtgga ctcccccatt gggaaggtgg tcgtttctgc   1500

tgtgtatgag cggggagctg ctgagcggca tggtggcatt gtgaaagggg acgagatcat   1560

ggcaatcaac ggcaagattg tgacagacta caccctggct gaggctgagg ctgccctgca   1620

gaaggcctgg aatcagggcg gggactggat cgaccttgtg gttgccgtct gcccccccaaa   1680

ggagtatgac gatgagctga ccttcttctg aagtccaaaa ggggaaacca aattcaccgt   1740

taggaaacag tgagctccgg ccccacctcg tgaacacaaa gcctcggatc agccttgaga   1800

gaggccacac tacacacacc agatggcatc cttgggacct gaatctatca cccaggaatc   1860

tcaaactccc tttggccctg aaccagggcc agataaggaa cagctcgggc cactcttctg   1920

aaggccaacg tggaggaaag ggagcagcca gccatttggg agaagatctc aaggatccag   1980

actctcattc ctttcctctg gcccagtgaa tttggtctct cccagctctg gggactcct   2040

tccttgaacc ctaataagac cccactggag tctctctctc tccatccctc tcctctgccc   2100

tctgctctaa ttgctgccag gattgtcact ccaaacctta ctctgagctc attaataaaa   2160

tagatttatt ttccagctta                                               2180
```

<210> SEQ ID NO 13
<211> LENGTH: 533
<212> TYPE: PRT
<213> ORGANISM: Homo sapiens

<400> SEQUENCE: 13

```
Met Asp Arg Lys Val Ala Arg Glu Phe Arg His Lys Val Asp Phe Leu
1               5                   10                  15

Ile Glu Asn Asp Ala Glu Lys Asp Tyr Leu Tyr Asp Val Leu Arg Met
            20                  25                  30

Tyr His Gln Thr Met Asp Val Ala Val Leu Val Gly Asp Leu Lys Leu
        35                  40                  45

Val Ile Asn Glu Pro Ser Arg Leu Pro Leu Phe Asp Ala Ile Arg Pro
    50                  55                  60

Leu Ile Pro Leu Lys His Gln Val Glu Tyr Asp Gln Leu Thr Pro Arg
65                  70                  75                  80

Arg Ser Arg Lys Leu Lys Glu Val Arg Leu Asp Arg Leu His Pro Glu
                85                  90                  95

Gly Leu Gly Leu Ser Val Arg Gly Gly Leu Glu Phe Gly Cys Gly Leu
            100                 105                 110

Phe Ile Ser His Leu Ile Lys Gly Gly Gln Ala Asp Ser Val Gly Leu
        115                 120                 125

Gln Val Gly Asp Glu Ile Val Arg Ile Asn Gly Tyr Ser Ile Ser Ser
    130                 135                 140

Cys Thr His Glu Glu Val Ile Asn Leu Ile Arg Thr Lys Lys Thr Val
```

-continued

```
145                 150                 155                 160

Ser Ile Lys Val Arg His Ile Gly Leu Ile Pro Val Lys Ser Ser Pro
                165                 170                 175

Asp Glu Pro Leu Thr Trp Gln Tyr Val Asp Gln Phe Val Ser Glu Ser
            180                 185                 190

Gly Gly Val Arg Gly Ser Leu Gly Ser Pro Gly Asn Arg Glu Asn Lys
        195                 200                 205

Glu Lys Lys Val Phe Ile Ser Leu Val Gly Ser Arg Gly Leu Gly Cys
    210                 215                 220

Ser Ile Ser Ser Gly Pro Ile Gln Lys Pro Gly Ile Phe Ile Ser His
225                 230                 235                 240

Val Lys Pro Gly Ser Leu Ser Ala Glu Val Gly Leu Glu Ile Gly Asp
                245                 250                 255

Gln Ile Val Glu Val Asn Gly Val Asp Phe Ser Asn Leu Asp His Lys
            260                 265                 270

Glu Gly Arg Glu Leu Phe Met Thr Asp Arg Glu Arg Leu Ala Glu Ala
        275                 280                 285

Arg Gln Arg Glu Leu Gln Arg Gln Glu Leu Leu Met Gln Lys Arg Leu
    290                 295                 300

Ala Met Glu Ser Asn Lys Ile Leu Gln Glu Gln Gln Glu Met Glu Arg
305                 310                 315                 320

Gln Arg Arg Lys Glu Ile Ala Gln Lys Ala Ala Glu Glu Asn Glu Arg
                325                 330                 335

Tyr Arg Lys Glu Met Glu Gln Ile Val Glu Glu Glu Glu Lys Phe Lys
            340                 345                 350

Lys Gln Trp Glu Glu Asp Trp Gly Ser Lys Glu Gln Leu Leu Leu Pro
        355                 360                 365

Lys Thr Ile Thr Ala Glu Val His Pro Val Pro Leu Arg Lys Pro Lys
    370                 375                 380

Tyr Asp Gln Gly Val Glu Pro Glu Leu Glu Pro Ala Asp Asp Leu Asp
385                 390                 395                 400

Gly Gly Thr Glu Glu Gln Gly Glu Gln Asp Phe Arg Lys Tyr Glu Glu
                405                 410                 415

Gly Phe Asp Pro Tyr Ser Met Phe Thr Pro Glu Gln Ile Met Gly Lys
            420                 425                 430

Asp Val Arg Leu Leu Arg Ile Lys Lys Glu Gly Ser Leu Asp Leu Ala
        435                 440                 445

Leu Glu Gly Gly Val Asp Ser Pro Ile Gly Lys Val Val Val Ser Ala
    450                 455                 460

Val Tyr Glu Arg Gly Ala Ala Glu Arg His Gly Gly Ile Val Lys Gly
465                 470                 475                 480

Asp Glu Ile Met Ala Ile Asn Gly Lys Ile Val Thr Asp Tyr Thr Leu
                485                 490                 495

Ala Glu Ala Glu Ala Ala Leu Gln Lys Ala Trp Asn Gln Gly Gly Asp
            500                 505                 510

Trp Ile Asp Leu Val Val Ala Val Cys Pro Pro Lys Glu Tyr Asp Asp
        515                 520                 525

Glu Leu Thr Phe Phe
    530
```

<210> SEQ ID NO 14
<211> LENGTH: 695
<212> TYPE: PRT
<213> ORGANISM: Homo sapiens

<400> SEQUENCE: 14

Met Ala Glu Ala Pro Pro Arg Arg Leu Gly Leu Gly Pro Pro Pro Gly
1               5                   10                  15

Asp Ala Pro Arg Ala Glu Leu Val Ala Leu Thr Ala Val Gln Ser Glu
            20                  25                  30

Gln Gly Glu Ala Gly Gly Gly Gly Ser Pro Arg Arg Leu Gly Leu Leu
        35                  40                  45

Gly Ser Pro Leu Pro Pro Gly Ala Pro Leu Pro Gly Pro Gly Ser Gly
    50                  55                  60

Ser Gly Ser Ala Cys Gly Gln Arg Ser Ser Ala Ala His Lys Arg Tyr
65                  70                  75                  80

Arg Arg Leu Gln Asn Trp Val Tyr Asn Val Leu Glu Arg Pro Arg Gly
                85                  90                  95

Trp Ala Phe Val Tyr His Val Phe Ile Phe Leu Leu Val Phe Ser Cys
            100                 105                 110

Leu Val Leu Ser Val Leu Ser Thr Ile Gln Glu His Gln Glu Leu Ala
        115                 120                 125

Asn Glu Cys Leu Leu Ile Leu Glu Phe Val Met Ile Val Val Phe Gly
    130                 135                 140

Leu Glu Tyr Ile Val Arg Val Trp Ser Ala Gly Cys Cys Cys Arg Tyr
145                 150                 155                 160

Arg Gly Trp Gln Gly Arg Phe Arg Phe Ala Arg Lys Pro Phe Cys Val
                165                 170                 175

Ile Asp Phe Ile Val Phe Val Ala Ser Val Ala Val Ile Ala Ala Gly
            180                 185                 190

Thr Gln Gly Asn Ile Phe Ala Thr Ser Ala Leu Arg Ser Met Arg Phe
        195                 200                 205

Leu Gln Ile Leu Arg Met Val Arg Met Asp Arg Arg Gly Gly Thr Trp
    210                 215                 220

Lys Leu Leu Gly Ser Val Val Tyr Ala His Ser Lys Glu Leu Ile Thr
225                 230                 235                 240

Ala Trp Tyr Ile Gly Phe Leu Val Leu Ile Phe Ala Ser Phe Leu Val
                245                 250                 255

Tyr Leu Ala Glu Lys Asp Ala Asn Ser Asp Phe Ser Ser Tyr Ala Asp
            260                 265                 270

Ser Leu Trp Trp Gly Thr Ile Thr Leu Thr Thr Ile Gly Tyr Gly Asp
        275                 280                 285

Lys Thr Pro His Thr Trp Leu Gly Arg Val Leu Ala Ala Gly Phe Ala
    290                 295                 300

Leu Leu Gly Ile Ser Phe Phe Ala Leu Pro Ala Gly Ile Leu Gly Ser
305                 310                 315                 320

Gly Phe Ala Leu Lys Val Gln Glu Gln His Arg Gln Lys His Phe Glu
                325                 330                 335

Lys Arg Arg Met Pro Ala Ala Asn Leu Ile Gln Ala Ala Trp Arg Leu
            340                 345                 350

Tyr Ser Thr Asp Met Ser Arg Ala Tyr Leu Thr Ala Thr Trp Tyr Tyr
        355                 360                 365

Tyr Asp Ser Ile Leu Pro Ser Phe Arg Glu Leu Ala Leu Leu Phe Glu
    370                 375                 380

His Val Gln Arg Ala Arg Asn Gly Gly Leu Arg Pro Leu Glu Val Arg
385                 390                 395                 400

Arg Ala Pro Val Pro Asp Gly Ala Pro Ser Arg Tyr Pro Pro Val Ala

```
                405                 410                 415

Thr Cys His Arg Pro Gly Ser Thr Ser Phe Cys Pro Gly Glu Ser Ser
            420                 425                 430

Arg Met Gly Ile Lys Asp Arg Ile Arg Met Gly Ser Ser Gln Arg Arg
        435                 440                 445

Thr Gly Pro Ser Lys Gln His Leu Ala Pro Pro Thr Met Pro Thr Ser
    450                 455                 460

Pro Ser Ser Glu Gln Val Gly Glu Ala Thr Ser Pro Thr Lys Val Gln
465                 470                 475                 480

Lys Ser Trp Ser Phe Asn Asp Arg Thr Arg Phe Arg Ala Ser Leu Arg
                485                 490                 495

Leu Lys Pro Arg Thr Ser Ala Glu Asp Ala Pro Ser Glu Glu Val Ala
            500                 505                 510

Glu Glu Lys Ser Tyr Gln Cys Glu Leu Thr Val Asp Asp Ile Met Pro
        515                 520                 525

Ala Val Lys Thr Val Ile Arg Ser Ile Arg Ile Leu Lys Phe Leu Val
    530                 535                 540

Ala Lys Arg Lys Phe Lys Glu Thr Leu Arg Pro Tyr Asp Val Lys Asp
545                 550                 555                 560

Val Ile Glu Gln Tyr Ser Ala Gly His Leu Asp Met Leu Gly Arg Ile
                565                 570                 575

Lys Ser Leu Gln Thr Arg Val Asp Gln Ile Val Gly Arg Gly Pro Gly
            580                 585                 590

Asp Arg Lys Ala Arg Glu Lys Gly Asp Lys Gly Pro Ser Asp Ala Glu
        595                 600                 605

Val Val Asp Glu Ile Ser Met Met Gly Arg Val Val Lys Val Glu Lys
    610                 615                 620

Gln Val Gln Ser Ile Glu His Lys Leu Asp Leu Leu Leu Gly Phe Tyr
625                 630                 635                 640

Ser Arg Cys Leu Arg Ser Gly Thr Ser Ala Ser Leu Gly Ala Val Gln
                645                 650                 655

Val Pro Leu Phe Asp Pro Asp Ile Thr Ser Asp Tyr His Ser Pro Val
            660                 665                 670

Asp His Glu Asp Ile Ser Val Ser Ala Gln Thr Leu Ser Ile Ser Arg
        675                 680                 685

Ser Val Ser Thr Asn Met Asp
    690                 695


<210> SEQ ID NO 15
<211> LENGTH: 4116
<212> TYPE: DNA
<213> ORGANISM: Homo sapiens

<400> SEQUENCE: 15

agccatgcgt ctctgagcgc cccgagcgcg cccccgcccc ggaccgtgcc cgggccccgg      60

cgcccccagc ccggcgccgc ccatggccga ggcccccccg cgccgcctcg gcctgggtcc     120

cccgcccggg gacgcccccc gcgcggagct agtggcgctc acggccgtgc agagcgaaca     180

gggcgaggcg ggcgggggcg gctccccgcg ccgcctcggc ctcctgggca gcccccctgcc     240

gccgggcgcg cccctccctg ggccgggctc cggctcgggc tccgcctgcg gccagcgctc     300

ctcggccgcg cacaagcgct accgccgcct gcagaactgg gtctacaacg tgctggagcg     360

gccccgcggc tgggccttcg tctaccacgt cttcatattt ttgctggtct tcagctgcct     420

ggtgctgtct gtgctgtcca ctatccagga gcaccaggaa cttgccaacg agtgtctcct     480
```

-continued

```
catcttggaa ttcgtgatga tcgtggtttt cggcttggag tacatcgtcc gggtctggtc    540
cgccggatgc tgctgccgct accgaggatg gcagggtcgc ttccgctttg ccagaaagcc    600
cttctgtgtc atcgacttca tcgtgttcgt ggcctcggtg gccgtcatcg ccgcgggtac    660
ccagggcaac atcttcgcca cgtccgcgct gcgcagcatg cgcttcctgc agatcctgcg    720
catggtgcgc atggaccgcc gcggcggcac ctggaagctg ctgggctcag tggtctacgc    780
gcatagcaag gagctgatca ccgcctggta catcgggttc ctggtgctca tcttcgcctc    840
cttcctggtc tacctggctg agaaggacgc caactccgac ttctcctcct acgccgactc    900
gctctggtgg gggacgatta cattgacaac catcggctat ggtgacaaga caccgcacac    960
atggctgggc agggtcctgg ctgctggctt cgccttactg ggcatctctt tctttgccct   1020
gcctgccggc atcctaggct ccggctttgc cctgaaggtc caggagcagc accggcagaa   1080
gcacttcgag aagcggagga tgccggcagc caacctcatc caggctgcct ggcgcctgta   1140
ctccaccgat atgagccggg cctacctgac agccacctgg tactactatg acagtatcct   1200
cccatccttc agagagctgg ccctcttgtt tgagcacgtg caacgggccc gcaatggggg   1260
cctacggccc ctggaggtgc ggcgggcgcc ggtacccgac ggagcaccct cccgttaccc   1320
gcccgttgcc acctgccacc ggccgggcag cacctccttc tgccctgggg aaagcagccg   1380
gatgggcatc aaagaccgca tccgcatggg cagctcccag cggcggacgg gtccttccaa   1440
gcagcatctg gcacctccaa caatgcccac ctccccaagc agcgagcagg tgggtgaggc   1500
caccagcccc accaaggtgc aaaagagctg gagcttcaat gaccgcaccc gcttccgggc   1560
atctctgaga ctcaaacccc gcacctctgc tgaggatgcc ccctcagagg aagtagcaga   1620
ggagaagagc taccagtgtg agctcacggt ggacgacatc atgcctgctg tgaagacagt   1680
catccgctcc atcaggattc tcaagttcct ggtggccaaa aggaaattca aggagacact   1740
gcgaccgtac gacgtgaagg acgtcattga gcagtactca gcaggccacc tggacatgct   1800
gggccggatc aagagcctgc aaactcgggt ggaccaaatt gtgggtcggg ggcccgggga   1860
caggaaggcc cgggagaagg gcgacaaggg gccctccgac gcggaggtgg tggatgaaat   1920
cagcatgatg ggacgcgtgg tcaaggtgga gaagcaggtg cagtccatcg agcacaagct   1980
ggacctgctg ttgggcttct attcgcgctg cctgcgctct ggcacctcgg ccagcctggg   2040
cgccgtgcaa gtgccgctgt tcgaccccga catcacctcc gactaccaca gccctgtgga   2100
ccacgaggac atctccgtct ccgcacagac gctcagcatc tcccgctcgg tcagcaccaa   2160
catggactga gggacttctc agaggcaggg cagcacacgg ccagccccgc ggcctggcgc   2220
tccgactgcc ctctgaggcc tccggactcc tctcgtactt gaactcactc cctcacgggg   2280
agagagacca cacgcagtat tgagctgcct gagtgggcgt ggtacctgct gtgggtgcca   2340
gcgccccttc cccacctcag gagcgtgaga tgccaggtcg cacagagggc agcagcagcg   2400
gccgtcccgc ggcctctggg ccccccagtg ccctgcccac tccatcaagg ccctatgtgg   2460
cccacctggc aggggcacag ccccgggagt gggagcgggc gctggggccc tgggccctga   2520
cccagcttcc agctatgcaa ggtgaggtct ctggcccacc cttcggacac agcagggaag   2580
ccctcccgcc aagtccccgc cccacttggg ggtgggccaa ggtgccccca caggtaccca   2640
caaagcacag gaccctgcca caaggcaggt ggacaccata tatgcaaacc atgttaaata   2700
tgcaactttg gggaccccca tggggtctct ctgtccctcc cccattggga gctgggcccc   2760
cagcagtagc tggtctcagg ctgcttggcc accaccctgt ccctattctt tggcttatca   2820
```

-continued

```
ctccttcccc tcccagcatg gggcctgttt ctcccctgcc ctctcctaag ggcaatgcct   2880

gggcctttct tcccatttgc aagtgtcagc tcccaggggc tccctcctcc tgctgggtgg   2940

ccactcccct ccttggccct ccagacacca ctcatagtca gcacaggttt ctgtatcctc   3000

cccaaaactc ccagacagtg cttcgtggac gatcgcacaa acatagcctt ttagtttctc   3060

cagacaggaa gaaagcctct cacacttaaa catgcaatga cgtgacacac ttggagacat   3120

gagtgcagag ccactcagcc gctcctgggc ctctgcagca gatgccagtg gactggcctt   3180

gcagggtgac gaccactaag aggaagaccc ccaactccat ctgagcagga gaaggagctt   3240

tgaagtaacc cgagagctct ccaggcccca cccagacctt tacccgctcc ccttcttcaa   3300

gaagatctcc tcctctctgg tccaggagcc ctaacccact gcctctgcct gtccccaagg   3360

gcccgcctcc gtgtctccac agcacaactc gggcccaggc ctgacaccac tggagagacc   3420

ccaggcccac ttctagccag gcctgtgcct tcctagtcac tctaactccc agagagaata   3480

agaatgcatg taatagctat accaaccgcg catccggctt tcacatgcac tgtctcccct   3540

ccctccacac cccacttctt cacttcaatt ggcagcgcca catccaggcg tcagccccca   3600

ttcactccag gaacactttc ttatccccac ccctttgctc ctcttctgca aagccaatgc   3660

aggtggcagg aaggtgaggg gtagtggacc aatggcaacc ctctgtggga acaaggggcc   3720

gaggccacgc tgcctgcatc tcgtgctggg gacctgcatg cgccagcacc agggcttgga   3780

ctggatctta ctcagtccat ggtgcccagc ctctgcccca acatgccctc tgcatgtgac   3840

cgtcatgccc tggatggagc cactcctggc tcaccccacc tgcactgcac tgtccccaga   3900

gagccacccc tccacccact cagagacagc tgtggagagg gccaggagaa tgggattacc   3960

ctatgaccaa ggagacatgg gaagaagccc tccttccttc cacgatcgag gttccgccat   4020

caactcggtt ctcggatatg caagtacctc actttgttaa cttattaact tattggtttc   4080

attaaagttt tcaagaggaa aaaaaaaaaa aaaaaa                             4116
```

<210> SEQ ID NO 16
<211> LENGTH: 508
<212> TYPE: DNA
<213> ORGANISM: Homo sapiens

<400> SEQUENCE: 16

```
acgcgtccgg cttcccggcc ccgcgcgctg cccccgccac gcggttcggc ccaggcacca     60

actcggccgc ccgtgcgccc tgccccgccg cctgctccgc gcgttccctc cctccgcctc    120

gcctcgcttg ctcgctcgct ccctcccgat ttgggaaggc ggccgcgggg cgggcggggg    180

aggggcgggg cgggggaggg tgacatgtga gcggcgcgcg ccggtggcag gtggaaaggc    240

gagcggcatg gagcgcgtaa taagagagtt ggagtcggaa agagcagccc cagtcgccgg    300

ggaagcggga ggtcagtgcg ggctccggcg gcccccaggc tccgagcgcc cgcccgcggc    360

cccggcccgg cccctagccc ccgccgcccg cgcccgcccc gggtcgcccc tctggccccg    420

ggtccgagcc atgcgtctct gagcgccccg agcgcgcccc cgccccggac cgtgcccggg    480

ccccggcgcc cccagcccgg cgccgccc                                       508
```

<210> SEQ ID NO 17
<211> LENGTH: 453
<212> TYPE: PRT
<213> ORGANISM: Homo sapiens

<400> SEQUENCE: 17

Met Gly Glu Asn Asp Pro Pro Ala Val Glu Ala Pro Phe Ser Phe Arg

-continued

```
1               5                   10                  15

Ser Leu Phe Gly Leu Asp Asp Leu Lys Ile Ser Pro Val Ala Pro Asp
            20                  25                  30

Ala Asp Ala Val Ala Ala Gln Ile Leu Ser Leu Leu Pro Leu Lys Phe
        35                  40                  45

Phe Pro Ile Ile Val Ile Gly Ile Ile Ala Leu Ile Leu Ala Leu Ala
    50                  55                  60

Ile Gly Leu Gly Ile His Phe Asp Cys Ser Gly Lys Tyr Arg Cys Arg
65                  70                  75                  80

Ser Ser Phe Lys Cys Ile Glu Leu Ile Ala Arg Cys Asp Gly Val Ser
                85                  90                  95

Asp Cys Lys Asp Gly Glu Asp Glu Tyr Arg Cys Val Arg Val Gly Gly
            100                 105                 110

Gln Asn Ala Val Leu Gln Val Phe Thr Ala Ala Ser Trp Lys Thr Met
        115                 120                 125

Cys Ser Asp Asp Trp Lys Gly His Tyr Ala Asn Val Ala Cys Ala Gln
    130                 135                 140

Leu Gly Phe Pro Ser Tyr Val Ser Ser Asp Asn Leu Arg Val Ser Ser
145                 150                 155                 160

Leu Glu Gly Gln Phe Arg Glu Glu Phe Val Ser Ile Asp His Leu Leu
                165                 170                 175

Pro Asp Asp Lys Val Thr Ala Leu His His Ser Val Tyr Val Arg Glu
            180                 185                 190

Gly Cys Ala Ser Gly His Val Val Thr Leu Gln Cys Thr Ala Cys Gly
        195                 200                 205

His Arg Arg Gly Tyr Ser Ser Arg Ile Val Gly Gly Asn Met Ser Leu
    210                 215                 220

Leu Ser Gln Trp Pro Trp Gln Ala Ser Leu Gln Phe Gln Gly Tyr His
225                 230                 235                 240

Leu Cys Gly Gly Ser Val Ile Thr Pro Leu Trp Ile Ile Thr Ala Ala
                245                 250                 255

His Cys Val Tyr Asp Leu Tyr Leu Pro Lys Ser Trp Thr Ile Gln Val
            260                 265                 270

Gly Leu Val Ser Leu Leu Asp Asn Pro Ala Pro Ser His Leu Val Glu
        275                 280                 285

Lys Ile Val Tyr His Ser Lys Tyr Lys Pro Lys Arg Leu Gly Asn Asp
    290                 295                 300

Ile Ala Leu Met Lys Leu Ala Gly Pro Leu Thr Phe Asn Glu Met Ile
305                 310                 315                 320

Gln Pro Val Cys Leu Pro Asn Ser Glu Glu Asn Phe Pro Asp Gly Lys
                325                 330                 335

Val Cys Trp Thr Ser Gly Trp Gly Ala Thr Glu Asp Gly Gly Asp Ala
            340                 345                 350

Ser Pro Val Leu Asn His Ala Ala Val Pro Leu Ile Ser Asn Lys Ile
        355                 360                 365

Cys Asn His Arg Asp Val Tyr Gly Gly Ile Ile Ser Pro Ser Met Leu
    370                 375                 380

Cys Ala Gly Tyr Leu Thr Gly Gly Val Asp Ser Cys Gln Gly Asp Ser
385                 390                 395                 400

Gly Gly Pro Leu Val Cys Gln Glu Arg Arg Leu Trp Lys Leu Val Gly
                405                 410                 415

Ala Thr Ser Phe Gly Ile Gly Cys Ala Glu Val Asn Lys Pro Gly Val
            420                 425                 430
```

```
Tyr Thr Arg Val Thr Ser Phe Leu Asp Trp Ile His Glu Gln Met Glu
        435                 440                 445

Arg Asp Leu Lys Thr
    450


<210> SEQ ID NO 18
<211> LENGTH: 2460
<212> TYPE: DNA
<213> ORGANISM: Homo sapiens

<400> SEQUENCE: 18

accgggcacc ggacggctcg ggtactttcg ttcttaatta ggtcatgccc gtgtgagcca      60

ggaaagggct gtgtttatgg gaagccagta acactgtggc ctactatctc ttccgtggtg     120

ccatctacat ttttgggact cgggaattat gaggtagagg tggaggcgga gccggatgtc     180

agaggtcctg aaatagtcac catgggggaa aatgatccgc ctgctgttga agccccccttc    240

tcattccgat cgctttttgg ccttgatgat ttgaaaataa gtcctgttgc accagatgca     300

gatgctgttg ctgcacagat cctgtcactg ctgccattga agttttttcc aatcatcgtc     360

attgggatca ttgcattgat attagcactg gccattggtc tgggcatcca cttcgactgc     420

tcagggaagt acagatgtcg ctcatccttt aagtgtatcg agctgatagc tcgatgtgac     480

ggagtctcgg attgcaaaga cggggaggac gagtaccgct gtgtccgggt gggtggtcag     540

aatgccgtgc tccaggtgtt cacagctgct tcgtggaaga ccatgtgctc cgatgactgg     600

aagggtcact acgcaaatgt tgcctgtgcc caactgggtt tcccaagcta tgtgagttca     660

gataacctca gagtgagctc gctggagggg cagttccggg aggagtttgt gtccatcgat     720

cacctcttgc cagatgacaa ggtgactgca ttacaccact cagtatatgt gagggaggga     780

tgtgcctctg gccacgtggt taccttgcag tgcacagcct gtggtcatag aaggggctac     840

agctcacgca tcgtgggtgg aaacatgtcc ttgctctcgc agtggccctg gcaggccagc     900

cttcagttcc agggctacca cctgtgcggg ggctctgtca tcacgcccct gtggatcatc     960

actgctgcac actgtgttta tgacttgtac ctccccaagt catggaccat ccaggtgggt    1020

ctagtttccc tgttggacaa tccagcccca tcccacttgg tggagaagat tgtctaccac    1080

agcaagtaca agccaaagag gctgggcaat gacatcgccc ttatgaagct ggccgggcca    1140

ctcacgttca atgaaatgat ccagcctgtg tgcctgccca actctgaaga gaacttcccc    1200

gatggaaaag tgtgctggac gtcaggatgg ggggccacag aggatggagg tgacgcctcc    1260

cctgtcctga accacgcggc cgtccctttg atttccaaca agatctgcaa ccacagggac    1320

gtgtacggtg gcatcatctc cccctccatg ctctgcgcgg gctacctgac gggtggcgtg    1380

gacagctgcc agggggacag cggggggccc ctggtgtgtc aagagaggag gctgtggaag    1440

ttagtgggag cgaccagctt tggcatcggc tgcgcagagg tgaacaagcc tggggtgtac    1500

acccgtgtca cctccttcct ggactggatc cacgagcaga tggagagaga cctaaaaacc    1560

tgaagaggaa ggggacaagt agccacctga gttcctgagg tgatgaagac agcccgatcc    1620

tcccctggac tcccgtgtag gaacctgcac acgagcagac acccttggag ctctgagttc    1680

cggcaccagt agcaggcccg aaagaggcac ccttccatct gattccagca caaccttcaa    1740

gctgcttttt gtttttttgtt tttttgagat ggagtctcgc tctgttgccc aggctggagt    1800

gcagtggcga aatccctgct cactgcagcc tccgcttccc tggttcaagc gattctcttg    1860

cctcagcttc cccagtagct gggaccacag gtgcccgcca ccacacccaa ctaatttttg    1920
```

-continued

```
tatttttagt agagacaggg tttcaccatg ttggccaggc tgctctcaaa cccctgacct   1980

caaatgatgt gcctgcttca gcctcccaca gtgctgggat tacaggcatg ggccaccacg   2040

cctagcctca cgctcctttc tgatcttcac taagaacaaa agaagcagca acttgcaagg   2100

gcggcctttc ccactggtcc atctggtttt ctctccaggg gtcttgcaaa attcctgacg   2160

agataagcag ttatgtgacc tcacgtgcaa agccaccaac agccactcag aaaagacgca   2220

ccagcccaga agtgcagaac tgcagtcact gcacgttttc atctctaggg accagaacca   2280

aacccaccct ttctacttcc aagacttatt ttcacatgtg gggaggttaa tctaggaatg   2340

actcgtttaa ggcctatttt catgatttct ttgtagcatt tggtgcttga cgtattattg   2400

tcctttgatt ccaaataata tgtttccttc cctcattgaa aaaaaaaaaa aaaaaaaaaa   2460


<210> SEQ ID NO 19
<211> LENGTH: 1775
<212> TYPE: PRT
<213> ORGANISM: Homo sapiens

<400> SEQUENCE: 19

Met Ala Leu Ser Leu Trp Pro Leu Leu Leu Leu Leu Leu Leu Leu Leu
1               5                   10                  15

Leu Leu Ser Phe Ala Val Thr Leu Ala Pro Thr Gly Pro His Ser Leu
            20                  25                  30

Asp Pro Gly Leu Ser Phe Leu Lys Ser Leu Leu Ser Thr Leu Asp Gln
        35                  40                  45

Ala Pro Gln Gly Ser Leu Ser Arg Ser Arg Phe Phe Thr Phe Leu Ala
    50                  55                  60

Asn Ile Ser Ser Ser Phe Glu Pro Gly Arg Met Gly Glu Gly Pro Val
65                  70                  75                  80

Gly Glu Pro Pro Pro Leu Gln Pro Pro Ala Leu Arg Leu His Asp Phe
                85                  90                  95

Leu Val Thr Leu Arg Gly Ser Pro Asp Trp Glu Pro Met Leu Gly Leu
            100                 105                 110

Leu Gly Asp Met Leu Ala Leu Leu Gly Gln Glu Gln Thr Pro Arg Asp
        115                 120                 125

Phe Leu Val His Gln Ala Gly Val Leu Gly Gly Leu Val Glu Val Leu
    130                 135                 140

Leu Gly Ala Leu Val Pro Gly Gly Pro Pro Thr Pro Thr Arg Pro Pro
145                 150                 155                 160

Cys Thr Arg Asp Gly Pro Ser Asp Cys Val Leu Ala Ala Asp Trp Leu
                165                 170                 175

Pro Ser Leu Leu Leu Leu Leu Glu Gly Thr Arg Trp Gln Ala Leu Val
            180                 185                 190

Gln Val Gln Pro Ser Val Asp Pro Thr Asn Ala Thr Gly Leu Asp Gly
        195                 200                 205

Arg Glu Ala Ala Pro His Phe Leu Gln Gly Leu Leu Gly Leu Leu Thr
    210                 215                 220

Pro Thr Gly Glu Leu Gly Ser Lys Glu Ala Leu Trp Gly Gly Leu Leu
225                 230                 235                 240

Arg Thr Val Gly Ala Pro Leu Tyr Ala Ala Phe Gln Glu Gly Leu Leu
                245                 250                 255

Arg Val Thr His Ser Leu Gln Asp Glu Val Phe Ser Ile Leu Gly Gln
            260                 265                 270

Pro Glu Pro Asp Thr Asn Gly Gln Cys Gln Gly Gly Asn Leu Gln Gln
        275                 280                 285
```

-continued

```
Leu Leu Leu Trp Gly Val Arg His Asn Leu Ser Trp Asp Val Gln Ala
    290                 295                 300

Leu Gly Phe Leu Ser Gly Ser Pro Pro Pro Pro Pro Ala Leu Leu His
305                 310                 315                 320

Cys Leu Ser Thr Gly Val Pro Leu Pro Arg Ala Ser Gln Pro Ser Ala
                325                 330                 335

His Ile Ser Pro Arg Gln Arg Arg Ala Ile Thr Val Glu Ala Leu Cys
            340                 345                 350

Glu Asn His Leu Gly Pro Ala Pro Pro Tyr Ser Ile Ser Asn Phe Ser
        355                 360                 365

Ile His Leu Leu Cys Gln His Thr Lys Pro Ala Thr Pro Gln Pro His
    370                 375                 380

Pro Ser Thr Thr Ala Ile Cys Gln Thr Ala Val Trp Tyr Ala Val Ser
385                 390                 395                 400

Trp Ala Pro Gly Ala Gln Gly Trp Leu Gln Ala Cys His Asp Gln Phe
                405                 410                 415

Pro Asp Glu Phe Leu Asp Ala Ile Cys Ser Asn Leu Ser Phe Ser Ala
            420                 425                 430

Leu Ser Gly Ser Asn Arg Arg Leu Val Lys Arg Leu Cys Ala Gly Leu
        435                 440                 445

Leu Pro Pro Pro Thr Ser Cys Pro Glu Gly Leu Pro Pro Val Pro Leu
    450                 455                 460

Thr Pro Asp Ile Phe Trp Gly Cys Phe Leu Glu Asn Glu Thr Leu Trp
465                 470                 475                 480

Ala Glu Arg Leu Cys Gly Glu Ala Ser Leu Gln Ala Val Pro Pro Ser
                485                 490                 495

Asn Gln Ala Trp Val Gln His Val Cys Gln Gly Pro Thr Pro Asp Val
            500                 505                 510

Thr Ala Ser Pro Pro Cys His Ile Gly Pro Cys Gly Glu Arg Cys Pro
        515                 520                 525

Asp Gly Gly Ser Phe Leu Val Met Val Cys Ala Asn Asp Thr Met Tyr
    530                 535                 540

Glu Val Leu Val Pro Phe Trp Pro Trp Leu Ala Gly Gln Cys Arg Ile
545                 550                 555                 560

Ser Arg Gly Gly Asn Asp Thr Cys Phe Leu Glu Gly Leu Leu Gly Pro
                565                 570                 575

Leu Leu Pro Ser Leu Pro Pro Leu Gly Pro Ser Pro Leu Cys Leu Thr
            580                 585                 590

Pro Gly Pro Phe Leu Leu Gly Met Leu Ser Gln Leu Pro Arg Cys Gln
        595                 600                 605

Ser Ser Val Pro Ala Leu Ala His Pro Thr Arg Leu His Tyr Leu Leu
    610                 615                 620

Arg Leu Leu Thr Phe Leu Leu Gly Pro Gly Ala Gly Gly Ala Glu Ala
625                 630                 635                 640

Gln Gly Met Leu Gly Arg Ala Leu Leu Leu Ser Ser Leu Pro Asp Asn
                645                 650                 655

Cys Ser Phe Trp Asp Ala Phe Arg Pro Glu Gly Arg Arg Ser Val Leu
            660                 665                 670

Arg Thr Ile Gly Glu Tyr Leu Glu Gln Asp Glu Glu Gln Pro Thr Pro
        675                 680                 685

Ser Gly Phe Glu Pro Thr Val Asn Pro Ser Ser Gly Ile Ser Lys Met
    690                 695                 700
```

-continued

```
Glu Leu Leu Ala Cys Phe Ser Pro Val Leu Trp Asp Leu Leu Gln Arg
705                 710                 715                 720

Glu Lys Ser Val Trp Ala Leu Gln Ile Leu Val Gln Ala Tyr Leu His
                725                 730                 735

Met Pro Pro Glu Asn Leu Gln Gln Leu Val Leu Ser Ala Glu Arg Glu
            740                 745                 750

Ala Ala Gln Gly Phe Leu Thr Leu Met Leu Gln Gly Lys Leu Gln Gly
        755                 760                 765

Lys Leu Gln Val Pro Pro Ser Glu Glu Gln Ala Leu Gly Arg Leu Thr
    770                 775                 780

Ala Leu Leu Leu Gln Arg Tyr Pro Arg Leu Thr Ser Gln Leu Phe Ile
785                 790                 795                 800

Asp Leu Ser Pro Leu Ile Pro Phe Leu Ala Val Ser Asp Leu Met Arg
                805                 810                 815

Phe Pro Pro Ser Leu Leu Ala Asn Asp Ser Val Leu Ala Ala Ile Arg
            820                 825                 830

Asp Tyr Ser Pro Gly Met Arg Pro Glu Gln Lys Glu Ala Leu Ala Lys
        835                 840                 845

Arg Leu Leu Ala Pro Glu Leu Phe Gly Glu Val Pro Ala Trp Pro Gln
    850                 855                 860

Glu Leu Leu Trp Ala Val Leu Pro Leu Leu Pro His Leu Pro Leu Glu
865                 870                 875                 880

Asn Phe Leu Gln Leu Ser Pro His Gln Ile Gln Ala Leu Glu Asp Ser
                885                 890                 895

Trp Pro Ala Ala Gly Leu Gly Pro Gly His Ala Arg His Val Leu Arg
            900                 905                 910

Ser Leu Val Asn Gln Ser Val Gln Asp Gly Glu Glu Gln Val Arg Arg
        915                 920                 925

Leu Gly Pro Leu Ala Cys Phe Leu Ser Pro Glu Glu Leu Gln Ser Leu
    930                 935                 940

Val Pro Leu Ser Asp Pro Thr Gly Pro Val Glu Arg Gly Leu Leu Glu
945                 950                 955                 960

Cys Ala Ala Asn Gly Thr Leu Ser Pro Glu Gly Arg Val Ala Tyr Glu
                965                 970                 975

Leu Leu Gly Val Leu Arg Ser Ser Gly Gly Ala Val Leu Ser Pro Arg
            980                 985                 990

Glu Leu Arg Val Trp Ala Pro Leu  Phe Ser Gln Leu Gly  Leu Arg Phe
        995                 1000                1005

Leu Gln  Glu Leu Ser Glu Pro  Gln Leu Arg Ala Met  Leu Pro Val
    1010                1015                1020

Leu Gln  Gly Thr Ser Val Thr  Pro Ala Gln Ala Val  Leu Leu Leu
    1025                1030                1035

Gly Arg  Leu Leu Pro Arg His  Asp Leu Ser Leu Glu  Glu Leu Cys
    1040                1045                1050

Ser Leu  His Leu Leu Leu Pro  Gly Leu Ser Pro Gln  Thr Leu Gln
    1055                1060                1065

Ala Ile  Pro Arg Arg Val Leu  Val Gly Ala Cys Ser  Cys Leu Ala
    1070                1075                1080

Pro Glu  Leu Ser Arg Leu Ser  Ala Cys Gln Thr Ala  Ala Leu Leu
    1085                1090                1095

Gln Thr  Phe Arg Val Lys Asp  Gly Val Lys Asn Met  Gly Thr Thr
    1100                1105                1110

Gly Ala  Gly Pro Ala Val Cys  Ile Pro Gly Gln Pro  Ile Pro Thr
```

-continued

```
    1115                1120                1125

Thr Trp  Pro Asp Cys Leu Leu  Pro Leu Leu Pro Leu  Lys Leu Leu
    1130                1135                1140

Gln Leu  Asp Ser Leu Ala Leu  Leu Ala Asn Arg Arg  Arg Tyr Trp
    1145                1150                1155

Glu Leu  Pro Trp Ser Glu Gln  Gln Ala Gln Phe Leu  Trp Lys Lys
    1160                1165                1170

Met Gln  Val Pro Thr Asn Leu  Thr Leu Arg Asn Leu  Gln Ala Leu
    1175                1180                1185

Gly Thr  Leu Ala Gly Gly Met  Ser Cys Glu Phe Leu  Gln Gln Ile
    1190                1195                1200

Asn Ser  Met Val Asp Phe Leu  Glu Val Val His Met  Ile Tyr Gln
    1205                1210                1215

Leu Pro  Thr Arg Val Arg Gly  Ser Leu Arg Ala Cys  Ile Trp Ala
    1220                1225                1230

Glu Leu  Gln Arg Arg Met Ala  Met Pro Glu Pro Glu  Trp Thr Thr
    1235                1240                1245

Val Gly  Pro Glu Leu Asn Gly  Leu Asp Ser Lys Leu  Leu Leu Asp
    1250                1255                1260

Leu Pro  Ile Gln Leu Met Asp  Arg Leu Ser Asn Glu  Ser Ile Met
    1265                1270                1275

Leu Val  Val Glu Leu Val Gln  Arg Ala Pro Glu Gln  Leu Leu Ala
    1280                1285                1290

Leu Thr  Pro Leu His Gln Ala  Ala Leu Ala Glu Arg  Ala Leu Gln
    1295                1300                1305

Asn Leu  Ala Pro Lys Glu Thr  Pro Val Ser Gly Glu  Val Leu Glu
    1310                1315                1320

Thr Leu  Gly Pro Leu Val Gly  Phe Leu Gly Thr Glu  Ser Thr Arg
    1325                1330                1335

Gln Ile  Pro Leu Gln Ile Leu  Leu Ser His Leu Ser  Gln Leu Gln
    1340                1345                1350

Gly Phe  Cys Leu Gly Glu Thr  Phe Ala Thr Glu Leu  Gly Trp Leu
    1355                1360                1365

Leu Leu  Gln Glu Ser Val Leu  Gly Lys Pro Glu Leu  Trp Ser Gln
    1370                1375                1380

Asp Glu  Val Glu Gln Ala Gly  Arg Leu Val Phe Thr  Leu Ser Thr
    1385                1390                1395

Glu Ala  Ile Ser Leu Ile Pro  Arg Glu Ala Leu Gly  Pro Glu Thr
    1400                1405                1410

Leu Glu  Arg Leu Leu Glu Lys  Gln Gln Ser Trp Glu  Gln Ser Arg
    1415                1420                1425

Val Gly  Gln Leu Cys Arg Glu  Pro Gln Leu Ala Ala  Lys Lys Ala
    1430                1435                1440

Ala Leu  Val Ala Gly Val Val  Arg Pro Ala Ala Glu  Asp Leu Pro
    1445                1450                1455

Glu Pro  Val Pro Asn Cys Ala  Asp Val Arg Gly Thr  Phe Pro Ala
    1460                1465                1470

Ala Trp  Ser Ala Thr Gln Ile  Ala Glu Met Glu Leu  Ser Asp Phe
    1475                1480                1485

Glu Asp  Cys Leu Thr Leu Phe  Ala Gly Asp Pro Gly  Leu Gly Pro
    1490                1495                1500

Glu Glu  Leu Arg Ala Ala Met  Gly Lys Ala Lys Gln  Leu Trp Gly
    1505                1510                1515
```

```
Pro Pro  Arg Gly Phe Arg Pro  Glu Gln Ile Leu Gln  Leu Gly Arg
    1520                 1525                 1530

Leu Leu  Ile Gly Leu Gly Asp  Arg Glu Leu Gln Glu  Leu Ile Leu
    1535                 1540                 1545

Val Asp  Trp Gly Val Leu Ser  Thr Leu Gly Gln Ile  Asp Gly Trp
    1550                 1555                 1560

Ser Thr  Thr Gln Leu Arg Ile  Val Val Ser Ser Phe  Leu Arg Gln
    1565                 1570                 1575

Ser Gly  Arg His Val Ser His  Leu Asp Phe Val His  Leu Thr Ala
    1580                 1585                 1590

Leu Gly  Tyr Thr Leu Cys Gly  Leu Arg Pro Glu Glu  Leu Gln His
    1595                 1600                 1605

Ile Ser  Ser Trp Glu Phe Ser  Gln Ala Ala Leu Phe  Leu Gly Thr
    1610                 1615                 1620

Leu His  Leu Gln Cys Ser Glu  Glu Gln Leu Glu Val  Leu Ala His
    1625                 1630                 1635

Leu Leu  Val Leu Pro Gly Gly  Phe Gly Pro Ile Ser  Asn Trp Gly
    1640                 1645                 1650

Pro Glu  Ile Phe Thr Glu Ile  Gly Thr Ile Ala Ala  Gly Ile Pro
    1655                 1660                 1665

Asp Leu  Ala Leu Ser Ala Leu  Leu Arg Gly Gln Ile  Gln Gly Val
    1670                 1675                 1680

Thr Pro  Leu Ala Ile Ser Val  Ile Pro Pro Pro Lys  Phe Ala Val
    1685                 1690                 1695

Val Phe  Ser Pro Ile Gln Leu  Ser Ser Leu Thr Ser  Ala Gln Ala
    1700                 1705                 1710

Val Ala  Val Thr Pro Glu Gln  Met Ala Phe Leu Ser  Pro Glu Gln
    1715                 1720                 1725

Arg Arg  Ala Val Ala Trp Ala  Gln His Glu Gly Lys  Glu Ser Pro
    1730                 1735                 1740

Glu Gln  Gln Gly Arg Ser Thr  Ala Trp Gly Leu Gln  Asp Trp Ser
    1745                 1750                 1755

Arg Pro  Ser Trp Ser Leu Val  Leu Thr Ile Ser Phe  Leu Gly His
    1760                 1765                 1770

Leu Leu
    1775


<210> SEQ ID NO 20
<211> LENGTH: 5515
<212> TYPE: DNA
<213> ORGANISM: Homo sapiens

<400> SEQUENCE: 20

gccctgccct cacctggcta tcccacacag gtgagaataa ccagaactca cctccggtac     60

cagtgttcac ttggaaacat ggctctcagc ctctggcccc tgctgctgct gctgctgctg    120

ctgctgctgc tgtcctttgc agtgactctg gcccctactg ggcctcattc cctggaccct    180

ggtctctcct tcctgaagtc attgctctcc actctggacc aggctcccca gggctccctg    240

agccgctcac ggttctttac attcctggcc aacatttctt cttcctttga gcctgggaga    300

atgggggaag gaccagtagg agagccccca cctctccagc cgcctgctct gcggctccat    360

gattttctag tgacactgag aggtagcccc gactgggagc caatgctagg gctgctaggg    420

gatatgctgg cactgctggg acaggagcag actccccgag atttcctggt gcaccaggca    480
```

-continued

```
ggggtgctgg gtggacttgt ggaggtgctg ctgggagcct tagttcctgg gggcccccct    540
accccaactc ggcccccatg cacccgtgat gggccgtctg actgtgtcct ggctgctgac    600
tggttgcctt ctctgctgct gttgttagag ggcacacgct ggcaagctct ggtgcaggtg    660
cagcccagtg tggaccccac caatgccaca ggcctcgatg ggagggaggc agctcctcac    720
tttttgcagg gtctgttggg tttgcttacc ccaacagggg agctaggctc caaggaggct    780
ctttggggcg gtctgctacg cacagtgggg gcccccctct atgctgcctt tcaggagggg    840
ctgctccgtg tcactcactc cctgcaggat gaggtcttct ccattttggg gcagccagag    900
cctgatacca atgggcagtg ccagggaggt aaccttcaac agctgctctt atggggcgtc    960
cggcacaacc tttcctggga tgtccaggcg ctgggctttc tgtctggatc accacccccca   1020
ccccctgccc tccttcactg cctgagcacg ggcgtgcctc tgcccagagc ttctcagccg   1080
tcagcccaca tcagcccacg ccaacggcga gccatcactg tggaggccct ctgtgagaac   1140
cacttaggcc cagcaccacc ctacagcatt tccaacttct ccatccactt gctctgccag   1200
cacaccaagc ctgccactcc acagccccat cccagcacca ctgccatctg ccagacagct   1260
gtgtggtatg cagtgtcctg ggcaccaggt gcccaaggct ggctacaggc ctgccacgac   1320
cagtttcctg atgagttttt ggatgcgatc tgcagtaacc tctccttttc agccctgtct   1380
ggctccaacc gccgcctggt gaagcggctc tgtgctggcc tgctcccacc ccctaccagc   1440
tgccctgaag gcctgccccc tgttcccctc accccagaca tcttttgggg ctgcttcttg   1500
gagaatgaga ctctgtgggc tgagcgactg tgtggggagg caagtctaca ggctgtgccc   1560
cccagcaacc aggcttgggt ccagcatgtg tgccagggcc ccaccccaga tgtcactgcc   1620
tccccaccat gccacattgg accctgtggg gaacgctgcc cggatggggg cagcttcctg   1680
gtgatggtct gtgccaatga caccatgtat gaggtcctgg tgcccttctg gccttggcta   1740
gcaggccaat gcaggataag tcgtgggggc aatgacactt gcttcctaga agggctgctg   1800
ggcccccttc tgccctctct gccaccactg ggaccatccc cactctgtct gacccctggc   1860
cccttcctcc ttggcatgct atcccagttg ccacgctgtc agtcctctgt cccagctctt   1920
gctcacccca cacgcctaca ctatctcctc cgcctgctga ccttcctctt gggtccaggg   1980
gctgggggcg ctgaggccca ggggatgctg ggtcgggccc tactgctctc cagtctccca   2040
gacaactgct ccttctggga tgcctttcgc ccagagggcc ggcgcagtgt gctacggacg   2100
attggggaat acctggaaca agatgaggag cagccaaccc catcaggctt tgaacccact   2160
gtcaacccca gctctggtat aagcaagatg gagctgctgg cctgctttag tcctgtgctg   2220
tgggatctgc tccagaggga aaagagtgtt tgggccctgc agattctagt gcaggcgtac   2280
ctgcatatgc cccagaaaa cctccagcag ctggtgcttt cagcagagag ggaggctgca   2340
cagggcttcc tgacactcat gctgcagggg aagctgcagg ggaagctgca ggtaccacca   2400
tccgaggagc aggccctggg tcgcctgaca gccctgctgc tccagcggta cccacgcctc   2460
acctcccagc tcttcattga cctgtcacca ctcatccctt tcttggctgt ctctgacctg   2520
atgcgcttcc caccatccct gttagccaac gacagtgtcc tggctgccat ccgggattac   2580
agcccaggaa tgaggcctga acagaaggag gctctggcaa agcgactgct ggcccctgaa   2640
ctgtttgggg aagtgcctgc ctggccccag gagctgctgt gggcagtgct gcccctgctc   2700
cccccacctcc ctctggagaa ctttttgcag ctcagccctc accagatcca ggccctggag   2760
gatagctggc cagcagcagg tctggggcca gggcatgccc gccatgtgct gcgcagcctg   2820
gtaaaccaga gtgtccagga tggtgaggag caggtacgca ggcttgggcc cctcgcctgt   2880
```

-continued ttcctgagcc ctgaggagct gcagagccta gtgcccctga gtgatccaac ggggccagta 2940
gaacgggggc tgctggaatg tgcagccaat gggaccctca gcccagaagg acgggtggca 3000
tatgaacttc tgggtgtgtt gcgctcatct ggaggagcgg tgctgagccc ccgggagctg 3060
cgggtctggg cccctctctt ctctcagctg ggcctccgct tccttcagga gctgtcagag 3120
ccccagctta gagccatgct tcctgtcctg cagggaacta gtgttacacc tgctcaggct 3180
gtcctgctgc ttggacggct ccttcctagg cacgatctat ccctggagga actctgctcc 3240
ttgcaccttc tgctaccagg cctcagcccc cagacactcc aggccatccc taggcgagtc 3300
ctggtcgggg cttgttcctg cctggcccct gaactgtcac gcctctcagc ctgccagacc 3360
gcagcactgc tgcagacctt tcgggttaaa gatggtgtta aaaatatggg tacaacaggt 3420
gctggtccag ctgtgtgtat ccctggtcag cctattccca ccacctggcc agactgcctg 3480
cttcccctgc tcccattaaa gctgctacaa ctggattcct tggctcttct ggcaaatcga 3540
agacgctact gggagctgcc ctggtctgag cagcaggcac agtttctctg gaagaagatg 3600
caagtaccca ccaaccttac cctcaggaat ctgcaggctc tgggcaccct ggcaggaggc 3660
atgtcctgtg agtttctgca gcagatcaac tccatggtag acttccttga agtggtgcac 3720
atgatctatc agctgcccac tagagttcga gggagcctga gggcctgtat ctgggcagag 3780
ctacagcgga ggatggcaat gccagaacca gaatggacaa ctgtagggcc agaactgaac 3840
gggctggata gcaagctact cctggactta ccgatccagt tgatggacag actatccaat 3900
gaatccatta tgttggtggt ggagctggtg caaagagctc cagagcagct gctggcactg 3960
accccccctcc accaggcagc cctggcagag agggcactac aaaacctggc tccaaaggag 4020
actccagtct caggggaagt gctggagacc ttaggccctt tggttggatt cctggggaca 4080
gagagcacac gacagatccc cctacagatc ctgctgtccc atctcagtca gctgcaaggc 4140
ttctgcctag gagagacatt tgccacagag ctgggatggc tgctattgca ggagtctgtt 4200
cttgggaaac cagagttgtg gagccaggat gaagtagagc aagctggacg cctagtattc 4260
actctgtcta ctgaggcaat ttccttgatc cccagggagg ccttgggtcc agagaccctg 4320
gagcggcttc tagaaaagca gcagagctgg gagcagagca gagttggaca gctgtgtagg 4380
gagccacagc ttgctgccaa gaaagcagcc ctggtagcag gggtggtgcg accagctgct 4440
gaggatcttc cagaacctgt gccaaattgt gcagatgtac gagggacatt cccagcagcc 4500
tggtctgcaa cccagattgc agagatggag ctctcagact ttgaggactg cctgacatta 4560
tttgcaggag acccaggact tgggcctgag gaactgcggg cagccatggg caaagcaaaa 4620
cagttgtggg gtcccccccg gggatttcgt cctgagcaga tcctgcagct tggtaggctc 4680
ttaataggtc taggagatcg ggaactacag gagctgatcc tagtggactg gggagtgctg 4740
agcaccctgg ggcagataga tggctggagc accactcagc tccgcattgt ggtctccagt 4800
ttcctacggc agagtggtcg gcatgtgagc cacctggact tcgttcatct gacagcgctg 4860
ggttatactc tctgtggact gcggccagag gagctccagc acatcagcag ttgggagttc 4920
agccaagcag ctctcttcct cggcaccctg catctccagt gctctgagga acaactggag 4980
gttctggccc acctacttgt actgcctggt gggtttggcc caatcagtaa ctgggggcct 5040
gagatcttca ctgaaattgg caccatagca gctgggatcc cagacctggc tctttcagca 5100
ctgctgcggg gacagatcca gggcgttact cctcttgcca tttctgtcat ccctcctcct 5160
aaatttgctg tggtgtttag tcccatccaa ctatctagtc tcaccagtgc tcaggctgtg 5220

-continued

```
gctgtcactc ctgagcaaat ggcctttctg agtcctgagc agcgacgagc agttgcatgg   5280

gcccaacatg agggaaagga gagcccagaa cagcaaggtc gaagtacagc ctggggcctc   5340

caggactggt cacgaccttc ctggtccctg gtattgacta tcagcttcct tggccacctg   5400

ctatgagcct gtctctacag tagaaggaga ttgtggggag agaaatctta agtcataatg   5460

aataaagtgc aaacagaagt gcatcctgat tattttcaga agctgatgag gaata        5515


<210> SEQ ID NO 21
<211> LENGTH: 585
<212> TYPE: PRT
<213> ORGANISM: Homo sapiens

<400> SEQUENCE: 21

Met Glu Asp Ser Gln Asp Leu Asn Glu Gln Ser Val Lys Lys Thr Cys
1               5                   10                  15

Thr Glu Ser Asp Val Ser Gln Ser Gln Asn Ser Arg Ser Met Glu Met
            20                  25                  30

Gln Asp Leu Ala Ser Pro His Thr Leu Val Gly Gly Gly Asp Thr Pro
        35                  40                  45

Gly Ser Ser Lys Leu Glu Lys Ser Asn Leu Ser Ser Thr Ser Val Thr
    50                  55                  60

Thr Asn Gly Thr Gly Val Ile Thr Ser Ser Gly Tyr Ser Pro Arg Ser
65                  70                  75                  80

Ala His Gln Tyr Ser Pro Gln Leu Tyr Pro Ser Lys Pro Tyr Pro His
                85                  90                  95

Ile Leu Ser Thr Pro Ala Ala Gln Thr Met Ser Ala Tyr Ala Gly Gln
            100                 105                 110

Thr Gln Tyr Ser Gly Met Gln Gln Pro Ala Val Tyr Thr Ala Tyr Ser
        115                 120                 125

Gln Thr Gly Gln Pro Tyr Ser Leu Pro Thr Tyr Asp Leu Gly Val Met
    130                 135                 140

Leu Pro Ala Ile Lys Thr Glu Ser Gly Leu Ser Gln Thr Gln Ser Pro
145                 150                 155                 160

Leu Gln Ser Gly Cys Leu Ser Tyr Ser Pro Gly Phe Ser Thr Pro Gln
                165                 170                 175

Pro Gly Gln Thr Pro Tyr Ser Tyr Gln Met Pro Gly Ser Ser Phe Ala
            180                 185                 190

Pro Ser Ser Thr Ile Tyr Ala Asn Asn Ser Val Ser Asn Ser Thr Asn
        195                 200                 205

Phe Ser Gly Ser Gln Gln Asp Tyr Pro Ser Tyr Thr Ala Phe Gly Gln
    210                 215                 220

Asn Gln Tyr Ala Gln Tyr Tyr Ser Ala Ser Thr Tyr Gly Ala Tyr Met
225                 230                 235                 240

Thr Ser Asn Asn Thr Ala Asp Gly Thr Pro Ser Ser Thr Ser Thr Tyr
                245                 250                 255

Gln Leu Gln Glu Ser Leu Pro Gly Leu Thr Asn Gln Pro Gly Glu Phe
            260                 265                 270

Asp Thr Met Gln Ser Pro Ser Thr Pro Ile Lys Asp Leu Asp Glu Arg
        275                 280                 285

Thr Cys Arg Ser Ser Gly Ser Lys Ser Arg Gly Arg Gly Arg Lys Asn
    290                 295                 300

Asn Pro Ser Pro Pro Pro Asp Ser Asp Leu Glu Arg Val Phe Val Trp
305                 310                 315                 320

Asp Leu Asp Glu Thr Ile Ile Val Phe His Ser Leu Leu Thr Gly Ser
```

-continued

```
                325                 330                 335

Tyr Ala Gln Lys Tyr Gly Lys Asp Pro Pro Met Ala Val Thr Leu Gly
            340                 345                 350

Leu Arg Met Glu Glu Met Ile Phe Asn Leu Ala Asp Thr His Leu Phe
        355                 360                 365

Phe Asn Asp Leu Glu Glu Cys Asp Gln Val His Ile Asp Asp Val Ser
    370                 375                 380

Ser Asp Asp Asn Gly Gln Asp Leu Ser Thr Tyr Ser Phe Ala Thr Asp
385                 390                 395                 400

Gly Phe His Ala Ala Ala Ser Ser Ala Asn Leu Cys Leu Pro Thr Gly
                405                 410                 415

Val Arg Gly Gly Val Asp Trp Met Arg Lys Leu Ala Phe Arg Tyr Arg
            420                 425                 430

Arg Val Lys Glu Leu Tyr Asn Thr Tyr Lys Asn Asn Val Gly Gly Leu
        435                 440                 445

Leu Gly Pro Ala Lys Arg Asp Ala Trp Leu Gln Leu Arg Ala Glu Ile
    450                 455                 460

Glu Gly Leu Thr Asp Ser Trp Leu Thr Asn Ala Leu Lys Ser Leu Ser
465                 470                 475                 480

Ile Ile Ser Thr Arg Ser Asn Cys Ile Asn Val Leu Val Thr Thr Thr
                485                 490                 495

Gln Leu Ile Pro Ala Leu Ala Lys Val Leu Leu Tyr Ser Leu Gly Gly
            500                 505                 510

Ala Phe Pro Ile Glu Asn Ile Tyr Ser Ala Thr Lys Ile Gly Lys Glu
        515                 520                 525

Ser Cys Phe Glu Arg Ile Val Ser Arg Phe Gly Thr Asn Ile Thr Tyr
    530                 535                 540

Val Val Ile Gly Asp Gly Arg Asp Glu Glu His Ala Ala Asn Gln His
545                 550                 555                 560

Asn Met Pro Phe Trp Arg Ile Ser Ser His Ser Asp Leu Leu Ala Leu
                565                 570                 575

His Gln Ala Leu Glu Leu Glu Tyr Leu
            580                 585
```

<210> SEQ ID NO 22
<211> LENGTH: 5393
<212> TYPE: DNA
<213> ORGANISM: Homo sapiens

<400> SEQUENCE: 22

```
tccggagttt tggctcctct cctttcctcc tccccctcgg agccggcttc tccctccgcc      60

ccgcttctcc cccgcttgtg tacgctattt gttgtggggt ggccgaaggg gatgtcctgt     120

tttcaccaga ggcacagcgc gaaggggaaa cttcgacact ggaaggaacg agaataaata     180

cttaattacg gacgcactga accgcggctg ggacagacac ttcgggaacc cgaggcggac     240

cgggcgacga gatagtcatt tttacttgaa ggaagctgct tctacttggg agtggcagga     300

gaagtgagaa aaccacatgg aagactccca ggatttaaat gaacaatcag taaagaaaac     360

gtgcacagaa tcagatgttt cacaatctca gaattccagg tctatggaaa tgcaggacct     420

agcaagtcct catactcttg ttggaggtgg tgatactcca ggtagctcca aactggaaaa     480

atctaatctc agcagcacat cagttactac aaatgggaca ggagtaatta caagtagtgg     540

ctacagcccc agatcagcac atcagtattc cccacagctg tatccttcca agccctatcc     600

acacattctt tctacaccag cagctcaaac aatgtctgcc tatgcaggcc agactcagta     660
```

```
ttcggggatg cagcagccag ccgtctacac agcctactca cagacaggac agccctacag    720
cttgcccact tacgatttgg gtgtgatgtt gccagccatc aagacagaga gtggactttc    780
ccaaactcag tccccattac agagtggctg cctcagttac agcccagggt tctctacccc    840
acagccaggc cagacacctt attcttacca aatgccaggt tctagttttg caccatcatc    900
tactatttat gcaaataatt cagtttccaa ttcaacgaat ttcagtggtt cacaacagga    960
ttatccatcc tatacagcct ttggccaaaa ccagtatgca cagtattatt cagcatcaac   1020
gtatggagcg tatatgacat cgaataacac agccgatggc acaccctctt caacctctac   1080
ttatcagttg caggaatctc tcccaggact gactaaccaa ccaggagagt tcgataccat   1140
gcagagtccc tccacaccca tcaaagatct tgatgagaga acctgtagga gttctgggtc   1200
aaagtccaga ggaagaggcc ggaaaaataa tccctccccg cctcctgata gtgacctgga   1260
gcgtgtgttt gtctgggatt tggatgaaac catcattgtt tttcactcac tgctcaccgg   1320
gtcttatgca cagaagtatg gcaaggatcc ccccatggct gtaacccttg gactccgcat   1380
ggaagaaatg atttttaatc ttgctgatac tcatttgttt tttaatgatt tagaggagtg   1440
tgatcaagtt catatagatg atgtttcctc tgatgataat gggcaggact taagtaccta   1500
cagttttgca actgatggct tccatgcagc tgcaagtagt gcaaaccttt gtttgccaac   1560
aggtgtaaga ggaggggttg actggatgag gaagttggct tttcgttaca gaagagtaaa   1620
agaattatat aacacctaca agaacaacgt tggaggactc cttggccctg ccaagaggga   1680
tgcctggcta cagttaaggg cagagattga aggtctgaca gattcctggc taacaaatgc   1740
acttaagtct ttatcaatta ttagcactag gagtaactgc ataaatgtct tggtaacgac   1800
aactcaactg atcccagcac ttgcgaaggt tctactctat agtttaggag gtgctttccc   1860
cattgagaat atttacagtg caactaaaat aggcaaggaa agctgttttg agcgtatagt   1920
gtccagattt ggcactaaca taacttatgt tgtgattgga gatggccgag atgaggagca   1980
tgccgctaac cagcacaaca tgcccttctg gaggatatcc agtcactcag acctcctggc   2040
tctccaccaa gcactggaat tagagtattt gtaactgtgt tctttagccg gagatccatt   2100
ttttatattt caagtacact gaatttttat gtgtgattca atgcctctgg ctctacacat   2160
ataaattgtc ttaatggatg aaatcatatt tggaataaaa attccagaat gaagaattca   2220
gattgctgaa tggagttaaa ctttagtgct acagaaaaga aactctatgg tcttatattt   2280
acaacacttt aatgggtttt ttaaaaatct gtggaggttg ctggtacaca ccaaatgagt   2340
ccaaactgga atgagcagct ttagcaaaga actcttaccc tggcaaagca gcaacacaca   2400
tgctccgtct gacaaggtgg tcaacaacat tcctcaaaat gggagatctt ctcagccctg   2460
aggtttgaat ctgactttag cctacctaac ccagaaaatc tgaattggaa tgcactcaga   2520
ctgtataagg acagtcctat ttagacatgt aatttgtgta aattattgat gaaaataatt   2580
tactgtgact ttattagcag ctgactttca aagtggatgc aatttttctt tcttttgttg   2640
gggaggggaa tgggagggga aatgggaata taatattgtc tctttttttaa gtttggcaaa   2700
cagaatgttc atactgatgt gttgtgcctt aaagacaaga cagcatttgt gtgttacaat   2760
gtaactttgg ttaaaatctc tgtagataat gaaaaaaaac aaaaaaaaaa acctttgtga   2820
tgattcttaa catgaccaaa tttaaaagtc aagctctcag agcttaatta ccgcatcagc   2880
aagaaactga gtatttttttg caataagaaa acaacaataa taaaggaaag cttgtgtttc   2940
atttgggttc ttaataattc caataattgt atgaggcaac tatttgcgca tccaaccatg   3000
```

-continued

```
agtggaaggt ttgggaaaga ctgtgggacc tttacttaga aagtgaaatg tatgtagaag   3060
tctcaagtac cccttctaca gttttactgg agaaaactaa gagccatatt catgacaact   3120
tgcacagttt tgaggttgag acttttgata tgtgtaagtt gcatagagga ggatattatc   3180
atgcaaatca tgagcaatta tcacataaac tttttagaa tgtgccatga acatggcata    3240
aaattcacat tgagtgcaca gggcttaaaa taaagctaag tatgtttatt cccaatgcca   3300
tggcaaaaat gataaatatca tcagaaatgg aaggcagttc tcccagatgg tgtctaatga  3360
aagcaatgag tctatgaaaa ttttacctag aatatcatca taaattaaat tagcaagtgc   3420
gctggatctt ggcagcgctg ctgaaatgac aacagtaaaa taatacctgg ttctccatct   3480
gaatacatca atgcaggttc tcctcgtaac agacttgcat atgtttgtta gtttctgcct   3540
gtattgtcac tgcgcaacgg atggcattca ttacaagaag agcccatcat cgttgtgttt   3600
gcatggtttt tttccttgtg tgtagcccat gttgggaaca cgatacaggt tctcctctta   3660
tttcctatga cacgatttcc cttgtggaaa tttaagactt taagaactag agtattttta   3720
tggtgtctgc acctgcagtt ctgtgtttaa aatgtcataa tgtggatcct ggagtcaggc   3780
tactagtcag tgcccctagc cagaggctgg ttcatgagtt catcaactga ggcctctgtg   3840
gcttcaataa agtctacatt ttgctcacag atcacaacat tcactgtgga aatatgattt   3900
catttcttta ggctacaaac ctgtatttct ttactgaatg ctaaggccat gtttatattg   3960
ggtagaaaga tattgagatc ccaattttgt acaagattgt gatttcatta tctaaacctt   4020
aaacttaatc ctttaaattt tgtagctttt ggctgcatct gccccaagta ctattccagg   4080
caaattaaag ttggaatacc tttaataata taaaaataat gatagtaaat cttatacttc   4140
tgttggccct tagcttgaaa atagcagtta aaaaaattta aatgttgcct tgattatcag   4200
tacttaatta tgttgtgcac taaaacctta aatatttatt actgtgaata aaaacaaatt   4260
atctttactg tatagctggt ttctttaaat gttgatagaa ttgtggcatt acatctaaat   4320
ttgtaagtct tttcatatca aacaagcaag gctttttatg ctgctaagtc tgtgggtgca   4380
gaaagaaaca ccccttggaa gggcaaagag aagccggctg gttgcatcac cccgtgcagt   4440
ttctcacaca catctctttt tctgattctg tgttcagaag aggctgccgg cataaaacct   4500
aaatgcaagg ttgacggaga acagcttgtc tggcacaaca atggtgcagg cccacgagcc   4560
agcatcacag cttggccatg ggacgttgag tatgcacaaa ctagaactct tcccttccca   4620
ccttaggaat agaaaatcct cttcctttct aatctgaaaa acgaaaactg aacaaacaca   4680
aaaccaaccc cttggcagtt cccacctcct attgacatat ggaatattgt gccttattgt   4740
aaaccagttt gaaaaatgtt ctgtaactaa agtgggtttt cggctattat gtatacagct   4800
tggtatatta ctacgaaaga taaccacctt gtgttgcacc ttaaaaatat caagaccatg   4860
taatttccat aacaaaatag gtggcctggc tatggtatta tagcatacaa ttaggacact   4920
atgcccctgc aaaattttgt aaatcaaatt cagaggcaaa aacatatttt agaatcatac   4980
agtttgcaca cgacaagtag gtaataactg tctctaaaaa tgttttctcc ttagtccgca   5040
atgagctaag attcagaata gtgtcaacag catgctccta tatgaagttg ttttttttaa   5100
agcacatttg tttatgacaa gcctacattc tcagtgaata tggcatttag tatttctttt   5160
gaaaacaaac ttaagcatca tgagccaaag ttgcactttg actcccaact acggtagcat   5220
tatggacatc tcacaatgtc aagggtttct gttatgtatt agtaaagtat agattattgg   5280
ggcctacata atttaaaaga aatgtaaatt aatattaaaa gcttgtaaaa atatgtatat   5340
ctttactatt tctcaataaa tacctttgca attgttttca tttccttcaa aaa          5393
```

<210> SEQ ID NO 23
<211> LENGTH: 964
<212> TYPE: DNA
<213> ORGANISM: Homo sapiens

<400> SEQUENCE: 23
tcttcacctg tcattttcaa ccagcctcag cctatctgct ctgtcacaat cactactaaa 60
atatgttcct aaattgcttg tttctagatc cttccttctc atatgctcag gtgaacacat 120
gggtgaaatt taatatggaa ttgaaatatg tactatgcaa gatagattcc ttaagaaatg 180
tttctctgat ttatatgaca taattgtatt ttactagttt acctgtccat ctgtaaaact 240
ttgttttgga gatttcatat attacaatgt ttaagaaata tgctataatg ttttgtatag 300
tatatttctt cgtgataacc ttatatacta ccagtcacac gtgtttgtaa aaatctaaag 360
agtacttttg gctcctacag aatgtgtgaa gttgtgaaat tgttttttttg ttttgttttg 420 ttttgttttt atgccccaaa gatgtggagg gcttcatata agagggtaga tttaatgaga 480
gagagaggga gagacagaga gaatgataaa agaagcttaa gagattattt tatcttgtca 540
acgacattgt tattgaatgt aagctgctaa acttcttaga taaagtaaaa cagtaaaaac 600
aaacacacaa aacagaacag agaatcatca gacaggctga cgaacacagt acaataaagc 660
agccagtacc gatgatcagt ggacatcaat ttgtcttttg ggctgtagca cctgctacta 720
attggtgcaa agcgctcacc agtcagtgcg tggtttagcg cactcagctg tctcctgtat 780
gtgctgcgag aagcaagata gctaattgct gttgcttcag tgccagtgaa atcaacgtgc 840
tgagctaata gcgacagata gagggcagac agattcctgc tagcagctta gtgttagttg 900
cttgtggtaa ctaaggcagg tggcatacat ctcagaacgt ggagaatgat ggtatgcttt 960
ctga 964

<210> SEQ ID NO 24
<211> LENGTH: 1040
<212> TYPE: DNA
<213> ORGANISM: Homo sapiens

<400> SEQUENCE: 24
tggtagcctc cctagagaca cagagctggg ccggatgagt ccaggcactg acgtgatcca 60
ttatctttca ccttaaagag taaaagggaa actaaagtta attacctcca cgaaacaaaa 120
aggtgccttc ttgtgcttca attacatgga tatattctac tagtctaaaa gtatcttctc 180
acttctttct gtcactgtga ggacttgagt cagaagaaag tttaaataca gtcattgagc 240
tggaaagagt ggaaagagaa gcaaagaggg ggaagctgta ggaaggacga agtcaccccc 300
aagatacatg gttactgctt acaccaagca agctgccttg ggaacgcttc ccccgagcag 360
ccagaatgct cagcagtgga agacacctct attcctgtag gcgagtcctg ggaagctggt 420
caatctgcaa atgccaattc ccagcagtga gctcggtcca cgtgtaaatc aagatttggg 480
gaaagagtag ggtgggtggc atggttgaca atgtcatcag ctccctcctc tgactcctgt 540
ggtcgtgccc ccatctactc tcactcagct acaccccacc ttcggatttg tgatggacgc 600
tgggtcccta gtaaccacag caagtgtctc ccccgcactt ccccccttccc cacccccacc 660 cccaccccca accaccaccc cagcgatgga gcctactctg ctccaagccg ccgctaagac 720
ccggagaagc ggaatttcac tttgaaattc ccttgcctcg tgagggccgg cgctgggcat 780
gctcagtagc cgcggcgctg ctgctgggct gctgggctgg cgcggagtcc accctgccgt 840

```
ctccgccttg gcttctgggc gtccagaagg ccaggcattt gccgcctctg agcgcttctg    900

ttccccttac ccgcaacctc ctactgctct tcctctctcc ctctcttagg gaggttgaag    960

ctggtgctgg tttctgtcgg cgccacagac tgactgctct gcaaacccca gccgaggacc   1020

tgaatcccgg agactagaag                                               1040
```

<210> SEQ ID NO 25
<211> LENGTH: 964
<212> TYPE: DNA
<213> ORGANISM: Homo sapiens

<400> SEQUENCE: 25

```
gcccagtgga attttcctag ttctttacac tagccatgta tttacctata aaatcaggag     60

aaatatgtat atatataata tattaaaaca tatatatatt taaatgggga aatatgtaac    120

aaacaaatag aaacaagggg agaaaggcat tgtatttgac aaaacacata tgttcaggtc    180

tgagaaggct cataaagaat gttgtctgct atactttgta gttgcttctg ttatcacaca    240

atcagtctgc atatacaggc gttttatata tatatttata tagactacat atatacgtat    300

attatatatg taaatatttc actgtctttg aggacggggg ccctgtcttt tttatctgtg    360

gttttgctta gatgtcctcc aacataatct taacacatag tatgctttta gaaatcgttg    420

actgaatgct aaggacgaaa aaccggtgac cagaaggcaa ccaggaaagg ctttgctgac    480

ctccggagtg gtggagttgg aggttctggg aaggcgacta gggagccagg caggggcggg    540

gtgggatggg atgtggacag cgcttttgcg gggggaaagc gtttttgctg ctggaattga    600

gcagtaggaa tgtgtcagtc acatccccac cttcccaatt cttgtcatct cggttcagga    660

aggtgaacgg tgttccgatt ccccgcggcg ggggcctgta gtgggagctc tgccccttcc    720

ccgcctctgc tgcaggcccc gcccctcgcc cggaaccccg gggcgctggc cgcggtgctg    780

aaacggcgcc ctccgcggac ggaggagggg gcggggctct cgggagccgt gagccgggaa    840

gagggagacg ggcagggcgg cgccagcagg ccctggtggg cttgggagga ggcaggagac    900

tggagacagc ctcggctaga gcggacacag gcacctggca agctttcctt gaccaaatca    960

aggt                                                                 964
```

<210> SEQ ID NO 26
<211> LENGTH: 477
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
tctagactgc agagggccct gcgtatgagt gcaagtgggt tttaggacca ggatgaggcg     60

gggtgggggt gcctacctga cgaccgaccc cgacccactg gacaagcacc caaccccccat   120

tccccaaatt gcgcatcccc tatcagagag gggggaggga aacaggatgc ggcgaggcgc    180

gtgcgcactg ccagcttcag caccgcggac agtgccttcg cccccgcctg gcggcgcgcg    240

ccaccgccgc ctcagcactg aaggcgcgct gacgtcactc gccggtcccc cgcaaactcc    300

ccttcccggc caccttggtc gcgtccgcgc cgccgccggc ccagccggac cgcaccacgc    360

gaggcgcgag atagggggc acgggcgcga ccatctgcgc tgcggcgccg gcgactcagc    420

gctgcctcag tctgcggtgg gcagcggagg agtcgtgtcg tgcctgagag cgcagtc       477
```

<210> SEQ ID NO 27

-continued

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Leu Ala Val Pro Phe Lys
1               5
```